US012773405B2

(12) United States Patent
Kroemer et al.

(10) Patent No.: US 12,773,405 B2
(45) Date of Patent: *Oct. 27, 2026

(54) COMBINATION OF LURBINECTEDIN AND IMMUNE CHECKPOINT INHIBITORS

(71) Applicant: PHARMA MAR, S.A., Madrid (ES)

(72) Inventors: Guido Kroemer, Villejuif (FR); Oliver Kepp, Villejuif (FR)

(73) Assignee: PHARMA MAR, S.A., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 19/190,098

(22) Filed: Apr. 25, 2025

(65) Prior Publication Data

US 2025/0295656 A1 Sep. 25, 2025

Related U.S. Application Data

(63) Continuation of application No. 18/023,804, filed as application No. PCT/EP2021/074425 on Sep. 3, 2021, now abandoned.

(30) Foreign Application Priority Data

Sep. 4, 2020 (WO) ................ PCT/EP2020/074860

(51) Int. Cl.

| | |
|---|---|
| ***A61K 31/4995*** | (2006.01) |
| ***A61K 39/39*** | (2006.01) |
| ***A61K 39/395*** | (2006.01) |
| ***A61P 35/00*** | (2006.01) |
| *A61K 39/00* | (2006.01) |

(52) U.S. Cl.

CPC ...... *A61K 31/4995* (2013.01); *A61K 39/3955* (2013.01); *A61P 35/00* (2018.01); *A61K 2039/505* (2013.01); *A61K 2039/507* (2013.01)

(58) Field of Classification Search

CPC ............ A61K 31/4995; A61K 39/3955; A61K 2039/505; A61K 2039/507; A61P 35/00

USPC ....................................................... 424/158.1

See application file for complete search history.

(56) References Cited

U.S. PATENT DOCUMENTS

| | | | |
|---|---|---|---|
| 5,089,273 | A | 2/1992 | Rinehart et al. |
| 5,149,804 | A | 9/1992 | Rinehart et al. |
| 5,256,663 | A | 10/1993 | Rinehart et al. |
| 5,478,932 | A | 12/1995 | Rinehart et al. |
| 5,654,426 | A | 8/1997 | Rinehart et al. |
| 5,721,362 | A | 2/1998 | Corey et al. |
| 5,929,059 | A | 7/1999 | Sanger et al. |
| 5,985,876 | A | 11/1999 | Rinehart et al. |
| 6,069,150 | A | 5/2000 | Spinelli et al. |
| 6,124,292 | A | 9/2000 | Corey |
| 6,124,293 | A | 9/2000 | Rinehart et al. |
| 6,316,214 | B1 | 11/2001 | Rinehart et al. |
| 6,348,467 | B1 | 2/2002 | Corey |
| 6,569,859 | B1 | 5/2003 | Corey |
| 6,686,470 | B2 | 2/2004 | Danishefsky et al. |
| 6,815,544 | B2 | 11/2004 | Corey |
| 6,867,334 | B2 | 3/2005 | Rinehart et al. |
| 6,936,714 | B2 | 8/2005 | Danishefsky et al. |
| 7,041,634 | B2 | 5/2006 | Weber et al. |
| 7,097,836 | B1 | 8/2006 | Seon |
| 7,763,615 | B2 | 7/2010 | Gallego et al. |
| RE41,614 | E | 8/2010 | Corey |
| 7,795,260 | B2 | 9/2010 | Barrasa et al. |
| 8,975,248 | B2 | 3/2015 | Zaknoen et al. |
| 12,324,806 | B2 | 6/2025 | Kahatt et al. |
| 12,433,890 | B2 | 10/2025 | Kahatt et al. |
| 12,440,490 | B2 | 10/2025 | Kahatt et al. |
| 2003/0216397 | A1 | 11/2003 | Flores et al. |
| 2004/0019056 | A1 | 1/2004 | Manzanares et al. |
| 2004/0059112 | A1 | 3/2004 | Rinehart et al. |
| 2004/0108086 | A1 | 6/2004 | Takahashi et al. |
| 2005/0267140 | A1 | 12/2005 | Miller et al. |
| 2006/0030571 | A1 | 2/2006 | Rinehart et al. |
| 2007/0082856 | A1 | 4/2007 | Gianni et al. |
| 2007/0093658 | A1 | 4/2007 | Barrasa et al. |
| 2007/0197517 | A1 | 8/2007 | Jani et al. |
| 2008/0234279 | A1 | 9/2008 | Rinehart et al. |
| 2008/0255132 | A1 | 10/2008 | Rowinsky et al. |
| 2009/0247533 | A1 | 10/2009 | Rinehart et al. |
| 2009/0253685 | A1 | 10/2009 | Provost et al. |
| 2012/0302629 | A1 | 11/2012 | Wang et al. |
| 2013/0266666 | A1 | 10/2013 | Moneo Ocaña et al. |
| 2018/0008602 | A1 | 1/2018 | Moneo Ocaña et al. |
| 2023/0310426 | A1 | 10/2023 | Kroemer et al. |
| 2024/0415834 | A1 | 12/2024 | Paz-Ares Rodriguez et al. |

FOREIGN PATENT DOCUMENTS

| | | | |
|---|---|---|---|
| CN | 1823794 | A | 8/2006 |
| CN | 103282037 | A | 9/2013 |
| CN | 106974902 | A | 7/2017 |
| CN | 111298122 | A | 6/2020 |

(Continued)

OTHER PUBLICATIONS

Jotte et al. (Journal of Thoracic Oncology, vol. 15 No. 8: 1351-1360, Apr. 14, 2020).*

ClinicalTrials.gov, Study of Lurbinectedin (PM01183) in Combination With Cisplatin in Patients With Solid Tumors. History of Changes for Study: NCT01980667, 7 pages, Jan. 25, 2017.

ClinicalTrials.gov, Study of Lurbinectedin in Combination With Doxorubicin Versus Doxorubicin Alone as First-line Treatment in Participants With Metastatic Leiomyosarcoma (SaLuDo). History of Changes for Study: NCT06088290, 5 pages, May 24, 2024.

(Continued)

*Primary Examiner* — Yan Xiao

(74) *Attorney, Agent, or Firm* — McCarter & English, LLP

(57) ABSTRACT

Described are combination therapies for the treatment of solid tumours, said therapies comprising lurbinectedin and an immune checkpoint inhibitor, for example, anti-PD-1, anti-PD-L1 or anti-CTLA-4 antibodies.

29 Claims, 5 Drawing Sheets

(56) References Cited

FOREIGN PATENT DOCUMENTS

| | | | |
|---|---|---|---|
| CN | 116284054 | A | 6/2023 |
| CN | 116332932 | A | 6/2023 |
| EP | 0309477 | A1 | 4/1989 |
| EP | 1806349 | A1 | 7/2007 |
| JP | 59-225189 | | 12/1984 |
| JP | 60-084288 | B2 | 5/1985 |
| JP | 2023-541010 | A | 9/2023 |
| TW | 202027750 | A | 8/2020 |
| WO | 1987/07610 | A2 | 12/1987 |
| WO | 1992/09607 | A1 | 6/1992 |
| WO | 1998/12198 | A1 | 3/1998 |
| WO | 1998/46080 | A1 | 10/1998 |
| WO | 1999/51238 | A1 | 10/1999 |
| WO | 1999/58125 | A1 | 11/1999 |
| WO | 2000/18233 | A1 | 4/2000 |
| WO | 2000/69862 | A2 | 11/2000 |
| WO | 2001/77115 | A1 | 10/2001 |
| WO | 2001/87894 | A1 | 11/2001 |
| WO | 2001/87895 | A1 | 11/2001 |
| WO | 2003/008423 | A1 | 1/2003 |
| WO | 2003/014127 | A1 | 2/2003 |
| WO | 2003/066638 | A2 | 8/2003 |
| WO | 2004/017964 | A1 | 3/2004 |
| WO | 2004/035613 | A2 | 4/2004 |
| WO | 2005/000852 | A2 | 1/2005 |
| WO | 2005/049031 | A1 | 6/2005 |
| WO | 2005/077341 | A1 | 8/2005 |
| WO | 2006/046079 | A1 | 5/2006 |
| WO | 2006/065780 | A2 | 6/2006 |
| WO | 2009/140675 | A2 | 11/2009 |
| WO | 2011/017145 | A2 | 2/2011 |
| WO | 2011/147828 | A1 | 12/2011 |
| WO | 2012/062920 | A1 | 5/2012 |
| WO | 2013/082660 | A1 | 6/2013 |
| WO | 2016/137985 | A1 | 9/2016 |
| WO | 2016/192680 | A1 | 12/2016 |
| WO | 2018/197663 | A1 | 11/2018 |
| WO | 2020/254471 | A1 | 12/2020 |
| WO | 2021/043949 | A1 | 3/2021 |
| WO | 2021/098992 | A1 | 5/2021 |
| WO | 2021/104442 | A1 | 6/2021 |
| WO | 2021/228414 | A1 | 11/2021 |
| WO | 2022/046594 | A1 | 3/2022 |
| WO | 2022/048775 | A1 | 3/2022 |
| WO | 2022/049270 | A1 | 3/2022 |
| WO | 2022/243482 | A1 | 11/2022 |
| WO | 2023/116861 | A1 | 6/2023 |

OTHER PUBLICATIONS

ClinicalTrials.gov, Study of PM01183 in Non-Colorectal Cancer Patients as a Days 1 and 8 Intravenous Short Infusion Every 3 Weeks. History of Changes for Study: NCT01405391, 7 pages, Jan. 14, 2016.
ClinicalTrials.gov, Study of Trilaciclib and Lurbinectidin. History of Changes for Study: NCT05578326, 4 pages, Nov. 14, 2023.
ClinicalTrials.gov, Study to Assess Safety, Tolerability, Efficacy of PM01183 and Atezolizumab in Patients w/Advanced Small Cell Lung Cancer. History of Changes for Study: NTC04253145. 13 pages, Nov. 15, 2023.
ClinicalTrials.gov, Study to Assess Safety, Tolerability, Efficacy of PM01183 and Atezolizumab in Patients w/Advanced Small Cell Lung Cancer. NCT04253145, 11 pages, Mar. 3, 2021.
ClinicalTrials.gov, Study to Assess Safety, Tolerability, Efficacy of PM01183 and Atezolizumab in Patients with Advanced Small Cell Lung Cancer. History of Changes for Study: NCT04253145. 6 pages, Mar. 2, 2021.
ClinicalTrials.gov, Study to Evaluate PM01183 in Combination With Olaparib in Advanced Solid Tumors. History of Changes for Study: NCT02684318, 12 pages, Jun. 21, 2017.
ClinicalTrials.gov, Study to Evaluate the Effect of Bosentan on the Pharmacokinetics of Lurbinectedin in Patients With Advanced Solid Tumors. NCT05072106, 7 pages, Oct. 8, 2021.
ClinicalTrials.gov, Talimogene Laherparepvec, Nivolumab and Trabectedin for Sarcoma (TNT). NCT03886311, 9 pages, Oct. 17, 2022.
ClinicalTrials.gov, To Assess the Effectiveness and Safety of Zepzelca in Adult Patients With Extensive Stage Small Cell Lung Cancer (SCLC) (SCLC). History of Changes for Study: NCT04894591, 6 pages, May 14, 2024.
Cojocaru et al., What's the latest with investigational drugs for soft tissue saroma? Expert Opinion on Investigational Drugs: 2022;31(11)1239-1253.
Corbellari et al., The immunocytokine L19-TNF eradicates sarcomas in combination with chemotherapy agents or with immune check-point inhibitors. Anticancer Drugs. Sep. 2020;31(8):799-805.
Cortinovis et al., Novel Cytotoxic Chemotherapies in Small Cell Lung Carcinoma. Cancers (Basel). Mar. 8, 2021;13(5):1152, 17 pages.
Cote et al., A phase II multi-strata study of lurbinectedin as a single agent or in combination with conventional chemotherapy in metastatic and/or unresectable sarcomas. Eur J Cancer. Feb. 2020;126:21-32.
Cruz et al., Multicenter Phase II Study of Lurbinectedin in BRCA-Mutated and Unselected Metastatic Advanced Breast Cancer and Biomarker Assessment Substudy. J Clin Oncol. Nov. 1, 2018;36(31):3134-3143.
Dalisay et al., Marine-Derived Anticancer Agents Targeting Apoptotic Pathways: Exploring the Depths for Novel Cancer Therapies. Mar Drugs. Feb. 28, 2024;22(3):114, 46 pages.
Damiano et al., Real-world evidence in extensive disease small cell lung cancer: The missing piece of the puzzle. Crit Rev Oncol Hematol. Mar. 2025;207:104618, 9 pages.
Das et al., Advances in Treatment of Recurrent Small Cell Lung Cancer (SCLC): Insights for Optimizing Patient Outcomes from an Expert Roundtable Discussion. Adv Ther. 2021;38:5431-5451.
De Francia et al., Report at Sep. 30, 2020, 9Months 2020 Highlights. PharmaMar. 10 pages, Nov. 3, 2020.
De Francia et al., Report at Sep. 30, 2021, Highlights of the Third Quarter 2021. PharmaMar. 10 pages, Oct. 28, 2021.
De Francia, PharmaMar Group reports financial resuts to Sep. 30, 2023. Press Release, 17 pages, Oct. 26, 2023.
De Francia, PharmaMar, Report as of Jun. 30, 2024, Milestones. 12 pages, Jul. 30, 2024.
De Francia, Report at Sep. 30, 2024, Milestones. PharmaMar. 13 pages, Oct. 29, 2024.
De Miguel Luken et al., Lurbinectedin in Combination with Pembrolizumab for Patients with Relapsed Small Cell Lung Cancer. LUPER Clinical Trial. Journal of Thoracic Oncology. 2021; 16:S501-S502, Abstract P48.06.
Desai et al., Lurbinectedin in Extrapulmonary Metastatic Neuroendocrine Carcinomas. Pancreas. Mar. 2022;51(3):e38, Abstract C-11.
Di Fonte et al., Cervical cancer benefits from trabectedin combination with the beta-blocker propranolol: in vitro and ex vivo evaluations in patient-derived organoids. Front Cell Dev Biol. Jun. 13, 2023;11:1178316, 14 pages.
Disselhorst et al., Immuno-oncology in malignant pleural mesothelioma. Lancet Respir Med. May 14, 2018;2 pages.
Domine et al., SEOM clinical guidelines for the treatment of small-cell lung cancer (SCLC) (2019). Clin Transl Oncol. Feb. 2020;22(2):245-255.
Drilon et al., Lurbinectedin (PM01183) plus paclitaxel (P), recommended does (RD) expansion results with or without the addition of bevacizumab (Bev) in patients (pts) with selected solid tumors. Annals of Oncology. Oct. 2016;27(Suppl 6):vi127, abstract 391P.
Drilon et al., Lurbinectedin (PM01183) plus Paclitaxel (P), Recommended Dose (RD) Expansion Results With or Without the Addition of Bevacizumab (Bev) in Patients (pts) With Selected Solid Tumors. PharmaMar. Oct. 2026; 1 page.
Dumoulin et al., Lurbinectedin shows clinical activity and immunemodulatory functions in patients with pre-treated small cell lung cancer and malignant pleural mesothelioma. European Journal of Cancer. 2022;172: 357-366.
Elez et al., First-In-Human Phase | Study of Lurbinectedin (PM01183) in Patients with Advanced Solid Tumors. Clinical Cancer Res. Apr. 15, 2014;20(8):2205-2214.

(56) References Cited

OTHER PUBLICATIONS

ENOT., TumGrowth: An open-access web tool for the statistical analysis of tumor growth curves. Oncoimmunology. 2018;7(9):e1462431, 3 pages.
EU Clinical Trials Register, A Phase III, Randomized, Open-label, Multicenter Study of Lurbinectedin in Combination with Atezolizumab Compared with Atezolizumab as Maintenance Therapy in Participants with Extensive-stage Small-cell Lung Cancer (ES-SCLC) Following First-line Induction Therapy with Carboplatin, Etoposide and Atezolizumab. 2021-001930-20, 8 pages, Dec. 28, 2021.
EU Clinical Trials Register, Lurbinectedin combined with durvalumab (MEDI 4736) in pre-treated patients with extensive stage small-cell lung cancer. 2022-001114-19, 9 pages, Apr. 3, 2023.
EU Clinical Trials Register, Phase I/II, Multicenter, Open-Label, Clinical and Pharmacokinetic Study of Lurbinectedin (PM01183) in Combination with Pembrolizumab in Patients with Relapsed Small Cell Lung cancer (the LUPER study). 2019-002261-35, 9 pages, Feb. 28, 2020.
EU Clinical Trials Register, Phase I-II Study to Assess the Safety, Tolerability and Efficacy of PM01183 and Atezolizumab in Patients with Advanced Small Cell Lung Cancer that Progressed Following Prior Therapy with Platinum-Based Chemotherapy. 2019-001553-12, 9 pages, Sep. 4, 2019.
EudraCT No. 2010-024292-30, A Phase II Study of PM01183 as Second-line Treatment in Patients with Metastatic Pancreatic Center. 34 pages, Mar. 10, 2011.
EudraCT No. 2011-002172-16, A phase II Controlled Study of PM01183 in Platinum-Resistant/Refractory Advanced Ovarian Cancer Patients. 35 pages, Aug. 9, 2011.
EudraCT No. 2011-006108-11, A Multicenter Phase II Clinical Trial of PM01183 in BRCA 1/2-Associated or Unselected Metastatic Breast Cancer. 42 pages, Feb. 10, 2012.
EudraCT No. 2013-000548-25, A Randomized-Controlled Three-arm Phase II Study of Lurbinectedin (PM01183) Alone or in Combination with Gemcitabine and a control arm with Docetaxel in Second-Line Treatment in Unresectable Non-Small Cell Lung Cancer (NSCLC) Patients. 38 pages, Apr. 9, 2013.
EudraCT No. 2014-003773-42, A Multicenter Phase II Clinical Trial of Lurbinectedin (PM01183) in Selected Advanced Solid Tumors. 58 pages, Jul. 29, 2015.
EudraCT No. 2014-005251-39, Phase III Randomized Clinical Trial of Lurbinectedin (PM01183) versus Pegylated Liposomal Doxorubicin or Topotecan in Patients with Platinum-resistant Ovarian Cancer (CORAIL Trial). 37 pages, Oct. 12, 2018.
EudraCT No. 2014-005251-39, Phase III Randomized Clinical Trial of Lurbinectedin (PM01183) versus Pegylated Liposomal Doxorubicin or Topotecan in Patients with Platinum-resistant Ovarian Cancer (CORAIL Trial). 44 pages, Jul. 17, 2015.
EudraCT No. 2015-000206-18, Evaluation of the Effect of Lurbinectedin (PM01183) on Cardiac Repolarization (QTc Duration) in Patients with Selected Solid Tumors. 21 pages, Jul. 10, 2015.
EudraCT No. 2015-000206-18, Evaluation of the effect of Lurbinectin (PM01183) on cardiac repolarisation (QTc duration) in patients with certain solid tumours. 12 pages, Nov. 27, 2019.
EudraCT No. 2015-001141-80, Phase Ib/II study to evaluate the efficacy and tolerability of PM01183 in combination with olaparib in patients with advanced solid tumors. 8 pages, Aug. 13, 2015.
EudraCT No. 2015-001641-89, Phase II Randomized Clinical Trial of Lurbinectedin (PM01183)/Doxorubicin (DOX) versus Cyclophosphamide (CTX), Doxorubicin (DOX) and Vincristine (VCR) (CAV) or Topotecan as Treatment in Patients with Small-Cell Lung Cancer (SCLC) Who Failed One prior Platinum-containing Line (ATLANTIS Trial). 60 pages, Oct. 21, 2016.
EudraCT No. 2015-003602-16, Phase I/II, Multicenter, Open-label, Clinical and Pharmacokinetic Study of Lurbinectedin in Combination with Irinotecan in Pretreated Patients with Selected Advanced Solid Tumors. 7 pages, Mar. 3, 2023.
ClinicalTrials.gov, A Phase II Clinical Study of Cadonilimab in Treatment-naive or Relapsed Extensive Small Cell Lung Cancer. NCT06406673. 5 pages, Dec. 31, 2024.
ClinicalTrials.gov, A Phase II Clinical Trial of PM01183 in BRCA 1/2-Associated or Unselected Metastatic Breast Cancer. History of Changes for Study: NCT01525589, 15 pages, Sep. 4, 2020.
ClinicalTrials.gov, A Phase II Multi-Strata Study of PM01183 as a Single Agent or in Combination With Conventional Chemotherapy in Metastatic and/or Unresectable Sarcomas. History of Changes for Study: NCT02448537, 9 pages, Feb. 9, 2021.
ClinicalTrials.gov, A Phase III, Open-Label Study of Maintenance Lurbinectedin in Combination With Atezolizumab Compared With Atezolizumab in Participants With Extensive-Stage Small-Cell Lung Cancer (IMforte). History of Changes for Study: NCT05091567. 8 pages, Jan. 11, 2024.
ClinicalTrials.gov, A Phase III, Open-Label Study of Maintenance Lurbinectedin in Combination With Atezolizumab Compared With Atezolizumab in Participants With Extensive-Stage Small-Cell Lung Cancer. NCT05091567, 9 pages, May 30, 2023.
ClinicalTrials.gov, A Study of Ifinatamab Deruxtecan Versus Treatment of Physician's Choice in Subjects With Relapsed Small Cell Lung Cancer (IDeate-Lung02). History of Changes for Study: NCT06203210, 9 pages, Apr. 19, 2024.
ClinicalTrials.gov, Clinical Pharmacokinetic Study of Lurbinectedin in Patients With Advanced Solid Tumors and Varying Degrees of Hepatic Impairment. History of Changes for Study: NCT05101265, 6 pages, Nov. 23, 2023.
ClinicalTrials.gov, Clinical Study of PM01183 in Patients With Acute Leukemia or Relapsed/Refractory Myelodysplastic Syndrome. History of Changes for Study: NCT01314599, 8 pages, Nov. 4, 2015.
ClinicalTrials.gov, Clinical Trial of Lurbinectedin (PM01183) in Platinum Resistant Ovarian Cancer Patients (CORAIL). History of Changes for Study: NCT02421588, 18 pages, Mar. 25, 2020.
ClinicalTrials.gov, Clinical Trial of Lurbinectedin (PM01183) in Selected Advanced Solid Tumors. History of Changes for Study: NCT02454972, 15 pages, Feb. 1, 2023.
ClinicalTrials.gov, Clinical Trial of Lurbinectedin (PM01183) in Selected Advanced Solid Tumors. History of Changes for STudy: NCT02454972. 6 pages, May 21, 2015.
ClinicalTrials.gov, Clinical Trial of Lurbinectedin (PM01183) in Selected Advanced Solid Tumors. NCT02454972, 8 pages, Mar. 2, 2023.
ClinicalTrials.gov, Clinical Trial of Lurbinectedin as Single-agent or in Combination With Irinotecan Versus Topotecan or Irinotecan in Patients With Relapsed Small-cell Lung Cancer (LAGOON). History of Changes for Study: NCT05153239, 13 pages, Apr. 30, 2024.
ClinicalTrials.gov, ClinicalTrial of Lurbinectedin (PM01183)/ Doxorubicin Versus CAV or Topotecan as Treatment in Patients With Small-Cell Lung Cancer (ATLANTIS). History of Changes for Study: NCT02566993, 39 pages, Sep. 29, 2021.
ClinicalTrials.gov, Dose Attenuated Chemotherapy in Compromised Patients With Lung Cancer. History of Changes for Study: NCT05800587, 4 pages, Mar. 25, 2024.
ClinicalTrials.gov, Durvalumab and Lurbinectedin for the Treatment of Relapsed or Refractory Small Cell Lung Cancer. History of Changes for Study: NCT04607954. 4 pages, Jul. 21, 2023.
ClinicalTrials.gov, Efficacy and Safety Study of Lurbinectedin and Dostarlimab in Cancer Patients: Protocol VHIO21001—LiDer (LiDer). History of Changes for Study: NCT06385548, 4 pages, May 9, 2024.
ClinicalTrials.gov, Escalating Doses of PM01183 in Combination With Gemcitabine in Patients With Specific Unresectable Solid Tumors. History of Changes for Study: NCT01970553, 6 pages, Mar. 31, 2015.
ClinicalTrials.gov, Evaluation of the Effect of Lurbinectedin (PM01183) on Cardiac Repolarization in Patients With Selected Solid Tumors. History of Changes for Study: NCT02451007, 7 pages, Nov. 6, 2019.
ClinicalTrials.gov, History of Changes for Study: NCT05734066. 5 pages, Feb. 15, 2023.
ClinicalTrials.gov, Immune Checkpoint Inhibition With Lurbinectedin Relapsed/Recurrent SCLC. History of Changes for Study: NCT04610658. 4 pages, Apr. 1, 2024.

(56) References Cited

OTHER PUBLICATIONS

ClinicalTrials.gov, LINNOVATE: Lurbinectedin, Ipilimumab and Nivolumab for Soft Tissue Sarcoma (LINNOVATE). History of Changes for Study: NCT05876715. 4 pages, May 17, 2023.
ClinicalTrials.gov, Lurbinectedin (PM01183) Combined With Pembrolizumab in Small Cell Lung Cancer. (LUPER). History of Changes for Study: NCT04358237. 5 pages, Feb. 1, 2024.
ClinicalTrials.gov, Lurbinectedin (PM01183) Combined With Pembrolizumab in Small Cell Lung Cancer. (LUPER). NCT04358237. 7 pages, Apr. 20, 2020.
ClinicalTrials.gov, Lurbinectedin + Doxorubicin in Leiomyosarcoma. History of Changes for Study: NCT05099666, 5 pages, Apr. 13, 2024.
ClinicalTrials.gov, Lurbinectedin Combined with Durvalumab in Pre-treated Patients With Extensive Stage Small-cell Lung Cancer (LURBIMUNE). History of Changes for Study: NCT05572476. 4 pages, Oct. 26, 2023.
ClinicalTrials.gov, Lurbinectedin in FET-Fused Tumors (LIFFT). History of Changes for Study: NCT05918640, 4 pages, Apr. 12, 2024.
ClinicalTrials.gov, Lurbinectedin in Patients With Advanced Gastrointestinal Malignancies With DNA Repair Mutations. History of Changes for Study: NCT05229588, 4 pages, Feb. 1, 2024.
ClinicalTrials.gov, Lurbinectedin Monotherapy in Participants With Advanced or Metastatic Solid Tumors (EMERGE-201) (EMERGE-201). History of Changes for Study: NCT05126433, 4 pages, Feb. 23, 2024.
ClinicalTrials.gov, Lurbinectedin Monotherapy in Patients With Progressive Malignant Pleural Mesothelioma. History of Changes for Study: NCT03213301, 4 pages, Jul. 13, 2021.
ClinicalTrials.gov, Lurbinectedin With Berzosertib, an ATR Kinase Inhibitor in Small Cell Cancers with High-Grade Neuroendorine Cancers. History of Changes for Study: NCT04802174, 8 pages, May 3, 2024.
ClinicalTrials.gov, Lurbinectedin With or Without Avelumab in Small Cell Carcinoma of the Bladder (LASER). History of Changes for Study: NCT06228066. 6 pages, Jan. 26, 2024.
ClinicalTrials.gov, Lurbinectedin With or Without Irinotecan in Treating Patients With Relapsed or High Risk Metastatic Ewing Sarcoma. History of Changes for Study: NCT05042934, 4 pages, Feb. 1, 2022.
ClinicalTrials.gov, Neoadjuvant Lurbinectedin and Preoperative Radiation for Treating Soft Tissue Sarcomas. History of Changes for Study: NCT06217536, 5 pages, Apr. 22, 2024.
ClinicalTrials.gov, Observational Study to Evaluate the Safety and Efficacy of Zepzelca Injection. NCT06021483, 3 pages, Sep. 1, 2023.
ClinicalTrials.gov, Palliative Radiotherapy With Lurbinectedin in Patients With Extensive Stage Small Cell Lung Cancer. History of Changes for Study: NCT05244239, 4 pages, Jan. 12, 2024.
ClinicalTrials.gov, Pharmacokinetic Study of Lurbinectedin in Combination With Irinotecan in Patients With Selected Solid Tumors. History of Changes for Study: NCT02611024, 7 pages, Apr. 26, 2024.
ClinicalTrials.gov, Pharmacokinetic Study of Lurbinectedin in Combination With Irinotecan in Patients With Selected Solid Tumors. NCT02611024, 13 pages, Dec. 13, 2022.
ClinicalTrials.gov, Phase 1b of Lurbinectedin in Combination With Weekly Paclitaxel and Bevacizumab in Platinum-resistant Ovarian Cancer. History of Changes for Study: NCT05636111, 4 pages, Mar. 11, 2024.
ClinicalTrials.gov, Phase I Study of Lurbinectedin (PM01183) in Combination With Paclitaxel, With or Without Bevacizumab, in Selected Advanced Solid Tumors. History of Changes for Study: NCT01831089, 18 pages, Mar. 24, 2020.
ClinicalTrials.gov, Phase I, Multicenter, Open-label, Dose-escalating, Clinical and Pharmacokinetic Study of PM01183 in Patients With Advanced Solid Tumors. History of Changes for Study: NCT00877474, 8 pages, Nov. 3, 2015.
ClinicalTrials.gov, Phase II Trial of Lurbinectedin Combined With Avelumab as Switch Maaintenance Firstline Therapy. History of Changes for Study: NCT05574504. 4 pages, Oct. 7, 2022.
ClinicalTrials.gov, RW Effectiveness of Lurbinectedin in Extensive Stage SCLC (LURBICLIN). History of Changes for Study: NCT05285033, 3 pages, Jan. 5, 2023.
ClinicalTrials.gov, Safety Tolerability Pharmacokinetic and Preliminary Efficacy in Chinese Advanced Sold Tumors Patients. History of Changes for Study: NCT04638491, 3 pages, Apr. 25, 2023.
ClinicalTrials.gov, SAINT: Trabecedtin, Ipilimumab and Nivolumab as First Line Treatment for Advanced Soft Tissue Sarcoma. History of Changes for Study: NCT03138161. 6 pages, May 4, 2022.
ClinicalTrials.gov, Study Comparing Tarlatamab With Standard of Care Chemotherapy in Relapsed Small Cell Lung Cancer (DeLLphi-304). History of Changes for Study: NCT05740566. 14 pages, Feb. 21, 2023.
ClinicalTrials.gov, Study Escalating Doses of PM01183 in Combination With Fixed Doxorubicin in Patients With Specific Advanced Unresectable Solid Tumors. History of Changes for Study: NCT01970540, 12 pages, Feb. 24, 2020.
ClinicalTrials.gov, Study Escalating Doses of PM01183 in Combination With Fixed Doxorubicin in Patients With Specific Advanced Unresectable Solid Tumors. NCT01970540, 39 pages, Mar. 9, 2020, includes history of changes.
ClinicalTrials.gov, Study of Lurbinectedin (PM01183) in Combination With Capecitabine in Patients With Metastatic Breast Cancer (MBC), Pancreatic Cancer (PC) or Metastatic Colorectal Cancer (CRC). History of Changes for Study: NCT02210364, 6 pages, Dec. 13, 2016.
PharmaMar, CNMV Submissions. 226 pages, Jan. 5, 2022.
PharmaMar, Consolidated Management Report 2023, 23 pages, (2023).
PharmaMar, Consolidated Management Report 2023. 44 pages, (2023).
PharmaMar, Consolidated Non-Financial Information Statement. 80 pages, (2020).
PharmaMar, Corporate Presentation. www.pharmamar.com. 34 pages, Aug. 2023.
PharmaMar, Financial Statements 2023. 142 pages, (2023).
PharmaMar, FY 2022 Results Presentation. 22 pages, Mar. 1, 2023.
PharmaMar, General Shareholders' Meeting. 103 pages, Jun. 29, 2022.
PharmaMar, General Shareholders' Meeting. 43 pages, May 31, 2023.
PharmaMar, Junta General de Accionistas 2021, 54 pages, Apr. 15, 2021.
PharmaMar, PM1183-A-003-10 (NCT01970540). Phase I Multicenter, Open-label, Clinical and Pharmacokinetic Study of PM01183 in Combination with Doxorubicin in Non-heavily Pretreated Patients wtih Selected Advanced Solid Tumors. Statistical Analysis Plan, Version V4.0. 121 pages, Feb. 12, 2018.
PharmaMar, PM1183-B-003-11, A Multicenter Phase II ClinicalTrial of PM01183 in BRCA 1/2-Associated or Unselected Metastatic Breast Cancer. NCT Code: 01525589, Version 3.0, 95 pages, Dec. 10, 2018.
PharmaMar, PM1183-B-005-14, A Multicenter Phase II Clinical Trial of Lurbinectedin (PM01183) in Selected Advanced Solid Tumors. Statistical Analysis Plan, Version 5.0, 150 pages, Nov. 11, 2020.
PharmaMar, PM1183-C-003-14, Phase III Randomized Clinical Trial of Lurbinectedin (PM01183)/Doxorubicin (DOX) versus Cyclophosphamide (CTX), Doxorubicin (DOX) and Vincristine (VCR) (CAV) or Topotecan as Treatment in Patients with Small-Cell Lung Cancer (SCLC) Who Failed One Prior Platinum-containing Line (ATLANTIS Trial). Statistical Analysis Plan, Version 3.0, 123 pages, Sep. 4, 2020.
PharmaMar, PM1183-C-004-14 (NCT02421588), Phase II Randomized Clinical Trial of Lurbinectedin (PM01183) versus Pegylated Liposomal Dokxorubicin or Topotecan in Patients with Platinum-resistant Ovarian Cancer (CORAIL Trial). Statistical Analysis Plan, Version 2.0, 93 pages, Aug. 30, 2017.
PharmaMar, Report as of Dec. 31, 2019, 2019 Milestones. 12 pages, Feb. 26, 2020.

(56) References Cited

OTHER PUBLICATIONS

PharmaMar, Report as of Mar. 31, 2020, 1Q20 Milestones. 10 pages, Apr. 23, 2020.
PharmaMar, Report as of Mar. 31, 2022, Milestones. 8 pages, Apr. 28, 2022.
PharmaMar, Report as of Sep. 30, 2023, Milestones. 13 pages, Oct. 26, 2023.
PharmaMar, Report at Jun. 30, 2020, 1H20 Highlights. 10 pages. Jul. 30, 2020.
PharmaMar, Report at Jun. 30, 2021, Milestones in 2021. PharmaMar. 10 pages, Jul. 29, 2021.
PharmaMar, Report at Jun. 30, 2022, Milestones. PharmaMar. 9 pages, Jul. 27, 2022.
PharmaMar, Report at Sep. 30, 2020, 9Months 2020 Highlights. 10 pages, Nov. 3, 2020.
PharmaMar, Report at Sep. 30, 2021, Highlights of the Third Quarter 2021. 10 pages, Oct. 28, 2021.
PharmaMar, Report at Sep. 30, 2022 Milestones. 11 pages, Oct. 27, 2022.
PharmaMar, Report at Dec. 31, 2020, 2021 Milestones. 10 pages, Feb. 26, 2021.
PharmaMar, Report at Dec. 31, 2021, Milestones in 2021. 10 pages, Feb. 28, 2022.
PharmaMar, Report at Dec. 31, 2022, Milestones. 9 pages, Feb. 28, 2023.
PharmaMar, Report at Dec. 31, 2023, Milestones. 13 pages, Feb. 28, 2024.
PharmaMar, Report at Mar. 31, 2021, 1Q21 Milestones. 9 pages, May 5, 2021.
PharmaMar, Report at Mar. 31, 2023, Milestones. 12 pages, Apr. 26, 2023.
PharmaMar, Report at Mar. 31, 2024, Milestones. 12 pages, Apr. 23, 2024.
PharmaMar, Report at Jun. 30, 2023, Milestones. 12 pages, Jul. 27, 2023.
PharmaMar, Separate Financial Statements 2019. Financial Statements and Auditors' Report. 132 pages, (2019).
PharmMar Annual Report 2022, 162 pages, (2022).
Pietrocola et al., Caloric Restriction Mimetics Enhance Anticancer Immunosurveillance. Cancer Cell. 2016;30:147-160.
Pink et al., Efficacy and safety of nivolumab and trabectedin in pretreated patients with advanced soft tissue sarcomas (STS)—preliminary results of a phase II trial of the German Interdisciplinary Sarcoma Group (GISG-15, NitraSarc) for the non-L sarcoma cohort. <https://d201v5jt9ylckg.cloudfront. net/273/13681/198005/198005_A2855_poster_big_1.jpg.> ASCO 2021, ID329799, 1 page, (2021).
Pink et al., Efficacy and safety of nivolumab and trabectedin in pretreated patients with advanced soft tissue sarcomas (STS): Preliminary results of a phase II trial of the German Interdisciplinary Sarcoma Group (GISG-15, NitraSarc) for the non-L sarcoma cohort. J Clin Oncol. 39(Suppl 15):584s, Abstract 11545. (2021).
Pivotal, POLA/ACOG1401: Clinical Study Report Synopsis. Pages II. Phase IB/II to evaluate the efficacy and tolerability of PM01183 in combination with olaparib in patients with advanced solid tumors. Protocol POLA/ACOG1401 version 6.0, 5 pages, Jan. 14, 2019.
Poirier et al., New Approaches to SCLC Therapy: From the Laboratory to the Clinic. Journal of Thoracic Oncology. Apr. 2020; 15(4):520-540.
Ponce Aix et al., 2SMALL (NCT04253145) Phase I Part: Lurbinectidine (LUR) in Combination with Atezolizumab (ATZ) for Second Line Extensive Stage Small Cell Lung Cancer (ES-SCLC) Patients (Pts). J Immunother Cancer. 2021;9(Suppl 2):A493, Abstract 464.
Ponce Aix et al., 2SMALL phase I part. Lurbinectedin (LUR) in combination with Atezolizumab (ATZ) for second line Extensive Stage Small Cell Lung Cancer (ES-SCLC) patients. Fundacion OncoSur. 1 pages, (2021).
Ponce Aix et al., Lurbinectedin (LUR) in combination with Irinotecan (IRI) in patients (pts) with advanced solid tumors: Updated results from a phase Ib-II trial. ASCO. 1 page, (2020).
Ponce Aix et al., Lurbinectedin (LUR) in combination with irinotecan (IRI) in patients (pts) with advanced solid tumours. Annals of Oncology. Oct. 2019; 30(Suppl 5):v178, Abstract 471P.
Ponce Aix et al., Lurbinectedin (LUR) in combination wtih Irinotecan (IRI) in patients (pts) with advanced solid tumors: Updated results from a phase ib-II trial. Journal of Clinical Oncology. May 20, 2020;38(Suppl 15):3514. 4 pages.
Ponce Aix, Lurbinectedin (LUR) in combination with Irinotecan (IRI) in patients (pts) with advanced solid tumors. Annals of Oncology. 2019;30(Suppl 5):v159-v193, Abstract 3811, 2 pages.
Ponce et al., Lurbinectedin (L) Combined with Paclitaxel (P) or Irinotecan (I) in Relapsed SCLC. Results from Two Phase LB trials. IASLC 2019 World Conference on Lung Cancer. WCLC2019. IASLC.org. Poster P2. 12-13, p. 854, (2019).
Ponce et al., Lurbinectedin (L) combined wtih Paclitaxel (P) or Irinotecan (I) in relapsed SCL. Results from two phase Ib trials. J Thorac Oncol. Poster 2.12-13, 1 page, Abstract No. 1588, Sep. 7-10, 2019.
Ponce et al., Lurbinectedin in combination with Irinotecan in patients with advanced solid tumors. ESMO Congress, Ann Oncol., 2019;30(Suppl 5):v178, Abstract 471P.
Pons-Tostivint et al., Second-line treatment outcomes after first-line chemotherapy plus immunotherapy in Extensive-Stage small cell lung cancer (ES-SCLC) patients: A large French multicenter study. Lung Cancer. Aug. 2024; 194:107887, 17 pages, pre-publication edition.
Poveda et al., Lurbinectedin (PM01183) activity in platinum-resistant/refractory ovarian cancer patients Updated results of an ongoing two-stage Phase II study. 1 page, (2012).
Poveda et al., Lurbinectedin (PM01183) activity in platinum-resistant/refractory ovarian cancer patients: Updated results of an ongoing two stage Phase II study. Annals of Oncology. 2012;S732, Abstract 3065.
Poveda et al., Lurbinectedin (PM01183) An Active compound in platinum-resistant/refractory ovarian cancer patients: Results of a two-stage, controlled phase II study. 2014 ASCO 50th Annual Meeting. 19 pages, May 20, 2014.
Poveda et al., Lurbinectedin (PM01183), an active compound i platinum resistant/refractory ovarian cancer (PRROC) patients: Results of a two-stage, controlled phase II study. 2014 ASCO Annual Meeting. 2014;2 pages, Abstract 5505.
Povo-Retana et al., Specific Effects of Trabectedin and Lurbinectedin on Human Macrophage Function and Fate—Novel Insights. Cancers. 2020;12:3060, 21 pages.
Povo-Retana et al., Trabectedin and Lurbinectedin Modulate the Interplay between Cells in the Tumour Microenvironment-Progresses in Their Use in Combined Cancer Therapy. Molecules. Jan. 9, 2024;29(2):331, 21 pages.
Pujol et al., A Randomized Non-Comparative Phase II Study of Anti-Programmed Cell Death-Ligand 1 Atezolizumab or Chemotherapy as Second-Line Therapy in Patients With Small Cell Lung Cancer: Results From the IFCT-1603 Trial. Journal of Thoracic Oncology. May 2019;209;14(5): 903-913.
Radaelli et al., Progress in histology specific treatments in soft tissue sarcoma. Expert Rev Anticancer Ther. Sep. 2024;24(9):845-868.
Ratain et al., Phase I study of lurbinectedin (PM1183) administered on days (D) 1 & 8 every 3 weeks (q3wk) in patients (pts) with solid tumors. Eur J Cancer. 2014;50(Suppl 6): 13-14, Abstract 23.
Ratti et al., Trabectedin Overrides Osteosarcoma Differentiative Block and Reprograms the Tumor Immune Environment Enabling Effective Combination with Immune Checkpoint Inhibitors. Clin Cancer Res. Sep. 1, 2017;23 (17):5149-5161.
Ray-Coquard et al., Lymphopenia as a prognostic factor for overall survival in advanced carcinomas, sarcomas, and lymphomas. Cancer Res. Jul. 1, 2009;69(13):5383-91.
Recine et al., Clinical and translational implications of immunotherapy in sarcomas. Front Immunol. Jun. 25, 2024;15:1378398, 10 pages.
Reck et al., Efficacy and safety on nivolumab (nivo) monotherapy versus chemotherapy (chemo) in recurrent small cell lung cancer (SCLC): Results from CheckMate 331. Annals of Oncology. Dec. 2018;29(Suppl 10):x43, abstract L8A5.

(56) References Cited

OTHER PUBLICATIONS

Reddy et al., Emerging drugs for small cell lung cancer: A focused review on immune checkpoint inhibitors. Expert Opinion on Emerging Drugs. 2020;25(3):353-366.
REec Identificador: 2022-502975-45-00 (CTIS), Randomized, Controlled, Open-label, Phase IIb/III Study of Lurbinectedin in Combination with Doxorubicin versus Doxorubicin Alone as First-line Treatment in Patients with Metastatic Leiomyosarcoma. 18 pages, Nov. 12, 2023.
REec Identifier: 2021-004471-13, Clinical trial of lurbinectedin as a single agent or in combination with irinotecan versus topotecan or irinotecan in patients with relapsed small cell lung cancer (CPCP) (LAGOON). 38 pages, Jun. 6, 2022.
REec, A study of lurbinectedin in combination with atezolizumab compared with atezolizumab as maintenance therapy in participants with extensive-stage small-cell lung cancer (ES-SCLC) following first-line induction therapy with carboplatin, etoposide and atezolizumab. 2021-001930-20, 14 pages, Dec. 23, 2021.
REec, Identifier: 2013-000548-25, A Clinical Study in Three-arm of Lurbinectedin (PM01183) alone or in combination wtih Gemcitabine and a control arm with Docetaxel as second-line treatment in Small Cell Lung Cancer (NSCLC) patients. 4 pages, Nov. 23, 2016.
REec, Identifier: 2014-003773-42, Clinical Trial of Lurbinectedin (PM01183) in Selected Advanced Solid Tumors. 5 pages, Sep. 17, 2020.
REec, Identifier: 2014-005251-39, CORAIL Trial. 5 pages, Oct. 8, 2018.
REec, Identifier: 2015-000206-18, Effect of Lurbinectedin (PM01183) on Cardiac Repolarization (QTc Duration) in Patients with Solid Tumors. 4 pages, Aug. 18, 2016.
REec, Identifier: 2015-001141-80, Phase Ib/II study to evaluate the efficacy and tolerability of PM01183 in combination with olaparib in patients with advanced solid tumors. 4 pages, May 5, 2019.
REec, Identifier: 2015-001641-89, Clinical Trial of Lurbinectedin (PM01183)/Doxoribicin (DOX) versus Cyclophosphamide (CTX), Doxorubicin (DOX) and Vincristine (VCR) (CAV) or Topotecan as Treatment in Patients with Small-Cell Lung Cancer (SCLC). 11 pages, Feb. 23, 2020.
REec, Identifier: 2015-003602-16, Estudio clinico y farmacocinetico de lurbinectedina en combinacion con irinotecan en pacientes con tumores solidos avanzados. 14 pages, Jan. 4, 2016.
REec, Phase I-II Study to Assess the Safety, Tolerability and Efficacy of PM01183 and Atezolizumab in Patients with Advanced Small Cell Lung Cancer that Progressed Following Prior Therapy with Platinum-Based Chemotherapy. 2019-001553-12. 19 pages, Nov. 28, 2019.
REec, Study of Lurbinectedin (PM01183) in Combination with Pembrolizumab in Patients with Relapsed Small Cell Lung Cancer. 2019-002261-35, 17 pages, Mar. 3, 2020.
Reguart et al., A cross-sectional analysis of treatment patterns in small-cell lung cancer in five European countries. Future Oncol. 2024;20(17):1151-1164, pre-publication edition.
Reguart et al., In Search of the Long-Desired 'Copernican Therapeutic Revolution' in Small-Cell Lung Cancer. Drugs. Feb. 2020;80(3):241-262.
Reichardt et al., Efficacy and safety of nivolumab and trabectedin in pretreated patients with advanced soft tissue sarcmoas (STS): Results of a phase II trial of the German Interdisciplinary Sarcoma Group (GISG-15, NitraSarc). American Society of Clinical Oncology. 1 page, Abstract 11500, (2023).
Reichardt et al., Efficacy and safety of nivolumab and trabectedin in pretreated patients with advanced soft tissue sarcomas (STS)—results of a phase II trial of the German Interdisciplinary Sarcoma Group (GISG-15, NitraSarc). 2023 ASCO Annual Meeting. 20 pages, (2023).
Ren et al., Recent advances in immunotherapy for small cell lung cancer. Curr Opin Oncol. Jan. 1, 2025;37(1):17-26.
Risnik et al., Immunoregulatory effects of Lurbinectedin in chronic lymphocytic leukemia. Cancer Immonology, Immunotherapy. Feb. 13, 2020;69:813-824.
Roberts et al., Provocative Questions in osteosarcoma basic and translational biology: a report from the Children's Oncology Group. Cancer. Oct. 15, 2020;125(20):3514-3525.
Saida et al., Extensive-Stage Small-Cell Lung Cancer: Current Landscape and Future Prospects. Onco Targets Ther. Aug. 2, 2023;16:657-671.
Salaroglio et al., Ecteinascidin synthetic analogues: a new class of selective inhibitors of transcription, exerting immunogenic cell death in refractory malignant pleural mesothelioma. J Exp Clin Cancer Res. Dec. 21, 2024;43(1):327, 17 pages.
Saltos et al., Breaking the Impasse: Advances in Treatment of Small Cell Lung Cancer. Clin Chest Med. Jun. 2020;41(2):269-280.
Sands et al., Treating patients with platinum-sensitive extensive-stage small-cell lung cancer in a real-world setting. Front Oncol. Dec. 22, 2023;13:1161931, 12 pages.
Sasi et al., Current stand on systemic therapy in localized soft tissue sarcomas: a clinician's perspective. Future Oncol. Oct. 2023;19(31):2135-2145. Pre-publication edition.
Scattolin et al., The emerging role of Schlafen-11 (SLFN11) in predicting response to anticancer treatments: Focus on small cell lung cancer. Cancer Treat Rev. Jul. 2024;128:102768, 9 pages.
Schallier et al., Antitumor Activity of Cabozantinib in Metastatic Adult Ewing Sarcoma: A Case Report. Anticancer Research. 2020;40:2265-2269.
Schroeder et al., Immunologic Gene Signature Analysis Correlates Myeloid Cells and M2 Macrophages with Time to Trabectedin Failure in Sarcoma Patients. Cancers (Basel). Mar. 2, 2022;14(5):1290, 14 pages.
Schwarz et al., Trabectedin enhances the antitumor effects of IL-12 in triple-negative breast cancer. Cancer Immunol Res. Jan. 7, 2025. 43 pages, pre-publication edition.
Sebio et al., The current landscape of early drug development for patients with sarcoma in the immunotherapy era. Future Oncology. May 2018;14(12):1197-1211. Pre-publication edition.
Seidel et al., Anti-PD-1 and Anti-CTLA-4 Therapies in Cancer: Mechanisms of Action, Efficacy, and Limitations. Friontiers in Oncology. Mar. 2018;8(86):1-14.
Shaw et al., Recent treatment patterns and real-world survival following first-line anti-PD-L1 treatment for extensive-stage small cell lung cancer. Oncologist. Dec. 6, 2024;29(12):1079-1089.
Shim et al., Real-World Outcomes with Lurbinectedin in Second Line and Beyond for Extensive Stage Small Cell Lung Cancer in Korea. Lung Cancer (Auckl). Oct. 30, 2024;15:149-159.
Sistigu et al., Cancer cell-autonomous contribution of type I interferon signaling to the efficacy of chemotherapy. Nature Medicine. Nov. 2014;20(11):1301-1312.
Solta et al., Small cells—big issues: biological implications and preclinical advancements in small cell lung cancer. Mol Cancer. Feb. 24, 2024;23(1):41, 25 pages.
Sonpavde et al., Phase II trial of lurbinectedin combined with avelumab as maintenance therapy for metastatic urothelial carcinoma with stable or responding disease following platinum-based chemotherapy. J Clin Oncol. Feb. 21, 2023;41(6):1 page, Abstract TPS590.
Spigel et al., RESILIENT Trial Investigators. RESILIENT Part 2: A Randomized, Open-Label Phase III Study of Liposomal Irinotecan Versus Topotecan in Adults With Relapsed Small Cell Lung Cancer. J Clin Oncol. Jul. 1, 2024;42(19):2317-2326.
Aobo et al., Combination of immune checkpoint inhibitors and anthracyclines as a potential first-line regimen for dedifferentiated liposarcoma: systematic review and meta-analysis. Cancer Immunology, Immunotherapy. Apr. 21, 2025;74:179, 14 pages.
Assi et al., Doxorubicin and trabectedin in leiomyosarcoma: pioneering a new era of smart combinations in soft tissue sarcomas. Future Oncology. Feb. 7, 2025;21(8):879-882.
Cerrato et al., AI-based classification of anticancer drugs reveals nucleolar condensation as a predictor of immunogenicity. Mol Cancer. Dec. 20, 2024;23(1):275, 26 pages.
Cespedes et al., Lurbinectedin induces depletion of tumor-associated macrophages, an essential component of its in vivo synergism with gemcitabine, in pancreatic adenocarcinoma mouse models. Dis Model Mech. Dec. 1, 2016;9(12):1461-1471.

(56) References Cited

OTHER PUBLICATIONS

Chakraborty et al., Protocol to co-culture SCLC cells with human CD8+ T cells to measure tumor cell killing and T cell activation. STAR Protocols. Jun. 20, 2025;6:103767, 13 pages.
Choudhury et al., Lurbinectedin with atezolizumab maintenance therapy in extensive-stage small-cell lung cancer. The Lancet. Jun. 14, 2025;405:2104-2106.
De Francia et al., Report at Mar. 31, 2025, Milestones. PharmaMar. 13 pages, Apr. 24, 2025.
Ganti et al., Real-world use, effectiveness, and safety of second-line lurbinectedin monotherapy in small cell lung cancer. Future Oncology. May 26, 2025;21(13):1675-1685.
Gupta et al., Targeting ovarian cancer: The promise of liposome-based therapies. International Journal of Pharmaceutics. 2025;677:125647, 19 pages.
Hakim et al., Multimodal treatment with cisplatin for metastatic disease in malignant peripheral nerve sheath tumors: a case report and review. Anticancer Drugs. Aug. 1, 2025;36(7):594-599, pre-publication edition.
Hofer et al., Conference on challenges in sarcoma (CCS) 2024: Expert opinions on non-evidence-based management aspects. European Journal of Cancer. 2025;220:115368, 22 pages.
Jozwiak-Hagymasy et al., Economic evaluations and health economic models of soft tissue sarcomas: Systematic literature review from a European and North American perspective. Critical Reviews in Oncology/Hematology. 2025;209:104661, 9 pages.
Kim et al., Small Cell Lung Cancer: A Review. JAMA. Mar. 31, 2025;E1-E12.
Krayim et al., Lurbinectedin for extensive stage—small cell lung cancer (ES-SCLC): real world response patterns and survival outcomes. Lung Cancer. 2025;205:108598, 6 pages.
Lai et al., The origin and polarization of Macrophages and their role in the formation of the Pre-Metastatic niche in osteosarcoma. International Immunopharmacology. 2025;150:114260, 16 pages.
Legallois et al., Identification of Anticancer Drugs Associated to Cancer Therapy-Related Cardiac Dysfunction: A VigiBase® Disproportionality Analysis. Eur Heart J Cardiovasc Pharmacother. Apr. 24, 2025:pvaf027, 24 pages, pre-publication edition.
Lim et al., Current and future perspectives in extensive-stage small-cell lung cancer. Ther Adv Med Oncol. 2025;17:1-25.
Morand et al., Clinical characterization and therapeutic targeting of fusion genes in oncology. Future Oncology. 2025;21(10):1249-1260.
Mountzios et al., Tarlatamab in Small-Cell Lung Cancer after Platinum-Based Chemotherapy. New England Journal of Medicine. Jun. 2, 2025;672 pages.
Paz-Ares et al., Efficacy and safety of first-line maintenance therapy with lurbinectedin plus atezolizumab in extensive-stage small-cell lung cancer (IMforte): a randomised, multicentre, open-label, phase 3 trial. The Lancet. Jun. 14, 2025;405(10495):2129-2143.
Paz-Ares et al., Lurbinectedin (lurbi) + atezolizumab (atezo) as first-line (1L) maintenance treatment (tx) in patients (pts) with extensive-stage small cell lung cancer (ES-SCLC): Primary results of the phase 3 IMforte trial. 2025 ASCO Annual Meeting, Abstract 8006. 1 page, (2025).
Paz-Ares et al., Lurbinectedin + atezolizumab as first-line maintenance treatment in patients with extensive-stage small cell lung cancer: Primary results of the Phase 3 IMforte trial. 2025 ASCO Annual Meeting, Presentation. Abstract 8006, 28 pages, (2025).
Paz-Ares et al., Unmet Needs in Maintenance Therapy for Extensive Stage Small Cell Lung Cancer. Clin Lung Cancer. May 2025;26(3):168-178, pre-publication edition.
Peranzoni et al., Macrophages impede CD8 T cells from reaching tumor cells and limit the efficacy of anti-PD-1 treatment. Proc Natl Acad Sci U S A. Apr. 24, 2018;115(17):E4041-E4050.
PharmaMar, FDA Grants Priority for Zepzelca (lubinectedin) and atezolizumab (Tecentriq) combination in Extensive Stage Small Cell Lung Cancer. Press Release. 2 pages, Jun. 10, 2025.
PharmaMar, PharmaMar Group announces financial results for first quarter 2025. Press Release. 4 pages, Apr. 24, 2025.
PharmaMar, PharmaMar has submitted EU marketing authorization application for lurbinectedin in combination with atezolizumab in first-line maintenance therapy for extensive-stage small cell lung cancer. Press Release. 2 pages May 21, 2025.
PharmaMar, PharmaMar presents at ASCO that the Zepzelca (lubinectedin) and atezolizumab (Tecentriq) combination significantly improves survival as first-line maintenance therapy for extensive-stage small cell lung cancer. Press Release. 4 pages, Jun. 3, 2025.
PharmaMar, PharmaMar's lurbinectedin transformative data in combination with atezolizumab for small cell lung cancer will be shared as oral presentation at ASCO 2025. Press Release. 3 pages, Apr. 24, 2025.
PharmaMar, Separate Financial Statements 2024. 142 pages, (2024).
Povo-Retana et al., Immunometabolic actions of trabectedin and lurbinectedin on human macrophages: relevance for their anti-tumor activity. Front Immunol. Aug. 22, 2023;14:1211068, 20 pages.
Rao et al., Retrospective Analysis of BRCA-Altered Uterine Sarcoma Treated With Poly(ADP-ribose) Polymerase Inhibitors. JCO Precis Oncol. Mar. 2025;9:e2400765, 14 pages.
Romero, Adding lurbinectedin to maintenance therapy improves outcomes in ES-SCLC. Nat Rev Clin Oncol. Jun. 12, 2025;22:545.
Schoche et al., Current and future pharmacological therapies for extensive-stage small-cell lung cancer. Magazine of European Medical Oncology. Apr. 28, 2025;18:116-124.
Serrano et al., SEOM-GEIS Spanish clinical guidelines for the management of soft-tissue sarcomas (2024).Clinical and Translational Oncology. Feb. 7, 2025;27:1460-1471.
Shields et al., Top advances of the year: Small cell lung cancer. Cancer. 2025;e35770, 9 pages.
Simon et al., A phase II study of lurbinectedin with or without avelumab in small cell carcinoma of the bladder (laser)-design and rationale. Future Oncol. Apr. 2025;21(10):1171-1177.
Singh et al., Combination of Lurbinectedin and Osimertinib for Treatment of EGFR-Mutated Transformed SCLC: A Brief Report. JTO Clinical and Research Reports. Feb. 13, 2025;6(6):100807, 6 pages.
Torrado et al., Advancing Understanding and Therapeutic Strategies for NUT Sarcomas: Comprehensive Review of the Literature and Two Cases. J Immunother Precis Oncol. 2025;8(2):113-120.
Xu et al., Targeting immune checkpoints on tumor—associated macrophages in tumor immunotherapy. Frontiers in Immunology. May 29, 2023;14:1199631, 22 pages.
Chile Office Action for Application No. 2023-00632, dated Jun. 11, 2025, 68 pages.
Abraham, Burger's Medicinal Chemistry & Drug Discovery, Sixth Edition, vol. 6: Nervous System Agents. Wiley-Interscience. 1080 pages. (2003).
Alexander et al., Lurbinectedin in small cell lung cancer: real-world experience of a multicentre national early access programme. Intern Med J. Jul. 2024;54(7):1087-1096.
Allavena et al., Effects of the Anti-Tumor Agents Trabectedin and Lurbinectedin on Immune Cells of the Tumor Microenvironment. Front Oncol. Mar. 1, 2022;12:851790, 8 pages.
Allavena et al., Effects of the Anti-Tumor Agents Trabectedin and Lurbinectedin on Immune Cells of the Tumor Microenvironment. Frontiers in Oncology. Mar. 1, 2022;12:8 pages.
Andrini et al., Challenges and future perspectives for the use of temozolomide in the treatment of SCLC. Cancer Treat Rev. Sep. 2024;129:102798, 8 pages.
Anju et al., An overview on liposarcoma subtypes: Genetic alterations and recent advances in therapeutic strategies. J Mol Histol. Jun. 2024;55(3):227-240.
Apetoh et al., The interaction between HMGB1 and TLR4 dictates the outcome of anticancer chemotherapy and radiotherapy. Immunological Reviews. 2007;220:47-59.
Apetoh et al., Toll-like receptor 4-dependent contribution of the immune stystem to anticancer chemotherapy and radiotherapy. Nature Medicine. Sep. 2007;13(9):1050-1059.
Arfan et al., Molecular Heterogeneity in Leiomyosarcoma and Implications for Personalised Medicine. Curr Treat Options Oncol. May 2024;25(5):644-658.

(56) References Cited

OTHER PUBLICATIONS

Arrieta et al., Carboplatin plus etoposide or topotecan for small-cell lung cancer. The Lancet. Sep. 2020 Sep;21:1132-1134.
Arrieta et al., New opportunities in a challenging disease: lurbinectedin for relapsed small-cell lung cancer. Lancet Oncol. May 2020;21(5):605-607.
Aviles et al., Mechanism of action in antitumor activity of PM01183. 2009 AACR Annual Meeting. Apr. 20, 2009;1 page, abstract 2679.
Ayodele et al., Immunotherapy in soft-tissue sarcoma. Current Oncology. Feb. 2020;27(1):17-23.
Badin, Considerations for selecting second-line treatment in patients with progressive small cell lung cancer and the use of Lurbinectedin in this setting. Cancer Treat Res Commun. 2024;39:100803, 8 pages.
Bailly et al., Combined cytotoxic chemotherapy and immunotherapy of cancer: modern times. NAR Cancer. 2020;2(1):1-20.
Belgiovine et al., Inhibition of tumor-associated macrophages by trabectedin improves the antitumor adaptive immunity in response to anti-PD-1 therapy. Eur J Immunol. Nov. 2021;51(11):2677-2686.
Belgiovine et al., Lurbinectedin reduces tumour-associated macrophages and the inflammatory tumour microenvironment in preclinical models. British Journal of Cancer. Jul. 6, 2017;117:628-638.
Berckmans et al., Drug Repurposing for Targeting Myeloid-Derived Suppressor-Cell-Generated Immunosuppression in Ovarian Cancer: A Literature Review of Potential Candidates. Pharmaceutics. 2023;15:1-19.
Blay et al., The current reality of soft tissue sarcomas: advances, controversies, areas for improvement, and promising new treatments. Expert Review of Anticancer Therapy. Apr. 2020;20(Suppl 1):29-39.
Borgoni et al., Depletion of tumor-associated macrophages switches the epigenetic profile of pancreatic cancer infiltrating T cells and restores their anti-tumor phenotype. Oncoimmunology. Nov. 13, 2017;7(2):e1393596, 10 pages.
Boulouta et al., Pathologic complete response in patients with localized soft tissue sarcoma treated with neoadjuvant therapy and its correlation with clinical outcomes: A systematic review. Cancer Treat Rev. Nov. 2024;130:102820, 6 pages.
Byrne et al., Phase II study of nab-paclitaxel with gemcitabine for relapsed/refractory small cell lung cancer. Front Oncol. Jul. 31, 2024;14:1303268, 9 pages.
Caliman et al., Challenges in the treatment of small cell lung cancer in the era of immunotherapy and molecular classification. Lung Cancer. 2023;175:88-100.
Calles et al., A phase 1/2 trial of lurbinectedin (L) in combination with pembrolizumab (P) in relapsed small cell lung cancer (SCLC): The LUPER study. 2022 ASCO Annual Meeting, Journal of Clinical Oncology. 2022;40;526s, Abstract #8581.
Calles et al., Lurbinectedin Plus Pembrolizumab in Relapsed SCLC: The Phase I/II Luper Study. J Thorac Oncol. Feb. 10, 2025:S1556-0864(25)00064-4. Pre-publication edition.
Calles et al., Phase 1/2 Trial of Lurbinectedin (L) in Combination with Pembrolizumab (P) in Relapsed Small Cell Lung Cancer (SCLC): The Luper Study. 2022 ASCO Annual Meeting. Jun. 2, 2022;1 page, Abstract #8581.
Calles et al., Unveiling the Mechanism of Lurbinectedin's Action and Its Potential in Combination Therapies in Small Cell Lung Cancer. Mol Cancer Ther. Dec. 5, 2024. 49 pages, pre-publication edition.
Calvo et al., Phase I study of lurbinectedin in combination with weekly paclitaxel with or without bevacizumab in patients with advanced solid tumors. Invest New Drugs. Aug. 10, 2022;11 pages.
Calvo et al., Phase I study of lurbinectedin in combination with weekly paclitaxel with or without bevacizumab in patients with advanced solid tumors. Invest New Drugs. Dec. 2022;40(6):1263-1273.
Cantini et al., Immune modulatory functions of lurbinectedin in small cell lung cancer and malignant pleural mesothelioma patients. Annals of Oncology. 2022;33(S2):S108, Abstract 164P.
Carlisle et al., Advancing immunotherapy in small cell lung cancer. Cancer. Nov. 15, 2023;129(22):3525-3534.
Casagrande et al., Trabectedin inhibits classical hodgkin lymphoma growth, monocytes immunosuppressive polarization by tumor cells and synergizes with the CCR5-Antagonist Maraviroc. 11th International Symposium on Hodgkin Lymphoma, ISHL 2018. HemaSphere. 2018;2(Suppl 3):1-2, Abstract T005(0077).
Casagrande et al., Trabectedin overcomes doxorubicin-resistance, counteracts tumor-immunosuppressive reprogramming of monocytes and decreases xenograft growth in Hodgkin lymphoma. Cancer Lett. Mar. 1, 2021;500:182-193. Pre-publication edition.
Casares et al., Caspase-dependent immunogenicity of doxorubicin-induced tumor cell death. J Exp Med. Dec. 19, 2005;202(12):1691-701.
Chakraborty et al., De Novo and Histologically Transformed Small-Cell Lung Cancer Is Sensitive to Lurbinectedin Treatment Through the Modulation of EMT and NOTCH Signaling Pathways. Clin Cancer Res. Sep. 1, 2023;29(17):3526-3540.
Chakraborty et al., Lurbinectedin sensitizes PD-L1 blockade therapy by activating STING-IFN signaling in small-cell lung cancer. Cell Rep Med. Dec. 17, 2024;5(12):101852, 26 pages.
Chawla et al., Cancer Immunotherapy Using Trabectedin and Nivolumab in Advanced Soft Tissue Sarcoma: A Retrospective Analysis. CTOS Connective Tissue Oncology Society, 22nd Annual Meeting. p. 61, Paper 020, #2794748, Nov. 8-11, 2017.
Chawla et al., Clinical experience with combination chemo-/immunotherapy using trabectedin and nivolumab for advanced soft tissue sarcoma. ASCO Meeting Library. ASCO American Society of Clinical Oncology, 54th Annual Meeting. J Clin Oncol. 2018;36:1 page, Abstract e23568.
Chawla et al., Clinical Experience with Combination Chemo-/Immunotherapy using Trabectedin and Nivolumab for Advanced Soft Tissue Sarcoma. J Sarcoma Res. 2018;2(1):1009, 5 pages.
Chawla et al., Interim Results of a Phase 2 Study Using Talimogene Laherparepvec, Nivolumab and Trabectedin for Advanced Leiomyosarcoma. 2023 ASCO Annual Meeting. May 31, 2023;1 page, Abstract #11556.
Chawla et al., Interim results of a phase 2 study using talimogene laherparepvec, nivolumab, and trabectedin for advanced leiomyosarcoma. Journal of Clinical Oncology. 2023;41:11556, poster session.
Chawla et al., The TNT protocol: A phase II study using talimogene laherparepvec (TVEC), nivolumab (N) and trabectedin (T) as first, second/third line therapy for advanced sarcoma, including desmoid tumor and chordoma. Journal of Clinial Oncology. May 25, 2020;38(15 Suppl): 3 pages, Abstract TPS11572.
Chawla et al., TNT: Talimogene Laherparepvec (An Oncolytic Virus Expressing GM-CSF), Nivolumab and Trabectedin for Advanced Leiomyosarcoma: A Phase 2 Study [NCT# 03886311]. Molecular Therapy. Apr. 2023;31(4S1):28, Abstract 54.
Cheng et al., A pivotal bridging study of lurbinectedin as second-line therapy in Chinese patients with small cell lung cancer. Sci Rep. Feb. 13, 2024;14(1):3598, 10 pages.
Chukwueke et al., Medical management of meningiomas. Handbook of Clinical Neurology, vol. 170 (3rd Series), Meningiomas, Part II. M.W. McDermott (Ed.). Elsevier B.V. Chapter 28, pp. 291-302, (2020).
Cigrang et al., Pan-inhibition of super-enhancer-driven oncogenic transcription by next-generation synthetic ecteinascidins yields potent anti-cancer activity. Nat Commun. Jan. 8, 2025;16(1):512, 21 pages.
ClinicalTrails.gov, Clinical Trial of Lurbinectedin (PM01183) in Patients With Advanced Solid Tumors. NCT05063318, 4 pages, Oct. 1, 2021.
ClinicalTrials.gov, A Clinical Study in Three-arm of Lurbinectedin (PM01183) Alone or in Combination With Gemcitabine and a Control Arm With Docetaxel as Second Line Treatment in Non-Small Cell Lung Cancer (NSCLC) Patients. History of Changes for Study: NCT01951157, 13 pages, Sep. 4, 2019.
ClinicalTrials.gov, A Multicenter Expanded Access Treatment Protocol of Lurbinectedin in Previously Treated SCLC in the USA. History of Changes for Study: NCT04291937, 2 pages, Jun. 17, 2020.

(56) References Cited

OTHER PUBLICATIONS

Subbiah et al., Efficacy and safety of lurbinectedin (PM1183) in Ewing sarcoma: Final results from a phase 2 study. J Clin Oncol. 2018;36:2 pages, Abstract 11519.
Sugiyama et al., A Case of Malignant Melanoma-like Spindle Sarcoma Treated with Nivolumab and Trabectedin. Pediatr Blood Cancer. 2017;64(Suppl 4): S41, Abstract O8-1-5.
Sun et al., Impact of metronomic trabectedin combined with low-dose cyclophosphamide on sarcoma microenvironment and correlation with clinical outcome: results from the TARMIC study. Mol Cancer. Feb. 19, 2024;23(1):37, 6 pages.
Takahashi et al., Preclinical Investigations of PM01183 (Lurbinectedin) as a Single Agent or in Combination with Other Anticancer Agents for Clear Cell Carcinoma of the Ovary. PLoS One. Mar. 17, 2016;11(3):e0151050, 17 pages.
Tang et al., Efficacy and toxicity of lurbinectedin in subsequent systemic therapy of extensive-stage small cell lung cancer: a meta-analysis. BMC Cancer. Nov. 4, 2024;24(1):1351, 13 pages.
Tariq et al., Update 2021: Management of Small Cell Lung Cancer. Lung. Dec. 2021;199(6):579-587.
Tejas et al., Uterine Sarcoma, Review of Advances in Management in the Last Decade. Indian Journal of Gynecologic Oncology. 2024;22:89, 12 pages.
Teruel et al., Exposure-Response Analyses and Clinical Utility Index to Justify the Dosage of Lurbinectedin in Small-cell Lung Cancer. J Thorac Oncol. Mar. 2021;16(Suppl 3):S509, Abstract P48.23.
Teruel et al., Semi-Mechanistic Models of the Time Course of Neutrophils and Platelets in Cancer Patients Treated With Lurbinectedin. Journal of Thoracic Oncology. Mar. 2021;16(3S):S508-S509, Abstract P48.00.
Tesniere et al., Immunogenic death of colon cancer cells treated with oxaliplatin. Oncogene. 2010;29:482-491.
Tian et al., PD-1/L1 inhibitor plus chemotherapy in the treatment of sarcomas. Front Immunol. Aug. 23, 2022;13:898255, 11 page.
Toledo et al., Deciphering the performance of macrophages in tumour microenvironment: a call for precision immunotherapy. J Hematol Oncol. Jun. 11, 2024;17(1):44, 34 pages.
Toulmonde et al., Trabectedin plus Durvalumab in Patients with Advanced Pretreated Soft Tissue Sarcoma and Ovarian Carcinoma (TRAMUNE): An Open-Label, Multicenter Phase Ib Study. Clin Cancer Res. May 2, 2022;28(9):1765-1772.
Toulmonde et al., TRAMUNE, a phase Ib study combining trabectedin and durvalumab, results of the expansion cohort in patients with advanced pretreated soft tissue sarcomas. Annals of Oncology. 2020;31(S4):S1199, abstract LBA67.
Trigo et al., Antitumor activity of single agent Lurbinectedin in patients with relapsed SCLC occurrring larger than or equal to 30 days after last platinum dose. ASCO 2019 Conference, Poster P1.12-03, 1 page, Abstract No. 1710.
Trigo et al., Lurbinectedin as second-line treatment for patients with small-cell lung cancer: a single-arm, open-label, phase 2 basket trial. Lancet Oncol. May 2020;21(5):645-654.
Tumini et al., The Antitumor Drugs Trabectedin and Lurbinectedin Induce Transcription-Dependent Replication Stress and Genome Instability. Mol Cancer Res. Mar. 2019;17(3):773-782.
Turano et al., Trabectedin for Treatment of Soft-tissue Sarcomas in Patients Failing Anthracycline Treatment. CTOS Connective Tissue Oncology Society, 17th Annual Meeting. p. 266, Nov. 14-17, 2012.
U.S. National Institutes of Health, History of Changes for Study NCT04358237: Lurbinectedin (PM01183) Combined With Pembrolizumab in Small Cell Lung Cancer. (LUPER). Mar. 2, 2023, 7 pages.
Vacchelli et al., Chemotherapy-induced antitumor immunity requires formyl peptide receptor 1. Science. Nov. 20, 2015;350(6263):972-979.
Vacchelli et al., Impact of Pattern Recognition Receptors on the Prognosis of Breast Cancer Patients Undergoing Adjuvant Chemotherapy. Cancer Research. Jun. 1, 2016;76(1):3122-3126.
Vadillo et al., PharmaMar presents new data on lurbinectedin for Small Cell Lung Cancer at ESMO 2023. Press Release. 5 pages, Oct. 18, 2023.
Vadillo, PharmaMar Announces Positive and Statistically Significant Overall Survival and Progression-Free Survival Results for Zepzelca (lurbinectedin) and Atezolizumab Combination in First-Line Maintenance Therapy for Extensive-Stage Small Cell Lung Cancer. Press Release, 3 pages, Oct. 15, 2024.
Vadillo, PharmaMar closes recruitment for the Phase III Neptuno trial with plitidepsin for the treatment of COVID-19. Press Release. 141 pages, Feb. 16, 2023.
Vadillo, PharmaMar completes enrollment for phase III Lagoon study with Zepzelca (lurbinectedin) for the treatment of small cell lung cancer. Press Release, 2 pages, Dec. 19, 2024.
Vadillo, PharmaMar Group presents its financial results as of Sep. 30, 2024. Press Release, 4 pages, Oct. 29, 2024.
Vadillo, PharmaMar Group reports 2023 annual results. Press Results, 17 pages, Feb. 28, 2024.
Vadillo, PharmaMar Group reports results for 1Q2023. Press Release, 16 pages, Apr. 26, 2023.
Vadillo, The PharmaMar Group presents financial results for the first quarter of 2024. Press Release, 16 pages, Apr. 23, 2024.
Van Houdt et al., Sarcoma: Last Year's Practice Changing Papers. Ann Surg Oncol. Mar. 2025;32(3):1497-1503.
Vanmeerbeek et al., Trial watch: chemotherapy-induced immunogenic cell death in immuno-oncology. Oncolmmunology. 2020;9(1):e1703449, 23 pages.
Vernadou et al., Subungual metastasis of an endometrial carcinoma. International Journal of Gynecological Cancer. 2019;29(4):2 pages, abstract EP648.
Villanueva et al., Antitumor effect of PM01183 in a patient-derived Cisplatin-sensitive and -resistant serous epithelial ovarian orthotopic tumor model. AACR Annual Meeting. Apr. 2, 2012;1 page, abstract 1778.
Vince et al., Real-world comparison of the efficacy and safety of atezolizumab versus durvalumab in extensive-stage small cell lung cancer. Lung Cancer. Dec. 2024;198:107999, 8 pages.
Wagner et al., A Phase 1/2 Trial Combining Avelumab and Trabectedin for Advanced Liposarcoma and Leiomyosarcoma. Clin Cancer Res. Jun. 1, 2022;28(11):2306-2312.
Wagner et al., A Phase I/II Trial Combining Avelumab and Trabectedin for Advanced Liposarcoma and Leiomyosarcoma. J Immunother Cancer 2020;8(Suppl 3):A476, Abstract 796.
Waldschmidt et al., Long-term disease control in dedifferentiated liposarcoma: a case report on trabectedin priming followed by PD-1 inhibition. Front Oncol. Jan. 16, 2025;14:1518775, 6 pages.
Wang et al., Current Diagnosis and Management of Small-Cell Lung Cancer. Thematic Review on Neoplastic Mayo Clin Proc. 2019;94(8):1599-1622.
Wasifuddin et al., Review of real-world experience with lurbinectedin in relapsed/refractory small cell lung cancer. J Chemother. Nov. 2024;36(7):587-592.
Xie et al., Lurbinectedin synergizes with immune checkpoint blockade to generate anticancer immunity. Oncolmmunology. 2019;8(11):e1656502, 9 pages.
Yang et al., Comprehensive Review of Uterine Leiomyosarcoma: Pathogenesis, Diagnosis, Prognosis, and Targeted Therapy. Cells. Jun. 26, 2024;13(13):1106, 31 pages.
Yang et al., Emerging therapies for small cell lung cancer. Journal of Hematology & Oncology. 2019;12:47, 11 pages.
Yu et al., Opportunities and obstacles of targeted therapy and immunotherapy in small cell lung cancer. J Drug Target. Jan. 2021;29(1):1-11.
Yu et al., The therapeutic potential and application of marine alkaloids treating breast cancer. Front Mar. 2024;11:30 pages.
Zappasodi et al., Improved Clinical Outcome in Indolent B-Cell Lymphoma Patients Vaccinated with Autologous Tumor Cells Experiencing Immunogenic Death. Cancer Res. 2010;70(22):9062-9072.
Zhou et al., Molecular characteristics and systemic treatment options of liposarcoma: A systematic review. Biomed Pharmacother. Sep. 2024; 178:117204, 11 pages.

(56) References Cited

OTHER PUBLICATIONS

Zhou et al., Oncolysis with DTT-205 and DTT-304 generates immunological memory in cured animals. Cell Death Dis. Oct. 23, 2018;9(11):1086, 14 pages.
Zhou et al., Review of Personalized Medicine and Pharmacogenomics of Anti-Cancer Compounds and Natural Products. Genes (Basel). Apr. 8, 2024;15(4):468, 19 pages.
Zhu et al., The significance and therapeutic potential of PD-1 and its ligands in ovarian cancer: A systematic review. Gynecol Oncol. Jul. 2016;142(1):184-189.
Zitvogel et al., Immune parameters affecting the efficacy of chemotherapeutic regimens. Nat Rev Clin Oncol. Mar. 2011;8:151-160.
Humeau et al., An unexpected link between immunogenic cell death and inhibition of gene transcription. Oncolmmunology. 2020;9(1):1792039, 4 pages.
Humeau et al., Gold Standard Assessment of Immunogenic Cell Death in Oncological Mouse Models. Cancer Immunosurveillance: Methods and Protocols, Methods in Molecular Biology, vol. 1884, Alejandro Lopez-Soto (Ed.). Springer Science+Business Media, LLC. Chapter 21, pp. 297-315, (2019).
Humeau et al., Inhibition of transcription by dactinomycin reveals a new characteristic of immunogenic cell stress. EMBO Mol Med. 2020;12:e11622, 22 pages.
Hwang et al., Clinical practice guidelines for uterine corpus cancer: an update to the Korean Society of Gynecologic Oncology guidelines. J Gynecol Oncol. Jan. 2025;36(1):e71, 10 pages.
Imai et al., Predicting Trabectedin Efficacy in Soft Tissue Sarcoma: Inflammatory Biomarker Analysis. Anticancer Res. May 2024;44(5):2125-2132.
Iribarren et al., Anticancer effects on anti-CD47 immunotherapy in vivo. Oncolmmunology. 2019;8(3):e1550619, 8 pages.
Jimenez et al., Enriching cancer pharmacology with drugs of marine origin. Br J Pharmacol. 2020;177:3-27.
Jimenez et al., Pharmacology of marine drugs: Pattern-, purpose- and prudence-driven innovations. Annual Reports in Medicinal Chemistry, vol. 61. Elsevier, Inc. Chapter Three, pp. 101-131, (2023).
Jimeno et al., Phase I study of lurbinectedin, a synthetic tetrahydroisoquinoline that inhibits activated transcription, induces DNA single- and double-strand breaks, on a weekly x 2 every-3-week schedule. Invest New Drugs. Aug. 2017;35(4):471-477.
Kalemkerian et al., Systemic Therapy for Small Cell Lung Cancer: ASCO Guideline Rapid Recommendation Update. J Clin Oncol. Jan. 2025;43(1):101-105.
Kang et al., Navigating the Complexity of Resistance in Lung Cancer Therapy: Mechanisms, Organoid Models, and Strategies for Overcoming Treatment Failure. Cancers (Basel). Nov. 28, 2024;16(23):3996, 20 pages.
Kauffmann-Guerrero et al., Orphan Drugs in Development for the Treatment of Small-Cell Lung Cancer: Emerging Data on Lurbinectedin. Lung Cancer (Auckl). Mar. 2, 2020;11:27-31.
Kepp et al., Clinical evidence that Immunogenic cell death sensitizes to PD-1/PD-L1 blockade. Oncolmmunology. 2019;8(10):e1637188, 3 pages.
Kepp et al., Lurbinectedin: an FDA-approved inducer of immunogenic cell death for the treatment of small-cell lung cancer. Oncoimmunology. 2020;9(1):1-3.
Khoury et al., A Comprehensive Review on the Role of Lurbinectedin in Soft Tissue Sarcomas. Curr Treat Options Oncol. Feb. 2024;25(2):176-190.
Kim et al., A phase II study of pembrolizumab and paclitaxel in patients with relapsed or refractory small-cell lung cancer. Lung Cancer. Oct. 2019;136:122-128.
Kournoutas et al., Objective Responses in Metastatic Pleomorphic Rhabdomyosarcoma Treated with Combination of Doxorubicin and Pembrolizumab: A Case Series. Case Rep Oncol. Feb. 23, 2024;17(1):344-351.
Kroemer et al., Natural and therapy-indiced immunosurveillance in breast cancer. Nature Medicine. Oct. 2015;21(10):1128-1138.
Kundu et al., SLFN11 biomarker status predicts response to lurbinectedin as a single agent and in combination with ATR inhibition in small cell lung cancer. Transl Lung Cancer Res. 2021;10(11):4095-4105.
Kuroda et al., PM01183 inhibits myeloid-derived suppressor cells in vitro and in vivo. Immunotherapy. 2017;9(10):805-817.
Kyriazoglou et al., Well-differentiated liposarcomas and dedifferentiated liposarcomas: Systemic treatment options for two sibling neoplasms. Cancer Treat Rev. Apr. 2024;125:102716, 9 pages.
Leal et al., PM01183, a new DNA minor groove covalent binder with potent in vitro and in vivo anti-tumour activity. British Journal of Pharmacology. 2010;161:1099-1110.
Lee et al., Novel pharmacotherapies for the treatment of liposarcoma: a comprehensive update. Expert Opin Pharmacother. Dec. 2024;25(17):2293-2306.
Lesterhuis et al., Cancer immunptherapy—revisited. Nature Reviews Drug Discovery. Aug. 2011;10:591-600.
Leung et al., Comparison of target agent treatment strategies for platinum-resistant recurrent ovarian cancer: A Bayesian network meta-analysis. Medicine (Baltimore). May 24, 2024;103(21):e38183, 9 pages.
Leventakos et al., MC1923 Phase II Clinical Trial of Durvalumab (MEDI4736) and Topotecan or Lurbinectedin in Patients with Relapsed Extensive Stage Small Cell Lung Cancer Previously Treated with Chemotherapy and Immunotherapy. 2022 ASCO Annual ASCO Meeting, Mayo Clinic Cancer Center. Jun. 2, 2022;1 page, Abstract #TPS8604.
Leventakos et al., MC1923 Phase II Clinical Trial of Durvalumab (MEDI4736) and Topotecan or Lurbinectedin in Patients with Relapsed Extensive Stage Small Cell Lung Cancer Previously Treated with Chemotherapy and Immunotherapy. J Clin Oncol. 2022;40(Suppl 16):532s, Abstract TPS8604. Abstract.
Leventakos et al., MC1923 Phase II Clinical Trial of Durvalumab (MEDI4736) and Topotecan or Lurbinectedin in Patients with Relapsed Extensive Stage Small Cell Lung Cancer Previously Treated with Chemotherapy and Immunotherapy. J Clin Oncol. 2022;40(Suppl 16):532s, Abstract TPS8604. Poster.
Leventakos et al., MC1923 phase II clinical trial of durvalumab (MEDI4736) and topotecan or lurbinectedin in patients with relapsed extensive-stage small cell lung cancer previously treated with chemotherapy and immunotherapy. SCO 58th Annual Meeting. p. 532s, Abstract TPS8604, (2022).
Levesque et al., a synergistic triad of chemotherapy, immune checkpoint, and caloric restriction mimetics eradicates tumors in mice. Oncolmmunology. 2019;8(11):e1657375, 15 pages.
Li et al., Harnessing tumor-associated macrophages as aids for cancer immunotherapy. Molecular Cancer. 2019;18:177, 16 pages.
Li et al., Post-marketing safety evaluation of lurbinectedin: a pharmacovigilance analysis based on the FAERS database. Front Pharmacol. Mar. 14, 2024;15:1368763, 13 pages.
Liu et al., Advances of systemic treatment for adult soft-tissue sarcoma. Chin Clin Oncol. Aug. 2018;7(4):42, 13 pages.
Liu et al., Crizotinib-induced immunogenic cell death in non-small cell lung cancer. Nature Communications. 2019;10:1486, 17 pages.
Loi et al., Radiosensitizing Effect of Trabedectedin on Human Soft Tissue Sarcoma Cells. Int J Mol Sci. 2022;23:14305, 18 pages.
Lum et al., Technological and Therapeutic Advances in Advanced Small Cell Lung Cancer. Cancers. 2019;11:1570, 21 pages.
Lynch et al., Combinations of Chemotherapy and PD-1/PD-L1 Inhibitors in Sarcoma. Curr Treat Options Oncol. Dec. 2022;23(12):1861-1876.
Ma et al., Anticancer Chemotherapy-Induced Intratumoral Recruitment and Differentiation of Antigen-Presenting Cells. Immunity. Apr. 18, 2013;38:729-741.
Maio et al., Tremelimumab as second-line or third-line treatment in relapsed malignant mesothelioma (Determine): a multicentre, international, randomised, double-blind, placebo-controlled phase 2b trial. Lancet Oncol. Jul. 17, 2017;18:1261-1273.
Mannarino et al., Lurbinectedin down-regulates ASCL1 transcription factor in Small Cell Lung Cancer (SCLC). 2019 AACR-NCI-EORTC International Conference on Molecular Targets and Cancer Therapeutics. Poster No. LB-B13, (2019).
Martinez-Cava et al., PharmaMar and Jazz Pharmaceuticals announce initiation of confirmatory phase III clinical trial of Zepzelca

(56) References Cited

OTHER PUBLICATIONS (lurbinectedin) for the treatment of patients with relapsed Small Cell Lung Cancer. Press Release. 4 pages, Dec. 13, 2021.
Martinez-Cava et al., PharmaMar announces abstract to be presented at SITC 2021. Press Release. 2 pages, Nov. 10, 2021.
Martins et al., Restoration of the immunogenecity of cisplatin-induced cancer cell death by endosplasmic reticulum stress. Oncogene. 2011;30:1147-1158.
Mattarollo et al., Pivotal Role of Innate and Adaptive Immunity in Anthracycline Chemotherapy of Established Tumors. Cancer Res. 2011;71(14):4809-4820.
Mavroeidis et al., Novel Therapeutics in Soft Tissue Sarcoma. Cancers (Basel). Dec. 24, 2024;17(1):10, 30 pages.
Meftahpour et al., Prognostic significance and therapeutic potentials of immune checkpoints in osteosarcoma. Excli J. Jan. 12, 2022;21:250-268.
Meijer et al., Small cell lung cancer: Novel treatments beyond immunotherapy. Semin Cancer Biol. Nov. 2022;86(Pt 2):376-385.
Metaxas et al., Combination of cisplatin and lurbinectedin as palliative chemotherapy in progressive malignant pleural mesothelioma: Report of two cases. Lung Cancer. Dec. 2016;102:136-138.
Metaxas et al., Pembrolizumab as Palliative Immunotherapy in Malignant Pleural Mesothelioma. Journal of Thoracic Oncology. Nov. 2018;13(11):1784-1791.
Zugazagoitia et al., Facts and Hopes on Cancer Immunotherapy for Small Cell Lung Cancer. Clin Cancer Res. Jul. 15, 2024;30(14):2872-2883.
Australian Office Action for Application No. 2020466790, dated Feb. 19, 2025.
Chile Office Action for Application No. 2023-00632, dated Oct. 24, 2024.
International Search Report and Written Opinion for Application No. PCT/EP2020/074860, dated May 3, 2021, 9 pages.
International Search Report and Written Opinion for Application No. PCT/EP2021/074425, dated Nov. 2, 2021, 9 pages.
International Search Report and Written Opinion for Application No. PCT/EP2022/081155, dated Feb. 3, 2023, 9 pages.
Japanese Office Action for Application No. 2023-515171, dated Sep. 2, 2024, 13 pages.
Taiwan Office Action for Application No. 109130448, dated Feb. 17, 2024, 13 pages.
Metaxas et al., SAKK 17/16—Lurbinectedin monotherapy in patients with progressive malignant pleural mesothelioma: A multicenter, single-arm phase II trial. Annals of Oncology. 2018;29(Suppl 8):Viii644, Abstract 1817TiP.
Michaud et al., Autophagy-Dependent Anticancer Immune Responses Induced by Chemotherapeutic Agents in Mice. Science. Dec. 16, 2021;334:1573-1577.
Mispelaere et al., Natural course and clinical features of myxoid and round cell liposarcoma (MRCL)—a retrospective single center analysis. J Clin Oncol. 25(18S):1 page, Abstract 10066.
Moneo et al., Agents Causing DNA Damage or Proteasome Inhibition. 2009 AACR Annual Meeting. Apr. 21, 2009;1 page, Abstract 4525.
Moneo et al., PM01183 is a novel compound that binds DNA and displays cytotoxic effect in vitro and in vivo in human cancer cell lines. PharmaMar. 2009;1 page, Abstract #4525.
Moreno et al., PharmaMar announces abstracts to be presented at ASCO 2022. Press Release. 5 pages, Jun. 1, 2022.
Moura et al., HMGA1 regulates trabectedin sensitivity in advanced soft-tissue sarcoma (STS): A Spanish Group for Research on Sarcomas (GEIS) study. Cell Mol Life Sci. May 17, 2024;81(1):219, 18 pages.
Moura et al., Immune-checkpoint genes as predictive biomarkers of trabectedin in advanced soft-tiddue sarcoma (STS): A Spanish Group for Research on Sarcomas (GEIS) translational study. Journal of Clinical Oncology. May 20, 2020;38(Suppl 15):4 pages, Abstract 11546.
Muller et al., A non-randomized, open-label phase II trial evaluating efficacy and feasibility of combined treatment with trabectedin and nivolumab in patients with metastatic or inoperable soft tissue sarcomas (STS) after failure of an anthracycline-containing regimen. Annals of Oncology. 2020;31(S4):S991, Abstract 1669TiP.
Nandini et al., Therapeutic Strategies for Metastatic Triple-Negative Breast Cancers: From Negative to Positive. Pharmaceuticals. 2021;14:455, 18 pages.
Navarro et al., Analysis of patients with relapsed small cell lung cancer (SCLC) receiving single-agent lurbinectedin in the phase 3 Atlantis trial. 2022 ASCO Annual Meeting. p. 512s, Abstract 8524, (2022).
Navarro et al., Analysis of Patients With Relapsed Small Cell Lung Cancer (SCLC) Receiving Single-agent Lurbinectedin in the Phase 3 Atlantis Trial. ASCO Annual Meeting. Jun. 2022;1 page, Abstract 8524.
Nishio et al., Biology and Management of High-Grade Myxofibrosarcoma: State of the Art and Future Perspectives. Diagnostics (Basel). Sep. 22, 2023;13(19):3022, 16 pages.
Nunez et al., Lurbinectedin Specifically Triggers the Degradation of Phosphorylated RNA Polymerase II and the Formation of DNA Breaks in Cancer Cells. Mol Cancer Ther. 2016;15(10):2399-2412.
Obeid et al., Calreticulin exposure dictates the immunogenicity of cancer cell death. Nature Medicine. Jan. 2007;13(1):54-61.
Oronsky et al., A 2022 Update on Extensive Stage Small-Cell Lung Cancer (SCLC). Journal of Cancer. 2022;13:2945-2953.
Oronsky et al., Lost at SCLC: a review of potential platinum sensitizers. Cancer Metastasis Rev. Dec. 2024;43(4):1573-1578.
Ortin et al., PharmaMar announces the initiation of a study of lurbinectedin in combination with immunotherapy. Press Release. 3 pages, Jan. 14, 2020.
Ortin et al., PharmaMar has held its General Shareholders' Meeting today. Press Release. 6 pages, Apr. 15, 2021.
Ortin et al., PharmaMar receives positive opinion from EMA (COMP) for Orphan Drug Designation of lurbinectedin for Mesothelioma. Press Release. 2 pages, Jul. 28, 2021.
Ortin et al., PharmaMar will present new data for Zepzelca (lurbinectedin) at rescheduled IASLC 2020. Press Release. 3 pages, Jan. 13, 2021.
Ortin et al., PharmaMar's 2017 Group Annual General Shareholer's Meeting. Press Release. 5 pages, Jun. 28, 2018.
Ortin, PharmaMar announces its new immunotherapy research program. Press release, 3 pages, Apr. 9, 2019.
Ortin, PharmaMar Group reports first quarter 2021 earnings as of Mar. 31, 2021. Press Release, 13 pages, May 5, 2021.
Pacheco et al., Advancements in Small-cell Lung Cancer: The Changing Landscape Following IMpower-133. Clinical Lung Cancer. May 2019;20(3):148-160.
Pacheco et al., Systemic therapy options following first-line chemoimmunotherapy in small-cell lung cancer. J Thorac Dis. 2020;12(10):6264-6274.
Paudel et al., Myelomodulatory treatments augment the therapeutic benefit of oncolytic viroimmunotherapy in murine models of malignant peripheral nerve sheath tumors. Front Immunol. Jun. 25, 2024;15:1384623, includes Corrigendum, 20 pages.
Paz-Ares et al., Efficacy and Safety Profile of Lurbinectedin in Second-Line SCLC Patients: Results from a phase II single-agent trial. 2019 ASCO Annual Meeting. Slideshow, 22 pages, (2019).
Paz-Ares et al., Efficacy and safety profile of lurbinectedin in second-line SCLC patients: Results from a phase II single-agent trial. J Clin Oncol. 55th Annual Meeting. 1 page, May 31-Jun. 4, 2019.
Paz-Ares et al., IMforte: A Phase III Study of Lurbinectedin and Atezolizumab Versus Atezolizumab as Maintenance Therapy in ES-SCLC. IASLC 2022 World Conference Lung Cancer. 2022;1133, Abstract EP14.01-015.
Paz-Ares et al., IMforte: A Phase III Study of Lurbinectedin and Atezolizumab Versus Atezolizumab as Maintenance Therapy in ES-SCLC. Journal of Thoracic Oncology. 2022;17(9s):532-S533, Abstract EP14.01-015.
Paz-Ares et al., Phase I clinical and pharmacokinetic study of PM01183 (a tetrahydroisoquinoline, Lurbinectedin) in combination with gemcitabine in patients with advanced solid tumors. Invest New Drugs. Apr. 2017;35(2):198-206.

(56) References Cited

OTHER PUBLICATIONS

Peltonen et al., A Targeting Modality for Destruction of RNA Polymerase I that Possesses Anticancer Activity. Cancer Cell. 2014;25:77-90.
Perez et al., Efficacy and safety of lurbinectedin (PM1183) in small cell lung cancer (SCLC): Results from a phase 2 study. J Clin Oncol. 2018;36, 2 pages, Abstract 8570.
Pham et al., The Role of Macrophage/B-Cell Interactions in the Pathophysiology of B-Cell Lymphomas. Front Oncol. May 8, 2018;8:147, 14 pages.
PharmaMar Annual Report 2020, 160 pages, (2020).
PharmaMar Annual Report 2021, 164 pages, (2021).
PharmaMar Financial Statements 2020, 138 pages, (2020).
PharmaMar Financial Statements 2021, 144 pages, (2021).
PharmaMar Financial Statements 2022, 138 pages, (2022).
PharmaMar, 1H 2022 Results Presentation. 17 pages, Jul. 28, 2022.
PharmaMar, Annual Report 2019. 156 pages (2019).
PharmaMar, Annual Report 2023, 160 pages, (2023).
PharmaMar, Clinical Study Report, PM1183-C-004-14, Phase III Randomized Clinical Trial of LUrbinectedin (PM01183) Versus Pegylated Liposomal Doxorubicin or Topotecan in Patients with Platinum-Resistant Ovarian Cancer (CORAIL Trials). 15 pages, May 31, 2019.
PharmaMar, Clinical Trial Protocol, A Multicenter Phase II Clinical Trial of Lurbinectedin (PM01183) in Selected Advanced Solid Tumors. 105 pages, Jun. 5, 2020.
PharmaMar, Clinical Trial Protocol, Phase I Multicenter, Open-label, Clinical and Pharmacokinetic Study of PM01183 in Combination with Doxorubicin in Non-heavily Pretreated Patients with Selected Advanced Solid Tumors. PM1183-A-003-10, 106 pages, Oct. 17, 2014.
PharmaMar, Clinical Trial Protocol, PM1183-C-003-14, Phase III Randomized Clinical Trial of Lurbinectedin (PM01183)/Doxorubicin (DOX) versus Cyclophosphamide (CTX), Doxorubicin (DOX) and Vincristine (VCR) (CAV) or Topotecan as Treatment in Patients with Small-Cell Lung Cancer (SCLC) Who Failed One Prior Platinum-containing Line (Atlantis Trial). 117 pages, May 3, 2018.
PharmaMar, Clinical Trial Protocol, PM1183-C-004-14, Phase III Randomized Clinical Trial of Lurbinectedin (PM01183) versus Pegylated Liposomal Doxorubicin or Topotecan in Patients with Platinum-resistant Ovarian Cancer (COTRAIL trial). Final Version 1.0, 109 pages, Dec. 4, 2014.
PharmaMar, Clinical Trial Protocol. PM1183-B-003-11, A Multi-center Phase II Clinical Trial of PM01183 in BRCA 1/2-Associated or Unselected Metastatic Breast Cancer. 85 pages, Mar. 8, 2016.
PharmaMar, CNMV Submissions. 202 pages, Apr. 13, 2021.
EudraCT No. 2017-001016-11, Lurbinectedin Monotherapy in Patients with Progressive Malignant Pleural Mesothelioma. A Multicenter, Single-arm Phase II Trial. 35 pages, Jan. 13, 2021.
EudraCT No. 2021-004471-13, A Randomized, Multicenter, Open-label, Phase III Study of Lurbinectedin Single-Agent or Lurbinectedin in Combination with Irinotecan versus Investigator's Choice (Topotecan or Irinotecan) in Relapsed Small Cell Lung Cancer (SCLC) Patients (Lagoon Trial). 11 pages, Jun. 7, 2022.
EudraCT: 2015-000206-18, Evaluation of the effect of Lurbinectin (PM01183) on cardiac repolarisation (QTc duration) in patients with certain solid tumours. 24 pages, Nov. 27, 2019.
F Hoffman-La Roche Ltd., GO28753 Anti-PDL1 in NSCLC, A Phase II, Open Label, Multicenter, randomized Study to Investigate the Efficacy and Safety of MPDL3280A (Anti-PD-L1 Antibody) compared with Docetaxel in Patients with Non-Small Cell Lung Cancer after Platinum Failure. Eudract No. 2013-001142-34, NCT01903993. 5 pages, (2023).
F Hoffman-La Roche Ltd., GO28915-MPDL3280A or Docetaxel in Patients with NSCLC, A Phase III, Open-label, Multicentre, Randomised Study to Investigate the Efficacy and Safety of MPDL3280A (Anti-PD-L1 Antibody) Compared with Docetaxel in Patients with Non-small Cell Lung Cancer After Failure with Platinum-containing Chemotherapy. Eudract No. 2013-003331-30, NCT02008227. 5 pages, (2023).
Farago et al., Atlantis: a Phase III study of lurbinectedin/doxorubicin versus topotecan or cyclophosphamide/doxorubicin/vincristine in patients with small-cell lung cancer who have failed one prior platinum-containing line. Future Oncol. Jan. 2019;15(3):231-239.
Forster et al., Lurbinectedin (PM01183) with doxorubicin (DOX), an active treatment as second-line therapy in small cell lung cancer (SCLC). 2015 ASCO Annual Meeting, J Clin Oncol. 2015;33:2 pages, Abstract 7509.
Franza et al., New targeted therapies in liposarcoma: state of art and future perspectives. Curr Opin Oncol. Jul. 1, 2024;36(4):291-296.
Frapolli et al., Mechanism of Action and Antitumor Activity of PM01183. Mario Negro Istituto Di Ricerche Farmacologiche, PharmaMar. 1 page, Abstract #2679.
Fridman et al., The immunce contexture in cancer prognosis and treatment. Nature Reviews, Clinical Oncology. Dec. 2017;14:717-734.
Fucikova et al., Human Tumor Cells Killed by Anthracyclines Induce a Tumor-Specific Immune Response. Cancer Res. Jul. 15, 2011;71(14):4821-4833.
Fudio et al., A model-based head-to-head comparison of single-agent lurbinectedin in the pivotal Atlantis Study. Front Oncol. Jun. 15, 2023;13:1152371, 12 pages.
Fudio et al., Effect of lurbinectedin on the QTc interval in patients with advanced solid tumors: an exposure-response analysis. Cancer Chemother Pharmacol. Jan. 2021;87(1):113-124.
Fudio et al., Exposure-Response Analysis of Lurbinectedin alone or with Doxorubicin in Overall Survival in Small Cell Lung Cancer. 2021 World Conference on Lung Cancer. Slideshow, 11 pages, Sep. 8-14, 2021.
Fudio, Exposure-Response Analyses and Clinical Utility Index to Justify the Dosage of Lurbinectedin in Small-cell Lung Cancer. 2020 World Conference on Lung Cancer Singapore. Slideshow, 11 pages, Jan. 28-31, 2021.
Fudio, Exposure-Response Analysis of Lurbinectedin Alone or With Doxorubicin in Overall Survival in Small Cell Lung Cancer. J Thorac Oncol. 2021;16(Suppl 10):S1182-S1183, Abstract P63.02.
Fudio, Semi-Mechanistic Models of the Time Course of Neutrophils and Platelets in Cancer Patients Treated With Lurbinectedin. 2020 World Conference on Lung Cancer Singapore. Slideshow, 12 pages, Jan. 28-31, 2021.
Gaillard et al., Phase III trial of lurbinectedin versus PLD or topotecan in platinum-resistant ovarian cancer patients: Results of CORAIL trial. Annals of Oncology. 2018;29(Suppl 8): 1 page, Abstract 9320.
Gaillard et al., Phase III trial of Lurbinectedin versus PLD or Topotecan in platinum-resistant ovarian cancer patients: Results of CORAL trial. 2018 Munich ESMO Congress. Slideshow, 15 pages, (2018).
Galluzzi et al., Consensus guidelines for the definition, detection and interpretation of immunogenic cell death. Journal of Immunother Cancer. 2020;8:e000337, 22 pages.
Galluzzi et al., Immunostimulation with chemotherapy in the era of immune checkpoint inhibitors. Nature Reviews, Clinical Oncology. Dec. 2020;17:725-741.
Garcia et al., Activity of lurbinectedin as single agent and in combination in patients with advanced small cell lung cancer (SCLC). Annals of Oncology. 2017;28(Suppl 5):539-540, Abstract 1529PD.
Garcia San Andres et al., Cost comparison of adverse events and administration of lurbinectedin versus intravenous topotecan for relapsed small cell lung cancer in Spain and the United States. ISPOR International Society for Pharmacoeconomics and Outcomes Research. 1 page, (2019).
Garcia San Andres et al., Cost Comparison of Adverse Events and Treatment Administration of Lurbinectedin Versus Intravenous Topotecan for Relapsed Small Cell Lung Cancer in Spain and the United Kingdom. ISPOR International Society for Pharmacoeconomics and Outcomes Research. p. S462, Abstract PCN137, Nov. 2019.

(56) References Cited

OTHER PUBLICATIONS

Garralda et al., Lurbinectedin (PM01183) in combination with paclitaxel (P) in patients (pts) with advanced solid tumors. European Journal of Cancer. 2015;S66, Abstract 335.
Garralda et al., Lurbinectedin (PM01183) in Combination with Paclitaxel (P) in Patients (pts) with Advanced Solid Tumors. PharmaMar. Sep. 2015; 1 page.
Ghiringelli et al., Activation of the NLRP3 inflammasome in dendritic cells induces IL 1beta-dependent adaptive immunity against tumors. Nature Medicine. Oct. 2009;15(10):1170-1179.
Girard et al., Lurbinectedin in extensive-stage small-cell lung cancer: a brief report of the IFCT-2105 Lurbiclin study. ESMO Open. Dec. 2024;9(12):103968, 6 pages.
Gomez et al., Lurbinectedin is an effective alternative to platinum rechallenge and may restore platinum sensitivity in patients with sensitive relapsed small cell lung cancer. Expert Rev Anticancer Ther. Jan. 2025;25(1):27-40.
Gomez-Puerto et al., Emerging treatments for sarcoma: from 2024 onward. Expert Opin Emerg Drugs. Feb. 3, 2025:1-18. pre-publication edition.
Gomez-Randulfe et al., Recent advances and future strategies in first-line treatment of ES-SCLC. Eur J Cancer. Mar. 2024;200:113581, 8 pages.
Gordon et al., Cancer immunotherapy using trabectedin and nivolumab in advanced soft tissue sarcoma: A retrospective analysis. 2018 ASCO-SITC Clinical Immuno-Oncology Symposium. 2 pages, Abstract 40, (2018).
Gordon et al., Cancer Immunotherapy with sequential administration of trabectedin and nivolumab in advanced soft tissue sarcoma. Journal for Immuno Therapy of Cancer. 2017;5(Suppl 1):12, Abstract A42.
Gordon et al., Phase 1/2 Study of Safety/Efficacy Using Trabectedin, Ipilimumab and Nivolumab Triple Therapy as First Line Treatment of Advanced Soft Tissue Sarcoma (STS) (NCT03138161). ASCO American Society of Clinical Oncology, 54th Annual Meeting. Abstract TPS11591, 1 page, Jun. 1-5, 2018.
Gordon et al., Phase 1/2 study of safety/efficacy using trabectedin, ipilimumab and nivolumab triple therapy as first line treatment of advanced soft tissue sarcoma. J Clin Oncol. 2018;36:2 pages, Abstract TBP11591.
Gordon et al., SAINT: Results of an expanded phase II study using safe amounts of ipilimumab (I), nivolumab (N), and trabedectin (T) as first-line treatment of advanced soft tissue sarcoma. Journal of Clinical Oncology. May 20, 2020;38(Suppl 15);3 pages, Abstract 11520.
Gordon et al., The Saint: Initial Results of a Phase 1/2 Study of Safety/Efficacy Using Safe Amounts of Ipilimumab, Nivolumab and Trabectedin as First Line Treatment of Advanced Soft Tissue Sarcoma. CTOS Connective Tissue Oncology Society, 23rd Annual Meeting. pp. 357-358, Poster 237, Nov. 14-17, 2018.
Gordon et al., The Saint: Results of a Phase 1/2 Study of Safety/Efficacy Using Safe Amounts of Ipilimumab, Nivolumab and Trabectedin as First Line Treatment of Advanced Soft Tissue Sarcoma (NCT 03138161). CTOS Connective Tissue Oncology Society, 24th Annual Meeting. Page 444, Poster #192, Abstract 3255343, Nov. 13-16, 2019.
Guo et al., Advanced and challenges in imunotherapy of small cell lung cancer. Chinese Journal of Cancer Research. 2020;32(1):115-128.
Guo et al., Combined Tradectedin and anti-PD1 antibody produces a synergistic antitumor effect in a murine model of ovarian cancer. J Transl Med. 2015;247, 13 pages.
Guo et al., FZ-AD005, a Novel DLL3-Targeted Antibody-Drug Conjugate with Topoisomerase I Inhibitor, Shows Potent Antitumor Activity in Preclinical Models. Mol Cancer Ther. Oct. 1, 2024;23(10):1367-1377.
Guo et al., Leukemic progenitor cells enable immunosuppression and post-chemotherapy relapse via IL-36-inflammatory monocyte axis. Sci Adv. Oct. 8, 2021;7(41):eabg4167, 15 pages.
Gupta et al., Consensus recommendations for systemic therapies in the management of relapsed Ewing sarcoma: A report from the National Ewing Sarcoma Tumor Board. Cancer. Dec. 1, 2024;130(23):4028-4039.
Gutierrez et al., Actionable Driver Events in Small Cell Lung Cancer. Int J Mol Sci. Dec. 20, 2023;25(1):105, 21 pages.
Haddox et al., Diagnosis and management of dedifferentiated liposarcoma: A multidisciplinary position statement. Cancer Treat Rev. Dec. 2024;131:102846, 8 pages.
Harlow et al., Lurbinectedin Inactivates the Ewing Sarcoma Oncoprotein EWS-FLI1 by Redistributing It within the Nucleus. Cancer Res. Nov. 15, 2016;76(22):6657-6668.
He et al., A Scalable Total Synthesis of the Antitumor Agents Et-743 and Lurbinectedin. Angew Chem Int Ed Engl. Mar. 18, 2019;58(12):3972-3975.
Hendriks et al., Propsects of targeted and immune therapies in SCLC. Expert Review of Anticancer Therapy. 2018;17 pages.
Hodgkinson, International Association for the Study of Lung Cancer (IASLC)—22nd World Conference on Lung Cancer (WCLC 2021). Drugs of the Future. 2021;46(12):1033-1036.
Huang et al., Tumor-associated macrophages in non-small-cell lung cancer: From treatment resistance mechanisms to therapeutic targets. Crit Rev Oncol Hematol. Apr. 2024;196:104284, 14 pages.
Adeeku et al., Officer/Employee List for NDA 213702. Application No. 213702Orig1s000. Department of Health and Human Services. 2 pages, Jun. 10, 2020.
Alsheimer et al., The Effect of Lurbinectedin as a Monotherapy and in Combination with Ionizing Radiation on Sarcoma Cell Lines. Cancers (Basel). Sep. 7, 2025;17(17):2930, 24 pages.
Andreas et al., Second-line treatment strategies and clinical outcomes after progression on chemoimmunotherapy in extensive-stage small-cell lung cancer. Lung Cancer. Nov. 2025;209:108786, 8 pages.
Basharat et al., Lurbinectedin with immunotherapy in extensive-stage small cell lung cancer: Current insights and future prospects—A systematic review. J Clin Oncol. 2025;43:Abstract e20100.
Behrouzi et al., State of the art in treatment of small cell lung cancer. Ther Adv Med Oncol. Sep. 15, 2025;17:1-29.
Bustos Moran et al., Evaluation of the combination of lurbinectedin and atezolizumab in a humanized mouse model. J Clin Oncol. 2025;43:Abstract e14614.
Calles Blanco et al., Lurbinectedin (LUR) in combination with pembrolizumab (PBL) in relapsed small cell lung cancer (SCLC): The Phae I/II Luper study. Annals of Oncology. 2023;34(S2):S1060-S1061.
Calles et al., Lurbinectedin in Combination With Pembrolizumab in Relapsed Small Cell Lung Cancer (SCLC): The Phase 1/2 LUPER Study. ESMO, slideshow. 12 pages, Oct. 2023.
Chakraborty et al., Increasing the Efficacy of ICB by Lurbinectedin Mediated Re-Activation of Tumor Microenvironment in SCLC. Journal of Thoracic Oncology. 2025;20(8S2):S28.
Chakraborty et al., Lurbinectedin induces multimodal immune activation and augments the anti-tumor immune response in small-cell lung cancer. Cancer Res. 2024;84(Suppl. 6):Abstract 6554.
Cheng et al., IMforte: A new starting point and new challenges. Med. Aug. 8, 2025;6(8):100777, 3 pages.
Daley et al., New Approaches to Investigate Novel Agents in Ewing Sarcoma: A Report From the Children's Oncology Group Bone Tumor Committee. Pediatr Blood Cancer. Oct. 2025;72(10):e31917, 13 pages.
Donoghue, Supplement Approval. 4 pages, Apr. 1, 2022.
Dowlati et al., Phase 2 Open-Label Study of Sacituzumab Govitecan as Second-Line Therapy in Patients With Extensive-Stage SCLC: Results From TROPICS-03. J Thorac Oncol. Jun. 2025;20(6):799-808.
Florez et al., Clinical strategies for lung cancer management: Recommendations from the Bridging the Gaps Lung Cancer Consensus Conference 2024. Cancer. Sep. 1, 2025;131(17):e70060, 20 pages.
Gordon et al., Linnovate: A Phase 1/2 study of safety/efficacy using lurbinectedin, combined with ipilimumab and nivolumab for advanced soft tissue sarcomas (NCT05876715): Interim Analysis of Phase 1 Part. Sarcoma Oncology Center, 1 page, abstract 1739P, (2024).

(56) References Cited

OTHER PUBLICATIONS

Gordon et al., Linnovate: A Phase 1/2 study of safety/efficacy using lurbinectedin, combined with ipilimumab, and nivolumab for advanced soft tissue sarcomas (NCT05876715). Cancer Res. 2024;84(Suppl. 7):Abstract CT287.
Gordon et al., Linnovate: A Phase I/II study of safety/efficacy using lurbinectedin combined with ipilimumab and nivolumab for advanced soft tissue sarcoma (NCT05876715)—Interim analysis of phase I part. Annals of Oncology. 2024;35(S2): S1040, abstract 1739P.
Haddox et al., Leiomyosarcoma Therapeutic Approaches and Future Directions. Hematol Oncol Clin North Am. Aug. 2025;39(4):785-804.
Huang et al., Cost-effectiveness analysis of lurbinectedin plus atezolizumab as first-line treatment for extensive-stage small-cell lung cancer. Front Immunol. Sep. 23, 2025;16:1658740, 11 pages.
Iams et al., Patient characteristics and treatment patterns in extensive-stage small cell lung cancer (ES-SCLC). ISPOR. 1 page, Abstract HSD69, (2025).
Iams et al., Patient characteristics and treatment patterns in extensive-stage small cell lung cancer (ES-SCLC). Value in Health, ISPOR. Jul. 2025;28(6):S238, Abstract HSD69.
Jeffrey, Clinical benefit analysis of a phase I/II study using lurbinectedin combined with ipilimumab and nivolumab as first-line therapy for advanced soft tissue sarcoma (NCT05876715). Annals of Oncology. Sep. 2025 Sep;36(Suppl 2):S1443, Abstract 2706P.
Jeffrey, Clinical benefit analysis of a phase I/II study using lurbinectedin combined with ipilimumab and nivolumab as first-line therapy for advanced soft tissue sarcoma (NCT05876715). European Society for Medical Oncology (ESMO) Congress. Abstract 2706P. Oct. 17-21, 2025.
Jonczak et al., Liposarcoma: Novel Approaches to Systemic Therapy and Multidisciplinary Care. Hematol Oncol Clin North Am. Aug. 2025;39(4):805-824.
Korsah et al., Multi-Discipline Review, Application No. 213702Orig1s000. Center for Drug Evaluation and Research. 160 pages, Jun. 12, 2020.
Larkins, Supplement Approval/Fulfillment of Postmarketing Requirement. 6 pages, Oct. 2, 2025.
Larkins, Supplement Approval/Fulfillment of Postmarketing Requirement/Commitment. 5 pages, Jul. 28, 2023.
Mayasin et al., Targeting TAMs & CAFs in melanoma: New approaches to tumor microenvironment therapy. Oncol Res. Aug. 28, 2025;33(9):2221-2242.
Nie et al., Small-Cell Lung Cancer Updates. Semin Respir Crit Care Med. 12 pages, Aug. 7, 2025.
Nih, Atezolizumab Approved for Initial Treatment of Metastatic Lung Cancer. National Cancer Institute. 7 pages, Jan. 7, 2019.
Paz-Ares et al., Lung carcinoma: combination with lurbinectedin beats antibody monotherapy. Pneumology. 2025;79:611-612.
Paz-Ares et al., Lurbinectedin + atezolizumab as first-line maintenance treatment in patients with extensive-stage small cell lung cancer: Primary results of the phase 3 IMforte trial. Slideshow, 2025 ASCO Annual Meeting. 28 pages, Abstract 8006, (2025).
Paz-Ares, Patterns of disease progression (PD) and efficacy associated with tumour burden from the phase III IMforte study of lurbinectedin (lurbi)+atezolizumab (atezo) as first-line (1L) maintenance treatment (tx) in ES-SCLC. ESMO, Abstract 2762MO, 8 pages, (2025).
Paz-Ares, Patterns of disease progression and efficacy associated with tumour burden from the phase 3 IMforte study of lurbinectedin + atezolizumab as first-line maintenance treatment in ES-SCLC. ESMO, Slidshow, 11 pages, Abstract 4275, (2025).
Penel et al., Maintenance after first-line treatment for advanced soft tissue sarcoma. Crit Rev Oncol Hematol. Sep. 18, 2025;216:104959, 25 pages, pre-publication edition.
PharmaMar, FDA approves PharmaMar's Zepzelca (lurbinectedin) and Atezolizumab (Tecentriq) Combination as First-line Maintenance Therapy for Extensive-stage Small Cell Lung Cancer. Press Release, 3 pages, Oct. 3, 2025.
PharmaMar, PharmaMar receives US$50 million milestone payment from Jazz Pharmaceuticals for the FDA's approval of Zepzelca (lurbinectedin). Press release, 1 page, Oct. 15, 2025.
Ponce Aix et al., Safety and efficacy of lurbinectedin plus atezolizumab as second-line treatment for advanced small-cell lung cancer: Results of the 2SMALL phase 1/2 study (NCT04253145). 2025 ASCO Annual Meeting Slideshow. 11 pages, (2025).
Ponce Aix et al., Safety and efficacy of lurbinectedin plus atezolizumab as second-line treatment for advanced small-cell lung cancer: Results of the 2SMALL phase 1/2 study (NCT04253145). J Clin Oncol. 2025;43:Abstract 8013.
Russo-Cabrera et al., Lurbinectedin-induced transcriptional reprogramming: A pathway to sensitise SCLC to immunotherapy. Abstract 29-13-5837, (2025).
Russo-Cabrera et al., Lurbinectedin-induced transcriptional reprogramming: A pathway to sensitise SCLC to immunotherapy. Proceedings of the American Association for Cancer Research Annual Meeting. 2 pages, Abstract 5837, (2025).
Russo-Cabrera et al., Lurbinectedin-induced transcriptonal reprogramming: a pathway to sensitise SCLC to immunotherapy. Eur J Immunol. 2024;54(Suppl 1):1-1746, 2261-WS21.6.
Russo-Cabrera et al., Sensitization to immunotherapy through manipulation of tumour transcription by Lurbinectedin. Annals of Oncology. 2023;34(S2):S636, Abstract 1050P.
Russo-Cabrera et al., Sensitization to immunotherapy through manipulation of tumour transcription by Lurbinectedin. ESMO, 1 page (2023).
Sammarco et al., Risk Assessment and Risk Mitigation Review(s), Application No. 213702Orig1s000. Center for Drug Evaluation and Research. 12 pages, Jun. 8, 2020.
Sawyer et al., Review of outcomes in a veteran treated with lurbinectedin long-term for extensive-stage small cell lung cancer: A case report. Current Problems in Cancer: Case Reports. 2025;17:100350, 6 pages.
Scattolin et al., Outcome and safety of lurbinectedin as compassionate use in extensive stage small cell lung cancer: A multicentric international cohort. Eur J Cancer. Aug. 26, 2025;226:115595, 6 pages.
Sen, Lubinectedin induces multimodal immune activation and augments the anti-tumor immune response in small cell lung cancer. Anals of Oncology. 2024;9(S3):7, Abstract 207P.
Sen, Lubinectedin: A DNA minor groove inhibitor launches a multimodal immune response through activationof the cytosolic DNA-sensing cGAS-STING pathway. Anals of Oncology. 2023;20(S):2, Abstract 167P.
Simon et al., A phase II study of lurbinectedin with or without avelumab in small cell carcinoma of the bladder (Laser). J Clin Oncol. May 29, 2024;42(Suppl. 16):Abstract TPS4629.
Simon et al., A phase II study of Lurbinectedin with or without Avelumab in Small cell carcinoma of the bladder (Laser). National Cancer Institute. 1 page, Abstract TPS4629. (2024).
Singh et al., Immune checkpoint inhibitors: a promising anticancer therapy. Drug Discovery Today. Jan. 2020;25(1):223-229.
Srivastava et al., Therapeutic Effects of Lurbinectedin in PARP Inhibitor-Resistant High-Grade Serous Ovarian Cancer Using Patient-Derived Cell Lines and Organoid Models. Int J Mol Sci. Sep. 11, 2025;26(18):8866, 16 pages.
Stewart et al., Proprietary Name Review(s), Application No. 213702Orig1s000. Center for Drug Evaluation and Research. 22 pages, May 20, 2020.
Theoret, Zepzelca approval letter. 9 pages, Jun. 15, 2020.
Tummala et al., Preclinical analysis of ONC206 and ONC212 with lurbinectedin in pancreatic cancer. Proceedings of the American Association for Cancer Research Annual Meeting. Cancer Res. 2025;85(8 Suppl. 1):Abstract 7212.
Tummala et al., Synergistic combinations of lurbinectedin with ONC212 in pancreatic cancer. Cancer Res. 2024;84(Suppl. 6):Abstract 4550.
Underdown et al., Ewing Sarcoma, Desmoplastic Small Round Cell Tumor, and Other Round Cell Sarcomas. Hematol Oncol Clin North Am. Aug. 2025;39(4):709-726.
Vellanki, Supplement Approval/Fulfillment of Postmarketing Requirement. 5 pages, Apr. 30, 2025.

(56) References Cited

OTHER PUBLICATIONS

Wang, Product Quality Review(s), Application No. 213702Orig1s000. Center for Drug Evaluation and Research. 22 pages, May 21, 2020.
Woods, Administrative and Correspondence Documents, Application No. 213702Orig1s000. Center for Drug Evaluation and Research. 59 pages, Dec. 12, 2018.
Zepzelca, (lurbinectedin) for injection, for intravenous use Initial U.S. Approval: 2020. Label. 16 pages, Jun. 2020.
Zepzelca, (lurbinectedin) for injection, for intravenous use Initial U.S. Approval: 2020. Label. 18 pages, Apr. 2022.
Zepzelca, (lurbinectedin) for injection, for intravenous use Initial U.S. Approval: 2020. Label. 19 pages, Jul. 2023.
Zepzelca, (lurbinectedin) for injection, for intravenous use Initial U.S. Approval: 2020. Label. 20 pages, Apr. 2025.
Zepzelca, (lurbinectedin) for injection, for intravenous use Initial U.S. Approval: 2020. Label. 31 pages, Oct. 2025.
Zhang et al., Sacituzumab govitecan: another emerging treatment option for patients with relapsed small cell lung cancer. Transl Lung Cancer Res. Sep. 30, 2025;14(9):4165-4169.
Zheng et al., Other Review(s), Application No. 213702Orig1s000. Center for Drug Evaluation and Research. 26 pages, Mar. 4, 2020.
Australian Office Action for Application No. 2025204567, dated Sep. 15, 2025, 4 pages.
Canada Office Action for Application No. 3,191,207, dated Sep. 16, 2025, 5 pages.
Korean Office Action for Application No. 10-2023-7010697, dated Jul. 20, 2025, 19 pages.
New Zealand Office Action for Application No. 798309, dated Sep. 23, 2025, 4 pages.
Hande, Topoisomerase II inhibitors. Update on Cancer Therapeutics. 2008;3:13-26.
He et al., Renieramycins E and F from the Sponge Reniera sp.: Reassignment of the Stereochemistry of the Renieramycins. J Org Chem. 1989;54:5822-5824.
Heilig et al., Randomized phase II study of trabectedin/olaparib compared to physician's choice in subjects with previously treated advanced or recurrent solid tumors harboring dna repair deficiencies. Annals of Oncology. Oct. 2019;30(Suppl 5):V795-V796, Abstract 1979TiP.
Heilig et al., Randomized phase II study of trabectedin/olaparib compared to physician's choice in subjects with previously treated advanced or recurrent solid tumors harboring DNA repair deficiencies. Annals of Oncology. 2022;33 (S7):S762-S763, Abstract 487P.
Heilig et al., Randomized Phase II Study of Trabectedin/Olaparib Compared to Physician's Choice in Subjects with Previously Treated Advanced or Recurrent Solid Tumors Harboring DNA Repair Deficiencies. Oncol Res Treat. 2024;47(Suppl 2):122, Abstract V894.
Heilig et al., TOP-ART/PMO-1603: Randomized Phase 2 Study of Trabectedin/Olaparib Compared to Physician's Choice in Subjects with Previously Treated Advanced or Recurrent Solid Tumors Harboring DNA Repair Deficiencies. ESMO Congress. 1 page, (2019).
Hendriks et al., High antitumor activity of ET743 in human tumor xenograft models. Proceedings of the American Association for Cancer Research. Mar. 1996;37:389, Abstract 2653.
Hendriks et al., High antitumour activity of ET743 against human tumour xenografts from melanoma, non-small-cell lung and ovarian cancer. Ann Oncol. Oct. 1999; 10(10):1233-40.
Hensley et al., Efficacy and safety of trabectedin or dacarbazine for the treatment of patients with uterine leiomyosarcoma after prior chemotherapy: A subgroup analysis of the randomized phase 3 SAR-3007 study. Gynecologic Oncology. 2016; 141:3, Abstract 3.
Hensley et al., Efficacy and safety of trabectedin or dacarbazine in patients with advanced uterine leiomyosarcoma after failure of anthracycline-based chemotherapy: Subgroup analysis of a phase 3, randomized clinical trial. Gynecol Oncol. Sep. 2017;146(3):531-537.
Hergert, NCCN Guidelines Recommend Lurbinectedin as Second-Line Treatment in Relapsed SCLC. MJH Life Sciences. 7 pages, Jul. 15, 2020.
Herman et al., Effect of cyclosporin A on DNA repair and cancer incidence in kidney transplant recipients. J Lab Clin Med. Jan. 2001; 137(1):14-20.
Hesketh et al., Antiemetics: American Society of Clinical Oncology Clinical Practice Guideline Update. J Clin Oncol. Oct. 1, 2017;35(28):3240-3261.
Heymann et al., Heymann D. Bone sarcomas in the immunotherapy era. Br J Pharmacol. May 2021; 178 (9):1955-1972.
Highleyman, FDA Approves Zepzelca for Metastatic Small-Cell Lung Cancer, Lurbinectedin shrank tumors in a third of people with this less common type of lung cancer. Cancer Health, 2 pages, Jun. 16, 2020.
Hofsli et al., Reversal of multidrug resistance by lipophilic drugs. Cancer Res. Jul. 1, 1990;50(13):3997-4002.
Hojo et al., Cyclosporine induces cancer progression by a cell-autonomous mechanism. Nature. Feb. 11, 1999;397 (6719):530-4.
Hollander et al., ATREUS Trial: A Phase II Study On The Activity Of Trabectedin In Pretreated Epithelioid Or Biphasic/Sarcomatoid Malignant Pleural Mesothelioma (MPM). Annals of Oncology. 2015;26(Suppl 6):vi87.
Holt, The Isolation and Structural Characterization of the Ecteinascidins. Thesis, Submitted in partial fulfillment of the requirements for the degree of Doctor of Philosophy in Chemistry. 152 pages, (1986).
Horn et al., First-Line Atezolizumab plus Chemotherapy in Extensive-Stage Small-Cell Lung Cancer. N Engl J Med. Dec. 6, 2018;379(23):2220-2229.
Hourani et al., Tumor Associated Macrophages: Origin, Recruitment, Phenotypic Diversity, and Targeting. Front Oncol. Dec. 20, 2021;11:788365, 20 pages.
Hurley, Dna and associated targets for drug design. J Med Chem. Sep. 1989;32(9):2027-33.
Hurwitz et al., New advances in the second-line treatment of small cell lung cancer. Oncologist. Oct. 2009; 14 (10):986-94.
Hycamtin, Highlights of Prescribing Information. 15 pages, Oct. 2019.
Hycamtin, Prescribing Information. 16 pages, (1998).
Ikeda et al., Safracins, new antitumor antibiotics. I. Producing organism, fermentation and isolation. J Antibiot (Tokyo). Oct. 1983;36(10):1279-83.
Ikeda et al., Safracins, new antitumor antibiotics. II. Physicochemical properties and chemical structures. J Antibiot (Tokyo). Oct. 1983;36(10):1284-9.
Inanez et al., Modulation of EMT Increases the Activity of Lurbinectedin in Small Cell Lung Cancer. IASLC 2024 World Conference on Lung Cancer, WCLC 2024. 1 page, Sep. 7-10, 2024.
Italiano et al., Targeting Microenvironment and Cellular Immunity in Sarcomas with Weekly Trabectedin Combined with Metronomic Cyclophosphamide (Tarmic). CTOS 23rd Annual Meeting. Page 222, Poster 086, Abstract 3042845, (2018).
Italiano et al., Targeting Microenvironment and Cellular Immunity in Sarcomas with Weekly Trabectedin Combined with Metronomic Cyclophosphamide (Tarmic). CTOS 23rd Annual Meeting. Page 222, Poster 086, Abstract 3042845, Poster, (2018).
Ito, High-speed Countercurrent Chromatography. Critical Reviews in Analytical Chemistry. 1986; 17(1):65-143.
IUPAC acyl groups (A00123), retrieved online at: <https://doi.org/10.1351/goldbook.A00123.> 2 pages, Feb. 24, 2014.
IUPAC Compendium of Chemical Terminology, Electronic version. Retrieved online at: <http://goldbook.iupacorg/ A00123.html.> 1 page, retrieved Jul. 20, 2023.
Ixempra, Highlights of Prescribing Information. 35 pages, (2018).
Izbicka et al., In vitro antitumor activity of the novel marine agent, ecteinascidin-743 (ET-743, NSC-648766) against human tumors explanted from patients. Ann Oncol. Sep. 1998;9(9):981-7.
Jain et al., The portrayal of macrophages as tools and targets: A paradigm shift in cancer management. Life Sci. Mar. 1, 2023;316:121399, 20 pages.
Jang et al., Therapeutic Targeting of Macrophage Plasticity Remodels the Tumor-Immune Microenvironment. Cancer Res. Jul. 18, 2022;82(14):2593-2609.

(56) References Cited

OTHER PUBLICATIONS

Janota, Continuous Flow Fast Atom Bombardment and Electrospray Ionization Mass Spectrometry in Natural Products Research. Thesis Submitted in partial fulfillment of the requirements for the degree of Doctor of Philosophy in Chemistry in the Graduate College of teh University of Illinois at Urbana-Champaign. 164 pages, (1995).
Jansen et al., Chemosensitisation of malignant melanoma by BCL2 antisense therapy. Lancet. Nov. 18, 2000;356 (9243):1728-33.
Jazz Pharmaceuticals, Jazz Pharmaceuticals Announces U.S. Fda Accelerated Approval of Zepzelca (lurbinectedin) for the Treatment of Metastatic Small Cell Lung Cancer. Press Release, 4 pages, Jun. 15, 2020.
Jazz Pharmaceuticals, Jazz Pharmaceuticals Announces Zepzelca (lurbinectedin) and Atezolizumab (Tecentriq) Combination Significantly Improves Survival as First-Line Maintenance Therapy for Extensive-Stage Small Cell Lung Cancer. Press Release, 4 pages, Jun. 2, 2025.
Jazz Pharmaceuticals, PharmaMar and Jazz Pharmaceuticals Sign Exclusive License Agreement for Lurbinectedin in the U.S. Press Release, 3 pages, Dec. 19, 2019.
Jimeno et al., Progress in the acquisition of new marine-derived anticancer compounds: development of ecteinascidin-743 (ET-74e). Drugs of the Future. 1996;21(11):1155-1165.
Jin et al., Ecteinascidin 743, a transcription-targeted chemotherapeutic that inhibits MDR1 activation. Proc Natl Acad Sci U S A. Jun. 6, 2000;97(12):6775-9.
Jo et al., The Novel ATR Inhibitor M1774 Induces Replication Protein Overexpression and Broad Synergy with DNA- targeted Anticancer Drugs. Mol Cancer Ther. Jul. 2, 2024;23(7):911-923, pre-publication edition.
Johnston et al., Farnesyl transferase inhibitors: a novel targeted therapy for cancer. Lancet Oncol. Jan. 2001;2 (1):18-26.
Jones et al., Cardiac safety of trabectedin monotherapy or in combination with pegylated liposomal doxorubicin in patients with sarcomas and ovarian cancer. Cancer Med. Jun. 2021; 10(11):3565-3574.
Jones et al., Efficacy and safety of trabectedin in an elderly patient subgroup (greater than or equal to 65 years) with advanced leiomyosarcoma (LMS) or liposarcoma (LPS) from the Expanded Access Program (EAP). Annals of Oncology. 2017 Sept;28(Suppl 5):529, Abstract 1498P.
Jones et al., Efficacy and Safety of Trabectedin in an Elderly Patient Subgroup (greater than or equal to 65 Years) with Advanced Leiomyosarcoma (LMS) or Liposarcoma (LPS) from the Expanded Access Program (Eap). Ctos 22nd Annual Meeting. pp. 257-258, Poster 223, Abstract 2785250, (2017).
Jones et al., Efficacy and safety of trabectedin or dacarbazine in an elderly patient subgroup (greater than or equal to 65 years) with advanced leiomyosarcoma or liposarcoma after prior chemotherapy. 18th ECCO, 40th ESMO Congress. Poster 1321, Poster board P108, 1 page, (2015).
Schultz et al., ATR inhibition augments the efficacy of lurbinectedin in small-cell lung cancer. EMBO Mol Med. Aug. 7, 2023; 15(8):e17313, 47 pages.
Schwoppe et al., Comparative pharmacokinetics (PK) of targeted tissue factor tTF-NGR when intravenously applied alone or in combination with preceding trabectedin. Cancer Res. 2025;85(8 Suppl 1): Abstract 824.
Scotlandi et al., Effectiveness of Ecteinascidin-743 against drug-sensitive and -resistant bone tumor cells. Clin Cancer Res. Dec. 2002;8(12):3893-903.
Scotto et al., Transcription of the multidrug resistance gene MDR1: a therapeutic target. Mol Interv. Jun. 2001; 1 (2):117-25.
Seaman et al., An Ecteinascidin-DNA hydorgen bond network plays a major role in determining DNA sequence specificity of Et 736 Et 743 for their favored three base target sequences. 10th NCI-EORTC symposium on new drugs in cancer therapy. p. 138, Abstract 530, Jun. 16-19, 1998.
Seaman et al., Comparative NMR and modeling study of ET 743, ET 736, and ET 729 adducts of DNA duplexes containing either the favored or less-favored target sequences. Clinical Cancer Research. Nov. 1999;5:3851s, Abstract 604.
Seaman et al., Comparative NMR and Modeling study of Et 743, Et 736, and Et 729 adducts of DNA duplexes containing either the favored or less-favored target sequences. Proceedings of the 1999 AACR-NCI-EORTC International Conference. 1999; 123, Abstract 604.
Seaman et al., Molecular Basis for the DNA Sequence Selectivity of Ecteinascidin 736 and 743: Evidence for the Dominant Role of Direct Readout via Hydrogen Bonding. J Am Chem Soc. 1998; 120:13028-13041.
Sessa et al., Phase I clinical and pharmacokinetic study of trabectedin and doxorubicin in advanced soft tissue sarcoma and breast cancer. Eur J Cancer. May 2009;45(7):1153-1161.
Shah et al., The relevance of drug sequence in combination chemotherapy. Drug Resist Updat. Dec. 2000;3 (6):335-356.
Shamma et al., Carbon-13 NMR Shift Assignments of Amines and Alkaloids. Plenum Press, New York. Page 206 (1979).
Shang et al., Subverted macrophages in the triple-negative breast cancer ecosystem. Biomed Pharmacother. Oct. 2023; 166:115414, 14 pages.
Sharma et al., Efficacy and safety of pharmacological interventions in second- or later-line treatment of patients with advanced soft tissue sarcoma: a systematic review. BMC Cancer. Aug. 13, 2013;13:385, 21 pages.
Shen et al., The Reactions of Indoles in Aqueous Solution Initiated by One-electron Oxidation. J Chem Soc Perkin Trans. 1990;2:597-603.
Shepherd et al., Prospective, randomized, double-blind, placebo-controlled trial of marimastat after response to first-line chemotherapy in patients with small-cell lung cancer: a trial of the National Cancer Institute of Canada-Clinical Trials Group and the European Organization for Research and Treatment of Cancer. J Clin Oncol. Nov. 15, 2002;20 (22):4434-9.
Shi et al., Lurbinectedin-induced Pneumonitis and DAH in Recurrent Stage IV SCLC: Possible Pulmonary Toxicity From a Novel Alkylating Agent. Am J Respir Crit Care Med. 2025;211:A751, 2 pages.
Shi et al., Lurbinectedin-induced Pneumonitis and DAH in Recurrent Stage IV SCLC: Possible Pulmonary Toxicity From a Novel Alkylating Agent. Pulmonary Toxicities and Treatment-related Complications in Thoracic Oncology. Abstract A80-1, May 18, 2025.
Shields et al., ISL1: A Novel Neuroendocrine Subtype in Small Cell Lung Cancer Predicts Durable Response to Lurbinectedin. Mol Cancer Ther. Jan. 22, 2026. doi: 10.1158/1535-7163.MCT-25-0663. pre-publication edition.
Shim et al., Real-world outcomes with lurbinectedin in second-line and beyond for small cell lung cancer in Korea. J Clin Oncol. Aug. 2024;42(23 Suppl):211.
Shimada et al., Does the Use of Peripheral Immune-Related Markers Indicate Whether to Administer Pazopanib, Trabectedin, or Eribulin to Advanced Soft Tissue Sarcoma Patients? J Clin Med. Oct. 26, 2021; 10(21):4972, 10 pages.
Shtil, Signal transduction pathways and transcriptional mechanisms as targets for prevention of emergence of multidrug resistance in human cancer cells. Curr Drug Targets. Mar. 2001;2(1):57-77.
Shulgin et al., Structure-activity relationships of one-ring psychotomimetics. Nature. Feb. 8, 1969;221(5180):537-41.
Shunyakov et al., Place in therapy of key treatments for platinum-sensitive, relapsed, extensive-stage small cell lung cancer with a focus on lurbinectedin: a narrative review with case studies. Drugs Context. Oct. 29, 2025;14:2025-7-9, 2 pages.
Sica et al., Targeting tumour-associated macrophages. Expert Opin Ther Targets. Sep. 2007; 11(9):1219-29.
Sica et al., Tumour-associated macrophages are a distinct M2 polarised population promoting tumour progression: potential targets of anti-cancer therapy. Eur J Cancer. Apr. 2006;42(6):717-27.
Sigel et al., A Substance from the Marine Tunicate Ecteinascidia turbinata with Selective Action on Macrophages. Mononuclear Phagocyte Biology. 1984;24:451-471.
Sigel et al., Immunostimulatory activity of Ecteinascidia turbinata (Ete) extract on a variety of animal species. Prog Clin Biol Res. 1984; 161:543-54.

(56) References Cited

OTHER PUBLICATIONS

Sill et al., Comments on: "Docetaxel plus trabectedin appears active in recurrent or persistent ovarian and primary peritoneal cancer after up to three prior regimens" (Monk BJ, Sill MW, Hanjani P, Edwards R, Rotmensch J, De Geest K, et al. Gynecol Oncol. Mar. 2011; 120(3):459-63). Gynecologic Oncology. 2011;122(2):462.
Silverman, Drug Metabolism. The Organic Chemistry of Drug Design and Drug Action. Chapter 7, pp. 405-495, (2004).
Simetic et al., The treatment of locally advanced or metastatic soft tissue sarcomas in the era of innovative therapies and hystorical review of therapies in Croatia Single center experience - University Hospital Centre Zagreb. Lib Oncol. 2017;45(suppl 1):72, Abstract P27.
Simon et al., Cell biological mechanisms of multidrug resistance in tumors. Proc Natl Acad Sci U S A. Apr. 26, 1994;91 (9):3497-504.
Simone, Oncology. Cecil Textbook of Medicine, 20th Edition, vol. 1. W.B. Saunders Company, Philadelphia, J. Claude Bennett (Ed.). Chapter 154, pp. 1004-1010, (1996).
Simoni et al., Heterocycle-containing retinoids. Discovery of a novel isoxazole arotinoid possessing potent apoptotic activity in multidrug and drug-induced apoptosis-resistant cells. J Med Chem. Jul. 5, 2001;44(14):2308-18.
Simos et al., Third-line chemotherapy in small-cell lung cancer: an international analysis. Clin Lung Cancer. Mar. 2014; 15(2):110-8.
Sinder et al., Bone Mass Is Compromised by the Chemotherapeutic Trabectedin in Association With Effects on Osteoblasts and Macrophage Efferocytosis. J Bone Miner Res. Oct. 2017; 32(10):2116-2127.
Sinder et al., The Chemotherapeutic Trabectedin Negativity Impacts Osteal Macrophages, Bone Formation and Bone Healing. ASBMR 2017 Annual Meeting, Page S387, Abstract MO0687, (2017).
Siontis et al., A Phase II Multi-center Trial of Trabectedin in Combination with Olaparib in Patients with Advanced Unresectable or Metastatic Sarcoma. Clin Res. 26 pages, (2025).
Siontis et al., Phase II Multi-center, Single Arm Trial of Trabectedin in Combination with Olaparib in Advanced Unresectable or Metastatic Sarcoma. CTOS 27th Annual Meeting. Abstract, 4 pages, (2022).
Siontis et al., Phase II Multi-center, Single Arm Trial of Trabectedin in Combination with Olaparib in Advanced Unresectable or Metastatic Sarcoma. CTOS 27th Annual Meeting. Slideshow, 12 pages, (2022).
Sleijfer et al., Trial methodology in soft tissue sarcomas; the 'one plus one is three or zero' phenomenon. Onkologie. Feb. 2008;31(1-2):6-8.
Slotman et al., Prophylactic cranial irradiation in extensive small-cell lung cancer. N Engl J Med. Aug. 16, 2007;357 (7):664-72.
Soares et al., The DNA damage response to monofunctional anti-cancer DNA binders. Drug Discovery Today: Disease Models. 2012;9(2):e59-e67.
Soares et al., Trabectedin and its C subunit modified analogue PM01183 attenuate nucleotide excision repair and show activity toward platinum-resistant cells. Mol Cancer Ther. Aug. 2011; 10(8):1481-9.
Soares, The marine product Tryptamicidin shows activity toward platinum-resistant cells and attenuates nucleotide excision repair. Universite Pierre & Marie Curie Science A Paris. 31st EORTC-PAMM (Pharmacology and Molecular Mechanisms). Group Annual Winter Meeting. 20 pages, Jan. 27-30, 2010.
Sobczuk et al., Systemic inflammation index is a predictive and prognostic factor in patients with liposarcoma or leiomyosarcoma treated with trabectedin. Sci Rep. Feb. 12, 2025;15(1):5247, 10 pages.
Soto, Lurbinectedin (PMO1183) for the Treatment of Ewing Sarcoma and Neuroblastoma. Pediatric Oncology Subcommittee of the Oncology Drug Advisory Committee (ODAC). 27 pages, slideshow, Jun. 21, 2017.
Sparidans et al., Search for metabolites of ecteinascidin 743, a novel, marine-derived, anti-cancer agent, in man. Anticancer Drugs. Sep. 2001;12(8):653-66.
Stacchiotti et al., Patient-derived solitary fibrous tumour xenografts predict high sensitivity to doxorubicin/ dacarbazine combination confirmed in the clinic and highlight the potential effectiveness of trabectedin or eribulin against this tumour. Eur J Cancer. May 2017;76:84-92.
Stanley et al., Effects of the Immunomodulator Ecteinascidia turbinata Extract on Edwardsiella ictaluri Infection on Channel Catfish. Journal of Aquatic Animal Health. 1995;7:141-146.
Stanley et al., Use of the Immunomodulator Ecteinascidia turbinata Extract (Ete) in Association with Edward siella ictaluri infections of Channel Catfish. 92nd General Meeting of the ASM. 1992;81, Abstract B-335.
Urban et al., Bioactive Marine Alkaloids. Current Organic Chemistry. 2000;4:765-807.
Usach et al., Subcutaneous Injection of Drugs: Literature Review of Factors Influencing Pain Sensation at the Injection Site. Adv Ther. Nov. 2019;36(11):2986-2996.
Vaillet et al., Etoposide and doxorubicin antagonize the in vitro activity of paclitaxel in human non-small cell lung cancer cell lines. Lung Cancer. Aug. 1996; 15(1):93-101.
Vaillet et al., Tallimustine is inactive in patients with previously treated small cell lung cancer. A phase II trial of the National Cancer Institute of Canada Clinical Trials Group. Lung Cancer. Nov. 1996; 15(3):367-73.
Valeri et al., Development of an in vitro model for the simultaneous study of the efficacy and hematotoxicity of antileukemic compounds. Toxicol Lett. Dec. 15, 2010; 199(3):317-22.
Valoti et al., Ecteinascidin-743, a new marine natural product with potent antitumor activity on human ovarian carcinoma xenografts. Clin Cancer Res. Aug. 1998;4(8):1977-83.
Van Kesteren et al., Pharmacokinetics and pharmacodynamics of the novel marine-derived anticancer agent ecteinascidin 743 in a phase I dose-finding study. Clin Cancer Res. Dec. 2000;6(12):4725-32.
Van Kesteren et al., Yondelis (trabectedin, ET-743): the development of an anticancer agent of marine origin. Anticancer Drugs. Aug. 2003; 14(7):487-502.
Vanderwerf et al., Immunosuppressive Effect of Ecteinascidia Turbinata in Mice. Surgical Forum. Jan. 1, 1973;24:326-328.
Vejzovic et al., Drug screening reveals differential drug response in primary and metastatic clear cell sarcoma. Cancer Lett. Jan. 16, 2026;637:218131, 49 pages, pre-publication edition.
Veluvolu et al., Exploiting lurbinectedin-driven nucleolar relocalization of EWS-FLI1 to develop novel combination therapies for Ewing sarcoma. Cancer Res. 2024;84(6 Suppl):Abstract 1082.
Vengerovsky, Pharmacological incompatibility. Bulletin of Siberian Medicine. 2003;3:49-56.
Verweij, Alveolar soft part sarcoma: should we be targeting the tumor or targeting the vasculature? Onkologie. 2012;35(5):237-8.
Verweij, Ecteinascidin-743 (ET-743): early test or effective treatment in soft tissue sarcomas? J Clin Oncol. Aug. 20, 2005;23(24):5420-3.
Villalona-Calero et al., Final Results of a Phase I and Pharmacokinetic (PK) Study of the Marine Minor Groove Binder ET-743 on a Daily X 5 Schedule. Clinical Pharmacology. 1999; 18:180a, Abstract 691.
Vincenzi et al., M1-polarized macrophages as predictor of poor response to trabectedin treatment in myxoid liposarcoma. J Clin Oncol. 2016;34:Abstract e22537.
Vincenzi et al., Wide-spectrum characterization of trabectedin: biology, clinical activity and future perspectives. Pharmacogenomics. Jun. 2010; 11(6):865-78.
Vistica, Cytotoxicity as an indicator for transport mechanism: evidence that murine bone marrow progenitor cells lack a high-affinity leucine carrier that transports melphalan in murine L1210 leukemia cells. Blood. Sep. 1980;56(3):427-9.
Von Mehren et al., A phase I study of the safety and pharmacokinetics of trabectedin in combination with pegylated liposomal doxorubicin in patients with advanced malignancies. Ann Oncol. Oct. 2008; 19(10):1802-9.
Von Mehren et al., Efficacy and Safety of Trabectedin (T) or Dacarbazine (D) in Advanced Leiomyosarcoma (LMS) or Liposarcoma

(56) References Cited

OTHER PUBLICATIONS (LPS) After Prior Chemotherapy: Elderly Patient (Age greater than or equal to 65 years) Subgroup Analysis. CTOS 20th. p. 215, Abstract 128, (2015).
Von Mehren et al., Efficacy and safety of trabectedin (T) or dacarbazine (D) in an elderly patient subgroup (greater than or equal to 65 years) with advanced leiomyosarcoma (LMS) or liposarcoma (LPS) after prior chemotherapy. European Journal of Cancer. 2015;3(51):S194, Abstract 1321.
Von Pawel et al., Phase II comparator study of oral versus intravenous topotecan in patients with chemosensitive small-cell lung cancer. J Clin Oncol. Mar. 15, 2001; 19(6):1743-9.
Von Pawel et al., Randomized phase III trial of amrubicin versus topotecan as second-line treatment for patients with small-cell lung cancer. J Clin Oncol. Dec. 10, 2014;32(35):4012-9.
Von Pawel et al., Topotecan versus cyclophosphamide, doxorubicin, and vincristine for the treatment of recurrent small-cell lung cancer. J Clin Oncol. Feb. 1999; 17(2):658-67.
Wagner et al., A Phase 1/2 Trial Combining Avelumab and Trabectedin for Advanced Liposarcoma and Leiomyosarcoma. Clin Cancer Res. Jun. 1, 2022;28(11):2306-2312, 27 pages, pre-publication edition.
Wagner et al., A retrospective chart review of drug treatment patterns and clinical outcomes among patients with metastatic or recurrent soft tissue sarcoma refractory to one or more prior chemotherapy treatments. BMC Cancer. Mar. 25, 2015;15:175, 7 pages.
Waldschmidt et al., Trabectedin priming and subsequent PD-1 inhibition for long-term disease control in a patient with dedifferentiated liposarcoma. Oncol Res Treat. 2024;47(Suppl 2):296-297, Abstract P1055.
Wang et al., Dose-related immunomodulatory effects of recombinant TRAIL in the tumor immune microenvironment. J Exp Clin Cancer Res. Aug. 22, 2023;42(1):216, 21 pages.
Wang et al., Efficacy outcomes between tarlatamab and real-world physicians' choice of therapies for previously treated extensive stage small cell lung cancer. Oncologist. Sep. 1, 2025;30(9):oyaf256, 10 pages.
Wang et al., Molecular Recognition of DNA Minor Groove Binding Drugs. Crystallographic and modeling methods in molecular design. Springer, New York. pp. 123-150, (1990).
Washington et al., Cell Membranes, Epithelial Barriers, and Drug Absorption. Physiological Pharmaceutics, Barriers to Drug Absorption, Second Edition. CRC Press, Boca Raton. Chapter 1, pp. 1-18, (2001).
Wasifuddin et al., Correlations between overall response rate, progression-free survival and overall survival in refractory small cell lung cancer treated with lurbinectedin. J Clin Oncol. 2023;41(Suppl 16), Abstract e20623.
Waters et al., Phase I clinical and pharmacokinetic study of bcl-2 antisense oligonucleotide therapy in patients with non-Hodgkin's lymphoma. J Clin Oncol. May 2000; 18(9):1812-23.
Widler et al., 7-Alkyl- and 7-cycloalkyl-5-aryl-pyrrolo[2,3-d]pyrimidines-potent inhibitors of the tyrosine kinase c-Src. Bioorg Med Chem Lett. Mar. 26, 2001;11(6):849-52.
Wilkinson, Pharmacokinetics, The Dynamics of Drug Absorption, Distribution, and Elimination. Goodman & Gilman's The Pharmacological Basis of Therapeutics, Tenth Edition. McGraw-Hill, Medical Publishing Edition, New York. Chapter 1, pp. 3-29, (2001).
Williams, Drug Metabolism. Principles of Medicinal Chemistry, Fourth Edition. William O. Foye (Ed.), Lippincott Williams & Wilkins, Philadelphia. Chapter 8, pp. 83-140, (1995).
Witherington et al., 6-aryl-pyrazolo[3,4-b]pyridines: potent inhibitors of glycogen synthase kinase-3 (GSK-3). Bioorg Med Chem Lett. Sep. 15, 2003;13(18):3055-7.
Witten et al., Structures of two cockroach neuropeptides assigned by fast atom bombardment mass spectrometry. Biochem Biophys Res Commun. Oct. 30, 1984;124(2):350-8.
Woll et al., Phase II trial of raltitrexed ('Tomudex') in advanced small-cell lung cancer. Br J Cancer. 1997;76(2):264-5.
Wong et al., Abdominal monophasic synovial sarcoma is a morphological and immunohistochemical mimic of gastrointestinal stromal tumour. Histopathology. Jun. 2015; 66(7):974-81.
Wong, Properties and Reaction of Tryptamine-4,5-Dione with Glutathione and Central Toxicity and Potential Mechanisms of Action of Their Reaction Product 7-S-Glutathionyl-Tryptamine-4,5-Dione. A Dissertation Submitted to the Graduate Faculty in partial fulfillment of the requirements for the degree of Doctor of Philosophy. 243 pages, (1992).
Woods et al., Antagonism between tamoxifen and doxorubicin in the MCF-7 human breast tumor cell line. Biochem Pharmacol. Apr. 20, 1994;47(8):1449-52.
Wright et al., Antitumor Tetrahydroisoquinoline Alkaloids from the Colonial Ascidian Ecteinascidia turbinata. J Org Chem. 1990;55:4508-4512.
Xiang et al., Efficacy and safety of lurbinectedin in Chinese patients with extensive-stage small cell lung cancer (ES-SCLC): A multicenter, retrospective real-world study. Annals of Oncology. 2024;35(S4):S1667, Abstract 703P.
Xiang et al., MCL-1 inhibition in cancer treatment. Onco Targets Ther. Oct. 23, 2018; 11:7301-7314.
Xing et al., Phase 2 dose-ranging study to evaluate the efficacy and safety of liposomal irinotecan (LY01610) as a second-line treatment for patients with relapsed small cell lung cancer. EClinicalMedicine. Sep. 3, 2024;75:102791, 12 pages.
Yang et al., Structural studies of atom-specific anticancer drugs acting on DNA. Pharmacol Ther. Sep. 1999;83 (3):181-215.
Yazawa et al., Bioconversions of saframycin A specific to some genera of actinomycetes. J Antibiot (Tokyo). Jul. 1982;35(7):915-7.
Yazawa et al., Isolation and structural elucidation of new saframycins Y3, Yd-1, Yd-2, Ad-1, Y2b and Y2b-d. J Antibiot (Tokyo). Dec. 1986;39(12):1639-50.
Yondelis, Highlights of Prescribing Information. 20 pages, Jul. 2016.
Jones et al., Efficacy and tolerability of trabectedin in elderly patients with sarcoma: subgroup analysis from a phase 3, randomized controlled study of trabectedin or dacarbazine in patients with advanced liposarcoma or leiomyosarcoma. Annals of Oncology. 2018;29(9):1995-2002. pre-publication edition.
Jones et al., Trabectedin Reduces Skeletal Prostate Cancer Tumor Size in Association with Effects on M2 Macrophages and Efferocytosis. Neoplasia. Feb. 2019;21(2):172-184.
Jonsson et al., Differential activity of topotecan, irinotecan and SN-38 in fresh human tumour cells but not in cell lines. Eur J Cancer. Oct. 2000; 36(16):2120-7.
Joss et al., Ondansetron plus dexamethasone is superior to ondansetron alone in the prevention of emesis in chemotherapy-naive and previously treated patients. Swiss Group for Clinical Cancer Research (SAKK). Ann Oncol. Mar. 1994;5(3):253-8.
Jumaniyazova et al., Immune Cells in the Tumor Microenvironment of Soft Tissue Sarcomas. Cancers (Basel). Dec. 8, 2023; 15(24):5760, 18 pages.
Kania, The First Enantioselective Total Syntheses of Dolabellatrienone and Ecteinascidin 743. Thesis, The Department of Chemistry and Chemical Biology in partial fulfillment of the requirements for the degree of Doctor of Philosophy. 239 pages, Sep. 1997.
Kano et al., Effects of CPT-11 in combination with other anti-cancer agents in culture. Int J Cancer. Feb. 20, 1992;50 (4):604-10.
Kantidakis et al., New benchmarks to design clinical trials with advanced or metastatic liposarcoma or synovial sarcoma patients: An EORTC—Soft Tissue and Bone Sarcoma Group (STBSG) meta-analysis based on a literature review for soft-tissue sarcomas. Eur J Cancer. Oct. 2022; 174:261-276.
Kartner et al., Multidrug Resistance in Cancer. Scientific American. Mar. 1989;44-51.
Kasper et al., Recent advances and further challenges in lyophilization. Eur J Pharm Biopharm. Oct. 2013; 85 (2):162-9, pre-publication edition.
Kawakami et al., Synthesis and evaluation of novel rhodacyanine dyes that exhibit antitumor activity. J Med Chem. Sep. 26, 1997;40(20):3151-60.

(56) References Cited

OTHER PUBLICATIONS

Kawano et al., Combination treatment with trabectedin and irinotecan or topotecan has synergistic effects against ovarian clear cell carcinoma cells. Int J Gynecol Cancer. Jun. 2014;24(5):829-37.
Kaye, New antimetabolites in cancer chemotherapy and their clinical impact. Br J Cancer. 1998;78 Suppl 3(Suppl 3):1-7.
Keegan, Center for Drug Evaluation and Research, Application No. 207953Orig1s000, Summary Review. NDA 207953, Yondelis. 30 pages, Oct. 23, 2015.
Keisling et al., Effects of Acoustic Immune Priming with Low-intensity Focused Ultrasound (LORJ) and Trabectedin on a Murine Model of Osteosarcoma. J Immunother Cancer. 2020;8(Suppl 3):A348-A349, Abstract 581.
Kemeny et al., Targeting the (Un)differentiated State of Cancer. Cancer Cell. May 14, 2018;33(5):793-795.
Kepp et al., FDA approves lurbinectedin in combination with atezolizumab for extensive-stage small cell lung cancer. Oncoimmunology. Dec. 31, 2025;14(1):2584898, 5 pages.
Kim et al., Experience of the use of trabectedin (ET-743) in patients with advanced soft tissue sarcoma failing doxurubicin and/or ifosfamide in Korea. J Clin Oncol. 2010;28:Abstract e20518, 2 pages.
Kimura et al., Adjuvant immunotherapy with interleukin 2 and lymphokine-activated killer cells after noncurative resection of primary lung cancer. Lung Cancer. Aug. 1995; 13(1):31-44.
Koenig, The Applicability of Asymmetric Homogeneous Catalytic Hydrogenation. Asymmetric Synthesis, Chiral Catalysis, vol. 5. Academic Press, Inc., Orlando. Chapter 3, p. 71, (1985).
Koeppel et al., Acquired irofulven resistance is accompanied by decreased tumorigenicity withough changes in sensitivity to irradiation or to other anticancer agents. Proceedings of the American Association for Cancer Research. Jul. 2003; 44:480, Abstract 2450.
Kofron et al., A Convenient Method for Estimation of Alkyllithium Concentrations. J Org Chem. 1976;41 (10):1879-1880.
Koh et al., The impact of reducing osteal macrophages and their efferocytotic function on bone turnover and bone mass. ASBMR 2015 Annual Meeting. Abstract SU0167, 2 pages, Oct. 11, 2015.
Kola et al., Can the pharmaceutical industry reduce attrition rates? Nat Rev Drug Discov. Aug. 2004;3(8):711-5.
Kotha et al., A Novel LC-MS/MS Technique for the Quantitation of Lurbinectedin in Human Plasma: Application of Stability Studies. International Journal of Applied Pharmaceutics. 2025; 17(6):7 pages.
Kraljevic et al., Accelerating drug discovery. EMBO Rep. Sep. 2004;5(9):837-42.
Kratz et al., Serum proteins as drug carriers of anticancer agents: a review. Drug Deliv. 1998;5(4):281-99.
Krayim et al., Lurbinectedin in small cell lung cancer (SCLC): Response patterns and survival outcomes by line of therapy. J Clin Oncol. 2025;43(Suppl 16):Abstract e20128.
Kristeleit et al., Lurbinectedin in patients with pretreated endometrial cancer: results from a phase 2 basket clinical trial and exploratory translational study. Invest New Drugs. Oct. 2023; 41(5):677-687.
Kristensen et al., Anti-vascular endothelial growth factor therapy in breast cancer. Int J Mol Sci. Dec. 11, 2014;15 (12):23024-41.
Kubo et al., Structure of saframycin D, a new dimeric isoquinolinequinone antibiotic. Chem Pharm Bull (Tokyo). Jan. 1987;35(1):440-2.
Kuffel et al., Cytochrome P450 catalyzed metabolism of Ecteinascidin 743 by rat and human liver microsomes. Proceedings of the American Association for Cancer Research. Mar. 1997;38:596, Abstract 4003.
Kurdow et al., Apoptosis by gemcitabine in non-small cell lung cancer cell line KNS62 is induced downstream of caspase 8 and is profoundly blocked by Bcl-xL over-expression. Langenbecks Arch Surg. Jun. 2005;390(3):243-8.
Kuroshima et al., Multimodality therapy for the patients with advanced or recurrent uterine leiomyosarcoma. 70th Annual Congress, JSOG. 2018;44(8):1610, Abstract ISP-38-7.
Kuter et al., General Aspects of Thrombocytopenia, Platelet Transfusions, and Thrombopoietic Growth Factors. Consultative Hemostasis and Thrombosis. Elsevier eBooks. Chapter 7, pp. 108-126, (2019).
Kuter et al., Managing thrombocytopenia associated with cancer chemotherapy. Oncology (Williston Park). Apr. 2015;29(4):282-94.
Laharwal et al., Real-world effectiveness of lurbinectedin in extensive stage small cell lung cancer (ES-SCLC). J Clin Oncol. 2025;43(Suppl 16): Abstract e20133.
Lambden et al., Metastatic Myxofibrosarcoma with Durable Response to Temozolomide Followed by Atezolizumab: A Case Report. Oncologist. Jul. 2021;26(7):549-553.
Larionova et al., Interaction of tumor-associated macrophages and cancer chemotherapy. Oncoimmunology. Apr. 13, 2019;8(7):1596004, 15 pages.
Laroche-Clary et al., Synergistic Effects of ATR Inhibition and Lurbinectedin in Soft-Tissue Sarcomas: The Predictive Role of SLFN11 Expression. Clin Cancer Res. Sep. 2, 2025;31(17):3796-3804. pre-publication edition.
Laznicek et al., The effect of lipophilicity on the protein binding and blood cell uptake of some acidic drugs. J Pharm Biomed Anal. Jun. 1995; 13(7):823-8.
Lazo et al., Antiproliferative actions of tamoxifen to human ovarian carcinomas in vitro. Cancer Res. Jun. 1984;44 (6):2265-71.
Le Cesne et al., Assessing the clinical impact of trabectedin in patients with leiomyosarcomas or liposarcomas (Lsarcomas) progressing despite prior conventional chemotherapy: clinical benefit rate, growth modulation index and tumor variation as parameters of treatment e. European Journal of Cancer Supplements. Sep. 2007; 5(4):405, abstract P#7512. 2 pages.
Le Cesne et al., Assessing the Clinical Impact of Trabectedin in Patients with Leiomyosarcomas or Liposarcomas (L-sarcomas) Progressing Despite Prior Conventional Chemotherapy: Clinical Benefit Rate, Growth Modulation Index and Tumor Variation as Parameters of Treatment Effect in a Randomized International Trial of Two Trabectedin Dosing Regimens. ECCO 14—the European Cancer Conference. 1 page, Sep. 23-27, 2007.
Le et al., Ecteinascidins. A review of the chemistry, biology and clinical utility of potent tetrahydroisoquinoline antitumor antibiotics. Nat Prod Rep. Feb. 2015;32(2):328-47.
Le Tourneau et al., mTORC1 inhibitors: is temsirolimus in renal cancer telling US how they really work? Br J Cancer. Oct. 21, 2008;99(8):1197-203.
Leal et al., Molecular pharmacology and antitumor activity of in several human cancer cell lines. Biochemical Pharmacology. 2009;78(2):162, 33 pages.
Leary et al., Pooled Safety Analysis of Single-Agent Lurbinectedin in Patients With Advanced Solid Tumours. Eur J Cancer. Oct. 2023; 192:113259, 23 pages, pre-publication edition.
Leblond et al., Tumor-Associated Macrophages in Bladder Cancer: Biological Role, Impact on Therapeutic Response and Perspectives for Immunotherapy. Cancers (Basel). Sep. 21, 2021;13(18):4712, 30 pages.
Lee et al., Advancements in small cell lung cancer. Semin Cancer Biol. Aug. 2023; 93:123-128.
Pharmamar, PharmaMar presents new results for lurbinectedin at ASCO Genitourinary Cancers symposium. Press Release, 3 pages, Jan. 29, 2024.
Pharmamar, PharmaMar presents new results with lurbinectedin as a single agent in patients with recurrent small-cell lung cancer at ASCO 2018. Press Release, 3 pages, Jun. 4, 2018.
Pharmamar, PharmaMar presents positive results from a Phase II study of lurbinectedin in Ewing's sarcoma at the CTOS International Congress. Press Release, 3 pages, Nov. 13, 2017.
Pharmamar, PharmaMar presents the Overall Survival data from the Phase I/II Study of lurbinectedin in combination with doxorubicin for relapsed Small Cell Lung Cancer. Press Release, 3 pages, Sep. 24, 2018.
Pharmamar, PharmaMar reaches an agreement with Impilo Pharma, a part of Immedica Group, for the promotion and distribution of Yondelis in the Nordic countries and Easter Europe. Press Release, 3 pages, Jul. 27, 2018.

(56) References Cited

OTHER PUBLICATIONS

Pharmamar, PharmaMar receives authorization to initiate the Phase III Neptuno clinical trail with plitidepsin for the treatment of COVID-19. Press Release, 3 pages, Apr. 29, 2021.
Pharmamar, PharmaMar receives Orphan Drug Designation for lurbinectedin from the Swiss Agency for Therapeutic Products for Malignant Mesothelioma. Press Release, 2 pages, Dec. 27, 2022.
Pharmamar, PharmaMar receives Orphan Drug Designation for lurbinectedin from the Swiss Agency for Therapeutic Products for Small Cell Lung Cancer. Press Release, 2 pages, Nov. 26, 2019.
Pharmamar, PharmaMar receives positive opinion from Ema (Comp) for orphan drug designation of Zepsyre (lurbinectedin) for small-cell lung cancer. Press Release, 2 pages, Jan. 24, 2019.
Pharmamar, PharmaMar receives the first commercial milestone payment from Jazz Pharmaceuticals for US$25 million. Press Release, 2 pages, Mar. 4, 2022.
Pharmamar, PharmaMar receives US$10 million milestone payment from Janssen. Press Release, 2 pages, Dec. 12, 2022.
Pharmamar, PharmaMar receives US$10 million milestone payment from Janssen. Press Release, 2 pages, Nov. 6, 2023.
Pharmamar, PharmaMar reports EBITDA of euro20.6 million (+6%) in the first quarter of 2022. Press Release, 3 pages, Apr. 28, 2022.
Pharmamar, PharmaMAr reports net profit of euro5 million at the end of the third quarter of 2018. Press Release, 3 pages, Oct. 30, 2018.
Pharmamar, PharmaMar reports positive results for Aplidin against coronavirus HCoV-229E. Press Release, 2 pages, Mar. 13, 2020.
Pharmamar, PharmaMar requests the modification from primary endpoint to OS for the ATLANTIS trial. Press Release, 2 pages, Jun. 12, 2018.
Pharmamar, PharmaMar sells Zelnova for euro33.4 million. Press Release, 2 pages, Jun. 28, 2019.
Pharmamar, PharmaMar signs a commercialization and distribution license agreement for Aplidin (plitidepsin) with Megapharm in Israel. Press Release, 2 pages, Jan. 2, 2018.
Pharmamar, PharmaMar signs a commercialization and distribution license agreement for Aplidin with Pint Pharma International. Press Release, 2 pages, Jun. 11, 2018.
Pharmamar, PharmaMar signs a licensing agreement with R-Pharm to commercialize Yondelis in Russia, Armenia, Azerbaijan, Belarus, Kazakhstan, Kyrgyzstan, Moldova, Tajikistan, Uzbekistan, Turkmenistan, Ukraine and Georgia. Press Release, 3 pages, Dec. 23, 2020.
Pharmamar, PharmaMar signs a licensing and commercialization agreement with Lotus Pharmaceutical for lurbinectedin in Taiwan. Press Release, 3 pages, Nov. 11, 2021.
Pharmamar, PharmaMar signs a new agreement with Adium Pharma S.A. to commercialize Yondelis in Latin America. Press Release, 3 pages, Jul. 27, 2020.
Pharmamar, PharmaMar signs a new agreement with Adium to commercialize Zepzelca (lurbinectedin) in Latin America. Press Release, 3 pages, Mar. 1, 2021.
Pharmamar, PharmaMar signs a new agreement with Megapharm to commercialize Yondelis in Israel. Press Release, 3 pages, Dec. 13, 2019.
Pharmamar, PharmaMar signs a new agreement with Onko to commercialize Yondelis in Turkey. Pree Release, 3 pages, Aug. 10, 2020.
Pharmamar, PharmaMar signs a new licensing and commercialization agreement wtih Eczacibasi for lurbinectedin in Turkey. Press Release, 3 pages, Dec. 22, 2021.
Pharmamar, PharmaMar signs a new licensing, development and commercialization agreement with Merck for lurbinectedin in Japan. Press Release, 2 pages, Apr. 3, 2025.
Pharmamar, PharmaMar signs an agreement with Immedica Pharma to market lurbinectedin in Easter Europe, the UK, Ireland, the Nordic countries and some Middle Eastern countries. Press Release, 2 pages, Apr. 29, 2020.
Pharmamar, PharmaMar signs an agreement with Jazz Pharmaceuticals for lurbinectedin in Canada. Press Release. 2 pages, Oct. 15, 2020.
Pharmamar, PharmaMar signs an agreement with Valeo Pharma to commercialize Yondelis in Canada. Press Release, 3 pages, Jan. 21, 2020.
Pharmamar, PharmaMar starts a quadruple combination study with Aplidin for the treatment of multiple myeloma. Press Release, 2 pages, Aug. 9, 2017.
Pharmamar, PharmaMar starts clinical studies with a new compound—PM14—in patients with solid tumors. Press Release, 2 pages, Sep. 19, 2017.
Pharmamar, PharmaMar study of the combination of lurbinectedin and irinotecan on Small Cell Lung Cancer has been selected for a presentation at ASCO. Press Release, 4 pages, Apr. 25, 2024.
Pharmamar, PharmaMar submits the Marketing Authorisation Application for Aplidin in Switzerland. Press Release, 2 pages, Oct. 4, 2017.
Pharmamar, PharmaMar to attend the China Healthcare Investment Conference (CHIC). Press Release, 2 pages, Mar. 26, 2019.
Pharmamar, PharmaMar to Hold Fourth Quarter Financial Results Conference Call and Webcast on Friday, Feb. 24, 2017. Press Release, 3 pages, Feb. 22, 2017.
Pharmamar, PharmaMar to host Conference Call with Webcast on Wednesday, Jan. 4, 2017 to discuss the license and Commercialization agreement with Chugai Pharmaceuticals for Lurbinectedin in Japan. Press Release, 2 pages, Jan. 3, 2017.
Pharmamar, PharmaMar to Host Research and Development Event on Apr. 24, 2017, 2 pages, Apr. 6, 2017.
Pharmamar, PharmaMar To Host Virtual KOL Event on Lurbinectedin. Press Release, 2 pages, Jun. 3, 2020.
Pharmamar, PharmaMar to Participate at the 19th Annual Needham Virtual Healthcare Conference on April 14th, at 11:40 Am Est (17:40CET). Press Release, 2 pages, Apr. 13, 2020.
Pharmamar, PharmaMar to present at the Stifel 2017 Healthcare Conference. Press Release, 1 page, Nov. 14, 2017.
Pharmamar, PharmaMar to Present at the Upcoming Virtual European Biotech Investor Day 2020. Press Release, 2 pages, Jun. 23, 2020.
Pharmamar, PharmaMar to present new data on lurbinectedin at the IASLC 2023 World Lung Cancer Congress. Press Release, 4 pages, Sep. 8, 2023.
Pharmamar, PharmaMar unites Europe's leading experts in Soft Tissue Sarcoma in Madrid. Press Release, 2 pages, Apr. 22, 2022.
Pharmamar, PharmaMar will commercialize PM1183 with the trade name of Zepsyre. Press Release, 2 pages, Jun. 16, 2017.
Pharmamar, PharmaMar will host a conference call with investors after lurbinectedin results are presented at ASCO. Press Release, 3 pages, Jun. 3, 2019.
Pharmamar, PharmaMar will participate in the Solebury Trout KOL Day in New York on Nov. 15, 2019. Press Release, 3 pages, Nov. 7, 2019.
Pharmamar, PharmaMar will present at ESGO new data on Yondelis for gynecological cancers. Press Release, 4 pages, Nov. 3, 2017.
Pharmamar, PharmaMar will present at ESMO results of the phase Iii Corail study with lurbinectedin in platinum- resistant Ovarian Cancer. Press Release, 4 pages, Oct. 18, 2018.
Pharmamar, PharmaMar will present data for Zepzelca (lurbinectedin) and Yondelis (trabectedin) at ESMO 2020. Press Release, 5 pages, Sep. 14, 2020.
Takahashi et al., Phase I study of lurbinectedin in Japanese patients with pretreated advanced tumours: Final results. ESMO Virtual Congress 2020. Poster, Sep. 19-21, 2020.
Takahashi et al., Phase I trial of lurbinectedin (PM1183) in Japanese patients with advanced tumors. Results of the dose escalation part. ASCO American Society of Clinical Oncology, 54th Annual Meeting. 1 page, poster, Jun. 1-5, 2018.
Takahashi et al., Phase I trial of lurbinectedin (PM1183) in Japanese patients with advanced tumors: Results of the dose escalation part. J Clin Oncol. Jun. 4, 2018;36. Abstract 2551.
Takuro et al., Nivolumab for gastric cancer. Immunotherapy inhibitor. Immunotherapy. Sep. 1, 2018;266(9):711-716.

(56) References Cited

OTHER PUBLICATIONS

Tan et al., Navitoclax enhances the efficacy of taxanes in non-small cell lung cancer models. Clin Cancer Res. Mar. 15, 2011;17(6):1394-404.
The Medical Letter, Lurbinectedin (Zepzelca) for Small-Cell Lung Cancer. The Medical Letter on Drugs and Therapeutics. Nov. 14, 2022;64:e198-e199.
Toublanc et al., Second-line lurbinectedin as a new treatment option for small-cell lung cancer: Preliminary results in real-clinical practice. Thorac Cancer. Aug. 2022;13(15):2248-2252.
Trigo et al., Antitumor activity of single agent Lurbinectedin in patients with relapsed SCLC occurring greater than or equal to 30 days after last platinum dose. IASLC 20th World Conference on Lung Cancer. 1 page, poster, Sep. 7-10, 2019.
Trigo et al., Efficacy and safety of lurbinectedin (PM1183, Zepsyre) in small cell lung cancer (SCLC): Results from a phase 2 study. ASCO American Society of Clinical Oncology, 54th Annual Meeting. 1 page, poster, Jun. 1-5, 2018.
Trigo Perez et al., Antitumor Activity of Single Agent Lurbinectedin in Patients with Relapsed SCLC Occurring greater than or equal to 30 Days After Last Platinum Dose. IASLC 2019 World Confernce on Lung Cancer. Page 560, Abstract P1.12-03, (2019).
Trigo Perez et al., Efficacy and safety of lurbinectedin (PM1183) in small cell lung cancer (SCLC): Results from a phase 2 study. J Clin Oncol. 2018;36:Abstract 8570.
Tummala et al., Synergistic combinations of lurbinectedin with irinotecan and ONC212 in pancreatic cancer. Cancer Res.83(7 Suppl):Abstract 2674.
Uruchurtu et al., Molecular analysis of small cell lung cancer provides insights into mechanism of action underlying the novel drug combination of lurbinectedin and TIC10/ONC201. Cancer Res. 83(7 Suppl):Abstract 4909.
Vaidya et al., Lurbinectedin exhibits combinatorial activity with BCL2/BCL2L1 inhibitors in vitro and in vivo by modulation of MCL1 expression. Cancer Res. 2023;83(7 Suppl):Abstract 6155.
Van Andel et al., Development and validation of a liquid chromatography-tandem mass spectrometry assay for the quantification of lurbinectedin in human plasma and urine. J Pharm Biomed Anal. Sep. 5, 2018;158:160-165.
Vidal et al., Lurbinectedin (PM01183), a new DNA minor groove binder, inhibits growth of orthotopic primary graft of cisplatin-resistant epithelial ovarian cancer. Clin Cancer Res. Oct. 1, 2012; 18(19):5399-411.
Villanueva et al., Antitumor effect of PM01183 in a patient-derived Cisplatin-sensitive and -resistant serous epithelial ovarian orthotopic tumor model. AACR Annual Meeting. Apr. 2, 2012;1 page, Poster, abstract 1778.
Vogler, Targeting BCL2-Proteins for the Treatment of Solid Tumours. Adv Med. 2014;2014:943648, 14 pages.
Wahab et al., Lurbinectedin-Induced Tumor Lysis Syndrome in Small Cell Neuroendocrine Cancer of the Cecum: A First-Ever Case Report. Am J Case Rep. Jun. 14, 2021;22:e932081, 5 pages.
Wang et al., Characterization of Real-World Use of Lurbinectedin in Adult Small Cell Lung Cancer Patients in the United States. Journal of Thoracic Oncology. Sep. 2022; 17(9S):S553-S554, Abstract EP14.05.023.
Wang et al., Targeting MCL-1 in cancer: current status and perspectives. J Hematol Oncol. Apr. 2, 20211;14(1):67, 18 pages.
Waybackmachine, Drug Development and Drug Interactions, Table of Substrates, Inhibitors and Inducers. 17 pages, Aug. 24, 2022.
Wertz et al., Sensitivity to antitubulin chemotherapeutics is regulated by MCL1 and FBW7. Nature. Mar. 3, 2011;471 (7336):110-4.
Yakobson et al., Metastatic small cell lung cancer—an aggressive disease: a case report and literature review. Anti-Cancer Drugs. 4 pages, (2021), pre-publication edition.
Yan et al., BET inhibition induces vulnerability to MCL1 targeting through upregulation of fatty acid synthesis pathway in breast cancer. Cell Rep. Sep. 13, 2022;40(11):111304, 25 pages.
Yang et al., Synthetic strategies and therapeutic insights into FDA-approved indole-containing drugs. J Enzyme Inhib Med Chem. Dec. 2026;41(1):2616556, 24 pages.
Yasuda et al., MCL1 inhibition is effective against a subset of small-cell lung cancer with high MCL1 and low BCL-XL expression. Cell Death Dis. Mar. 9, 2020;11(3):177, 15 pages.
Yecies et al., Acquired resistance to ABT-737 in lymphoma cells that up-regulate MCL-1 and BFL-1. Blood. Apr. 22, 2010;115(16):3304-13.
Yokoi et al., Lurbinectedin (PM01183), a selective inhibitor of active transcription, effectively eliminates both cancer cells and cancer stem cells in preclinical models of uterine cervical cancer. Invest New Drugs. Oct. 2019; 37(5):818-827.
Yokoyama, Lurbinectedin Approved in the U.S. for Advanced Small Cell Lung Cancer. Nikkei Business Publications. 2 pages, Jun. 18, 2020.
Yu et al., Extensive-stage small-cell lung cancer: Current management and future directions. Int J Cancer. Jun. 1, 2023;152(11):2243-2256.
Zeltia, S.A. Audit report, annual financial statements e Management Report as of Dec. 31, 2001. 264 pages.
Zeltia, S.A. Auditor's Report, Annual Financial Statements and Management Report 2000, 252 pages.
Zepzelca, Highlights of prescribing information. 31 pages, Feb. 2026.
Zepzelca, How Zepzelca works, Retrieved online at: https://www.zepzelca.com/what-zepzelca-does/. 6 pages. (2025).
Zirkelbach et al., Improving Dose-Optimization Processes Used in Oncology Drug Development to Minimize Toxicity and Maximize Benefit to Patients. J Clin Oncol. Oct. 20, 2022;40(30):3489-3500.
Zugazagoitia et al., Extensive-Stage Small-Cell Lung Cancer: First-Line and Second-Line Treatment Options. J Clin Oncol. Feb. 20, 2022;40(6):671-680.
Huisman et al., Second-line chemotherapy and its evaluation in small cell lung cancer. Cancer Treat Rev. Aug. 1999;25(4):199-206.
Li et al., Lurbinectedin for the treatment of small cell lung cancer. Drugs Today (Barc). Jun. 2021;57(6):377-385. .
US non-final Office Action for U.S. Appl. No. 19/190,098, dated Aug. 7, 2025, 104 pages.
Zeltia, S.A., Informe de auditoria, cuentas anuales e informe de geston al 31 de diciembre de 2007. 170 pages.
Zeltia, S.A., Informe de auditoria, cuentas anuales e informe de geston al 31 de diciembre de 2006. 133 pages.
Zeltia, S.A., Informe de auditoria, cuentas anuales e informe de geston al 31 de diciembre de 2004. 134 pages.
Zeltia, S.A., Informe de auditoria, cuentas anuales e informe de geston al 31 de diciembre de 2003. 142 pages.
Zeltia, S.A., Informe de auditoria, cuentas anuales e informe de geston al 31 de diciembre de 2002. 170 pages.
U.S. Department of Health and Human Services, Common Terminology Criteria for Adverse Events (CTCAE), Version 4.0. 79 pages. May 28, 2009.
Center for Drug Evaluation and Research, Application No. 207953Orig1s000, Cross Discipline Team Leader Review. 32 pages, Oct. 23, 2015.
Center for Drug Evaluation and Research, Application No. 207953Orig1s000, Medical Review(s). 141 pages, Oct. 23, 2015.
Center for Drug Evaluation and Research, Application No. 207953Orig1s000, Office Director Memo. 9 pages, Oct. 23, 2015.
Center for Drug Evaluation and Research, Application No. 207953Orig1s000, Officer/Employee List. 2 pages, Oct. 23, 2015.
Center for Drug Evaluation and Research, Application No. 207953Orig1s000, Other Review(s). 80 pages, Oct. 23, 2015.
Center for Drug Evaluation and Research, Application No. 207953Orig1s000, Pharmacology Review(s). 19 pages, Oct. 23, 2015.
Center for Drug Evaluation and Research, Application No. 207953Orig1s000, Proprietary Name Review(s). 25 pages, Oct. 23, 2015.
Center for Drug Evaluation and Research, Application No. 207953Orig1s000, Risk Assessment and Risk Mitigation Review(s). 10 pages, Oct. 23, 2015.

(56) References Cited

OTHER PUBLICATIONS

Center for Drug Evaluation and Research, Application No. 207953Orig1s000, Statistical Review(s). 26 pages, Oct. 23, 2015.
Chahine et al., Experience of the use of trabectedin in pretreated unresectable, advanced, or metastatic soft tissue sarcoma in nine centers in Lebanon on a compassionate-use basis. J Clin Oncol. 2011;29:Abstract e20533, 2 pages.
Chamseddine et al., Modulating tumor-associated macrophages to enhance the efficacy of immune checkpoint inhibitors: A TAM-pting approach. Pharmacol Ther. Mar. 2022;231:107986, 71 pages, pre-publication edition.
Chawla et al., A phase 2 study of talimogene laherparepvec, nivolumab, and trabectedin (TNT) in advanced sarcoma. ASCO 57th Annual Meeting. 2021;39(Suppl 15):589s, Abstract 11567.
Chawla et al., Activity of TNT: a phase 2 study using talimogene laherparepvec, nivolumab and trabectedin for previously treated patients with advanced sarcomas (NCT# 03886311). Front Oncol. May 1, 20230; 13:1116937, 11 pages.
Chawla et al., An update on SOC-1882: a phase 2 study using talimogene laherparepvec, nivolumab, and trabectedin for advanced leiomyosarcoma. ASCO 60th Annual Meeting. 1 page, Abstract e23570, (2024).
Chawla et al., Cancer Immunotherapy Using Trabectedin and Nivolumab in Advanced Soft Tissue Sarcoma: A Retrospective Analysis. ASCO-SITC Clinical Immuno-Oncology Symposium 2018. J Clin Oncol. 2018; 36(Suppl. 5): Abstract 40.
Chawla et al., Cancer Immunotherapy Using Trabectedin and Nivolumab in Advanced Soft Tissue Sarcoma: A Retrospective Analysis. CTOS 22nd Annual Meeting. 1 page, Paper 20, Abstract 2794748, (2017).
Chawla et al., Clinical experience with combination chemo-/immunotherapy using trabectedin and nivolumab for advanced soft tissue sarcoma. ASCO 54th Annual Meeting, 1 page, (2018).
Chawla et al., Clinical tolerability of trabectedin administered by two different schedules (weekly for 3 of 4 weeks vs q3 weeks) in patients with advanced metastatic liposarcoma or leiomyosarcoma (Lsarcomas) progressing despite prior treatment with at least anthracyl. European Journal of Cancer Supplements. 2007;5(4):407, 2 pages.
Chawla et al., Clinical tolerability of Trabectedin administered by two different schedules (weekly for 3 of 4 weeks vs q3 weeks) in patients with advanced/metastatic liposarcoma or leiomyosarcoma (L-sarcomas) progressing despite prior treatment with at least Anthracycline and Ifosfamide. ECCO 14 - the European Cancer Conference. 1 page, Sep. 23-27, 2007.
Chawla et al., Results of a multivariate analysis for potential factors affecting outcome in translocation related sarcomas (TRS) treated with trabectedin or doxorubicin-based chemotherapy (DXCT) as first-line therapy. 17th ECCO, (2013).
Chawla et al., Results of a multivariate analysis for potential factors affecting outcome in translocation related sarcomas (TRS) treated with trabectedin or doxorubicin-based chemotherapy (DXCT) as first-line therapy. European Journal of Cancer. 2013;49:S885, Abstract 3829.
Chawla et al., Results of Tnt: A phase II study using talimogene laherparepvec, nivolumab and trabectedin for advanced leiomyosarcoma and liposarcoma [NCT# 03886311]. Annals of Oncology. 2024;35(S2):S1035-S1036, Abstract 1728P.
Chawla et al., Seven year update on SOC-1702: A phase 2 study using trabectedin (T) in combination with ipilimumab (I), nivolumab (N) and trabectedin (T) in previously untreated patients with advanced soft tissue sarcoma [NCT03138161]. Asco 60th Annual Meeting. 1 page, Abstract 11577, Poster, (2024).
Chawla, et al., Tnt: A Phase 2 Study Using Talimogene Laherparepvec, Nivolumab and Trabectedin as First, Second/Third Line Therapy for Advanced Soft Tissue Sarcoma, Including Desmoid Tumor and Chordoma. CTOS Annual Meeting. 1 page, Abstract 3463019, (2020).
Chekerov et al., Comparison of quality of life in patients with platinum-sensitive recurrent ovarian, fallopian tube and peritoneal cancer treated with trabectedin plus pegylated liposomal doxorubicin (PLD) or standard platinum-based therapy: Data look of the Noggo S16/COMPASS Trial. ESGO 2022, Abstract No. 672, Poster, (2022).
Chekerov et al., Comparison of Quality of Life in Patients with Platinum-sensitive Recurrent Ovarian, Fallopian Tube and Peritoneal Cancer Treated with Trabectedin Plus Pegylated Liposomal Doxorubicin (PLD) or Standard Platinum- based Therapy: Data Look of the NOGGO S16/Compass Trial. Int J Gynecol Cancer. 2022;32(Suppl 2):A252-A253, Abstract 2022-RA-672-ESGO.
Chen et al., Combination Therapy of Lurbinectedin and AZD6738 for Effective Elimination of ALT Cancer Cells. The 82nd Annual Meeting of the Japanese Cancer Association. 1 page, Abstract E-1026, Sep. 21, 2023.
Chib et al., Doxorubicin plus trabectedin for metastatic or unresectable leiomyosarcoma. Lancet Oncol. Oct. 2022; 23 (10): e443.
Chiodoni et al., Concomitant Reprogramming of tumor Cell Differentiation and Immune Environment Inhibits Osteosarcoma Metastatic Potential. CTOS 21st Annul Meeting. Page 171, Abstract 2559102, (2016).
Chou et al., Analysis of combined drug effects: a new look at a very old problem. TIPS. Nov. 1983, pp. 450-454.
Chou et al., Drug combination studies and their synergy quantification using the Chou-Talalay method. Cancer Res. Jan. 1, 20105;70(2):440-6.
Chou et al., Relationships between inhibition constants and fractional inhibition in enzyme-catalyzed reactions with different Nos. of reactants, different reaction mechanisms, and different types and mechanisms of inhibition. Mol Pharmacol. Mar. 1974; 10(2):235-47.
Christinat et al., Role of trabectedin in the treatment of soft tissue sarcoma. Onco Targets Ther. Feb. 18, 2009;2:105-13.
Chu et al., Phase I and Pharmacokinetic Study of Sequential Paclitaxel Followed by Trabectedin (ET-743) in 24-Hr Every 2 Weeks in Patients with Advanced or Metastatic Cancer. ESMO 29th Congress. 2004; 15(Suppl. 3):iii107. 1 page.
Chu et al., Phase I and Pharmacokinetic Study of Sequential Paclitaxel Followed by Trabectedin (ET-743) in 24-Hr Every 2 Weeks in Patients with Advanced or Metastatic Cancer. ESMO 29th Congress. 2004; 15(Suppl. 3):iii107. Abstract 398P, 1 page.
Chuk et al., A phase I trial and pharmacokinetic study of a 24-hour infusion of trabectedin (Yondelis®, ET-743) in children and adolescents with relapsed or refractory solid tumors. Pediatr Blood Cancer. Nov. 2012; 59(5):865-9.
Chute et al., Twenty years of phase III trials for patients with extensive-stage small-cell lung cancer: perceptible progress. J Clin Oncol. Jun. 1999; 17(6):1794-801.
Cigrang et al., Ectesacidins, When marine pharmacology targets the transcriptional dependence of cancer. medecine/sciences. Oct. 2025;41(10):720-723.
Cigrang et al., Novel synthetic esteinascidins echibit potent anti-melanoma activity by suppressing super-enhancer- driven oncogenic transcription. bioRxiv, 69 pages, Mar. 28, 2024.
Cigrang et al., Targeting Transcriptional Addiction in Melanoma with a new marine-derived drug. 21st Science Day of La Ligue Contre le Cancer. 1 page, Nov. 9, 2021.
Cinar et al., Androgen receptor mediates the reduced tumor growth, enhanced androgen responsiveness, and selected target gene transactivation in a human prostate cancer cell line. Cancer Res. Oct. 1, 2001;61(19):7310-7.
ClinicalTrial NCT02448537, A Phase II Multi-Strata Study of PM01183 as a Single Agent or in Combination With Conventional Chemotherapy in Metastatic and/or Unresectable Sarcomas. Protocol 15-083, 63 pages, Feb. 5, 2016.
Clinicaltrials.gov, A Phase III, Open-Label Study on Maintenance Lurbinectedin in Combination With Atezolizumab Compared With Atezolizumab in Participants With Extensive-Stage Small-Cell Lung Cancer (IMforte). NCT05091567, 39 pages, Oct. 29, 2024.
Clinicaltrials.gov, Clinical Pharmacokinetic Study of Lurbinectedin in Patients With Advanced Solid Tumors and Varying Degrees of Hepatic Impairment. 5 pages.
Clinicaltrials.gov, NCT00002904, Ecteinascidin 743 in Treating Adults With Advanced Solid Tumors. 24 pages, Jul. 2, 2012.

(56) References Cited

OTHER PUBLICATIONS

Clinicaltrials.gov, NCT00003939, Ecteinascidin 743 in Treating Patients With Advanced Soft Tissue Sarcoma. 12 pages, Sep. 24, 2012.
Clinicaltrials.gov, NCT00005625, Ecteinascidin 743 in Treating Patients With Previously Treated Metastatic Osteosarcoma. 10 pages, Jun. 19, 2013.
Clinicaltrials.gov, NCT00006463, Ecteinascidin 743 in Treating Children With Refractory Solid Tumors. 15 pages, Feb. 21, 2014.
Clinicaltrials.gov, Pharmacokinetic Study of PM01183 in Combination With Irinotecan in Patients With Selected Solid Tumors. History of Changes for Study: NCT02611024. 7 pages, Nov. 18, 2015.
Clinicaltrials.gov, Study to Assess Safety, Tolerability, Efficacy of PM01183 and Atezolizumab in Patients w/ Advanced Small Cell Lung Cancer. NCT04253145, 16 pages Nov. 18, 2023.
Akazawa et al., Chemotherapy Sensitivity for Recurrent Small-Cell Lung Cancer Based on Chemotherapy-Free Interval and Treatment Regimens. Journal of Thoracic Oncology. Oct. 2024; 19(10S): S668-S669, EP.13B.12.
Boyer et al., Cellular and Molecular Basis of Chemotherapy. The Basic Science of Oncology, Third Edition. Ian F. Tannock (Ed.), McGraw-Hill. Chapter 15, pp. 350-369, (1998).
Brunetto et al., Modest reductions in dose intensity and drug-induced neutropenia have no. major impact on survival of patients with non-small cell lung cancer treated with platinum-doublet chemotherapy. J Thorac Oncol. Sep. 2010;5(9):1397-403.
Clinicaltrials.gov, History of Changes for Study: NCT02454972, Clinical Trial of lurbinectedin (PM01183) in Selected Advanced Solid Tumors. 7 pages, Oct. 21, 2021.
Devita, Principles of Cancer Management: Chemotherapy. Cancer, Principles & Practice of Oncology, 5th Edition, vol. 1, Chapter 17, pp. 333-347. Lippincott-Raven Publishers, Philadelphia, (1997).
FDA, Camptosar, Highlights of Prescribing Information. 39 pages, Feb. 2019.
FDA, Doxil. Highlights of prescribing information. 29 pages, Aug. 2019.
FDA, Gemzar, Highlights of Prescribing Information. 25 pages, May 2019.
FDA, Pediatric Subcommittee of the Oncologic Drugs Advisory Committee Meeting. 86 pages, Jun. 21, 2017.
FDA, Taxol (paclitaxel) Injection, patient information included. 20 pages, Mar. 2015.
FDA, Taxotere, Highlights of prescribing information. 66 pages, Jun. 2019.
FDA, Topotecan Injection, Highlights of prescribing information. 19 pages, Feb. 2014.
Feng et al., Lambert-Eaton Myasthenic Syndrome During Immunotherapy in Extensive-Stage Small-Cell Lung Cancer: A Case Report. Br J Hosp Med (Lond). Apr. 17, 2026;87(4):53025, 12 pages.
Ibrahim, Supplemental Approval, Department of Health and Human Services, Nda 22-065/S-006, 4 pages, Oct. 18, 2011.
Monaca et al., Antibody-Drug Conjugates in Small-Cell Lung Cancer: DLL3, B7-H3, TROP2 and Beyond. J Thorac Oncol. Apr. 13, 2026:103726, pre-publication edition.
Moore et al., Pharmacology of Anticancer Drugs. The Basic Science of Oncology, Third Edition. lan F. Tannock (Ed.), McGraw-Hill. Chapter 16, pp. 370-391, (1998).
Owonikoko et al., A systematic analysis of efficacy of second-line chemotherapy in sensitive and refractory small-cell lung cancer. J Thorac Oncol. May 2012;7(5):866-72.
Soto, Lurbinectedin (PM01183) for the Treatment of Ewing Sarcoma and Neuroblastoma. Slideshow, PharmaMar, 27 pages, Jun. 21, 2017.
Weiss, NDA Approval, Department of Health and Human Services, NDA 22-065, 5 pages, Oct. 16, 2007.
Pink, A Non-randomized, Open-label Phase II Nitrasarc Trial of Trabectedin and Nivolumab in Patients with Metastatic or Inoperable Soft Tissue Sarcomas After Failure of an Anthracycline-containing Regimen: Interim Safety Analysis. CTOS 2020 Annual Meeting. Abstract 3446023, 1 page, (2020).
Pink, The NiTraSarc Trial—A Non-randomized, open-label phase II trial evaluating efficacy and feasibility of combined treatment with trabectedin and nivolumab in patients with metastatic or inoperable soft tissue sarcomas after failure of an anthracycline-containing regimen: Interim Safety Analysis. Ctos 2020 Annual Meeting. 1 page, Poster, (2020).
Pivotal, Phase Ib/II study to evaluate the efficacy and tolerability of PM01183 in combination with olaparib in patients with advanced solid tumors. PM01183 and Olaparib. 6 pages, Mar. 25, 2019.
Pivotal, POLA/ACOG1401: Clinical Study Report Synopsis Phase I. 2015-001141-80. 6 pages, Apr. 7, 2016.
Planting et al., Phase II study of ACNU as second-line treatment in small-cell lung cancer. EORTC Lung Cancer Cooperative Group. Cancer Chemother Pharmacol. 1992;29(5):409-11.
Polani et al., Exploring Outcomes in Second-line Therapy for Small Cell Lung Cancer with Brain Metastases: Lurbinectedin vs Others. J Thorac Oncol. Nov. 2023;18(11 Suppl):S709, Abstract EP13.07-07.
Pollock et al., Appropriate prescribing of medications: an eight-step approach. Am Fam Physician. Jan. 15, 2007;75 (2):231-6.
Pommier et al., DNA sequence- and structure-selective alkylation of guanine N2 in the DNA minor groove by ecteinascidin 743, a potent antitumor compound from the Caribbean tunicate Ecteinascidia turbinata. Biochemistry. Oct. 15, 1996;35(41):13303-9.
Pommier, Topoisomerase I inhibitors: camptothecins and beyond. Nat Rev Cancer. Oct. 2006;6(10):789-802.
Pons-Tostivint et al., Second-line treatment outcomes following first-line chemotherapy plus immunotherapy in patients with extensive-stage small cell lung cancer (Es-Sclc): A multicenter study. J Clin Oncol. May 2024;42(Suppl 16):Abstract e20122.
Porta et al., Tumor promotion by tumor-associated macrophages. Adv Exp Med Biol. 2007;604:67-86.
Poveda et al., OS Analysis by Treatments Received After Trabectedin/PLD or PLD Alone in Patients with Recurrent Ovarian Cancer: Platinum vs Non-Platinum. 16th Biennial Meeting of the International Cancer Society. 1 page, Oct. 29-31, 2016.
Poveda et al., OS Analysis by Treatments Received After Trabectedin/PLD or PLD Alone in Patients with Recurrent Ovarian Cancer: Platinum vs Non-Platinum. International Journal of Gynecological Cancer. Oct. 2016;26(Suppl 3):811.
Poveda et al., Platinum or nonplatinum in recurrent ovarian cancer: that is the question. Future Oncol. Oct. 2017; 13 (23s):11-16. pre-publication edition.
Povo-Retana et al., Correction: Povo-Retana et al. Trabectedin and Lurbinectedin Modulate the Interplay between Cells in the Tumour Microenvironment-Progresses in Their Use in Combined Cancer Therapy. Molecules 2024, 29, 331. Molecules. Jun. 5, 2025;30(11):2472.
Prenen et al., Tumor-associated macrophages: a short compendium. Cell Mol Life Sci. Apr. 2019; 76(8):1447-1458.
Pretsch et al., Tables of Spectral Data for Structure Determination of Organic Compounds, Second Edition. Springer-Verlag, Berlin. Page H125, (1983).
Preusser et al., Trabectedin for recurrent WHO grade 2 or 3 meningioma: A randomized phase II study of the EORTC Brain Tumor Group (EORTC-1320-BTG). Neuro Oncol. May 4, 2022;24(5): 755-767. pre-publication edition.
Preusser et al., Trabectedin for recurrent WHO grade Il or Ill meningioma: a randomized phase II study of the EORTC Brain Tumor Group (EORTC-1320-BTG). 2019 ASCO Annual Meeting. Slideshow, 23 pages, (2019).
Provencher et al., Characterization of four novel epithelial ovarian cancer cell lines. In Vitro Cell Dev Biol Anim. Jun. 2000;36(6):357-61.
PubChem CID 5284373, Cyclosporin A. 146 pages, Nov. 20, 2005.
Puglisi et al., Treatment options for small cell lung cancer - do we have more choice? Br J Cancer. Feb. 16, 2010;102(4):629-38.
Quan et al., Part III. Immunotherapy for Cancer: Harnessing the Hose Immune Defenses-Biologic Mechanisms and Results in Melanoma and Renal Cell Carcinoma. Disease-a-Month. Nov. 1997;43(11):755-808.

(56) References Cited

OTHER PUBLICATIONS

Ramanjooloo et al., Marine sponge-derived/inspired drugs and their applications in drug delivery systems. Future Med Chem. Mar. 2021;13(5):487-504.
Raymond et al., Oxaliplatin: a review of preclinical and clinical studies. Ann Oncol. Oct. 1998; 9(10):1053-71.
Reagan-Shaw et al., Dose translation from animal to human studies revisited. Faseb J. Mar. 2008;22(3):659-61.
Reck et al., MA11.04 Safety of lurbinectedin + atezolizumab as 1L maintenance treatment in ES-SCLC: results from the Phase 3 IMforte study. IASLC 2025 World Conference on Lung Cancer, Abstract Book. Page 190 (2025).
Reck et al., Safety of lurbinectedin + atezolizumab as 1L maintenance treatment in ES-SCLC: results from the Phase 3 IMforte study. 2025 World Conference on Lung Cancer. Slideshow, 10 pages, Sep. 6-9, 2025.
Redin et al., Lurbinectedin synergizes with selinexor by inhibiting DNA damage repair and enhancing immune cell infiltration in neuroendocrine lung and prostate tumors. Cancer Res. 2025;85(8 Suppl 1):Abstract 1166.
Redin et al., Lurbinectedin Synergizes with Selinexor by Inhibiting DNA Damage Repair and Enhancing Immune Cell Infiltration in Neuroendocrine Lung Tumors. IASLC 2024 World Conference on Lung Cancer, WCLC 2024. J Thorac Oncol. 2024;19(Suppl 10):S159, Abstract P1.03G.01.
Redini et al., Drugs targeting the bone microenvironment: new therapeutic tools in Ewing's sarcoma? Expert Opin Emerg Drugs. Sep. 2013;18(3):339-52.
Reedijk, The relevance of hydrogen bonding in the mechanism of action of platinum antitumor compounds. Inorganica Chimica Acta. 1992; 198-200:873-881.
Reghu et al., Harnessing the innate immune system by revolutionizing macrophage-mediated cancer immunotherapy. J Biosci. 2024;49:63, 12 pages.
Reichardt et al., Uncertainties that threaten the benefit/risk balance in early treatment lines for advanced or metastatic soft tissue sarcoma. Future Oncology. 2021;17(Suppl 21):7-10, pre-publication edition.
Reid et al., Preclinical pharmacology of ecteinascidin 729, a marine natural product with potent antitumor activity. Cancer Chemother Pharmacol. 1996;38(4):329-34.
Reiffen et al., Generic Drug Industry Dynamics. The Review of Economics and Statistics. Feb. 2005; 87(1):37-49.
Remers, Saframycins, Renieramycins, and Safracins. The Chemistry of Antitumor Antibiotics, vol. 2. John Wiley & Sons, New York. Chapter 3, pp. 93-119 (1988).
Ren et al., NB-506, an indolocarbazole topoisomerase I inhibitor, binds preferentially to triplex DNA. Febs Lett. Mar. 31, 2000;470(3):355-9.
Riccardi et al., Combination of trabectedin and irinotecan is highly effective in a human rhabdomyosarcoma xenograft. Anticancer Drugs. Sep. 2005;16(8):811-5.
Riccardi et al., Effective Combinations of ET-743 and Doxorubicin for Tumor Growth Inhibitions Against Murine and Human Sarcomas in Athymic Mice. Proceedings of the AACR. Mar. 2001;42, Abstract 1132.
Riccardi et al., Preclinical Activity and Biodistribution of Ecteinascidin 743 (ET-743) and Doxorubicin (DOX) Combinations in Human Rhabdomyosarcorna. AACR-NCI-EORTC Conference on Molecular Targets and Cancer Therapeutics. Abstract 405, Oct. 29-Nov. 2, 2001.
Richards et al., Monocytes and macrophages in cancer: development and functions. Cancer Microenviron. Aug. 2013;6(2):179-91.
Rinehart et al., Applications of High-Resolution Tandem FAB Mass Spectrometry. Biological Mass Spectrometry. Elsevier, Amsterdam, A.L. Burlingame (Ed.). pp. 233-257, (1990).
Rinehart et al., Bioactive compounds from aquatic and terrestrial sources. J Nat Prod. Jul. 1990-Aug. 53(4):771-92.
Rinehart et al., Biologically active natural products. Pure & Appl Chem. 1990;62(7):1277-1280.
Rinehart et al., Ecteinascidins 729, 743, 745, 759A, 759B, and 770: Potent Antitumor Agents from the Caribbean Tunicate Ecteinascidia turbinata. J Org Chem. 1990;55:4512-4515.
Rinehart et al., Novel Bioactive Natural Products from Marine Organisms. Topics in Pharmaceutical Sciences 1989. International Pharmaceutical Federation. D.D. Breimer (Ed.). Chater 44, pp. 613-626, (1989).
Rinehart et al., Preclinical Antitumor Development of a Marine Derived Natural Product. Annual Meeting of the American Association for Cancer Research. 1995;36:390, Abstract 2322.
Rinehart, Antitumor compounds from tunicates. Med Res Rev. Jan. 2000;20(1):1-27.
Rinehart, Antitumor, Antiviral, and Immunosuppressive Compounds from Marine Tunicates. Bioact Compd Mar Indo-US Symp. 1989;301-307.
Moura et al., Immune-checkpoint genes as predictive biomarkers of trabectedin in advanced soft-tissue sarcoma (STS): A Spanish Group Research on Sarcomas (GEIS) translational study. ASCO 56th Annual Meeting. 1 page, Poster, (2020).
Moura et al., Immune-checkpoint genes as predictive biomarkers of trabectedin in advanced soft-tissue sarcoma (STS): A Spanish Group Research on Sarcomas (GEIS) translational study. ASCO 56th Annual Meeting. 2 pages, (2020).
Moura, Immune-checkpoint genes as predictive biomarkers of trabectedin in advanced soft-tissue sarcoma (STS):A Spanish Group for Research on Sarcomas (GEIS) translational study. ASCO American Society of Clinical Oncology, 56th Annual Meeting, Virtual. May 31-Jun. 4, 2020. J Clin Oncol. 2020;38(Suppl. 15):Abstract 11546.
Moura, Immune-checkpoint genes as predictive biomarkers of trabectedin in advanced soft-tissue sarcoma (STS):A Spanish Group for Research on Sarcomas (GEIS) translational study. CTOS 2020 Annual Meeting. Virtual, Nov. 18-21, 2020.
Moussa et al., Clinical Efficacy of Lurbinectedin in Metastatic Neuroendocrine Carcinomas of the Genitourinary Tract—Multi-Institutional Real-World Experience. ASCO American Society of Clinical Oncology Genitourinary Cancers Symposium. 1 page, poster, Jan. 25-27, 2024.
Moussa et al., Clinical efficacy of lurbinectedin in metastatic neuroendocrine carcinomas of the genitourinary tract: Multi-institutional real-world experience. J Clin Oncol. Jan. 2024;42(Suppl 4):Abstract 601.
Moussa et al., Durable Objective Response to Lurbinectedin in Small Cell Bladder Cancer with TP53 Mutation: A Molecular-Directed Strategy. Curr Oncol. Jun. 13, 2024;31(6):3342-3349.
Muller et al., A non-randomized, open-label phase II trial evaluating efficacy and feasibility of combined treatment with trabectedin and nivolumab in patients with metastatic or inoperable soft tissue sarcomas after failure of an anthracycline-containing regimen. ESMO Virtual Congress 2020. Sep. 20-21, 2020. Ann Oncol. 2020;31(Suppl. 4):S991, Abstract 1669TiP.
Mullin, Drug R&D Costs Take Big Leap. Drug Development: The cost of bringing a drug to market approaches $3 billion. C&en. Nov. 24, 2014;92(47):6.
Murphy et al., Infusion of dendritic cells pulsed with HLA-A2-specific prostate-specific membrane antigen peptides: a phase II prostate cancer vaccine trial involving patients with hormone-refractory metastatic disease. Prostate. Jan. 1, 1999;38(1):73-8.
Myers et al., A Concise, Stereocontrolled Synthesis of (-)-Saframycin A by the Directed Condensation of a-Amino Aldehyde Precursors. J Am Chem Soc. 1999;121:10828-10829.
Nakagawa et al., Total Synthesis of (-)-Eudistomin L and (-)-Debromoeudistomin L. J Am Chem Soc. 1989;111:2721-2722.
Nakamura et al., A novel method of screening for immunomodulating substances, establishment of an assay system and its application to culture broths of microorganisms. J Antibiot (Tokyo). Aug. 1986;39(8):1148-54.
Navarria et al., Radiotherapy (RT) Combined with Trabectedine for Locally Advanced or Metastatic, Soft Tissue Sarcoma (STS): An Update of a Single Institution Experience. CTOS 23rd Annual Meeting. Page 220-221, Poster 084, Abstract 3040916, (2018).
Navarro et al., A phase II, multicenter, open-label, single-arm study of berzosertib plus topotecan in patients with relapsed platinum-

(56) References Cited

OTHER PUBLICATIONS resistant small-cell lung cancer (DDRiver SCLC 250). ESMO Open. Jan. 2026;11(1):105918, 9 pages.
Navarro et al., Efficacy of Platinum after Lurbinectedin + DOX or Topotecan/CAV in Sensitive Relapsed SCLC Patients in the ATLANTIS Trial. IASLC 2023 World Conference on Lung Cancer, WCLC 2023. 1 page, poster, Sep. 9-12, 2023.
Navarro et al., Efficacy of Platinum after Lurbinectedin + DOX or Topotecan/CAV in Sensitive Relapsed SCLC Patients in the ATLANTIS Trial. Journal of Thoracic Oncology. Nov. 2023; 18(11S):S380-S381.
Navelbine, Final Printed Label, 12 pages, (2000).
Nazzaro et al., Chemotherapy Agent Trabectedin Demonstrates Immunomodulatory Properties that Improve Efficacy of Anti-PD1 Immunotherapy and Delay Glioma Malignant Progression. J Immunother Cancer. 2024; 12(Suppl 2):A811, Abstract 709.
Nazzaro et al., Trabectedin modulates the glioma innate and adaptive immune microenvironment in vivo. J Immunol. 212(Suppl 1): 1461-5482, 1 page, May 1, 2024.
Nccn, National Comprehensive Cancer Network, Small Cell Lung Cancer, Version 4.2020. Retrieved online at: http://guide.medlive.cn/. Slideshow, 68 pages, Jul. 7, 2020.
NCI Staff, FDA Approves Trabectedin to Treat Two Types of Soft Tissue Sarcoma. NIH, National Cancer Institute. 5 pages, Dec. 4, 2015.
Neelam et al., Combination of flavone acetic acid (FAA) with adriamycin, cis-platinum and difluoromethylornithine (DFMO) in vitro against human colon cancer cells. Invest New Drugs. Aug. 1990;8(3):263-8.
Neidle et al., Crystallographic Insights into DNA Minor Groove Recognition by Drugs. Biopoly. 1997;44:105-121.
Nelson et al., Budget Impact Analysis of Trabectedin for Second-Line Treatment of Patients with Unresctable or Metastatic Liposarcoma or Leiomyosarcoma. JMCP. Apr. 2018;24(4-a):S91, Abstract M24.
Newman et al., Drugs and Drug Candidates from Marine Sources: An Assessment of the Current "State of Play". Planta Med. Jun. 2016;82(9-10):775-89.
Newman et al., The influence of natural products upon drug discovery. Nat Prod Rep. Jun. 2000; 17(3):215-34.
Nichols et al., Synthesis and evaluation of 2,3-dihydrobenzofuran analogues of the hallucinogen 1-(2,5-dimethoxy-4-methylphenyl)-2-aminopropane: drug discrimination studies in rats. J Med Chem. Feb. 1986;29(2):302-4.
Nitiss et al., Targeting DNA topoisomerase II in cancer chemotherapy. Nat Rev Cancer. May 2009;9(5):338-50.
Novartis Pharmaceuticals UK Ltd, Hycamtin 0.25mg hard capsule. 12 pages, Apr. 23, 2018.
Nuijen et al., Pharmaceutical development of anticancer agents derived from marine sources. Anticancer Drugs. Nov. 2000;11(10):793-811.
Nuzzo et al., A Retrospective Tumor Response Assessment in Locally Unresectable or Metastatic Soft Tissue Sarcoma (ASTS) Patients (PTS): A Three-years Regina Elena Cancer Institute (IRE) Experience with Trabectedin Therapy. CTOS 18th Annual Meeting. Page 312, Abstract PO 322, (2013).
Nuzzo et al., Tumor response assessment in locally unresectable or metastatic soft tissue sarcoma (aSTS) patients (pts): A three-year Regina Elena Cancer Institute (IRE) experience with trabectedin therapy. J Clin Oncol. 2013;31: Abstract e21517.
O'Brien et al., Phase III trial comparing supportive care alone with supportive care with oral topotecan in patients with relapsed small-cell lung cancer. J Clin Oncol. Dec 1, 2006;24(34):5441-7.
Oehler et al., The promise of anti-angiogenic cancer therapy. Br J Cancer. Feb. 2000;82(4):749-52.
Ojima et al., New taxanes as highly efficient reversal agents for multidrug resistance in cancer cells. Bioorg Med Chem Lett. Jan. 20, 1998;8(2):189-94.
OPM - Oncology Practice Management, Zepzelca New Therapy Approval for Metastatic Small-Cell Lung Cancer. Press Release, 4 pages, Jun. 15, 2020.
Otegui et al., EP.13.27 Co-Targeting SFKs and DNA Damaging Chemotherapy Drugs as a Novel Therapeutic Strategy in Sclc. Iaslc 2025 World Conference on Lung Cancer, Abstract Book. Page 1786, (2025).
Otterson et al., Phase II study of the histone deacetylase inhibitor Romidepsin in relapsed small cell lung cancer (Cancer and Leukemia Group B 30304). J Thorac Oncol. Oct. 2010;5(10):1644-8.
Owonikoko et al., IDeate-Lung02: a Phase 3 study of second-line ifinatamab deruxtecan in patients with relapsed small cell lung cancer. Future Oncol. Oct. 2025;21(25):3275-3282.
Ozaniak et al., Novel Insights into the Immunotherapy of Soft Tissue Sarcomas: Do We Need a Change of Perspective? Biomedicines. Aug. 1, 2021;9(8):935, 20 pages.
Paloma Colli et al., Trabectedin in pretreated pediatric patients with relapsed or progressive advanced sarcomas: Toxicity and efficacy. J Clin Oncol. 2012;30: Abstract e20005.
Panici et al., Phase II Trial of Weekly Trabectedin Plus Weekly Pegylated Liposomal Doxorubicin for Treatment of Advanced, Persistent or Recurrent Ovarian Carcinoma. 14th Biennial Meeting of the International Gynecologic Cancer Society (IGCS). 1 page, Oct. 13-16, 2012.
Panici et al., Phase II Trial of Weekly Trabectedin Plus Weekly Pegylated Liposomal Doxorubicin for Treatment of Advanced, Persistent or Recurrent Ovarian Carcinoma. 18th International Meeting of the European Society of Gynaecological Oncology (ESGO). 1 page, Oct. 19-22, 2013.
Panici et al., Phase II Trial of Weekly Trabectedin Plus Weekly Pegylated Liposomal Doxorubicin for Treatment of Advanced, Persistent or Recurrent Ovarian Carcinoma. International Journal of Gynecological Cancer. Oct. 2013;23(8 Suppl 1):573.
Panici et al., Phase II Trial of Weekly Trabectedin Plus Weekly Pegylated Liposomal Doxorubicin for Treatment of Advanced, Persistent or Recurrent Ovarian Carcinoma. The International Journal of Gynecological Cancer. Oct. 2012;22(8, Suppl. 3):E271.
Panici et al., Trabectedin Plus Cisplantin in Recurrent or Metastatic Cervical Cancer: A Phase I-II Dose-finding Study. 14th Biennial Meeting of the International Gynecologic Cancer Society (IGCS). 1 page, Oct. 13-16, 2012.
Panici et al., Trabectedin Plus Cisplantin in Recurrent or Metastatic Cervical Cancer: A Phase I-II Dose-finding Study. The International Journal of Gynecological Cancer. Oct. 2012;22(8 Suppl. 3):E561.
Parulekar et al., Bioactivity and chemical ecology of some intertidal animals. Bioactivity and Chemical Ecology. pp. 29-35, (1991).
Pasquali et al., A comparative assessment of selinexor with trabectedin or lurbinectedin in patient-derived xenografts (PDX) or dedifferentiated liposarcoma (DDLPS) highlights the effectiveness of their sequential or concomitant combination. Mol Cancer Ther. Dec. 1, 2023;22(Suppl 12):Abstract B096, 2 pages.
Abrams et al., New chemotherapeutic agents for breast cancer. Cancer. Aug. 1, 1994;74(3 Suppl):1164-76.
Abraxane, Highlights of Prescribing Information. 25 pages, Aug. 2018.
Adam et al., Efficacy and Safety of Trabectedin Versus Gemcitabine/Docetaxel in Patients with Sarcoma After Failure of Anthracycline and/or Ifosfamide. AOS Asian. 1 page, Abstract AOS-12, (2012).
Adam et al., Efficacy and Safety of Trabectedin Versus Gemcitabine/Docetaxel in Patients with Sarcoma After Failure of Anthracycline and/or Ifosfamide. European Journal of Cancer. 2012;48:S7-S8, Abstract AOS12.
Agarwal et al., Phase 2 study using talimogene laherparepvec, nivolumab, and trabectedin for advanced leiomyosarcoma and liposarcoma (NCT03886311). Asco 61st Annual Meeting. Abstract e23560, (2025).
Agarwal et al., Update on Saint: A phase II study using trabectedin (T) in combination with ipilimumab (I) and nivolumab (N) in previously treated soft tissue sarcoma. Annals of Oncology. 2024;35(S2):S1036, Abstract 1729P.
Ahmad et al., Immune Cell Modulation of the Extracellular Matrix Contributes to the Pathogenesis of Pancreatic Cancer. Biomolecules. Jun. 17, 2021;11(6):901, 25 pages.
Aldinucci et al., Formation of the Immunosuppressive Microenvironment of Classic Hodgkin Lymphoma and Therapeutic Approaches to Counter It. Int J Mol Sci. May 15, 2019;20(10):2416, 23 pages.

(56) References Cited

OTHER PUBLICATIONS

Allavena et al., Anti-inflammatory properties of the novel antitumor agent yondelis (trabectedin): inhibition of macrophage differentiation and cytokine production. Cancer Res. Apr. 1, 2005;65(7):2964-71.
Allavena et al., Trabectedin: A drug from the sea that strikes tumor-associated macrophages. Oncoimmunology. Jun. 1, 2013;2(6):e24614, 3 pages.
Almeida et al., Peripheral immune profiling of soft tissue sarcoma: perspectives for disease monitoring. Front Immunol. Oct. 21, 2024; 15:1391840, 20 pages.
Altmann, Microtubule-stabilizing agents: a growing class of important anticancer drugs. Curr Opin Chem Biol. Aug. 2001;5(4):424-31.
Alvarez et al., Trabectedin with Concomitant Radiation Therapy for Patients with Resectable Retroperitoneal Liposarcoma or Leiomyosarcoma: A Phase I/II Trial of Spanish (GEIS), Italian (ISG) and French (FSG) Groups. CTOS 2022 Annual Meeting. 6 pages, Abstract 1301234, Nov. 16-19, 2022.
Alvarez et al., Trabectedin with Concomitant Radiation Therapy for Patients with Resectable Retroperitoneal Liposarcoma or Leiomyosarcoma: A Phase I/II Trial of Spanish (GEIS), Italian (ISG) and French (FSG) Groups. CTOS 27th Annual Meeting. 1 page, poster (2022).
Alvarez-Breckenridge et al., Trabectedin for recurrent WHO grade 2 or 3 meningiomas-Paving the road for new opportunities. Neuro Oncol. May 4, 2022;24(5):768-769.
Amgen, Chemotherapy-induced thrombocytopenia (CIT). 2 pages, (2010).
An et al., Tumor-associated macrophage-targeted therapeutics in ovarian cancer. Int J Cancer. Jul. 1, 2021;149 (1):21-30. pre-publication edition.
Angarita et al., Trabectedin for Inoperable or Recurrent Soft Tissue Sarcoma in Adult Patients. CTOS 19th Annual Meeting p. 197, Abstract 110, (2014).
Angarita et al., Trabectedin for inoperable or recurrent soft tissue sarcoma in adult patients. CTOS 19th Annual Meeting. 1 page, (2014).
Angarita et al., Trabectedin for inoperable or recurrent soft tissue sarcoma in adult patients: a retrospective cohort study. BMC Cancer. Jan. 19, 2016;16:30, 11 pages.
Antoun et al., Low skeletal muscle density as predictive for febrile neutropenia in patients treated by doxorubicin/trabectedin/pegfilgrastim combination as a first-line treatment of advanced or metastatic leiomyosarcoma (Lms) (LMS02 study). 2014 ASCO Annual Meeting. 2 pages, Abstract e20640, (2014).
Antoun et al., Low Skeletal Muscle Density is Predictive for Febrile Neuropenia in Patients Treated by Doxorubicin/Trabectedin Combination as a First-line Treatment of Advanced or Metastatic Leiomyosarcoma (Lms) (LMS02 Study). CTOS 19th Annual. pp. 189-190, Poster 97, (2014).
Antoun et al., Low skeletal muscle density is predictive for febrile neuropenia in patients treated by doxorubicin/ trabectedin/ pegfilgrastim combination as a first-line treatment of advanced or metastatic leiomyosarcoma (LMS02 Study). CTOS (Connective Tissue Oncology Society). 1 pages, Oct. 15-18, 2014.
Antoun et al., Low skeletal muscle density is predictive for febrile neutropenia in patients treated by doxorubicin/ trabectedin/ pegfilgrastim combination as a first-line treatment of advanced or metastatic leiomyosarcoma (Lms) (LMS02 Study). 39th ESMO. 1 page, (2014).
Antoun et al., Low Skeletal Muscle Density is Predictive for Febrile Neutropenia in Patients Treated by Doxorubicin/ Trabectedin/ Pegfilgrastim Combination as a First-line Treatment of Advanced or Metastatic Leiomyosarcoma (LMS) (LMS02 Study). Annals of Oncology. 2014;25(Suppl 4):iv505, Abstract 1445P.
Anusha et al., Stability Indicating LC-ESI-MS/MS Method Development and Validation for the Quantitation of Lurbinectedin in Biological Matrices. International Journal of Applied Pharmaceutics. 2025;17(5):6 pages.
Anusha et al., Stability INdicating LC-ESI-MS/MS Method Development and Validation for the Quantitation of Lurbinectedin in Biological Matrices. Journal of Pharmaceutical Quality Assurance. 2024; 15(3):1120-1125.
Aquila et al., Trabectedin and Lurbinectedin Extend Survival of Mice Bearing C26 Colon Adenocarcinoma, without Affecting Tumor Growth or Cachexia. Cancers (Basel). Aug. 17, 2020;12(8):2312, 25 pages.
Arai et al., Directed biosynthesis of new saframycin derivatives with resting cells of Streptomyces lavendulae. Antimicrob Agents Chemother. Jul. 1985;28(1):5-11.
Arai et al., Increased production of saframycin A and isolation of saframycin S. J Antibiot (Tokyo). Sep. 1980;33 (9):951-60.
Arai et al., Isoquinolinequinones from Actinomycetes and Sponges. The Alkaloids, Chemistry and Pharmacology, vol. XXI. Academic Press, New York. Arnold Brossi, (Ed.). Chapter 3, pp. 55-100, (1983).
Arai et al., New antibiotics saframycins A, B, C, D and E. J Antibiot (Tokyo). Nov. 1977;30(11):1015-8.
Arai et al., The structure of a novel antitumor antibiotic, saframycin A. Experientia. Sep. 15, 1980;36(9):1025-7.
Arbuck et al., An overview of topoisomerase I-targeting agents. Semin Hematol. Jul. 1998;35(3 Suppl 4):3-12.
Arnold et al., Phase II study of vandetanib or placebo in small-cell lung cancer patients after complete or partial response to induction chemotherapy with or without radiation therapy: National Cancer Institute of Canada Clinical Trials Group Study BR.20. J Clin Oncol. Sep. 20, 2007;25(27):4278-84.
Asaoka et al., A New Saframycin, Saframycin R. The Journal of Antibiotics, vol. XXXV, No. 12, pp. 1708-1710 (1982).
ASCO 2019, Small-cell tumors: improvements in the second-line setting. ASCO:memo, Oncology. pp. 18-20, Feb. 2019.
Assi et al., Trabectedin and immune checkpoint inhibitors: a blissful combination or another failure in soft tissue sarcomas? Immunotherapy. Jan. 2023;15(1):5-8. pre-publication edition.
Assi et al., Trabectedin and radiotherapy in soft tissue sarcomas: friends or foes? Future Oncol. Sep. 2023;19(28):1893-1896. pre-publication edition.
Auernhammer et al., Personalized drug screening and risk assessment in patient-derived gastroenteropancreatic neuroendocrine neoplasms. J Clin Endocrinol Metab. Jan. 10, 2026:dgaf705, 42 pages, pre-publication edition.
Badin et al., Real-world safety and healthcare resource utilization (HCRU) of lurbinectedin (lurbi) in patients (pts) with small cell lung cancer (SCLC): Jazz EMERGE 402 updated analysis. J Clin Oncol. May 2024;42(Suppl 16): Abstract e23266.
Baggstrom et al., A phase II study of AT-101 (Gossypol) in chemotherapy-sensitive recurrent extensive-stage small cell lung cancer. J Thorac Oncol. Oct. 2011;6(10):1757-60.
Ballen et al., Adoptive immunotherapy. Curr Opin Oncol. Nov. 1997;9(6):579-83.
Ballon et al., Phase 2 Study Using Talimogene Laherparepvec, Nivolumab, and Trabectedin for Advanced Leiomyosarcoma and Liposarcoma (NCT03886311). 28th Annual Meeting ASGCT. Abstract 1704, (2025).
Banerjee et al., Molecular Landscape and Therapeutic Strategies of Lung Cancer Lineage Plasticity. J Thorac Oncol. Nov. 2025;20(11):1582-1593.
Banerjee et al., Trabectedin Reveals a Strategy of Immunomodulation in Chronic Lymphocytic Leukemia. Cancer Immunol Res. Dec. 2019;7(12):2036-2051.
Barman Balfour et al., Bendamustine. Drugs. 2001;61(5):631-638.
Barone et al., FDA Approval Summary: Trabectedin for Unresectable or Metastatic Liposarcoma or Leiomyosarcoma Following an Anthracycline-Containing Regimen. Clin Cancer Res. Dec. 15, 2017;23(24):7448-7453.
Barthomeuf et al., Marine metabolites overcoming or circumventing multidrug resistance mediated by ATP—dependent transporters: a new hope for patient with tumors resistant to conventional chemotherapy. Anticancer Agents Med Chem. Dec. 2008;8(8):886-903.

(56) References Cited

OTHER PUBLICATIONS

Barton et al., Synthesis and Properties of a Series of Sterically Hindered Guanidine Bases. J Chem Soc Perkin Trans 1. 1982:2085-2090.
Patel et al., A Randomized Controlled Phase-3 Study of Trabectedin (T) or Dacarbazine (D) for the Treatment of Patients (pts) with Advanced Leiomyosarcoma (LMS) or Liposarcoma (LPS): Final Overall Survival (OS) Analysis. CTOS 20th Annual. 2 pages, (2015).
Patel et al., Final overall survival (OS) analysis of the randomized phase 3 study of trabectedin (T) or dacarbazine (D) for the treatment of patients (pts) with advanced leiomyosarcoma (LMS) or liposarcoma (LPS). European Journal of Cancer. 2015;3(15):S689, Abstract 3403.
Patel et al., Overall survival and histology-specific subgroup analyses from a phase 3, randomized controlled study of trabectedin or dacarbazine in patients with advanced liposarcoma or leiomyosarcoma. Cancer. Aug. 1, 2019;125 (15):2610-2620.
Paul et al., How to improve R&D productivity: the pharmaceutical industry's grand challenge. Nat Rev Drug Discov. Mar. 2010;9(3):203-14.
Pautier et al., A randomized, multicenter phase-III study comparing doxorubicin (dox) alone versus dox with trabectedin (trab) followed by trab in non-progressive patients (pts) as first-line therapy, in pts with metastatic or unresectable leiomyosarcoma (LMS): Final results of the LMS-04 study. Annals of Oncology. 2023;34(S2):S1030, Abstract 1913O.
Pautier et al., A randomized, multicenter phase-III study comparing doxorubicin alone versus doxorubicin with trabectedin followed by trabectedin in non-progressive patients as first-line therapy, in patients with metastatic or unresectable leiomyosarcoma. Final results of the LMS-04 study. ESMO Congress. 10 pages, Slideshow, Oct. 21, 2023.
Pautier et al., Doxorubicin alone versus doxorubicin with trabectedin followed by trabectedin alone as first-line therapy for metastatic or unresectable leiomyosarcoma (LMS-04): a randomised, multicentre, open-label phase 3 trial. Lancet Oncol. Aug. 2022;23(8):1044-1054.
Pautier et al., Doxorubicin plus trabectedin for metastatic or unresectable leiomyosarcoma—Authors' reply. Lancet Oncol. Oct. 2022;23(10):e445.
Pautier et al., LMS-02: A Phase II single-arm multicenter study to determine the efficacy of doxorubicin in combination with trabectedin as a 1st line treatment of metastatic and/or locally advanced leiomyosarcoma of uterine (U-LMS) or soft tissue (ST-LMS) origin: results of the soft tissue group. 17th ECCO. 1 page, (2013).
Pautier et al., LMS-02: A Phase II single-arm multicenter study to determine the efficacy of doxorubicin in combination with trabectedin as a 1st line treatment of metastatic and/or locally advanced leiomyosarcoma of uterine (U-LMS) or soft tissue (ST-LMS) origin: results of the soft tissue group. European Journal of Cancer. 2013;49:S887, Abstract 3834.
Pautier et al., LMS-04 study: A randomised, multicenter, phase III study comparing doxorubicin alone versus doxorubicin with trabectedin followed by trabectedin in non-progressive patients as first-line therapy, in patients with metastatic or unresectable leiomyosarcoma—A French Sarcoma Group study. Annals of Oncology. 2021;32(S5):S1336, Abstract LBA59.
Pautier et al., Trabectedin in combination with doxorubicin for first-line treatment of advanced uterine or soft-tissue leiomyosarcoma (LMS-02): a non-randomised, multicentre, phase 2 trial. Lancet Oncol. Apr. 2015;16(4):457-64.
Paz, Antitumour Antibiotics. Anticancer Therapeutics. John Wiley & Sons, Sotiris Missailidis (Ed.). Chapter 8, pp. 111-131, (2008).
Paz-Ares et al., Efficacy and safety of lurbinectedin (LUR) with irinotecan (IRI) in patients (Pts) with relapsed small cell lung cancer (SCLC): Results from a phase 2 expansion cohort. Journal of Clinical Oncology. 2024;42(16):Abstract 8094.
Paz-Ares et al., Lung Carcinoma. Tumor Diagnosis and Therapy. 2025;46:462.
Paz-Ares et al., Trabectedin in pre-treated patients with advanced or metastatic soft tissue sarcoma: a phase II study evaluating co-treatment with dexamethasone. Invest New Drugs. Apr. 2012;30(2):729-40.
Paz-Ares, Phase III Randomized Clinical Trial of Lurbinectedin (PM01183)/Doxorubicin (DOX) versus Cyclophosphamide (CTX), Doxorubicin (DOX) and Vincristine (Vcr) (Cav) or Topotecan as Treatment in Patients with Small-cell Lung Cancer (SCLC) Who Failed One Prior Platinum-containing Line (ATLANTIS Trial). Clinical Study Report PM1183-C-003-14, 16 pages, Feb. 10, 2021.
Pazdur, Center for Drug Evaluation and Research, Application No. 207953Orig1s000, Labeling. 23 pages, Oct. 23, 2015.
Pazdur, Center for Drug Evaluation and Research, Approval Package for: Application No. 207953Orig1s000. Yondelis. 11 pages, Oct. 23, 2015.
Pazdur, Yondelis approval letter. Food and Drug Administration. NDA 207953. 8 pages, Oct. 23, 2015.
PDR, Cosemgen® (dactinomycin). Product Information. Physicians' Desk Reference, 54th Edition. pp. 1766-67, (2000).
PDR, Cytosar-UR (cytarabine). Product Information. Physicians' Desk Reference, 53rd Edition. pp. 2469-72, (1999).
PDR, Mithracin® (plicamycin). Product Information. Physicians' Desk Reference, 54th Edition. pp. 697-8, (2000).
PDR, Mutamycin® (mitomycin). Product Information. Physicians' Desk Reference, 54th Edition. pp. 309, 872-73, (2000).
PDR, Oncovin® (vincristine sulfate). Product Information. Physicians' Desk Reference, 54th Edition. pp. 1631-33, (2000).
PDR, Purinethol® (mercaptopurine). Product Information. Physicians' Desk Reference, 54th Edition. pp. 314, 1255-57, (2000).
PDR, Velban®. Product Information. Physicians' Desk Reference, 54th Edition. pp. 1647-49, (2000).
Pecorelli et al., Phase II of oral gimatecan in patients with recurrent epithelial ovarian, fallopian tube or peritoneal cancer, previously treated with platinum and taxanes. Ann Oncol. Apr. 2010;21(4):759-765.
Pelayo Alvarez et al., Chemotherapy versus best supportive care for extensive small cell lung cancer. Cochrane Database Syst Rev. Oct. 7, 2009;(4):CD001990, 27 pages.
Pellini, Dr. Pellini on the Challenges of Using Topotecan as a Comparator Arm in Recurrent ES-SCLC. Moffitt Cancer Center. 6 pages, May 19, 2021.
Peraza et al., Re-Education of Tumor Associated Macrophages by Trabectedin. Biophysical Journal. 2019;116 (3):539a-540a, Abstract 2675-Pos.
Peraza et al., Trabectedin modulates macrophage polarization in the tumor-microenvironment. Role of Kv1.3 and Kv1.5 channels. Biomedicine & Pharmacotherapy. 2023;161:114548, 15 pages.
Peraza et al., Trabectedin Re-Education Resting Peritoneal Macrophages into M1 Subtype. Biophysical Journal. Feb. 14, 2017;112(3):405a, Abstract 1995-Pos.
Perez-Ruixo et al., Population pharmacokinetic meta-analysis of trabectedin (ET-743, Yondelis) in cancer patients. Clin Pharmacokinet. 2007;46(10):867-84.
Petek et al., PM00104 (Zalypsis®): a marine derived alkylating agent. Molecules. Aug. 15, 2014;19(8):12328-35.
Peters et al., Basis for effective combination cancer chemotherapy with antimetabolites. Pharmacol Ther. Aug. 2000-Sep. 87(2-3):227-53.
Peters et al., Lurbinectedin in patients with small cell lung cancer with chemotherapy-free interval greater than or equal to 30 days and without central nervous metastases. Lung Cancer. Feb. 2024;188:107448, 8 pages.
Petrelli et al., Current data of targeted therapies for the treatment of triple-negative advanced breast cancer: empiricism or evidence-based? Expert Opin Investig Drugs. Oct. 2009;18(10):1467-77.
Petty et al., Tumor-associated macrophages: implications in cancer immunotherapy. Immunotherapy. Mar. 2017;9 (3):289-302.
Pfizer Limited, Topotecan Hospira 4 mg/4 ml concentrate for solution for infusion. 13 pages, Apr. 2019.
Pharmamar, Clinical Study Report PM1183-C-003-14, EudraCt No. 2015-001641-89. Synopsis. 16 pages, Feb. 24, 2020.
PharmaMar Group reports year to date results up to Sep. 30, 2019. Press Release, 2 pages, Oct. 23, 2019.

(56) References Cited

OTHER PUBLICATIONS

PharmaMar presents positive results of the pivotal Phase III trial with plitidepsin in multiple myeloma during the ASH meeting. Press Release, 7 pages, Dec. 11, 2017.
PharmaMar to present new data on its compounds at AACR 2023 Congress. Press Release, 3 pages, Apr. 17, 2023.
Pharmamar, According to international oncologists, trabectedin is the therapeutic option of reference for the second line treatment of sarcoma. Press Release, 3 pages, Apr. 7, 2017.
Pharmamar, Annual Report 2017. 148 pages, (2017).
Pharmamar, Annual Report 2018. 154 pages (2018).
Pharmamar, ASCO releases abstracts and publishes PharmaMar's lurbinectedin data in second line small cell lung cancer. Press Release, 4 pages, May 16, 2019.
Pharmamar, ASCO selects lurbinectedin second line small cell lung cancer abstract from "Best of ASCO" program. Press Release, 2 pages, May 15, 2019.
Pharmamar, ASCO selects PharmaMar's lurbinectedin monotherapy trial for an oral presentation. Press Release, 2 pages, Apr. 1, 2019.
Alard et al., Advances in Anti-Cancer Immunotherapy: Car-T Cell, Checkpoint Inhibitors, Dendritic Cell Vaccines, and Oncolytic Viruses, and Emerging Cellular and Molecular Targets. Cancers (Basel). Jul. 7, 2020;12(7):1826, 38 pages.
Arya et al., Updates in Small Cell Lung Cancer Treatment: No Longer Too Small to Ignore-A Review of Recent Therapeutic Advances. Am Soc Clin Oncol Educ Book. Jun. 2026;46(3) e524964, 14 pages.
Barba et al., Small cell lung cancer: a therapeutic update in the era of immunotherapy and beyond-a narrative review. Chin Clin Oncol. Apr. 2026;15(2):34, 16 pages.
Biswas et al., Outcomes of Lurbinectedin in Central Nervous System Metastases of Small Cell Lung Cancer: A Single-Institution Retrospective Case Series. Reports (MDPI). Jun. 7, 2026;9(2):179, 9 pages.
Borghaei et al., Nivolumab versus Docetaxel in Advanced Nonsquamous Non-Small-Cell Lung Cancer. N Engl J Med. Oct. 22, 2015;373(17):1627-39.
Brahmer et al., Safety and activity of anti-PD-L1 antibody in patients with advanced cancer. N Engl J Med. Jun. 28, 2012;366(26):2455-65.
Chen et al., Anti-PD-1/PD-L1 therapy of human cancer: past, present, and future. J Clin Invest. Sep. 2015;125(9):3384-91.
Chen et al., Application and mechanistic research of novel therapeutic strategies in cisplatin-resistant small cell lung cancer. Ann Med. Dec. 2026;58(1):2601401, 27 pages.
Dong et al., Tumor-associated B7-H1 promotes T-cell apoptosis: a potential mechanism of immune evasion. Nat Med. Aug. 2002;8(8):793-800.
EMA Summary of Product Characteristics. Zepzelca. 38 pages, Jun. 1, 2026.
EU Risk Management Plan for Zepzelca (lurbinectedin). EU Risk Management Plan version 1.0. 53 pages, Jun. 1, 2026.
European Medicines Agency, Assessment report, Zepzelca. Committee for Medicinal Products for Human Use (Chmp), EMA/87579/2026. 199 pages, Mar. 26, 2026.
European Medicines Agency, Orphan Maintenance Assessment Report. Zepzelca (lurbinectedin), Treatment of pulmonary neuroendocrine carcinoma. EMA/OD/0000304173. 17 pages, Mar. 31, 2026.
European Medicines Agency, Summary of opinion (initial authorisation), Zepzelca lurbinectedin. EMA/56282/2026. 1 page, Mar. 26, 2026.
European Medicines Agency, Zepzelca (lurbinectedin), A plain-language overview of Zepzelca and why it is authorised in the Eu. EMA/77801/2026, EMEA/H/C/006673. 3 pages, Jun. 1, 2026.
Falcon et al., Pooled safety analysis of lurbinectedin plus irinotecan in patients with advanced solid tumors. Invest New Drugs. May 4, 2026. doi: 10.1007/s10637-026-01616-0, 10 pages.
Freeman et al., Engagement of the PD-1 immunoinhibitory receptor by a novel B7 family member leads to negative regulation of lymphocyte activation. J Exp Med. Oct. 2, 2000;192(7):1027-34.
Gordon et al., PD-1 expression by tumour-associated macrophages inhibits phagocytosis and tumour immunity. Nature. May 25, 2017;545(7655):495-499.
Guan et al., Overcoming immunotherapy resistance in extensive-stage small cell lung cancer: Insights into mechanisms and therapeutic opportunities. Crit Rev Oncol Hematol. Jun. 1, 2026;225:105411, 13 pages.
Gunuganti et al., Lurbinectedin in treating CNS metastases from small cell neuroendocrine prostate cancer-a case report. Front Oncol. Jul. 9, 2026;16:1840883, 6 pages.
Han et al., PD-1/PD-L1 pathway: current researches in cancer. Am J Cancer Res. Mar. 1, 2020;10(3):727-742.
Herbst et al., Pembrolizumab versus docetaxel for previously treated, PD-L1-positive, advanced non-small-cell lung cancer (KEYNOTE-010): a randomised controlled trial. Lancet. Apr. 9, 2016;387(10027):1540-1550.
Hta Cg Member State Coordination Group on Health Technology Assessment, Joint Clinical Assessment Report of Lurbinectedin, Version 1.0. 211 pages, Jul. 8, 2026.
Iwai et al., Involvement of PD-L1 on tumor cells in the escape from host immune system and tumor immunotherapy by PD-L1 blockade. Proc Natl Acad Sci U S A. Sep. 17, 2002;99(19):12293-7.
JAZZ Pharmaceuticals, JAZZ Pharmaceuticals Provides Update on Zepzelca (lurbinectedin) Phase 3 LAGOON Trial in Second-Line Small Cell Lung Cancer. Press Release, 9 pages, Jun. 12, 2026.
Jiang et al., Comparative Efficacy and Safety of Anti-PD-1/PD-L1 for the Treatment of Non-Small Cell Lung Cancer: A Network Meta-Analysis of 13 Randomized Controlled Studies. Front Oncol. May 10, 2022;12:827050, 10 pages.
Liao et al., Comparative efficacy and safety of PD-1/PD-L1 inhibitors versus docetaxel in the treatment of non-small cell lung cancer: a systematic review and meta-analysis. J Thorac Dis. Oct. 31, 2025; 17(10):8662-8677.
Marchetti et al., Why anti-PD1/PDL1 therapy is so effective? Another piece in the puzzle. J Thorac Dis. Dec 2017;9 (12):4863-4866.
Nguyen et al., Ultramutagenesis through combined Msh2 depletion and proofreading-deficient DNA polymerase epsilon expression enhances small molecule target identification in forward genetic screens. bioRxiv. 30 pages, Jun. 29, 2026.
Oh et al., Evaluation of the Appropriateness, Efficacy, and Safety of Lurbinectedin in Patients with Metastatic Small Cell Lung Cancer: A Single-center Retrospective Study. J Kor Soc Health-Syst Pharm. 2026;43(2):129-143.
Petrelli et al., A decade of progress in small-cell lung cancer (2015-2025): a narrative review. Eur J Clin Pharmacol. Jun. 22, 2026;82(7):184, 12 pages.
Pfirschke et al., Immunogenic Chemotherapy Sensitizes Tumors to Checkpoint Blockade Therapy. Immunity. Feb. 16, 2016;44(2):343-54.
Pharmmar, PharmaMar Reports Update on Phase Iii Lagoon Trial in Second Line for Small Cell Lung Cancer Press Release. 3 pages, Jun. 12, 2026.
Rittmeyer et al., Atezolizumab versus docetaxel in patients with previously treated non-small-cell lung cancer (OAK): a phase 3, open-label, multicentre randomised controlled trial. Lancet. Jan. 21, 2017;389(10066):255-265.
Shen et al., Efficacy of PD-1 or PD-L1 inhibitors and PD-L1 expression status in cancer: meta-analysis. BMJ. Sep. 10, 2018;362:k3529, 9 pages.
Stenger, Asco Clinical Practice Guideline Update: Recommendations for the Use of White Blood Cell Growth Factors. Today in Oncology. 6 pages, Nov. 10, 2015.
Sunshine et al., PD-1/PD-L1 inhibitors. Curr Opin Pharmacol. Aug. 2015;23:32-8.
Tian et al., The Efficacy and Safety of Nab-Paclitaxel Plus Anlotinib in Small-Cell Lung Cancer for Second-Line Therapy. Thorac Cancer. May 2026;17(9):e70290, 7 pages.
Topalian et al., Safety, activity, and immune correlates of anti-PD-1 antibody in cancer. N Engl J Med. Jun. 28, 2012;366(26):2443-54.

(56) References Cited

OTHER PUBLICATIONS

Vargas et al., Can Immunogenic Chemotherapies Relieve Cancer Cell Resistance to Immune Checkpoint Inhibitors? Front Immunol. May 29, 2019;10:1181, 12 pages.
Wang et al., Wang et al., Comparative efficacy of tarlatamab and second-line therapies in extensive-stage small cell lung cancer: A network meta-analysis. Lung Cancer. Jul. 2026;217:109465, 10 pages.
WHO Expert Committee on Access to Medicines and Health Products (MHP). The Selection and Use of Essential Medicines (2015)—Who Trs 994. Granulocyte colony-stimulating factor (GCSF) (addition). pp. 187-189, Jan. 30, 2015.
Zak et al., Structure of the Complex of Human Programmed Death 1, PD-1, and Its Ligand PD-L1. Structure. Dec. 1, 2015;23(12):2341-2348.
Zambrano Iglesias et al., Decoding Small Cell Lung Cancer: Molecular Subtypes, Surface Antigens, and the Target-Modality Problem. Cancers (Basel). Jul. 7, 2026;18(13):2173, 20 pages.
Zepzelca: EPAR—All authorised presentations. 1 page, Jun. 1, 2026.
Zhang et al., Efficacy and Safety of PD-1/PD-L1 Checkpoint Inhibitors versus Anti-PD-1/PD-L1 Combined with Other Therapies for Tumors: A Systematic Review. Cancers (Basel). Jan. 22, 2023;15(3):682, 23 pages.
Zhao et al., Closing the evidence gap in older adults with extensive-stage small-cell lung cancer: a CGA-guided, risk- adapted treatment framework. Ther Adv Med Oncol. Jul. 13, 2026;18:17588359261463145, 22 pages.
Zhao et al., Zhao et al., Comparisons of Underlying Mechanisms, Clinical Efficacy and Safety Between Anti-PD-1 and Anti-PD-L1 Immunotherapy: The State-of-the-Art Review and Future Perspectives. Front Pharmacol. Jul. 7, 2021;12:714483, 13 pages.
Zhu et al., Cost-effectiveness of lurbinectedin with atezolizumab for extensive-stage small-cell lung cancer in the United States: impact of drug wastage reduction on economic outcomes. BMC Health Serv Res. May 4, 2026;26(1):839, 37 pages, pre-publication edition.
Zietse et al., Interchangeability of immune checkpoint inhibitors: an urgent need for action. Lancet Oncol. Nov. 2024;25(11):e611-e616.
Yondelis, Highlights of Prescribing Information. 21 pages, Jun. 2020.
Yondelis, Highlights of Prescribing Information. 21 pages, Dec. 2025.
Yondelis, Highlights of Prescribing Information. 21 pages, May 2017.
Yondelis, Highlights of Prescribing Information. 22 pages, Dec. 2018.
Yondelis, Highlights of Prescribing Information. 22 pages, Jun. 2018.
Yondelis, Prescribing Information Label. 21 pages, Oct. 2015.
Yubin et al., The extraction, separation and purification of alkaloids in the natural medicine. Journal of Chemical and Pharmaceutical Research. 2024;6(1):338-345.
Yue et al., Tumor-associated macrophages: a novel potential target for cancer treatment. Chin Med J (Engl). Sep. 2012;125(18):3305-11.
Zaman et al., The human multidrug resistance-associated protein MRP is a plasma membrane drug-efflux pump. Proc Natl Acad Sci U S A. Sep. 13, 1994;91(19):8822-6.
Zeltia, Annual Accounts of Zeltia and its Consolidated Group 2008. 761 pages, Mar. 30, 2009.
Zeltia, Annual Accounts of Zeltia and its Consolidated Group 2009. 677 pages. Mar. 25, 2010.
Zeltia, S.A., Annual Accounts and Management Report at Dec. 31, 2013 next to the Audit Report on the Annual Accounts. 647 pages, (2013).
Zeltia, S.A., Annual Accounts and Management Report at Dec. 31, 2014 next to the Audit Report on the Annual Accounts. 585 pages, (2014).
Zeltia, S.A., Annual Financial Statements and Management Report as of Dec. 31, 2011 next to the Audit Report on the Annual Accounts. 631 pages, (2011).
Zeltia, S.A., Annual Financial Statements and Management Report as of Dec. 31, 2012 next to the Audit Report on the Annual Accounts. 641 pages, (2012).
Zeltia, S.A., Audit Report, Annual Financial Statements and Management Report for 2010. 640 pages, (2010).
Zepzelca, Highlights of Prescribing Information, 16 pages, Jun. 2020.
Zepzelca, Highlights of Prescribing Information. 20 pages, Apr. 2025.
Zepzelca, Indications. Retrieved online at: https://www.zepzelcapro.com/mechanism-ofaction/. 7 pages, (2025).
Zewail Foote, The Antitumor Agent Ecteinascidin 743 (Et 743): Characterization of its Covalent DNA Adducts and its Effect on DNA Repair Mechanisms. Dissertation. Presented to the Faculty of the Graduate School of The University of Texas at Austin in Partial Fulfillment of the Requirements for the Degree of Doctor of Philosophy. 180 pages, Aug. 2000.
Zewail-Foote et al., Differential rates of reversibility of ecteinascidin 743-DNA covalent adducts from different sequences lead to migration to favored bonding sites. J Am Chem Soc. Jul. 11, 2001;123(27):6485-95.
Zewail-Foote et al., Ecteinascidin 743: a minor groove alkylator that bends DNA toward the major groove. J Med Chem. Jul. 15, 1999;42(14):2493-7.
Zhang et al., Anlotinib treatment in elderly patients with unresectable or metastatic soft tissue sarcoma: a retrospective study. Anticancer Drugs. Jan. 1, 2022;33(1):e519-e524.
Zhang et al., Can hepatocellular carcinoma be treated by Yondelis through targeting both tumor cells and tumor- associated macrophages? Hepatogastroenterology. Jan. 2010-Feb. 57(97):114-6.
Zhang et al., Tumor-associated macrophages: A promising target for a cancer immunotherapeutic strategy. Pharmacol Res. Nov. 2020; 161: 105111, 8 pages, pre-publication edition.
Zhao et al., Nanomedicine enables spatiotemporally regulating macrophage-based cancer immunotherapy. Biomaterials. Jan. 2021;268:120552, 26 pages.
Zhao et al., Simultaneous determination of SU5416 and its phase I and phase II metabolites in rat and dog plasma by LC/MS/MS. J Pharm Biomed Anal. Jul. 2001;25(5-6):821-32.
Zhou et al., Uptake and metabolism of vinca alkaloids by freshly isolated human hepatocytes in suspension. Anticancer Res. May 1994-Jun. 14(3A):1017-22.
Zhou, P3. 18.78 A Prospective Study of Lurbinectedin Plusivonescimab Assecond-Line Treatment for Extensive-Stage Small Cell Lung Cancer. IASLC 2025 World Conference on Lung Cancer, Abstract Book. p. 1300, (2025).
Zielinski et al., Combining annamycin, a non-cardiotoxic potent topo II poison, with azacitidine, cytarabine, gemcitabine, ifosfamide, trabectedin, or vincristine to synergize anticancer effects and identify potential clinical applications. Cancer Res. 2025;85(8 Suppl 1):Abstract 1683.
Zmijewski et al., The in vitro interaction of naphthyridinomycin with deoxyribonucleic acids. Chem Biol Interact. Jan. 1985;52(3):361-75.
Zugazagoitia et al., Efficacy and Safety of Lurbinectedin (LUR) in Combination with Irinotecan (IRI) in Patients (Pts) with Relapsed Small Cell Lung Cancer (SCLC): Results from a Phase 2 Expansion Cohort. ESMO Congress. 2024 Sep. 13-17, Abstract 356.
Zugazagoitia et al., Phase II data of lurbinectedin (LUR) and irinotecan (IRI) in relapsed small cell lung cancer (SCLC) patients (pts) with chemotherapy-free interval (CTFI)>30 days (d). ESMO Congress, 2024 Sep. 13-17. 1 page, poster, Abstract 1790P.
Zweifler et al., Parathyroid hormone and trabectedin have differing effects on macrophages and stress fracture repair. Bone. Feb. 2024; 179:116983, 24 pages, pre-publication edition.
U.S. Appl. No. 10/416,086, Interview Summary, Brandon J. Fetterolf, 2 pages, May 7, 2008.

(56) References Cited

OTHER PUBLICATIONS

Pharmamar, PharmaMar and Jazz Pharmaceuticals Announce the U.S. License Agreement for Lurbinectedin in Effective With the Expiration of the HSR Waiting Period. Press Release 328 pages, Jan. 22, 2020.
Pharmamar, PharmaMar presents positive results of the pivotal Phase III trial with plitidepsin in multiple myeloma during the ASH meeting. 8 pages, Dec. 11, 2017.
Pharmamar, PharmaMar receives positive opinion from EMA (Comp) for orphan drug designation of Zepsyre (lurbinectedin) for small-cell lung cancer. 145 pages, Jan. 24, 2019.
Pharmamar, Phase II study results of lurbinectedin in progressive mesothelioma will be presented in an oral session at ESMO 2019. Press Release, 4 pages, Sep. 23, 2019.
Pharmamar, Phase II trial of lurbinectedin in progressive mesothelioma finalizes its patient recruitment. Press Release, 2 pages, Dec. 17, 2018.
Pharmamar, R&D Day. Slideshow. 166 pages, Apr. 24, 2017.
Pharmamar, R&D Day. Slideshow. 319 pages, Apr. 24, 2017.
Pharmamar, Report as of Sep. 30, 2019, 9M19 Milestones. 10 pages, Oct. 23, 2019.
Pharmamar, Report as of Dec. 31, 2018, Milestones in 2018. 12 pages, Feb. 28, 2019.
Pharmamar, Report as of Mar. 31, 2019, 1Q19 Milestones. 10 pages, Apr. 26, 2019.
Pharmamar, Report at Jun. 30, 2018, 1H18 Highlights. 11 pages, Jul. 26, 2018.
Pharmamar, Report at Jun. 30, 2019, 1H19 Highlights. 10 pages, Jul. 29, 2019.
Pharmamar, Report at Sep. 30, 2018, 9 month Milestones 2018. 10 pages, Oct. 30, 2018.
Pharmamar, Report at Mar. 31, 2018, 1Q18 Milestones. 11 pages, Apr. 26, 2018.
Pharmamar, Report at Jun. 30, 2025, Milestones. 12 pages, Jul. 30, 2025.
Pharmamar, S.A.U., Auditor's report, financial statements as of Dec 31, 2004 and management report for the year ended Dec 31, 2004. 162 pages, (2004).
Ponce Aix et al., Combination lurbinectedin and doxorubicin versus physician's choice of chemotherapy in patients with relapsed small-cell lung cancer (ATLANTIS): a multicentre, randomised, open-label, phase 3 trial. Lancet Respir Med. Jan. 2023;11(1):74-86.
Ponce Aix et al., Lurbinectedin (LUR) in combination with Irinotecan (IRI) in patients (pts) with advanced solid tumors: Updated results from a phase Ib-II trial. ASCO American Society of Clinical Oncology, 56th Annual Meeting. 1 page, poster, May 31-Jun. 4, 2020.
Ponce Aix et al., Lurbinectedin (LUR) in combination with Irinotecan (IRI) in patients (pts) with advanced solid tumors: Updated results from a phase Ib-II trial. ASCO American Society of Clinical Oncology, 56th Annual Meeting. 2 pages, May 31-Jun. 4, 2020.
Ponce et al., Combination of Lurbinectedin plus Irinotecan: Preclinical and Early Clinical Results in Relapsed Small Cell Lung Cancer Patients. J Thorac Oncol. Mar. 4, 2026:103654, 40 pages, pre-publication edition.
Ponce et al., Efficacy and Safety Profile of Lurbinectedin-Irinotecan in Patients with Relapsed SCLC, Results from a phase Ib-II trial. 2020 World Conference on Lung Cancer Singapore. 14 pages, slideshow, (2020).
Ponce et al., Lurbinectedin (LUR) in combination with Irinotecan (IRI) in patients (pts) with advanced advanced sold tumors. Updated results from a phase lb-II trial. 2020 ASCO Annual Meeting. 5 pages, slideshow, (2020).
Ponce-Aix et al., Lurbinectedin With Irinotecan in Relapsed Small Cell Lung Cancer. Results From the Expansion Stage of a Phase I-II Trial. J Thorac Oncol. 2021;16(3):S127, Abstract OA11.04.
Poveda et al., A phase I dose-finding, pharmacokinetics and genotyping study of olaparib and lurbinectedin in patients with advanced solid tumors. Sci Rep. Feb. 24, 2021;11(1):4433, 11 pages.
Poveda et al., Phase 2 Trial (POLA Study) of Lurbinectedin plus Olaparib in Patients with Advanced Solid Tumors: Results of Efficacy, Tolerability, and the Translational Study. Cancers (Basel). Feb. 12, 2022;14(4):915, 16 pages.
Poveda et al., Phase I study to evaluate the tolerability, pharmacokinetics (PK) and pharmacodynamic (PD) of PM01183 (Lurbinectedin) in combination with olaparib in patients with advanced solid tumors. ASCO American Society of Clinical Oncology, 53rd Annual Meeting. 1 page, poster, Jun. 2-6, 2017.
Poveda et al., Phase I study to evaluate the tolerability, pharmacokinetics (PK) and pharmacodynamic (PD) of PM01183 (Lurbinectedin) in combination with olaparib in patients with advanced solid tumors. J Clin Oncol. 2017;35, Abstract 5573.
Poveda et al., Phase Ib/II study to evaluate the efficacy and tolerability of PM01183 (lurbinectedin) in combination with olaparib in patients with advanced solid tumors. 41st ESMO European Cancer Congress. 1 page, poster, Oct. 7-11, 2016.
Poveda et al., Phase Ib/II study to evaluate the efficacy and tolerability of PM01183 (lurbinectedin) in combination with olaparib in patients with advanced solid tumors. Annals of Oncology. Oct. 2016;27(Suppl 6): vi311, Abstract 901TİP.
Poveda et al., Phase II randomized study of PM01183 versus topotecan in patients with platinum-resistant/refractory advanced ovarian cancer. Ann Oncol. Jun. 1, 2017;28(6):1280-1287.
Preusser et al., Trabectedin for recurrent WHO grade II or III meningioma: A randomized phase II study of the EORTC Brain Tumor Group. ASCO 55th Annual Meeting. 1 page, Jun. 3, 2019.
Provencio et al., A multicenter phase II basket clinical trial of lurbinectedin (PM01183) in selected advanced solid tumors. ASCO American Society of Clinical Oncology, 51st Annual Meeting, 1 page, poster May 29-Jun. 2, 2015.
Provencio Pulla et al., A multicenter phase II basket clinical trial of lurbinectedin (PM01183) in selected advanced solid tumors. J Clin Oncol. 2015;33:TPS2604.
Pujade-Lauraine, New treatments in ovarian cancer. Annals of Oncology. 2017;28(Suppl 8):viii57-viii60.
Rajput et al., Treatment of Small Cell Lung Cancer with Lurbinectedin: A Review. Anticancer Agents Med Chem. 2022;22(5):812-820.
Ratain et al., First-in-man phase I study of PM01183 using an accelerated titration design. Eur J Cancer. 2010;8 (7):137-138, Abstract 434.
Ratain et al., Phase I study of lurbinectedin (PM1183) administered on days (D) 1 & 8 every 3 weeks (q3w) in patients (pts) with solid tumours. 26th EORTC-NCI-AACR Symposium on Molecular Targets and Cancer Therapeutics. 1 page, poster, Nov. 18-21, 2014.
Ratain et al., PM01183 clinical and pharmacokinetic (PK) preliminary results of the first-in-man phase I study following an accelerated titration design. 22nd EORTC-NCI-AACR Symposium on Molecular Targets and Cancer Therapeutics. 1 page, poster, Nov. 16-19, 2010.
Rengarajan et al., Indirect Treatment Comparison of Lurbinectedin vs. Other Second-Line Treatments form Small- Cell Lung Cancer. Int J Radiat Oncol Biol Phys. 2022;112(2):E18, Abstract 119.
Resano et al., Exportin 1 inhibition synergizes with lurbinectedin by altering the response to DNA damage in neuroendocrine lung tumors. Cancer Res. 83(7 Suppl):Abstract 6188.
Rittberg et al., Real-world patient eligibility for lurbinectedin/doxorubicin in small cell lung cancer. Annals of Oncology. 2022;33(S2)S101-S102, Abstract 151P.
Romano et al., Comparison of in vitro and in vivo biological effects of trabectedin, lurbinectedin (PM01183) and Zalypsis® (PM00104). Int J Cancer. Nov. 2013;133(9):2024-33.
Rosenmayr-Templeton, An industry update: Dec. 2019, what is new in the field of therapeutic delivery this month? Ther Deliv. May 2020;11(5):289-296.
Rosner et al., Relapsed small-cell lung cancer: a disease of continued unmet need. Lancet Respir Med. Oct. 14, 2022;11(1):6-8.
Rotte, Combination of CTLA-4 and PD-1 blockers for treatment of cancer. J Exp Clin Cancer Res. Jun. 13, 2019;38(1):255, 12 pages.
Sands et al., Phase 2 Basket Trial of Lurbinectedin in Small-Cell Lung Cancer (SCLC): Analysis of Efficacy by Baseline Characteristics. 2020 North America Conference on Lung Cancer. 1 page, Abstract MO01.09, Oct. 16-17, 2020.

(56) References Cited

OTHER PUBLICATIONS

Sands et al., Phase 2 Basket Trial of Lurbinectedin in Small-Cell Lung Cancer: Analysis of Efficacy by Baseline Characteristics. IASLC 2020 North America Conference on Lung Cancer. Poster, Abstract 110, Oct. 16-17, 2020.
Santamaria et al., Lurbinectedin (PM01183) specifically targets RNA Pol II for degradation via the proteasome pathway in a TC-NER-dependent fashion. AACR Annual Meeting. Abstract 5558, Apr. 6-10, 2013.
Santamaria et al., Lurbinectedin (PM01183) specifically targets RNA Pol II for degradation via the proteasome pathway in a TC-NER-dependent fashion. AACR Annual Meeting. Abstract 5558, poster, Apr. 6-10, 2013.
Santamaria et al., Lurbinectedin (PM01183) specifically targets RNA Pol II for degradation via the proteasome pathway in a transcription and TC-NER dependent fashion. Eur J Cancer. 2014;50(Suppl 6):20-21, Abstract 47.
Fernandez-Teruel et al., Population-Pharmacokinetic and Covariate Analysis of Lurbinectedin (PM01183), a New RNA Polymerase II Inhibitor, in Pooled Phase I/II Trials in Patients with Cancer. Clin Pharmacokinet. Mar. 2019;58 (3):363-374.
Fiebig et al., Phase II Clinical Trial of Lobaplatin (D-19466) in Pretreated Patients with Small-Cell Lung Cancer. Onkologie. 1996;19:328-332.
Fioramonti et al., M1 Macrophages as Predictor of Poor Response to Trabectedin Treatment in Myxoid Liposarcoma. CTOS 21st Annual Meeting. pp. 375-377, Abstract 2561280, (2016).
Fischer et al., Current status of clinical trials for small cell lung cancer. Rev Recent Clin Trials. Jan. 2008;3(1):40-61.
Flam, Chemical prospectors scour the seas for promising drugs. Science. Nov. 25, 1994;266(5189):1324-5.
Ford et al., Pharmacology of drugs that alter multidrug resistance in cancer. Pharmacol Rev. Sep. 1990;42(3):155-99.
Forouzesh et al., Phase I and pharmacokinetic study of trabectedin as a 1- or 3-hour infusion weekly in patients with advanced solid malignancies. Clin Cancer Res. May 15, 2009;15(10):3591-9.
Fregeau, Biologically Active Compounds from a Clam and a Tunicate. Thesis, Submitted in partial fulfillment of the requirements for the degree of Doctor of Philosophy in Chemistry. 311 pages, (1992).
Frincke et al., Antimicrobial Metabolites of the Sponge Reniera sp. J Am Chem Soc. 1982;104:265-269.
Fujiwara et al., Role of Tumor-Associated Macrophages in Sarcomas. Cancers (Basel). Mar. 3, 2021;13(5):1086, 17 pages.
Fukuyama et al., Stereocontrolled total synthesis of (+-)-saframycin B. Journal of the American Chemical Society. Sep. 1, 1982;104(18):4957-4958.
Fukuyama et al., Total Synthesis of (+-)-Saframycin A. J Am Chem Soc 1990;112:3713-3715.
Gadducci et al., A phase II randomised (calibrated design) study on the activity of the single-agent trabectedin in metastatic or locally relapsed uterine leiomyosarcoma. Br J Cancer. Aug. 2018;119(5):565-571.
Galletti et al., B cells and macrophages pursue a common path toward the development and progression of chronic lymphocytic leukemia. Leukemia. Dec. 2016;30(12):2293-2301.
Galmarini et al., Lurbinectedin (PM01183) synergizes with topoisomerase I inhibitors in vitro and in vivo. Cancer Res. 2013;78(8 Suppl): Abstract 5499.
Galmarini et al., Trabectedin and plitidepsin: drugs from the sea that strike the tumor microenvironment. Mar Drugs. Jan. 27, 2014;12(2):719-33.
Galmarini, New marine anticancer agents in development. PharmaMar, New Cytotoxics and Vaccines, Symposium IX. 1 page, Jun. 22-25, 2010.
Ganti et al., Effectiveness and Safety Profile of Lurbinectedin in Second-Line Small Cell Lung Cancer: A Real-World Study. IASLC 2023 World Conference on Lung Cancer, WCLC 2023. 1 page, Abstract 2807, poster, (2023).
Ganti et al., Effectiveness and Safety Profile of Lurbinectedin in Second-Line Small Cell Lung Cancer: A Real-World Study. Journal of Thoracic Oncology. Nov. 2023;18(11S):S378-S379, Abstract P2.17-02.
Ganti et al., Real-World Effectiveness and Safety Profile of Lurbinectedin and Other Second-Line Treatments in Small Cell Lung Cancer. Journal of Thoracic Oncology. Jul. 2024; 19(7S):e50-e51, Abstract PP01. 117.
Ganti et al., Small Cell Lung Cancer, Version 2.2022, NCCN Clinical Practice Guidelines in Oncology. J Natl Compr Canc Netw. Dec. 2021;19(12):1441-1464.
Gao et al., Direct Selection for Catalysis from Combinatorial Antibody Libraries Using a Boronic Acid Probe: Primary Amide Bond Hydrolysis. J Am Chem Soc. Mar. 18, 1998;120(10):2489-2491.
Garcia-Campelo et al., Correction to: SEOM-GECP Clinical guidelines for diagnosis, treatment and follow-up of small-cell lung cancer (SCLC) (2022). Clin Transl Oncol. Sep. 2023;25(9):2760-2762.
Garcia-Campelo et al., SEOM-GECP Clinical guidelines for diagnosis, treatment and follow-up of small-cell lung cancer (SCLC) (2022). Clin Transl Oncol. Sep. 2023;25(9):2679-2691.
Garcia-Carbonero et al., Lurbinectedin plus irinotecan in pre-treated gastroenteropancreatic neuroendocrine carconomas (GEP-NECs). ESMO Open. 2024;9(S2):1, Abstract 270.
Garcia-Nieto et al., Bending of DNA upon Binding of Ecteinascidin 743 and Phthalascidin 650 Studies by Unrestrained Molecular Dynamics Simulations. J Am Chem Soc. 2000; 122:7172-7182.
Garcia-Rocha et al., Characterisation of antimitotic products from marine organisms that disorganise the microtubule network: ecteinascidin 743, isohomohalichondrin-B and LL-15. Br J Cancer. Apr. 1996;73(8):875-83.
Gasparini, The rationale and future potential of angiogenesis inhibitors in neoplasia. Drugs. Jul. 1999;58(1):17-38.
Gautam et al., Inhibition of experimental lung metastasis by aerosol delivery of PEI-p53 complexes. Mol Ther. Oct. 2000;2(4):318-23.
Geffen et al., New drugs for the treatment of cancer, 1990-2001. Isr Med Assoc J. Dec. 2002;4(12):1124-31.
Gemzar, FDA Revised Label—Version 082598. 24 pages, (1998).
Genentech, FDA Approves Genentech's Tecentriq in Combination With Chemotherapy for the Initial Treatment of Adults With Extensive-Stage Small Cell Lung Cancer. Press Release, 9 pages, Mar. 18, 2019.
Genestie, Tumour-infiltrating immune cells as a predictive factor in advanced or metastatic leiomyosarcomas: Comparison between uterine and non-uterine tumors. Annals of Oncology. 2024;9(S2):16, 2 pages, Abstract 92P.
Georg et al., Taxane Anticancer Agents, Basic Science and Current Status. ACS Symposium Series. 4 pages, (1995).
Gerard et al., Lurbiclin real-world effectiveness and treatment sequences in patients (pts) with extensive-stage small cell lung cancer (ES-SCLC) who received lurbinectedin as part of the French Early Access Program (Eap-Atu). J Clin Oncol. 2023;41(Suppl 16), Abstract 8584.
Gerard et al., LURBICLIN: Real-world effectiveness and treatment sequences in patients with extensive-stage small cell lung cancer who received lurbinectedin as part of the French Early Access Program (Eap-Atu). Asco American Society of Clinical Oncology, 59th Annual Meeting. 1 page, Poster, IFCT-2105.
Gerardi et al., An Open-label, but Non-Comparative Phase II Study on Trabectedin and Bevacizumab with or without Carboplatin in Partially Platinum-sensitive (PPS) Ovarian Cancer. IGCS 15th Biennial Meeting. 1 page, (2014).
Gerardi et al., An Open-label, Randomized Phase I Study on Trabectedin and Bevacizumab with or Without Carboplatin in Partially Platinum-sensitive (PPS) Overian Cancer. International Journal of Gynecological Cancer. 2014;24(9):455-456.
Germano et al., Anti-inflammatory properties of the novel-anti-tumor agent trabectedin: Reducation of ccl2, il-6 and pentraxin-3 by monocytes/macrophages and tumor cells. AACR Annual Meeting. Abstract 1197, 1 page, (2008).
Germano et al., Role of macrophage targeting in the antitumor activity of trabectedin. Cancer Cell. Feb. 11, 2013;23(2):249-62.

(56) References Cited

OTHER PUBLICATIONS

Germano et al., Targeting of the innate immunity/inflammation as complementary anti-tumor therapies. Ann Med. Dec. 2011;43(8):581-93.
Gerson, Alkylating and Platinating Agents. Current Cancer Therapeutics, Fourth Edition. Current Medicine, Philadelphia, John M. Kirkwood, (Ed.). Chapter 1, pp. 1-36, (2001).
Gettys et al., New and emerging therapies for advanced or metastatic soft tissue sarcoma. J Oncol Pharm Pract. Aug. 2014;20(4):288-97.
Ghaffer et al., Immunomodulation by extract of Ecteinascidia turbinata. J Reticuloendothel Soc. Fourteenth Annual National Meeting. 1977;22:62A, abstract P-29.
Ghalib et al., A phase I safety and efficacy clinical trial of plocabulin and gemcitabine in patients with advanced solid tumors. Invest New Drugs. Oct. 2024;42(5):481-491.
Ghielmini et al., In vitro cytotoxicity of Ecteinascidin 743 (ET-743) against human hemopoietic progenitors and cancer cells. Ann Oncology. 1998;9(Suppl 2)139, Abstract 533.
Ghose et al., Prediction of Hydrophobic (Lipophilic) Properties of Small Organic Molecules Using Fragmental Methods: An Analysis of ALOGP and CLOGP Methods. J Phys Chem. 1998;102:3762-3772.
Giaccone et al., 4'-Deoxydoxorubicin, an inactive drug in small cell lung cancer. Eur J Cancer Clin Oncol. Sep. 1987;23(9):1407-8.
Gillam et al., Oxidation of indole by cytochrome P450 enzymes. Biochemistry. Nov. 14, 2000;39(45):13817-24.
Giordano et al., The cGAS-STING pathway is a master regulator of OCT4 expression in persistent sarcoma cells and enhances cellular immunotherapy with NK and CIK lymphocytes. Cancer Immunol Immunother. Sep. 23, 2025;74 (10):312, 18 pages.
Stein, Internal Medicine, Fourth Edition. Mosby, St. Louis. Pages 699-729, (1994).
Still et al., Rapid Chromatographic Technique for Preparative Separations with Moderate Resolution. 1978;43(14):2923-2925.
Su et al., Cost-effectiveness Modeling of Lurbinectedin as a Second-line Therapy in Patients with Small Cell Lung Cancer (SCLC). ISPOR Europe. Jun. 2023;26(Suppl 6):S87, Abstract EE152.
Subbiah et al., Data on FDA Approved Therapy for Relapsed/Refractory SCLC. OncLive News Network. 6 pages, Aug. 20, 2020.
Subbiah et al., Safety analysis of lurbinectedin versus topotecan in elderly patients. ASCO American Society of Clinical Oncology. J Clin Oncol. 2023;41(Suppl 16), Abstract e20632.
Summers, Supplement Approval, NDA 207953/S-003. Yondelis. 4 pages, May 18, 2017.
Summers, Supplement Approval, NDA 207953/S-004. Yondelis. 4 pages, Jun. 29, 2018.
Summers, Supplement Approval/Fulfillment of Postmarketing Requitement. Nda 207953/S-005. Yondelis. 5 pages, Dec. 28, 2018.
Summers, Supplement Approval/Fullfillment of Postmarketing Requirement, Nda 207953/S-001. Yondelis. 4 pages, Jul. 20, 2016.
Sun et al., Targeting microenvironment and cellular immunity in sarcomas with trabectedin combined with metronomic cyclophosphamide: The TARMIC study. Annals of Oncology. 2023;34(S2):S1035, Abstract 1924P.
Sundstrom et al., Cisplatin and etoposide regimen is superior to cyclophosphamide, epirubicin, and vincristine regimen in small-cell lung cancer: results from a randomized phase III trial with 5 years' follow-up. J Clin Oncol. Dec 15, 2002;20(24):4665-72.
Sutcuglu et al., Doxorubicin plus trabectedin for metastatic or unresectable leiomyosarcoma. Lancet Oncol. Oct. 2022;23(10):e444.
Suzuki et al., Intermittent adjuvant chemo-immunotherapy after resection of non-small cell lung cancer with multilevel mediastinal lymph node metastasis. Oncol Rep. May 2000-Jun;7(3):545-9.
Taamma et al., Ecteinascidin-743 (ET-743) 24 hour continuous intravenous infusion (CI) phase I study in solid tumors (ST) patients (pts). Proceedings of the American Association for Cancer Research. Mar. 1998;39:323, Abstract 2207.
Taamma et al., Phase I and pharmacokinetic study of ecteinascidin-743, a new marine compound, administered as a 24-hour continuous infusion in patients with solid tumors. J Clin Oncol. Mar. 1, 2001;19(5):1256-65.
Takahashi et al., Ecteinascidin 743 (ET-743) and doxorubicin produce synergistic cytotoxic effects in soft tissue sarcoma lines HT-1080 and HS-IS. Clinical Cancer Research. Nov. 2000;6:Abstract 208.
Takahashi et al., Microbial conversion of saframycin A to 25-dihydrosaframycin A and 21-decyano-25-dihydrosaframycin A (25-dihydrosaframycin B) and their biological activities. J Antibiot (Tokyo). Feb. 1982;35 (2):196-202.
Takahashi et al., Phase I STudy of Lurbinectedin in Japanese Patients with Pretreated Advanced Sold Tumors. Japanese Journal of Oncology and Clinical Research. 2023;4:106, 19 pages.
Takahashi et al., Sequence-dependent enhancement of cytotoxicity produced by ecteinascidin 743 (ET-743) with doxorubicin or paclitaxel in soft tissue sarcoma cells. Clin Cancer Res. Oct. 2001;7(10):3251-7.
Takahashi et al., Sequence-dependent synergistic cytotoxicity of ecteinascidin-743 and paclitaxel in human breast cancer cell lines in vitro and in vivo. Cancer Res. Dec. 1, 2002;62(23):6909-15.
Takebayashi et al., Poisoning of human DNA topoisomerase I by ecteinascidin 743, an anticancer drug that selectively alkylates DNA in the minor groove. Proc Natl Acad Sci U S A. Jun. 22, 1999;96(13):7196-201.
Takeyama et al., The Clinical Results of Trabectedin or Eribulin Chemotherapy in Advenced Soft Tissue Sarcoma. CTOS 24th Annual Meeting. pp. 661-662, Poster 18, Abstract 3255227, (2019).
Tallarida, Quantitative methods for assessing drug synergism. Genes Cancer. Nov. 2011;2(11):1003-8.
Tambaro et al., An escalating dose finding study of liposomal doxorubicin and vinorelbine for the treatment of refractory or resistant epithelial ovarian cancer. Ann Oncol. Sep. 2003;14(9):1406-11.
Tan et al., Chemotherapy for Patients with BRCA1 and BRCA2-Mutated Ovarian Cancer: Same or Different? Am Soc Clin Oncol Educ Book. 2015:114-21.
Tang et al., Targeted and immuno-based therapies in sarcoma: mechanisms and advances in clinical trials. Biochim Biophys Acta Rev Cancer. Dec. 2021;1876(2):188606, 31 pages.
Tannock et al., The Basic Science of Oncology, Fifth Edition. McGraw Hill Education/Medical, New York. 588 pages, (2013).
Tansir et al., A phase II study of gemcitabine and docetaxel combination in relapsed metastatic or unresectable locally advanced synovial sarcoma. BMC Cancer. Jul. 8, 2023;23(1):639, 10 pages.
TAXOL (pacliaxel) Injection. FDA label. 53 pages, Apr. 2011.
TAXOL (paclitaxel), label, 43 pages, Feb. 10, 2000.
Taxotere, Label, 32 pages, Dec. 23, 1999.
Tercero et al., Predicting sarcoma patients response to trabectedin treatment with molecular markers detected by immunohistochemistry. Clinical Cancer Research. 2008;14(9 Suppl):44, Abstract B8.
Tercero et al., Predicting sarcoma patients response to trabectedin treatment with molecular markers detected by immunohistochemistry. Clinical Cancer Research. 2008;14(9 Suppl):44, Abstract B-8. Poster.
Timmerman et al., Dendritic cell vaccines for cancer immunotherapy. Annu Rev Med. 1999;50:507-29.
Tosca et al., Modeling approaches for reducing safety-related attrition in drug discovery and development: a review on myelotoxicity, immunotoxicity, cardiovascular toxicity, and liver toxicity. Expert Opin Drug Discov. Nov. 2021;16(11):1365-1390.
Toulmonde, Tramune, a phase Ib study combining trabectedin and durvalumab, Results of the expansion cohort in patients with advanced pretreated soft tissue sarcomas. Virtual ESMO Congress. Slideshow, 23 pages, (2020).
Traxler et al., Use of a pharmacophore model for the design of EGFR tyrosine kinase inhibitors: isoflavones and 3- phenyl-4(1H)-quinolones. J Med Chem. Mar. 25, 1999;42(6):1018-26.
Trigo et al., Efficacy of Platinum Given after Lurbinectedin in Sensitive Relapsed SCLC Patients. IASLC 2023 World Conference on Lung Cancer, WCLC 2023. 1 page, Poster, Sep. 9-12, 2023.

(56) References Cited

OTHER PUBLICATIONS

Trigo et al., Efficacy of Platinum Given after Lurbinectedin in Sensitive Relapsed SCLC Patients. Journal of Thoracic Oncology. Nov. 2023;18(11S):S708-S709, Abstract EP13.07-06.
Trowizsch-Kienast et al., Isolierung und Strukturaufklarung der Saframycine Mx 1 und Mx 2, neue antitumor-aktive Antibiotika aus Myxococcus xanthus. Liebigs Ann Chem. 1988:475-481.
Tseng et al., A Pilot Feasibility Study of Immunotherapy with Combination Trabectedin and Nivolumab in Advanced Soft Tissue Sarcoma. CTOS 21st Annual Meeting. p. 373, Abstract 2555232, (2016).
Tsuji et al., Selective immunosuppression of prodigiosin 25-C and FK506 in the murine immune system. J Antibiot (Tokyo). Oct. 1990;43(10):1293-301.
Tummala et al., Preclinical Synergistic Combination Therapy of Lurbinectedin with Irinotecan and 5-Fluorouracil in Pancreatic Cancer. Curr Oncol. Oct. 31, 2023;30(11):9611-9626.
Tummala et al., Preclinical synergistic combination therapy of lurbinectedin with irinotecan and 5-fluorouracil in pancreatic cancer. Mol Cancer Ther. 2023;22(12 Suppl):Abstract B026.
Twelves et al., Phase I and pharmacokinetic study of Yondelis (Ecteinascidin-743; ET-743) administered as an infusion over 1 h or 3 h every 21 days in patients with solid tumours. Eur J Cancer. Sep. 2003;39(13):1842-51.
U.S. Department of Health and Human Services, Common Terminology Criteria For Adverse Events (CTCAE), Version 5.0. 147 pages, slideshow, Nov. 27, 2017.
Uboldi et al., The WEE1 inhibitor AZD-1775 has synergic activity with trabectedin or lurbinectedin in ovarian cancer cells. AACR Annual Meeting. 1 page, abstract 4821, Apr. 16-20, 2016.
Uboldi et al., The WEE1 inhibitor AZD-1775 has synergic activity with trabectedin or lurbinectedin in ovarian cancer cells. AACR Annual Meeting. 1 page, abstract 4821, Apr. 16-20, 2016. Poster.
Uma et al., Immunomodulators in Aquaculture. Seafood Export J. Jun. 1996;27(6):23-27.
Rinehart, Didemnin and its biological properties. Peptides, Chemistry and Biology. Garland R. Marshall (Ed. ), ESCOM, Leiden. pp. 626-631, (1988).
Rinehart, Prospect for pharmaceutials from marine organisms. Medicinal Chemistry: Today and Tomorrow. Proceedings of the AFMC International Chemistry Symposium. Blackwell Science. pp. 7-14, (1995).
Ringwalt et al., Synergistic mechanisms against pediatric bone sarcoma models: Trabectedin enhances oncolytic virotherapy intratumoral spread and antitumor immune activation. Cancer Res. 2024;84(Suppl 6): Abstract 1087.
Ringwalt et al., Trabectedin Enhances Oncolytic Virotherapy by Reducing Barriers to Virus Spread and Cytotoxic Immunity in Preclinical Pediatric Bone Sarcoma. bioRxiv [Preprint]. Mar. 3, 2024:2024.03.02.582994, 44 pages.
Ringwalt et al., Trabectedin promotes oncolytic virus antitumor efficacy, viral gene expression, and immune effector function in models of bone sarcoma. Mol Ther Oncol. Sep. 26, 2024;32(4):200886, 16 pages.
Riou et al., Cellular uptake and efflux of doctaxel (Taxotere) and paclitaxel (Taxol) in P388 cell line. Proceedings of the American Association for Cancer Research. Mar. 1994; 35:385, Abstract 2292.
Robert et al., Pharmacokinetics of doxorubicin in sarcoma patients. Eur J Clin Pharmacol. 1987;31(6):695-9.
Rodrigues-Santos et al., Immune monitoring of trabectedin therapy in refractory soft tissue sarcoma patients—the IMMUNYON study. Front Immunol. Feb. 11, 2025;16:1516793, 16 pages.
Roston et al., Liquid Chromatographic Determination of Phenolic Acids of Vegetabel Origin. Journal of Liquid Chromatography. 1982;5(Suppl 1):75-103.
Roth et al., Gene Therapy for Non-Small Cell Lung Cancer: A Preliminary Report of a Phase I Trial of Adenoviral p53 Gene Replacement. Semin Oncol. 1998;25(Suppl 8):33-37.
Rudin et al., Ifinatamab Deruxtecan in Patients With Extensive-Stage Small Cell Lung Cancer: Primary Analysis of the Phase II IDeate-Lung01 Trial. J Clin Oncol. Feb. 2026;44(4):261-273.
Rudin et al., Phase II study of single-agent navitoclax (ABT-263) and biomarker correlates in patients with relapsed small cell lung cancer. Clin Cancer Res. Jun. 1, 2012;18(11):3163-9.
Ruiz Torres et al., Lurbinectedin/Irinotecan as a new therapeutic combination for small cell lung cancer. Cancer Res. 2025;85(8 Suppl 1):Abstract 5986.
Ruiz Torres et al., Lurbinectedin/Irinotecan as a new therapeutic combination for Small Cell Lung Cancer. Cancer Res. 2025;85(8 Suppl 1):Abstract 5986. Poster.
Ryan et al., Phase I and pharmacokinetic study of ecteinascidin 743 administered as a 72-hour continuous intravenous infusion in patients with solid malignancies. Clin Cancer Res. Feb. 2001; 7(2):231-42.
Saada et al., Rechallenge with trabectedin in patients with locally advanced or metastatic soft tissue sarcoma following drug holiday: The experience of the French Sarcoma Group (FSG). Asco 48th Annual Meeting. 1 page, (2012).
Saada et al., Rechallenge with trabectedin in patients with locally advanced or metastatic soft tissue sarcoma following drug holiday: The experience of the French Sarcoma Group (FSG). J Clin Oncol. 2012;30:Abstract 10062.
Saito et al., Synthesis of Saframycins. 3. Preparation of a Key Tricyclic Lactam Intermediate to Saframycin A. J Org Chem. 1989;54:5391-5395.
Sakai et al., Additional antitumor ecteinascidins from a Caribbean tunicate: crystal structures and activities in vivo. Proc Natl Acad Sci U S A. Dec. 1, 1992;89(23):11456-60.
Sakai et al., Ecteinascidins: Putative Biosynthetic Precursors and Absolute Stereochemistry. J Am Chem Soc. 1996;118:9017-9023.
Sakai, Biologically Active Compounds from Tunicates and a Sponge. Thesis submitted in partial fulfillment of the requirements for the degree of Doctor of Philosophy in Chemistry. 126 pages, (1991).
Samuels et al., Randomized Phase II study of trabectedin (ET-743) given by two different dosing schedules in patients with leiomyosarcomas or liposarcomas refractory to conventional doxorubicin and ifosfamide chemotherapy. ASCO 40th Annual Meeting. 2004;22(14s):818s, 26 pages, slideshow.
Samuels et al., Randomized Phase II study of trabectedin (ET-743) given by two different dosing schedules in patients with leiomyosarcomas or liposarcomas refractory to conventional doxorubicin and ifosfamide chemotherapy. Journal of Clinical Oncology. 2004;22(14):814, Abstract 9000.
Sanchez Becerra et al., Promising response to lurbinectedin in NUT carcinoma: a case report and review of emerging therapeutic strategies. Ann Oncol. Feb. 2025;36(2):225-227, pre-publication edition.
Sanchez et al., Challenges of cancer drug design: a drug metabolism perspective. Curr Cancer Drug Targets. May 2001;1(1):1-32.
Sanchez Sevilla Urucurtu et al., Chk1/2 inhibition enhances response to lurbinectedin treatment in small cell lung cancer. Cancer Res. 2024;84(6 Suppl):Abstract 3191.
Sanchez-Becerra et al., New therapeutic approaches in NUT carcinoma: An unmet need. AACR American Association for Cancer Resesarch, Annual Meeting. 1 page, Poster, Abstract 5996, (2025).
Sanchez-Becerra et al., New therapeutic approaches in NUT carcinoma: An unmet need. Cancer Res. 2025;85 (Suppl 1):Abstract 5996.
Sankar et al., Real-World Treatment Patterns and Clinical Outcomes in Patients With Extensive-Stage Small Cell Lung Cancer Treated With First-Line Platinum-Based Chemotherapy and greater than or equal to 2 Subsequent Lines of Therapy in the United States. Adv Ther. Jan. 2026;43(1):214-230.
Sanwald et al., Characterization of the cytochrome P450 enzymes involved in the in vitro metabolism of dolasetron. Comparison with other indole-containing 5-HT3 antagonists. Drug Metab Dispos. May 1996;24(5):602-9.
Sanwald et al., Simultaneous measurement of the major metabolites of dolasetron mesilate in human urine using solid-phase extraction and high-performance liquid chromatography. J Chromatogr B Biomed Appl. Nov. 4, 1994;661 (1):101-7.

(56) References Cited

OTHER PUBLICATIONS

Sanz et al., Costs Associated With the Administration, Post-Infusion Monitoring, and Management of Adverse Events (AEs) Related to Novel Drugs for Second-Line (2L) Treatment of Small-Cell Lung Cancer (SCLC). ISPOR Europe 2025, 1 page, Abstract EE289, Nov. 9-12, 2025.
Saponara et al., The safety and efficacy of trabectedin for the treatment of liposarcoma or leiomyosarcoma. Expert Rev Anticancer Ther. May 2016;16(5):473-84.
Sasi et al., Doxorubicin plus trabectedin for metastatic or unresectable leiomyosarcoma. Lancet Oncol. Oct. 2022;23(10):e442.
Sato et al., Oxidation of 1,2,4,5-Tetramethoxybenzene to a Cation Radical by Cytochrome P450. J Am Chem Soc. 2000; 122:8099-8100.
Saulnier et al., Discovery of a fluoroindolo[2,3-a]carbazole clinical candidate with broad spectrum antitumor activity in preclinical tumor models superior to the marketed oncology drug, CPT-11. J Med Chem. Apr. 7, 2005;48(7):2258-61.
Scaife et al., Antimetabolites in Cancer Therapy. Anticancer Therapeutics. John Wiley & Sons, Sotiris Missailidis (Ed.). Chapter 7, pp. 91-110, (2008).
Scambia et al., Randomized phase III trial on trabectedin (ET-743) single agent versus clinician's choice chemotherapy in recurrent ovarian, primary peritoneal, or fallopian tube cancers of BRCA-mutated or BRCAness phenotype patients (MITO23). Asco 58th Annual Meeting. 1 page, Abstract LBA5504, (2022).
Scambia et al., Randomized phase III trial on trabectedin (ET-743) single agent vs clinician's choice chemotherapy in recurrent ovarian, primary peritoneal, or fallopian tube cancers in BRCA mutated or BRCAness phenotype patients the MITO 23 study. ASCO 58th Annual Meeting. 22 pages, slideshow, (2022).
Scattolin et al., EP.13.15 Outcome and Safety of Lurbinectedin as Compassionate Use in SCLC: A Retrospective Multicentric International Study. IASLC 2025 World Conference on Lung Cancer, Abstract Book. p. 1772, (2025).
Scattolin et al., SLFN11 detection in patients with small cell lung cancer treated with lurbinectedin: A retrospective translational analysis. Ann Oncol. 2024;9(S6):3-4, Abstract 14P.
Schabel et al., Testing Therapeutic Hypotheses in Mice and Man: Observations on the Therapeutic Activity Against Advanced Solid Tumors of Mice Treated with Anticancer Drugs that Have Demonstrated or Potential Clinical Utility for Treatment of Advanced Solid Tumors of Man. Methods in Cancer Research, vol. XVII, Cancer Drug Development, Part B. Vincent T. DeVita, Jr. (Ed). Academic Press, New York. Chapter 1, pp. 3-51, (1979).
Schenk et al., A Randomized Double-Blind Phase II Study of the Seneca Valley Virus (NTX-010) versus Placebo for Patients with Extensive-Stage SCLC (ES SCLC) Who Were Stable or Responding after at Least Four Cycles of Platinum-Based Chemotherapy: North Central Cancer Treatment Group (Alliance) N0923 Study. J Thorac Oncol. Jan. 2020;15(1):110-119.
Schiller et al., Topotecan versus observation after cisplatin plus etoposide in extensive-stage small-cell lung cancer: E7593—a phase III trial of the Eastern Cooperative Oncology Group. J Clin Oncol. Apr. 1, 20015;19(8):2114-22.
Schlenk et al., Randomized Phase 2 Study of Trabectedin/Olaparib Compared to Physician's Choice in Subjects with Previously Treated Advanced or Recurrent Solid Tumors Haboring DNA Repair Deficiencies. Oncol Res Treat. 2018;41(Suppl 1):120-121, Abstract 236.
Schlenk et al., Randomized phase II study of trabectedin/olaparib compared to physician's choice in subjects with previously treated advanced or recurrent solid tumors harboring DNA repair deficiencies. Annals of Oncology. 2024;35(S2):S294, Abstract 196P.
Schmidt et al., Mitotic drug targets and the development of novel anti-mitotic anticancer drugs. Drug Resist Updat. Aug. 2007-Oct. 10(4-5):162-81.
Schoffski et al., Eribulin versus dacarbazine in previously treated patients with advanced liposarcoma or leiomyosarcoma: a randomised, open-label, multicentre, phase 3 trial. Lancet. Apr. 16, 2016;387(10028):1629-37.
Schuetze et al., Cardiac safety analysis of trabectedin (T) vs. dacarbazine (D) in patients (Pts) with advanced leiomyosarcoma (LMS) or liposarcoma (LPS) after prior anthracycline chemotherapy. J Clin Oncol. 2016;34:Abstract 11060.
PharmaMar, Boryung Pharmaceutical, PharmaMar's partner in South Korea, announces superior potent results for plitidepsin (Aplidin) against SARS-CoV-2. Press Release, 3 pages, Jul. 2, 2020.
PharmaMar, Chinese health authorities approve lurbinectedin for "urgent clinical use." Press Release, 2 pages, Jul. 18, 2022.
PharmaMar, CNIO and PharmaMar have signed a collaboration agreement to identify new anti-tumour therapies from the marine environment. Press Release, 3 pages, Mar. 21, 2017.
PharmaMar, CNMV INforme Financiero Semestral Correspondiente al Ano. 33 pages, (2022).
PharmaMar, ESMO includes lurbinectedin in its Clinical Practice Guidelines. Press Release, 2 pages, Apr. 15, 2021.
PharmaMar, European Commission grants orphan drug designation to PharmaMar's lurbinectedin for the treatment of Soft Tissue Sarcoma. Press Release, 2 pages, May 12, 2023.
PharmaMar, FDA chooses Zepsyre (PM1183) from PharmaMar to explore potential development for pediatric cancers. Press Release, 2 pages, Jun. 20, 2017.
PharmaMar, Final data on phase I/II in small-cell lung cancer with Zepsyre presented at the IASCLC 18th World Conference on Lung Cancer in Japan. Press Release, 2 page, Oct. 18, 2017.
PharmaMar, Genomica (PharmaMar Group) & Huasin Science completes the first CLART diagnostic equipment for the China market. Press Release, 4 pages, Nov. 27, 2019.
PharmaMar, Genomica (PharmaMar Group) presented the comparative results of the CLART HPV4s genotyping system for liquid cytology at the EUROGIN 2019 congress. Press Release, 3 pages, Dec. 10, 2019.
PharmaMar, Genomica and HuaSin advancing fight against cervical cancer in China. Press Release, 3 pages, Feb. 18, 2019.
PharmaMar, Genomica presents a new liquid biopsy test for the detection of mutations in lung cancer. Press Release, 3 pages, Sep. 11, 2017.
PharmaMar, Genomica, PharmaMar Group, announces that they have validated their PCR testing kit for saliva based sampling. Press Release, 3 pages, Jan. 28, 2021.
PharmaMar, Genomica, PharmaMar Group, is developing a kit to detect the new Wuhan coronavirus. Press Release, 2 pages, Jan. 30, 2020.
PharmaMar, Genomica, PharmaMar Group, launches a new PCR test that can detect and differentiate SARS-CoV-2, Influenza A and B and Respiratory Syncytial Virus (RSV). Press Release 3, pages, Nov. 24, 2020.
PharmaMar, IASLC publishes lurbinectedin (PharmaMar) abstracts titles for small cell lung cancer. Press Release, 2 pages, Aug. 12, 2019.
PharmaMar, In real-life, Yondelis improves the results obtained in previous clinical trials in soft tissue sarcoma. Press Release, 3 pages, Oct. 24, 2017.
PharmaMar, Life Science Alliance journal publishes results of plitidepsin in patients with COVID-19, which includes additional data on its antiviral activity against Delta and Omicron variants. Press Release, 3 pages, Jan. 11, 2022.
PharmaMar, Lurbinectedin "Named Patient Program" for Small-Cell Lung Cancer launched in Hong Long. Press Release, 2 pages, Jan. 9, 2023.
PharmaMar, Lurbinectedin data in Progressive Malignant Peural Mesothelioma presented at ESMO. Press Release, 3 pages, Oct. 1, 2019.
PharmaMar, Lurbinectedin receives innovative drug designation from UK MHRA . Press Release, 6 pages, Aug. 5, 2022.
PharmaMar, Lurbinectedin receives Orphan Drug designation from the TGA for Small-Cell Lung Cancer in Australia. Press Release, 2 pages, Feb. 19, 2020.
PharmaMar, New positive data on PM1183 sees a response rate of 36% as single agent in patients with advanced and relapsed small-cell lung cancer. Press Release, 3 pages, Sep. 12, 2017.

(56) References Cited

OTHER PUBLICATIONS

PharmaMar, New results with Yondelis (trabectedin) in sarcoma will be presented at ESMO 2021. Press Release, 3 pages, Sep. 20, 2021.
PharmaMar, Pediatric Subcommittee Oncology Drug Advisory Committee Meeting. Briefing Package. 30 pages, Jun. 21, 2017.
Pharmamar, Pharma Mar group reports first half financial results. Press Release, 2 pages, Jul. 26, 2017.
PharmaMar, Pharma Mar group revenues totalled euro140 million in the first nine months of the year. Press Release, 2 pages, Oct. 24, 2017.
PharmaMar, Pharma Mar S.A. submitted the Marketing Authorisation Application in the European Union at the end of 2016. 2 pages, May 4, 2017.
PharmaMar, Pharma Mar, S.A. announces that based on the preliminary feed-back ("trend vote") from the European Medicines Agency (EMA) Committee for Medicinal Products for Human Use. Press Release, 1 page, Nov. 8, 2017.
PharmaMar, PharmaMar and Bionical Emas launch Expanded Access Program for lurbinectedin in relapsed Small Cell Lung Cancer in the U.S. Press Release, 3 pages, Jan. 27, 2020.
PharmaMar, PharmaMar and Boryung Pharm sign a licensing agreement for Zepsyre (lurbinectedin) in Korea. Press Release, 2 pages, Nov. 7, 2017.
PharmaMar, PharmaMar and Chugai agree to terms for early termination of the license agreement for Zepsyre in Japan. Press Release, 3 pages, Jun. 26, 2018.
PharmaMar, PharmaMar and Eczacibasi sign a licensing agreement for Aplidin in Turkey. Press Release, 3 pages, May 25, 2017.
PharmaMar, PharmaMar and Jazz Pharmaceuticals Announce FDA Acceptance and Priority Review of New Drug Application for Lurbinectedin in Relapsed Small Cell Lung Cancer. Press Release, 3 pages, Feb. 17, 2020.
PharmaMar, PharmaMar and Jazz Pharmaceuticals announce results of the Atlantis phase III study with lurbinectedin. Press Release, 4 pages, Dec. 3, 2020.
PharmaMar, PharmaMar and Jazz Pharmaceuticals Announce the U.S. License Agreement for Lurbinectedin is Effective With the Expiration of the HSR Waiting Period. Press Release, 4 pages, Jan. 22, 2020.
PharmaMar, PharmaMar and Jazz Pharmaceuticals Sign Exclusive License Agreement for Lurbinectedin in the U.S. Press Release, 5 pages, Dec. 19, 2019.
PharmaMar, PharmaMar and Key Oncologics have signed an exclusive agreement to commercialize Yondelis in the Republic of South Africa, Namibia and Botswana. Press Release, 3 pages, May 19, 2020.
PharmaMar, PharmaMar and Luye Pharma announce the acceptance of New Drug Application for lurbinectedin in China. Press Release, 3 pages, Jun. 6, 2023.
PharmaMar, PharmaMar and Luye Pharma have started a clinical trial with lurbinectedin in China. Press Release, 3 pages, Dec. 1, 2020.
PharmaMar, PharmaMar and Luye Pharma sign License agreement for Development and Commercialization of lurbinectedin in China territories. Press Release, 3 pages, Apr. 26, 2019.
PharmaMar, PharmaMar and Megapharm sign a licensing agreement for lurbinectedin in Israel. Press Release, 2 pages, May 11, 2020.
PharmaMar, PharmaMar and Specialised Therapeutics Asia sign licensing and marketing agreement for lurbinectedin covering Australia, New Zealand and several Asian countries. Press Release, 3 pages, May 17, 2017.
PharmaMar, PharmaMar and Specialized Therapeutics Asia meet in Madrid to define new agreements. Press Release, 2 pages, Apr. 2019.
PharmaMar, PharmaMar and STADA sign agreement to commercialize Yondelis (trabectedin) in the MENA region. Press Release, 4 pages, Nov. 17, 2020.
PharmaMar, PharmaMar and TTY Biopharm entered into an exclusive agreement to commercialize Yondelis in Taiwan, Hong Kong and Macao. Press Release, 3 pages, Jun. 9, 2020.
PharmaMar, PharmaMar announces abstracts to be presented at ASCO 2020. Press Release, 4 pages, May 14, 2020.
PharmaMar, PharmaMar announces abstracts to be presented at ASCO 2021. Press Release, 3 pages, May 20, 2021.
PharmaMar, PharmaMar announces abstracts to be presented during the IASLC 2021 World Conference on Lung Cancer. Press Release, 3 pages, Sep. 2, 2021.
PharmaMar, PharmaMar announces abstracts to be presented to ASCO 2023. Press Release, 4 pages, May 26, 2023.
PharmaMar, PharmaMar will present final data on PM1183 during the 18th World Lung Conference in Japan. Press Release, 3 pages, Oct. 10, 2017.
PharmaMar, PharmaMar will present in the ESMO congress results of lurbinectedin on Ovarian Cancer. Press Release. 1 page, Aug. 10, 2018.
PharmaMar, PharmaMar will present in the IASLC congress results of lurbinectedin on Small-Cell Lung Cancer. Press Release, 1 page, Aug. 13, 2018.
PharmaMar, PharmaMar will present new clinical data on PM1183 during ESMO 2017. Press Release, 4 pages, Aug. 31, 2017.
PharmaMar, PharmaMar will present new data for Zepzelca (lurbinectedin) and Yondelis (trabectedin) for advanced Soft-Tissue Sarcoma at CTOS 2020. Press Release, 4 pages, Nov. 11, 2020.
PharmaMar, PharmaMar will present the results of the Phase I/II Study with lurbinectedin in combination with doxorubicin in relapsed small-cell lung cancer during the IASLC World Conference. Press Release, 3 pages, Sep. 6, 2018.
PharmaMar, PharmaMar will submit NDA for lurbinectedin under accelerated approval in SCLC in the USA. Press Release, 2 pages, Aug. 19, 2019.
PharmaMar, PharmaMar, S.A. announces the results of the Phase III clinical trial (CORAIL) with Zepsyre (lurbinectedin) in platinum-resistant ovarian cancer patients. Press Release, 1 page, Jan. 18, 2018.
PharmaMar, PharmaMar's Lurbinectedin Atlantis trial design and data in small-cell lung cancer will be an oral presentation at the IASCLC's annual meeting. Press Release, 3 pages, Feb. 20, 2018.
PharmaMar, PharmaMar's Zepsyre Atlantis trial in small-cell lung cancer will be an oral presentation at the IASLC's Targeted Therapies annual meeting. Press Release, 2 pages, Feb. 20, 2019.
PharmaMar, PharmaMar's Zepzelca (lurbinectedin) receives approval in China for the treatment of Small Cell Lung Cancer. Press Release, 2 pages, Dec 3, 2024.
PharmaMar, PharmaMar's Zepzelca (lurbinectedin) receives commercialization approval for the treatment of relapsed small cell lung cancer in Argentina. Press Release, 2 pages, May 19, 2025.
PharmaMar, PharmMar to participate at the 21st Morgan Stanley Annual Global Healthcare Conference. Press Release. 2 pages, Sep. 7, 2023.
PharmaMar, Phase II Study results of trabectedin combined with low-dose radiation therapy for Soft Tissue Sarcoma are presented at ESMO. Press Release, 2 pages, Sep. 30, 2019.
PharmaMar, Phase III trial with Zepsyre in small-cell lung cancer (Atlantis) to continue on the basis of positive recommendation by IDMC. Press Release, 2 pages, Nov. 15, 2017.
PharmaMar, Plitidepsin (PharmaMar) shows activity against the cells responsible for the destruction of bone in myeloma multiple. Press Release, 3 pages, Dec. 11, 2017.
PharmaMar, Positive recommendation of IDMC to Zepsyre to continue the Phase III trial with in small-cell lung cancer (Atlantis). Press Release, 2 pages, May 29, 2018.
PharmaMar, Positive results of lurbinectedin Phase II trial (PharmaMar) for the treatment of relapsed small cell lung cancer are presented at ASCO. Press Release, 3 pages, Jun. 1, 2019.
PharmaMar, Pursuant to article 228 of the consolidated text of the Spanish Securities Market Act, we hereby inform you of the following Significant Event. Press Release, p. 1, Mar. 21, 2018.
PharmaMar, Results of the phase II trial with lurbinectedin for the treatment of patients with relapsed Ewing Sarcoma. Press Release, 2 pages, May 3, 2022.

(56) References Cited

OTHER PUBLICATIONS

PharmaMar, Results presented at ASCO demonstrating the synergy of PharmaMar's combination of lurbinectedin with irinotecan in patients with relapsed small cell lung cancer. Press Release, 3 pages, Jun. 4, 2024.
PharmaMar, S.A., Annual Financial Statements and Management Report as of Dec 31, 2015, next to the Auditors' Report on the Annual Financial Statements. 672 pages, (2015).
PharmaMar, S.A., Financial Statements and Directors' Report as a Dec 31, 2016. 254 pages, (2016).
PharmaMar, S.A.U., Audit Report, Annual Financial Statements and Management Report for 2012. 150 pages, (2012).
PharmaMar, S.A.U., Audit Report, Annual Financial Statements and Management Report for 2013. 156 pages, (2013).
PharmaMar, Separate Financial Statements 2017. 122 pages, (2017).
PharmaMar, Separate Financial Statements 2018. 128 pages, (2018).
PharmaMar, Soft Tissue Sarcoma requires a multidisciplinary approach to reduce patient relapses and improve patient survival. Press Release, 3 pages, Mar. 21, 2019.
PharmaMar, Swiss medical authority approves PharmaMar's Zepzelca (lurbinectedin) and Atezolizumab (Tecentriq) combination as first-line maintenance therapy for extensive-stage small cell lung cancer. Press Release, 3 pages, Nov. 24, 2025.
PharmaMar, The Australian TGA approves Yondelis (trabectedin) for Soft Tissue Sarcoma (Liposarcoma or Leiomyosarcoma). Press Release, 2 pages, Apr. 23, 2021.
PharmaMar, The CHMP confirms its earlier trend towards a negative vote for the commercialization of plitidepsin in Europe. Press Release, 2 pages, Dec. 15, 2017.
PharmaMar, The General Court of the European Union agrees with PharmaMar on the ruling on Aplidin (plitidepsin). Press Release, 2 pages, Oct. 28, 2020.
PharmaMar, The Lancet Oncology journal chooses a PharmaMar poster as one of the most relevant of the ASCO 2018 congress. Press Release, 2 pages, Jul. 13, 2018.
PharmaMar, The Peer Review Journal Science confirms the potent activity of PharmaMar's plitidepsin against SARS-CoV-2. Press Release, 2 pages, Jan. 26, 2021.
PharmaMar, The PROFARMA program awards PharmaMar an "Excellent" company rating once again. Press Release, 1 page, Jul. 10, 2023.
PharmaMar, The PROFARMA program grants PharmaMar an "Excellent" company reating. Press Release, 3 pages, Oct. 14, 2022.
PharmaMar, The Spanish Agency of Medicines and Medical Devices gives their approval to PharmaMar's new facilities. Press Release, 2 pages, Dec 5, 2018.
PharmaMar, The success of sarcoma treatment, seen by prestigious international oncologists. Press Release, 4 pages, Mar. 29, 2017.
PharmaMar, The U.S. Food and Drug Administration (FDA) has granted Orphan Drug designation to PharmaMar's lurbinectedin. Press Release, 2 pages, Aug. 3, 2018.
PharmaMar, The World Health Organization grants the name ecubectedin to PharmaMar's anti-tumor compound PM14. Press Release, 2 pages, Sep. 13, 2021.
PharmaMar, PharmaMar signs a new agreement with STA to commercialize Yondelis in Australia, New Zealand and South East Asia. Press Release, 3 pages, Oct. 14, 2019.
PharmaMar, UK approves the initiation of the Phase III Neptuno clinical trial with PharmaMar's Aplidin (plitidepsin) for the treatment of patients with COVID-19. Press Release, 2 pages, Feb. 17, 2021.
PharmaMar, Zepsyre receives positive recommendation of the IDMC to continue with the Phase III trial in small-cell lung cancer (Atlantis). Press Release, 2 pages, Oct. 26, 2018.
PhRMA, Biopharmaceutical Research & Development, The Process Behind New Medicines. R&D Brochure, 24 pages, (2015).
Pink et al., Efficacy and safety of nivolumab and trabectedin in pretreated patients with advanced soft tissue sarcomas (STS)—preliminary results of a phase II trial of the German Interdisciplinary Sarcoma Group (GISG-15, NitraSarc) for the non-L sarcoma cohort. ASCO 57th Annual Meeting. Poster, 1 page, (2021).
Pink et al., Efficacy and safety of nivolumab and trabectedin in pretreated patients with advanced soft tissue sarcomas (STS): Preliminary results of a phase II trial of the German Interdisciplinary Sarcoma Group (GISG-15, NitraSarc) for the non-L sarcoma cohort. ASCO 57th Annual Meeting. 2021;39(Suppl 15):584s, Abstract 11545.
Pink et al., Efficacy of trabectedin in patients with advanced or metastatic alveolar soft-part sarcoma. Onkologie. 2012;35(5):249-52.
Pink et al., Which patients with pre-treated locally advanced or metastatic sarcoma benefit most from trabectedin treatment: First results of a retrospective study of the German interdisciplinary Sarcoma Group (GISG-14-ReTraSarc). ASCO 56th Annual Meeting. 1 page, (2020).
Glennon et al., 2-Substituted tryptamines: agents with selectivity for 5-HT(6) serotonin receptors. J Med Chem. Mar. 9, 2000;43(5):1011-8.
Gmeiner, Antimetabolite incorporation into DNA: structural and thermodynamic basis for anticancer activity. Biopolymers. Nov. 5, 2002;65(3):180-9.
Goldwasser et al., Characterization of ecteinascidin 743-induced DNA damages in cells. Proceedings of the American Association for Cancer Research. Mar. 1998;39:598, Abstract 4066.
Goodbody, The Ascidian Fauna of Two Contrasting Lagoons in the Netherlands Antilles: Piscadera BAAI, Curacao, and the LAC of Bonaire. Studies of the Fauna of Curacao and Other Caribbean Islands: No. 202. pp. 21-61.
Goodman & Gilman, The Pharmacological Basis of Therapeutics. Chapter 1, p. 36, (1975).
Gordon et al., A phase 2 study using ipilimumab nivolumab, and trabectedin for previously untreated metastatic soft tissue sarcoma. ASCO 57th Annual Meeting. Page 588s, Poster 11562, 1 page, (2021).
Gordon et al., Five-year results of a phase 2 trial using ipilimumab (I), nivolumab (N), and trabectedin (T) for previously untreated advanced soft tissue sarcoma (NCT03138161). Asco 58th Annual Meeting. p. 680s, Abstract 11573, (2022).
Gordon et al., Five-year results of a phase 2 trial using ipilimumab (I), nivolumab (N), and trabectedin (T) for previously untreated advanced soft tissue sarcoma [NCT03138161]. Asco 58th Annual Meeting. Abstract 11573, Poster, (2022).
Gordon et al., Results of a phase I/II combination regimen with ipilimumab (I), Nivolumab (N) and trabectedin (T) as first line therapy for advanced leiomyosarcoma. Annals of Oncology. 2022;33(S7):S1225, Abstract 14830.
Gordon et al., Saint: A Phase I/Expanded Phase II Study Using Safe Amounts of Ipilimumab, Nivolumab and Trabectedin as First-Line Treatment of Advanced Soft Tissue Sarcoma. Cancers (Basel). Jan. 31, 2023;15(3):906, 12 pages.
Gordon et al., SAINT: An Expanded Phase 2 Study Using Safe Amounts of Ipilimumab (I), Nivolumab (N), and Trabectedin (T) as First-line Treatment of Advanced Soft Tissue Sarcoma [NCT03138161]. Asco 57th Annual Meeting. 1 page, Poster (2021).
Gordon et al., Seven year update on SOC-1702: A phase 2 study using trabectedin (T) in combination with ipilimumab (I), nivolumab (N) and trabectedin (T) in previously untreated patients with advanced soft tissue sarcoma. ASCO 60th Annual Meeting. 1 page, Abstract 11577, (2024).
Gordon et al., The Saint: Initial Results of Phase 1/2 Study of Safety/Efficacy Using Safe Amounts of Ipilimumab, Nivolumab and Trabectedin as First Line Treatment of Advanced Soft Tissue Sarcoma. CTOS 23rd Annual Meeting. pp. 357-358, Poster 237, Abstract 3042637, (2018).
Gordon et al., The Saint: Results of a Phase 1/2 Study of Safety/Efficacy Using Safe Amounts of Ipilimumab, Nivolumab and Trabectedin as First Line Treatment of Advanced Soft Tissue Sarcoma (NCT 03138161). CTOS 24th Annual Meeting. p. 444, Poster 192, Abstract 3255343, (2019).
Gordon et al., The Saint: Results of a Phase 1/2 Study of Safety/Efficacy Using Safe Amounts of Ipilimumab, Nivolumab and

(56) References Cited

OTHER PUBLICATIONS

Trabectedin as First Line Treatment of Advanced Soft Tissue Sarcoma [NCT03138161]. Asco 55th Annual Meeting. 1 page, Abstract 11016, Poster (2019).
Gordon, Saint: An Expanded Phase 2 Study Using Safe Amounts of Ipilmumab (I), Nivolumab (N), and Trabectedin (T) as First-line Treatment of Advanced Soft Tissue Sarcoma [NCT03138161]. Ctos Annual Meeting. Abstract 3465078, 1 page, (2020).
Gore et al., Phase I combination study of trabectedin (T) and capecitabine (C) in patients with advanced malignancies. J Clin Oncol. Jun. 2, 20060;24(18):Abstract 2079.
Gourley et al., Angiogenesis: new targets for the development of anticancer chemotherapies. Curr Pharm Des. Mar. 2000;6(4):417-39.
Goyal et al., Oxidation chemistry and biochemistry of indole and effect of its oxidation product in albino mice. Bioelectrochemistry and Bioenergetics. 1998;45:47-53.
Grant et al., Single-agent chemotherapy trials in small-cell lung cancer, 1970 to 1990: the case for studies in previously treated patients. J Clin Oncol. Mar. 1992;10(3):484-98.
Greene et al., Protective Groups in Organic Synthesis, Third Edition. John Wiley & Sons, Inc., New York. pp. 17-23, 494-503, (1999).
Gronchi et al., Trabectedin and RAdiotherapy in Soft Tissue Sarcoma (TRASTS): Results of a Phase I Study in Myxoid Liposarcoma from Spanish (GEIS), Italian (ISG), French (FSG) Sarcoma Groups. EClinicalMedicine. Mar. 11, 2019;9:35-43.
Gronchi et al., Trabectedin and radiotherapy in soft-tissue sarcoma (TRASTS) study: An international prospective, phase I/II trial—A collaborative Spanish (GEIS), Italian (ISG), and French (FSG) group study. 2017 ASCO Annual Meeting. 1 page, (2017).
Gronchi et al., Trabectedin and radiotherapy in soft-tissue sarcoma (TRASTS) study: An international prospective, phase I/II trial—A collaborative Spanish (GEIS), Italian (ISG), and French (FSG) group study. J Clin Oncol. 2017;35:Abstract 11061.
Gronchi et al., Trabectedin and radiotherapy in soft-tissue sarcoma (TRASTS) study: An international prospective, phase II trial in localized myxoid liposarcoma—A collaborative Spanish (GEIS), Italian (ISG) and French (FSG) group study. ASCO 56th Annual Meeting. 2 pages, Abstract 11514, (2020).
Gronchi et al., Trabectedin and RAdiotherapy in Soft-Tissue Sarcoma (TRASTS) study: An international prospective, phase II trial. A collaborative Spanish (GEIS), Italian (ISG) and French (FSG) Sarcoma group study. ASCO 56th Annual Meeting. 1 page, Abstract 11514, poster, (2020).
Gronchi, Surgery in soft tissue sarcoma: the thin line between a surgical or more conservative approach. Future Oncology. 2021;17(Suppl 21):3-6, pre-publication edition.
Grosso et al., A Phase II Randomized -Non Comparative- Study on the Activity of Trabectedin or Gemcitabine + Docetaxel in Metastatic or Locally Relapsed Uterine Leiomyosarcoma Pretreated with Standard Chemotherapy. CTOS 21st Annual Meeting. pp. 140-141, Abstract 2570383, (2016).
Grosso et al., A Phase II Randomized -Non Comparative- Study on the Activity of Trabectedin or Gemcitabine + Docetaxel in Metastatic or Locally Relapsed Uterine Leiomyosarcoma Pretreated with Standard Chemotherapy. Trabectedin in Advanced Uterine Leiomyosarcoma TAUL Study. CTOS 21st Annual Meeting. Slideshow, 18 pages, (2016).
Guan et al., Molecular and crystal structures of ecteinascidins: potent antitumor compounds from the Caribbean tunicate Ecteinascidia turbinata. J Biomol Struct Dyn. Apr. 1993; 10(5):793-818.
Gulavita et al., Antimicrobial Constituents of a Spong-Nudibranch Pair from Sri Lanka. Bioactive Compounds from Marine Organisms, With Emphasis on the Indian Ocean, An Indo-United States Symposium. Oxford & IBH Publishing Co. Pvt. Ltd., New Delhi. Pages 229-233, (1991).
Gundle et al., Multiplexed Evaluation of Microdosed Antineoplastic Agents In Situ in the Tumor Microenvironment of Patients with Soft Tissue Sarcoma. Clin Cancer Res. Aug. 1, 2020;26(15):3958-3968.
Guo, Recent advances in the synthesis and activity of analogues of bistetrahydroisoquinoline alkaloids as antitumor agents. Eur J Med Chem. Dec. 15, 2023;262:115917, 16 pages.
Gupta et al., Chemotherapy (gemcitabine, docetaxel plus gemcitabine, doxorubicin, or trabectedin) in inoperable, locally advanced, recurrent, or metastatic uterine leiomyosarcoma: a clinical practice guideline. Curr Oncol. Oct. 2013;20(5):e448-54.
Gupta et al., High SLFN11 Expression Predicts Response but Is Not Required to Confer Sensitivity to Lurbinectedin. 2024 World Conference on Lung Cancer. 11 pages, Slideshow, Sep. 7-10, 2024.
Gupta et al., High SLFN11 Expression Predicts Response but is not Required to Confer Sensitivity to Lurbinectedin. J Thorac Oncol. 2024 Sep. 7-10;19(10 Suppl):S458, Abstract EP.03G.04.
Gupta et al., Systematic chemotherapy for inoperable, locally advanced, recurrent, or metastatic uterine leiomyosarcoma: a systematic review. Clin Oncol (R Coll Radiol). Jun. 2013;25(6):346-55.
Habeck, To approve or not approve? Lancet Oncol. Nov. 2003;4(11):646.
Hadoux et al., Multimodal treatment with doxorubicin, cisplatin, and ifosfamide for the treatment of advanced or metastatic uterine leiomyosarcoma: a unicentric experience. Int J Gynecol Cancer. Feb. 2015;25(2):296-302.
Hafezi et al., Targeting BCL-2 in Cancer: Advances, Challenges, and Perspectives. Cancers (Basel). Mar. 14, 2021;13(6):1292, 15 pages.
Hahn et al., Taxol in combination with doxorubicin or etoposide. Possible antagonism in vitro. Cancer. Nov. 1, 1993;72(9):2705-11.
Hakala et al., The Potential Value of In Vitro Screening. Methods in Cancer Research vol. XVI, Cancer Drug Development, Part A. Vincent T. DeVita, Jr., (Ed.), Academic Press, New York. Chapter VI, pp. 247-287, (1979).
Halmos et al., Efficacy and Safety of Lurbinectedin for Small Cell Lung Cancer in a Real-World Setting: Jazz EMERGE 402 Study. 2024 World Conference of Lung Cancer. 1 p. Abstract P1.13A. 10. poster, Sep. 7-10, 2024.
Halmos et al., Efficacy and Safety of Lurbinectedin for Small Cell Lung Cancer in a Real-World Setting: Jazz EMERGE 402 Study. 2024 World Conference of Lung Cancer. 12 p. Abstract P1.13A. 10. Slideshow, Sep. 7-10, 2024.
Halmos et al., Efficacy and Safety of Lurbinectedin for Small Cell Lung Cancer in a Real-World Setting: Jazz EMERGE 402 Study. 2024 World Conference of Lung Cancer. 2 p. Abstract P1.13A. 10. Sep. 7-10, 2024.
Halmos et al., P3.13.31 Real-World Effectiveness and Safety of Lurbinectedin for Small Cell Lung Cancer (SCLC): Updates from Jazz EMERGE 402. IASLC 2025 World Conference on Lung Cancer, Abstract Book. p. 1166 (2025).
Halmos et al., Real-world Safety and Dosing of Lurbinectedin-Treated Patients with Small Cell Lung Cancer: Jazz EMERGE 402 Preliminary Analysis. J Thorac Oncol. Nov. 2023; 18(11 Suppl): S381, Abstract P2.17-07.
Halmos et al., Real-world Safety and Dosing of Lurbinectedin-Treated Patients with Small Cell Lung Cancer: Jazz EMERGE 402 Preliminary Analysis. IASLC 2023 World Conference on Lung Cancer, WCLC 2023, Abstract 2717, 1 page, Sep. 9-12, 2023.
Halmos et al., Real-World Use of Lurbinectedin in Patients with Small Cell Lung Cancer: Jazz EMERGE 402 Updated Analysis. Journal of Thoracic Oncology. Jul. 2024;19(7S):e52, Abstract PP01. 119.
Hande, Clinical applications of anticancer drugs targeted to topoisomerase II. Biochim Biophys Acta. Oct. 1, 1998;1400 (1-3):173-84.
Ahfs, Lurbinectedin. Am J Health Syst Pharm. 2020;77(22):1815-1817. pre-publication edition.
Allavena et al., Lurbinectedin reduces Tumor Associated Macrophages and the production of inflammatory cytokines, chemokines, and angiogenic factors in preclinical models. AACR American Association for Cancer Research, 107th Annual Meeting. Abstract 1284, 1 page, poster, Apr. 16-20, 2016.
Allavena et al., Lurbinectedin reduces tumor-associated macrophages and the production of inflammatory cytokines, chemokines, and angiogenic factors in preclinical models. AACR Annual Meeting. Abstract 1284, Apr. 16-20, 2016.

(56) References Cited

OTHER PUBLICATIONS

Andres et al., Phase II Study to Evaluate the Efficacy, Tolerability, and Biomarkers of PM01183 with Olaparib in Patients with Advanced Gynecological Tumors. Int J Gynecol Cancer. 2018 Sept;28(Suppl 2):626, Abstract IGCS8-0961.
Anobile et al., Evaluation of the Preclinical Efficacy of Lurbinectedin in Malignant Pleural Mesothelioma. Cancers (Basel). May 1, 20212;13(10):2332, 14 pages.
Aquila et al., Lurbinectedin delays the onset of splenomegaly and extends survival of C26 tumor-bearing mice. Eur J Transl Myol. 2020;30(3):40, Abstract p. 01.
Australian Prescriber, Lurbinectedin. Aust Prescr. Feb. 2022;45:31.
Aviles et al., Lurbinectedin (PM01183): Pharmacokinetics/Pharmacodynamic (PK/PD) Properties in Pancreas, Ovarian and NSCLC Xenografts. Eur J Cancer. Nov. 7, 2012;48(Suppl 6):67, Abstract 222.
Aviles et al., Metabolic Disposition of Lurbinectedin, a Potent Selective Inhibitor of Active Transcription of Protein- Coding Genes, in Nonclinical Species and Patients. Drug Metab Dispos. Apr. 2022;50(4):327-340.
Aviles et al., Synergism of lurbinectedin (PM01183) combined with 5-fluorouracil (5-FU): in vitro and in vivo studies. AACR Annual Meeting. Abstract 5498, Apr. 4-10, 2013.
Aviles et al., Synergism of lurbinectedin (PM01183) combined with 5-fluorouracil (5-FU): in vitro and in vivo studies. AACR Annual Meeting. Abstract 5498, poster, Apr. 4-10, 2013.
Awada et al., Antitumor activity of lurbinectedin in combination with oral capecitabine in patients with metastatic breast cancer. ESMO Open. Dec. 2022;7(6):100651, 9 pages.
Awada et al., Anti-tumor activity of PM1183 (lurbinectedin) in combination with capecitabine in metastatic breast cancer patients: results from a phase I trial. ASCO American Society of Clinical Oncology, 54th Annual Meeting. 1 page, poster, Jun. 1-5, 2018.
Awada et al., Anti-tumor activity of PM1183 (lurbinectedin) in combination with capecitabine in metastatic breast cancer patients: Results from a phase I trial. J Clin Oncol. 2018;36, Abstract 1072.
Balmana et al., Anti-tumor activity of PM01183 (lurbinectedin) in BRCA1/2-associated metastatic breast cancer patients: results of a single-agent phase II trial. 41st ESMO European Cancer Congress. 18 pages, Slideshow, Oct. 7-11, 2016.
Balmana et al., Anti-tumor activity of PM01183 (lurbinectedin) in BRCA1/2-associated metastatic breast cancer patients: results of a single-agent phase II trial. Annals of Oncology. 2016;27(Suppl 6):vi68, Abstract 2230.
Balmana et al., Lurbinectedin (PM01183) activity in BRCA 1/2-associated or unselected metastatic breast cancer: interim results of an ongoing phase II trial. 37th San Antonio Breast Cancer Symposium (SABCS). 1 page, poster, Dec. 9-13, 2014.
Balmana et al., Lurbinectedin (PM01183) activity in BRCA1/2-associated or unselected metastatic breast cancer. Interim results of an ongoing phase II trial. 2014 San Antonio Breast Cancer Symposium. Publication No. P3-13-01, 1 page, (2014).
Baena et al., Lurbinectedin in the treatment of relapsed small cell lung cancer. Future Oncol. Jun. 2021; 17 (18):2279-2289.
Benjamin et al., Accelerated approval requirements for lurbinectedin. Lancet Oncol. May 2022;23(5):e206.
Benton et al., Phase I study of lurbinectedin (PM11083) in patients with advanced AML and Mds. J Clin Oncol. 2017;35, Abstract e18521.
Benton et al., Safety and tolerability of lurbinectedin (PM01183) in patients with acute myeloid leukemia and myelodysplastic syndrome. Hematol Oncol. Feb. 2019; 37(1):96-102.
Berton-Rigaud et al., Lurbinectedin (PM01183) Activity in Platinum-resistant/Refractory Ovarian Cancer Patients. Preliminary Results of an Ongoing Two-stage Phase II Study. Annals of Oncology. 2012;23(Suppl 9):Abstract 9680.
Berton-Rigaud et al., Lurbinectedin (PM01183) activity in platinum-resistant/refractory ovarian cancer. Preliminary results of an ongoing Phase II study. 2012 ESMO Congress. 15 pages, slideshow, (2012).
Bishop et al., Antitumor effect and tumor distribution of PM01183 in human pancreatic and breast xenograft mouse model. AACR Annual Meeting. Abstract 1779. Mar. 31-Apr. 4, 2012.
Bishop et al., Antitumor effect and tumor distribution of PM01183 in human pancreatic and breast xenograft mouse model. AACR Annual Meeting. Abstract 1779. Poster, 1 page, Mar. 31-Apr. 4, 2012.
Bolomsky et al., MCL-1 inhibitors, fast-lane development of a new class of anti-cancer agents. J Hematol Oncol. Dec. 11, 2020;13(1):173, 19 pages.
Boni et al., Lurbinectedin in patients with pretreated BRCA1/2-associated metastatic breast cancer: Results from a phase II basket study. ASCO American Society of Clinical Oncology, 58 Annual Meeting. 1 page, Poster, Jun. 3-7, 2022.
Boni et al., Lurbinectedin in patients with pretreated BRCA1/2-associated metastatic breast cancer: Results from a phase II basket study. J Clin Oncol. 2022;40(Suppl 16):58s, Abstract 1092.
Boni et al., Lurbinectedin, a selective inhibitor of oncogenic transcription, in patients with pretreated germline BRCA1/2 metastatic breast cancer: results from a phase II basket study. ESMO Open. Oct. 2022;7(5):100571, 8 pages.
Boudin et al., Lurbinectedin for metastatic small-cell bladder carcinoma. Eur J Cancer. Jul. 2021;151:1-2.
Boyne et al., Synthetic control arm (SCA) analysis of lurbinectedin compared to the standard of care (SoC) among patients with small cell lung cancer (SCLC) previously treated with platinum-based chemotherapy. Annals of Oncology. 2022;33(S7):S1249, Abstract 1536P.
Boyne et al., Synthetic Control Arm Analysis of Lurbinectedin Compared to the Standard of Care Among Patients With Small Cell Lung Cancer Previously Treated With Platinum-Based Chemotherapy. ESMO Congress 2022. Poster, Abstract 1536P, Sep. 9-13, 2022.
Buikhuisen et al., Second line therapy in malignant pleural mesothelioma: A systematic review. Lung Cancer. Sep. 2015;89(3):223-31, pre-publication edition.
Bushunow et al., EMERGE 402: Preliminary Real-world Characteristics and Safety of Lurbinectedin in Patients With Small-cell Lung Cancer. Journal of Thoracic Oncology. Sep. 2022;17(9S):S145-S146, Abstract P2. 10-02.
Byrne et al., Modified RECIST criteria for assessment of response in malignant pleural mesothelioma. Ann Oncol. Feb. 2004;15(2):257-60.
Calabuig, Molecular Modeling of the Interaction of Antitumor Drugs and Nucleases with DNA. Department of Pharmacology, University of Alcala. Doctoral Thesis. 492 pages, (2011).
Calvo et al., Activity and Safety of the Combination of PM01183 and Doxorubicin in Relapsed SCLC. Final Results of a Phase Ib Trial. Journal of Thoracic Oncology. 2017;12(11S2):S1800, Abstract MA 01.05.
Calvo et al., Antitumor activity of lurbinectedin (PM01183) and doxorubicin in relapsed small-cell lung cancer: results from a phase I study. Ann Oncol. Oct. 1, 2017;28(10):2559-2566.
Calvo et al., Lurbinectedin (PM01183) in combination with doxorubicin (DOX): Preliminary results of a phase Ib study. Eur J Cancer. 2013;49(Suppl 2): 178-179, Abstract 860.
Calvo et al., Lurbinectedin (PM01183) in combination with doxorubicin (DOX): Preliminary results of an ongoing phase Ib study. 17th ECCO—38th ESMO—32nd ESTRO European Cancer Congress. Poster, Sep. 27-Oct. 1, 2013.
Calvo et al., Lurbinectedin (PM01183) in Combination with Gemcitabine (GEM). Preliminary Results of an Ongoing Phase IB Study. Annals of Oncology. Sep. 2012;23(Suppl 9):ix166-ix167, Abstract 484P.
Calvo et al., Phase Ib study of lurbinectedin (PM01183) in combination with gemcitabine (GEM) Preliminary ongoing results. 37th ESMO Congress. 1 pages, poster, (2012).
Cespedes et al., Antitumor effect of PM01183 in a human pancreatic adenocarcinoma orthotopic model. AACR Annual Meeting. Abstract 1777, Mar. 31-Apr. 4, 2012.
Cespedes et al., Antitumor effect of PM01183 in a human pancreatic adenocarcinoma orthotopic model. AACR Annual Meeting. Abstract 1777, poster, Mar. 31-Apr. 4, 2012.

(56) References Cited

OTHER PUBLICATIONS

Cespedes et al., Lurbinectedin (PM01183): Pharmacokinetic/Pharmacodynamic (PK/PD) Properties in Pancreas, Ovarian and NSCLC Xenografts. 24th EORTC-NCI-AACR Symposium on Molecular Targets and Cancer Therapeutics. 1 page, poster, Nov. 6-9, 2012.
Chakraborty et al., De Novo and Histologically Transformed Small-Cell Lung Cancer Is Sensitive to Lurbinectedin Treatment Through the Modulation of EMT and NOTCH Signaling Pathways. Clin Cancer Res. Sep. 1, 2023;29 (17):3526-3540, pre-publication edition.
Chakraborty et al., Preclinical analysis identifies predictive biomarker and potential pathways of resistance to lurbinectedin treatment in small cell lung cancer. Cancer Res. 83(8 Suppl): Abstract LB233.
Chawla et al., The TNT protocol: A phase II study using talimogene laherparepvec (TVEC), nivolumab (N) and trabectedin (T) as first, second/third line therapy for advanced sarcoma, including desmoid tumor and chordoma. Journal of Clnical Oncology. 2020;38(15):Abstract TPS11572.
Chawla et al., The TNT protocol: A phase II study using talimogene laherparepvec (TVEC), nivolumab (N) and trabectedin (T) as first, second/third line therapy for advanced sarcoma, including desmold tumor and chordoma. Journal of Clinical Oncology. 38(15 Suppl):Abstract TPS11572, (2020).
Colby et al., High-dose carboplatin and regimen-related toxicity following autologous bone marrow transplant. Bone Marrow Transplant. Mar. 2002;29(6):467-72.
Coleman et al., A phase 3 study of trabectedin (T) plus pegylated liposomal doxorubicin (PLD) versus PLD for treatment of advanced-relapsed epithelial ovarian, primary peritoneal, or fallopian tube cancer. 2014 ASCO Annual Meeting. 2 pages, Abstract TPS5612, May 31, 2014.
Coleman et al., A Phase 3 Study of Trabectedin plus Pegylated Liposomal Doxorubicin (PLD) versus PLD for Treatment of Advanced Relapsed Epithelial Ovarian, Primary Peritoneal, or Fallopian Tube Cancer. 2014 ASCO Annual Meeting. 1 page, Poster No. 393B, May 31, 2014.
Coleman et al., A phase III study of trabectedin (T) plus pegylated liposomal doxorubicin (PLD) versus PLD for treatment of advanced-relapsed epithelial ovarian, primary peritoneal, or fallopian tube cancer. J Clin Oncol. 2015;33: Abstract TPS5606, 2 pages.
Collins et al., Lurbinectedin in Relapsed Extensive-stage Small Cell Lung Cancer Demonstrates Similar Efficacy to Phase II Basket Trial. J Invest Med. 2025;73(1):199-200, Abstract 157.
Colombo et al., Multicenter, randomised, open-label, non-comparative phase 2 trial on the efficacy and safety of the combination of bevacizumab and trabectedin with or without carboplatin in women with partially platinum-sensitive recurrent ovarian cancer. Br J Cancer. Oct. 2019;121(9):744-750.
Colombo et al., Randomized, non comparative, phase II trial on the efficacy and safety of the combination of bevacizumab and trabectedin with or without carboplatin in women with platinum partially sensitive recurring ovarian cancer. IGCS 16th Biennial. 1 page, (2016).
Colombo et al., Randomized, non-comparative phase II trial of bevacizumab and trabectedin with or without carboplatin in partially platinum-sensitive recurrent ovarian cancer (ROC) women. 20th International Meeting of the ESGO. 1 page, (2017).
Cook et al., Tumour-associated macrophages and cancer. Curr Opin Pharmacol. Aug. 2013;13(4):595-601.
Cooper et al., Structure of the quinone antibiotic EM5519 and the behavior of quinones in fast atom bombardment mass spectrometry. J Antibiot (Tokyo). Jan. 1985;38(1):24-30.
Cope et al., Targeting the Molecular and Immunologic Features of Leiomyosarcoma. Cancers (Basel). Mar. 31, 2023;15(7):2099, 24 pages.
Corey et al., Enantioselective Total Synthesis of Ecteinascidin 743. J Am Chem Soc. 1996;118:9202-9203.
Cote et al., Efficacy and Safety of Lurbinectedin (LUR) with Irinotecan (IRI) in a Phase 2 Expansion Cohort of Patients (Pts) with Synovial Sarcoma (SS). Asco American Society of Clinical Oncology, 60th Annual Meeting. Poster, Abstract 486, May 31-Jun. 4, 2024.
Cote et al., Efficacy and safety of lurbinectedin (LUR) with irinotecan (IRI) in a phase 2 expansion cohort of patients (Pts) with synovial sarcoma (SS). J Clin Oncol. 2024;42(Suppl 16):Abstract 11560.
Cote et al., Efficacy of combination lurbinectedin (LURBI) + doxorubicin (DOX) from the phase 1B soft-tissue sarcoma (STS) lead-in to a randomized phase 2 trial in leiomyosarcoma (Lms). J Clin Oncol. 2023;41(Suppl 16), Abstract 11507.
Cote et al., Efficacy of combination lurbinectedin + doxorubicin from the phase 1B soft-tissue sarcoma lead-in to a randomized phase 2 trial in leiomyosarcoma. ASCO American Society of Clinical Oncology, 59th Annual Meeting, 32 pages, slideshow Jun. 2-6, 2023.
Cote et al., Randomized Controlled, Open-label, Phase IIb/III Study of Lurbinectedin in Combination with Doxorubicin versus Doxorubicin Alone as First-line Treatment in Patients with Metastatic Leimyosarcoma. ASCO American Society of Clinical Oncology, 60th Annual Meeting. 1 page, poster, May 31-Jun. 4, 2024.
Cote et al., Randomized controlled, open-label, phase IIB/III study of lurbinectedin in combination with doxorubicin versus doxorubicin alone as first-line treatment in patients with metastatic leimyosarcoma. J Clin Oncol. 2024;42(Suppl 16):Abstract TPS11590.
Cote et al., Safety and efficacy of the combination lurbinectedin plus doxorubicin from a phase 1b trial in patients with advanced/metastatic soft-tissue sarcoma. Clinical Cancer Research. 2024;30(13):2702-2708, pre-publication edition.
Cote et al., Saludo: a randomized phase IIb/III study of lurbinectedin plus doxorubicin as first-line treatment in leiomyosarcoma. Future Oncol. Apr. 2025;21(8):943-951.
Cousin et al., Efficacy and safety of lurbinectedin in elderly patients with relapsed SCLC. 2023 ASCO Annual Meeting. 7 pages, slideshow, (2023).
Cousin et al., Efficacy and safety of lurbinectedin in elderly patients with relapsed Sclc. Asco American Society of Clinical Oncology, 59th Annual Meeting. Abstract 8591 poster, Jun. 2-6, 2023.
Cousin et al., Efficacy and safety of lurbinectedin in elderly patients with relapsed Sclc. J Clin Oncol. 2023;41(Suppl 16), Abstract 8591.
Cromie, Potent cancer drugs made - sea squirts provide recipe. The Harvard Gazette. 6 pages, May 4, 2000.
Cuevas et al., Ecteinascidin-743 (Yondelis), Aplidin, and Irvalec. Anticancer Agents from Natural Products, Second Edition. CRC Press, Gordon M. Cragg (Ed.). Chapter 12, pp. 291-316, (2012).
Cuevas et al., Semisynthesis Approach of Ecteinascidin 743 (ET-473, Yondelis). Drug Discovery from Natural Products. Chapter 1, pp. 5-12, (2012).
Cuevas et al., Synthesis of ecteinascidin ET-743 and phthalascidin Pt-650 from cyanosafracin B. Org Lett. Aug. 10, 2000;2(16):2545-8.
Cuevas, Development of Lurbinectedin for the Treatment of Sclc. Xiv Ecmnp, European Conference on Marine Natural Products. 1 page, Abstract IL 3, (2025).
Curt et al., Understanding Real-Life Response to Lurbinectedin as Second Line Therapy in Patients with Extensive Stage Small-Cell Lung Cancer. Journal of Thoracic Oncology. Nov. 2023; 18(11S): S705-S706, Abstract EP13.07-01.
Cvitkovic et al., Final Results of a Phase I Study of Ecteinascidin-743 (ET-743) 24 Hour (h) Continuous Infusion (CI) in Advanced Solid Tumors (AST) Patients (pts). Clinical Pharmacology. 1999;18:180a, Abstract 690.
Da Rocha et al., Natural products in anticancer therapy. Curr Opin Pharmacol. Aug. 2001;1(4):364-9.
D'Ambrosia et al., TOMAS2; A randomized phase II study from the Italian Sarcoma Group (ISG) of trabectedin plus olaparib (T+O) or trabectedin (T) in advanced, metastatic, or unresectable soft tissue sarcomas (STS) after failure of standard treatments. Annals of Oncology. 2023;34(S2):S1332, Abstract LBA91.
D'Ambrosia et al., Trabectedin-olaparib combination or trabectedin in advanced soft tissue sarcomas after failure of anthracycline-based treatment (TOMAS2): a randomized phase 2 study from the Italian Sarcoma Group. Annals of Oncology. 35 pages, (2025). pre-publication edition.

(56) References Cited

OTHER PUBLICATIONS

Daniela, The combination of ET-743 and Irinotecan is active in preclinical models in rhabdomyosarcoma. 16th EORTC-NCI-AARC Symposium on Molecular Targets and Cancer Therapeutics. Slideshow, 11 pages, Oct. 1, 2004.
David-Cordonnier et al., DNA and non-DNA targets in the mechanism of action of the antitumor drug trabectedin. Chem Biol. Nov. 2005;12(11):1201-10.
De Angelo et al., Phase II Study of Irinotecan (CPT-11) in Relapsed or Refractory Soft Tissue Sarcoma (Sts). Asco Annual Meeting. Abstract 2186, (2000).
De Lima et al., Consecutive Inhibition of Telomerase and Alternative Lengthening Pathway Promotes Hodgkin's Lymphoma Cell Death. Biomedicines. Sep. 16, 2022;10(9):2299, 15 pages.
Del Campo et al., Phase II randomized study of trabectedin given as two different every 3 weeks dose schedules (1.5 mg/m2 24 h or 1.3 mg/m2 3 h) to patients with relapsed, platinum-sensitive, advanced ovarian cancer. Ann Oncol. Nov. 2009;20(11):1794-802.
Delaloge et al., Preliminary Safety and Activity Results of Trabectedin in a Phase II Dedicated to Triple Negative (Er-, Pr-, HER2-), HER2+, or BRCA1/2 Germline-mutated Metastatic Breast Cancer (MBC) patients (pts). ASCO. Poster, 1 page, (2009).
Delaloge et al., Preliminary safety and activity results of trabectedin in a phase II trial dedicated to triple-negative (Er-, Pr-, HER2-), HER2+++, or BRCA1/2 germ-line-mutated metastatic breast cander (MBC) patients (pts). Journal of Clinical Oncology. 2009;27(15):43s, Abstract 1010.
Demetri et al., A Randomized Phase 3 Study of Trabectedin or Dacarbazine for the Treatment of Patients With Advanced Liposarcoma (LPS) or Leiomyosarcoma (Lms). Asco Annual '15 Meeting. 27 pages, (2015).
Demetri et al., A randomized phase III study of trabectedin (T) or dacarbazine (D) for the treatment of patients (pts) with advanced liposarcoma (LPS) or leiomyosarcoma (Lms). J Clin Oncol. 2015;33:Abstract 10503, 2 pages.
Demetri et al., Efficacy and safety of trabectedin (T) or dacarbazine (D) for treatment of patients (pts) with advanced leiomyosarcoma (LMS) or liposarcoma (LPS) after prior chemotherapy. p. S700, Abstract 3436, (2015).
Demetri et al., Efficacy and safety of trabectedin in patients with advanced or metastatic liposarcoma or leiomyosarcoma after failure of prior anthracyclines and ifosfamide: results of a randomized phase II study of two different schedules. J Clin Oncol. Sep. 1, 2009;27(25):4188-96.
Demetri et al., Efficacy and Safety of Trabectedin or Dacarbazine for Metastatic Liposarcoma or Leiomyosarcoma After Failure of Conventional Chemotherapy: Results of a Phase III Randomized Multicenter Clinical Trial. J Clin Oncol. Mar. 10, 2016;34(8):786-93.
Demetri et al., Efficacy and safety of trabectedin or dacarbazine for treatment of patients with advanced leiomyosarcoma or liposarcoma after prior chemotherapy. 1 page, (2015).
Demetri et al., Impact of independent review on efficacy outcomes in a randomised multicenter trial of trabectedin given by two dosing regimens in patients (pts) with progressing leiomyosarcomas or liposarcomas (Lsarcomas). ECCO 14—the European Cancer Conference. European Journal of Cancer Supplements. 2007 Sept;5(4):401, Abstract O#7500, 2 pages.
Demetri et al., Long-term results of a randomized phase II study of trabectedin by two different dose and schedule regimens in patients with advanced liposarcoma or leiomyosarcoma after failure of prior anthracyclines and ifosfamide. ASCO 45th Annual Meeting. Abstract 10509. Slideshow, 20 pages, (2009).
Demetri et al., Long-term results of a randomized phase II study of trabectedin by two different dose and schedule regimens in patients with advanced liposarcoma or leiomyosarcoma after failure of prior anthracyclines and ifosfamide. Journal of Clinical Oncology. 2009;27(15):538s, Abstract 10509.
Demetri et al., Patient-reported outcomes from randomized, phase-3 study of trabectedin (T) vs. dacarbazine (D) in advanced leiomyosarcoma (LMS) or liposarcoma (Lps). J Clin Oncol. 34:Abstract 10061.
Health Product InfoWatch, Health Products Mentioned in this Issue. Health Canada. 7 pages, Jan. 2023.
Herdon et al., A design alternative for two-stage, phase II, multicenter cancer clinical trials. Control Clin Trials. Oct. 1998;19(5):440-50.
Hoda et al., Trabectedin Is Active against Malignant Pleural Mesothelioma Cell and Xenograft Models and Synergizes with Chemotherapy and Bcl-2 Inhibition In Vitro. Mol Cancer Ther. Oct. 2016;15(10):2357-2369.
Hu et al., An oral and selective CDK12 inhibitor demonstrates robust anti-tumor activity. Cancer Res. 2022;82(12 Suppl):Abstract 5393.
Isakoff et al., Multicenter phase II trial of the novel compound PM01183 (lurbinectedin) in BRCA1/2-associated or unselected metastatic breast cancer. San Antonio Breast Cancer Symposium (SABCS). 1 page, poster, Dec. 10-14, 2013.
Isakoff et al., Multicenter phase II trial of the novel compound PM01183 (P) in BRCA1/2-associated or unselected metastatic breast cancer (MBC). Cancer Res. 2013;73(24 Suppl):Abstract OT1-4-01.
Jackman et al., Small-cell lung cancer. Lancet. Oct. 15-21, 2005;366(9494):1385-96.
Jimenez et al., Marine Natural Products in Medicinal Chemistry. ACS Med Chem Lett. Sep. 13, 2018;9(10):959-961.
Jorger et al., Safety profile and associated costs of therapies for relapsed small cell lung cancer in Switzerland. Annals of Oncology. 2022;33(S2):S102, Abstract 153P.
Jung et al., On the estimation of the binomial probability in multistage clinical trials. Stat Med. Mar. 30, 2004;23(6):881-96.
Kaland et al., U.S. Food and Drug Administration Analysis of Newly Identified Adverse Events With Lurbinectedin: Extravasation, Rhabdomyolysis, and Tumor Lysis Syndrome. Clin Lung Cancer. Dec. 2022;23(8):e556-e562. pre-publication edition.
Kashima et al., Advances in biology and novel treatments of SCLC: The four-color problem in uncharted territory. Semin Cancer Biol. Nov. 2022; 86(Pt 2):386-395. pre-publication edition.
Kawaguchi et al., Extraskeletal myxoid chondrosarcoma: a Multi-Institutional Study of 42 Cases in Japan. Cancer. Mar. 1, 2003;97(5):1285-92.
Keogh et al., Emerging Biomarkers and the Changing Landscape of Small Cell Lung Cancer. Cancers (Basel). Aug. 3, 2022;14(15):3772, 22 pages.
Khurshid et al., Multidisciplinary assessment of patients with extensive stage small cell lung cancer: A geriatric tumor board. CA Cancer J Clin. Nov. 2025-Dec. 75(6):475-484.
Kim et al., Antibody-Drug Conjugate Targeting c-Kit for the Treatment of Small Cell Lung Cancer. Int J Mol Sci. Feb. 18, 2022;23(4):2264, 14 pages.
King et al., Quantitative determination of lurbinectedin, its unbound fraction and its metabolites in human plasma utilizing ultra-performance Lc-Ms/Ms. PLoS One. Mar. 30, 2023;18(3):e0283783, 20 pages.
Kristeleit et al., Doxorubicin plus lurbinectedin in patients with advanced endometrial cancer: results from an expanded phase I study. Int J Gynecol Cancer. Nov. 2021;31(11):1428-1436.
Kundu et al., Characterization of lurbinectedin as a single agent and in combinations with DNA damage response inhibitor for the treatment and bio-marker discovery of SCLC. Cancer Res. 2021;81(13 Suppl):Abstract 1022.
Leary et al., Pooled safety analysis of single-agent lurbinectedin versus topotecan (Results from a randomized phase III trial CORAIL and a phase II basket trial). ASCO American Society of Clinical Oncology, 56th Annual Meeting, May 31-Jun. 4, 2020.
Leary et al., Pooled safety analysis of single-agent lurbinectedin versus topotecan (Results from a randomized phase III trial CORAIL and a phase II basket trial). J Clin Oncol. 2020;38(15 Suppl), 2 pages, (2020).

(56) References Cited

OTHER PUBLICATIONS

Leverson et al., Exploiting selective BCL-2 family inhibitors to dissect cell survival dependencies and define improved strategies for cancer therapy. Sci Transl Med. Mar. 18, 2015;7(279):279ra40, 11 pages.
Liang et al., An update of new small-molecule anticancer drugs approved from 2015 to 2020. Eur J Med Chem. Aug. 5, 2021;220:113473, 43 pages.
Liguori et al., Absence of Biomarker-Driven Treatment Options in Small Cell Lung Cancer, and Selected Preclinical Candidates for Next Generation Combination Therapies. Front Pharmacol. Aug. 31, 2021;12:747180, 11 pages.
Liguori et al., Preclinical studies with ONC201/TIC10 and lurbinectedin as a novel combination therapy in small cell lung cancer (SCLC). Am J Cancer Res. Feb. 15, 2022;12(2):729-743.
Liguori et al., Synergistic activity of Lurbinectedin plus ONC201 in SCLC is associated with ATF4, Chop and pChk1 induction. Cancer Res. 82(12 Suppl):Abstract 4064.
Lin et al., Tumor-associated macrophages in tumor metastasis: biological roles and clinical therapeutic applications. J Hematol Oncol. Jul. 12, 2019;12(1):76, 16 pages.
Liu et al., Biomimetic 3D-Bioprinted organoids of thymic epithelial tumors for translational drug screening and biomarker identification. Mater Today Bio. Feb. 11, 2026;37:102878, 16 pages.
Liu et al., New pharmaceuticals approved by FDA in 2020: Small-molecule drugs derived from amino acids and related compounds. Chirality. Jan. 2022;34(1):86-103.
Lochmann et al., BCL-2 inhibition is a promising therapeutic strategy for small cell lung cancer. Oncoscience. Aug. 14, 2018;5(7-8):218-219.
Loeuille et al., Physicochemical stability of lurbinectedin reconstituted at 500mg/mL and diluted at 15, 30, and 70mg/mL in 0.9% sodium chloride and 5% dextrose. European Journal of Oncology Pharmacy. 2021;4(3):e032, 7 pages.
Longo-Munoz et al., Lurbinectedin in patients with pretreated neuroendocrine tumours: Results from a phase II basket study. Eur J Cancer. Sep. 2022;172:340-348.
Lopez-Casas et al., Lurbinectedin (PM01183) in Combination with Gemcitabine in Patient-Derived, Pancreatic Ductal Adenocarcinoma (PDA) Xenografts. Eur J Cancer. Nov. 7, 2012;48(Suppl 6):66-67, Abstract 221.
Lopez-Casas et al., Lurbinectedin (PM01183) in Combination wtih Gemcitabine in Patient-Derived (AVATAR), Pancreatic Ductal Adenocarcinoma (PDA) Xenografts. 24th EORTC-NCI-AACR Symposium on Molecular Targets and Cancer Therapeutics. 1 page, poster, Nov. 6-9, 2012.
Lubomirov et al., Population pharmacokinetic-based targeted exome sequencing (PopPK-TES) approach to assess the impact of genetic variants on pharmacokinetics of lurbinectedin in patients with advanced cancer. 27th Annual Meeting of the Population Approach Group in Europe. Abstract 8489, May 29-Jun. 1, 2018.
Lubomirov et al., Population pharmacokinetic-based targeted exome sequencing (PopPK-TES) approach to assess the impact of genetic variants on pharmacokinetics of lurbinectedin in patients with advanced cancer. 27th Annual Meeting of the Population Approach Group in Europe. Poster IV-16, (2018).
Luvero et al., Ovarian cancer relapse: From the latest scientific evidence to the best practice. Crit Rev Oncol Hematol. Aug. 2019; 140:28-38.
Mallarkey et al., Targeted therapies in medical oncology: successes, failures and next steps. Ther Adv Med Oncol. Jan. 2013;5(1):5-16.
Mangues et al., Lurbinectedin (PM01183) Synergizes with Gemcitabine in NSCLC, Ovarian and Pancreas Tumor Xenografts. 24th EORTC-NCI-AACR Symposium on Molecular Targets and Cancer Therapeutics. 1 page, poster, Nov. 6-9, 2012.
Mangues et al., Lurbinectedin (PM01183) Synergizes with Gemcitabine in NSCLC, Ovarian and Pancreas Tumor Xenografts. Eur J Cancer. Nov. 7, 2012;48(Suppl 6):67-68, Abstract 223.
Manzo et al., Lurbinectedin in small cell lung cancer. Front Oncol. Aug. 3, 20220; 12:932105, 8 pages.
Marchetti et al., An overview of early investigational therapies for chemoresistant ovarian cancer. Expert Opin Investig Drugs. 2015;24(9):1163-83.
Mark et al., Long-term benefit of lurbinectedin as palliative chemotherapy in progressive malignant pleural mesothelioma (MPM): final efficacy and translational data of the SAKK 17/16 study. ESMO Open. Jun. 2022; 7(3):100446, 8 pages.
Markham et al., Lurbinectedin: First Approval. Drugs. Sep. 2020;80(13):1345-1353.
Martinez Diez et al., Lurbinectedin shows potent activity in all four molecular subtypes of Small Cell Lung Cancer (SCLC) and POU2F3 and SLFN11 and biomarkers for a better response. AACR Annual Meeting 2023, poster, 1 page, (2023).
Martinez Diez et al., Lurbinectedin shows potent activity in all four molecular subtypes of small cell lung cancer (SCLC) and POU2F3 and SLFN11 and biomarkers for a better response. Cancer Res. 83(7 Suppl):Abstract 6247.
Masacchio et al., Preclinical and Clinical Evidence of Lurbinectedin in Ovarian Cancer: Current Status and Future Perspectives. Front Oncol. Feb. 23, 2022;12:831612, 6 pages.
Matsui et al., High mRNA expression of POU2F3 in small cell lung cancer cell lines predicts the effect of lurbinectedin. Thorac Cancer. Apr. 2022;13(8):1184-1192.
PharmaMar, PharmaMar Group presents results for 2019. 3 pages, Feb. 26, 2020.
PharmaMar, PharmaMar Group presents results for the first quarter 2020. Press Release, 2 pages, Apr. 23, 2020.
PharmaMar, PharmaMar Group presents results up to Sep. 30, 2020. Press Release, 3 pages, Nov. 3, 2020.
PharmaMar, PharmaMar Group reported net profit euro113.8M at Jun. 30, 2020. Press Release, 3 pages, Jul. 30, 2020.
PharmaMar, PharmaMar Group reports 2018 results. Press Release, 3 pages, Feb. 28, 2019.
PharmaMar, PharmaMar Group reports 2022 annual results. Press Release, 5 pages, Feb. 28, 2023.
PharmaMar, PharmaMar Group reports 9 month 2021 financial results. Press Release, 4 pages, Oct. 28, 2021.
PharmaMar, PharmaMar Group reports a 27% increase in recurring business, revenues plus royalties, in 2021, to euro 165 million. Press Release, 4 pages, Feb. 28, 2022.
PharmaMar, PharmaMar Group reports euro45.5 million in revenues (+8%). Press Release, 2 pages, Apr. 27, 2017.
PharmaMar, PharmaMar Group reports first quarter financial results. Press Release, 2 pages, Apr. 26, 2018.
PharmaMar, PharmaMar Group reports H1 2021 Financial Results. Press Release, 4 pages, Jul. 29, 2021.
PharmaMar, PharmaMar Group reports nine months 2022 financial results. Press Release, 3 pages, Oct. 27, 2022.
PharmaMar, PharmaMar Group reports record results for 2020. Press Release, 4 pages, Feb. 26, 2021.
PharmaMar, PharmaMar Group reports results for the first half 2023. Press Release, 4 pages, Jul. 27, 2023.
PharmaMar, PharmaMar Group reports results for the first half of 2022. Press Release, 3 pages, Jul. 27, 2022.
PharmaMar, PharmaMar Group reports results for the first quarter of 2019. Press Release, 2 pages, Apr. 26, 2019.
PharmaMar, PharmaMar Group reviews 2016 at its annual general shareholders' meeting. Press Release, 3 pages, Jun. 29, 2017.
PharmaMar, PharmaMar has announced that the Spanish Medicines Agency has authorized the APLICOV-PC clinical trial with APlidin (plitidepsin) for the treatment of patients with COVID-19. Press Release, 4 pages, Apr. 28, 2020.
PharmaMar, PharmaMar has announced the sale of Xylazel for euro21.8 million. Press Release, 2 pages, Sep. 20, 2018.
PharmaMar, PharmaMar has filed for approval of lurbinectedin for the treatment of metastatic Small Cell Lung Cancer in the UK. Press Release, 2 pages, May 4, 2022.
PharmaMar, PharmaMar has filed lurbinectedin for Temporary Marketing Authorisation with the Swiss Agency for Therapeutic Products. Press Release, 2 pages, Jul. 20, 2020.
PharmaMar, PharmaMar has filed New Drug Application for lurbinectedin with the FDA for the treatment of relapsed small cell lung cancer. Press Release, 3 pages, Dec. 17, 2019.

(56) References Cited

OTHER PUBLICATIONS

PharmaMar, PharmaMar has held its General Shareholders Meeting today. Press Release, 4 pages, Jun. 18, 2020.
PharmaMar, PharmaMar has presented new results for Zepzelca (lurbinectedin) in sensitive patients with Small-Cell Lung Cancer, candidates for "re-challenge." Press Release, 4 pages, Sep. 17, 2020.
PharmaMar, PharmaMar has presented results of its antitumor compounds trabectedin and plocabulin at the CTOS Congress. Press Release, 4 pages, Nov. 18, 2019.
PharmaMar, PharmaMar has presented Yondelis data in ovarian cancer at ESGO. Press Release, 2 pages, Nov. 4, 2019.
PharmaMar, PharmaMar has published the results of its antibody conjugate active in breast, ovarian and gastric cancers that express HER2. Press Release, 3 pages, Feb. 16, 2018.
PharmaMar, PharmaMar has requested the process of re-examination for Aplidin from the EMA. Press Release, 2 pages, Jan. 3, 2018.
PharmaMar, PharmaMar has submitted a Phase II clinical trial of Aplidin (plitidepsin) for the treatment of COVID-19 to the Spanish Medicines Agency. Press Release, 3 pages, Apr. 2, 2020.
PharmaMar, PharmaMar holds its Annual General Shareholders' Meeting. Press Release, 3 pages, Jun. 26, 2019.
PharmaMar, PharmaMar in San Francisco during the J.P. Morgan Annual Healthcare Conference in San Francisco. Press Release, 2 pages, Jan. 9, 2020.
PharmaMar, PharmaMar increased R&D investment in oncology by 23% in 2022. Press Release, 3 pages, Sep. 22, 2023.
PharmaMar, PharmaMar initiates a Phase IIb/III clinical trial of Zepzelca (lurbinectedin) for the treatment of patients with metastatic leiomyosarcoma. Press Release, 3 pages, Oct. 31, 2023.
PharmaMar, PharmaMar initiates first human clinical trial of a molecule, PM534, for cancer patients. Press Release, 2 pages, Dec. 30, 2022.
PharmaMar, PharmaMar is announcing its intention to conduct a registered public offering of American Depositary Shares. Press Release. 2 pages, Sep. 7, 2018.
PharmaMar, PharmaMar is present wtih its Atlantis study at the IASLC Congress on small cell lung cancer in New York. Press Release, 2 pages, Apr. 8, 2019.
PharmaMar, PharmaMar launches clinical trial on solid tumors with its new molecule PM54. Press Release, 1 page, May 4, 2023.
PharmaMar, PharmaMar launches its new corporate website. Press Release, 2 pages, Dec. 10, 2021.
PharmaMar, PharmaMar leads the ONCOLIBETRYX consortium together with four research centers to develop new marine-based oncology drug administration strategies. Press Release, 3 pages, Dec. 2, 2022.
PharmaMar, PharmaMar leads the TERINMUN initiative, a research consortium in search of immunotherapies based on marine-derived compounds. Press Release, 3 pages, Dec. 22, 2022.
PharmaMar, PharmaMar licences lurbinectedin to Key Oncologics (Pty) Ltd for its marketing and distribution in Africa. Press Release, 3 pages, Sep. 12, 2023.
PharmaMar, PharmaMar licenses fully synthetic marine-derived payloads to Seattle Genetics for use in drug conjugates. Press Release, 2 pages, Feb. 14, 2018.
PharmaMar, PharmaMar maintains that there was a conflict of interest in the Aplidin (plitidepsin) case. Press Release, 3 pages, Feb. 6, 2023.
PharmaMar, PharmaMar presents a new Antibody Drug Conjugate at the World ADC Congress in San Diego. Press Release, 2 pages, Nov. 12, 2018.
PharmaMar, PharmaMar presents at MaNaPro & ECMNP its latest advances in the development of compounds of marine origin. Press Release, 3 pages, Sep. 2, 2019.
PharmaMar, PharmaMar presents in oral session at ASCO the ADMYRE study's adjusted overall survival with plitidepsin. Press Release, 2 pages, Jun. 5, 2018.
PharmaMar, PharmaMar presents new data on the treatment of multiple myeloma and ovarian cancer at the AACR Congress. Press Release, 3 pages, Apr. 4, 2017.
PharmaMar, PharmaMar presents new data on Yondelis (trabectedin) in combination with immunotherapy at ESMO. Press Release, 3 pages, Sep. 21, 2020.
PharmaMar, PharmaMar presents new data on Zepzelca (lurbinectedin) in combination with irinotecan at an oral session at (rescheduled) IASLC 2020. Press Release, 3 pages, Feb. 1, 2021.
PharmaMar, PharmaMar presents new lurbinectedin data at the World Conference on Lung Cancer. Press Release, 3 pages, Sep. 9, 2019.
Bartsch et al., Growth-inhibiting effect of crude pineal extracts on human melanoma cells in vitro is different from that of known synthetic pineal substances. J Neural Transm. 1987;69(3-4):299-311.
Bednarek et al., Liver metastasis or a pseudocyst? A rare presentation of leiomyosarcoma's metastasis in the liver. Contemp Oncol (Pozn). 2022;26(4):306-309.
Benedetti Panici et al., Phase II Trial of Weekly Trabectedin Plus Weekly Pegylated Liposomal Doxorubicin for Treatment of Advanced, Persistent or Recurrent Ovarian Carcinoma. International Journal of Gynecological Cancer. Nov. 2014;24(Suppl 4):123.
Berdel et al., Trabectedin plus CD13-targeted tissue factor tTF-NGR against advanced relapsed or refractory soft tissue sarcoma: Translational data, clinical safety and efficacy. Annals of Oncology. 2025;36(S2):S1445, Abstract 2711P.
Bergamini et al., Treatment of Ovarian Cancer Cells with Olaparib and Trabectedin Modulates the Expression of Immune-related Molecules and the Killing Ability of TCR-edited T Cells. Int J Gynecol Cancer. 2024;34(Suppl 1):A504, Abstract 780.
Beroukhim et al., The landscape of somatic copy-number alteration across human cancers. Nature. Feb. 18, 2010;463(7283):899-905.
Besse et al., A phase III study of lurbinectedin alone or in combination with irinotecan vs investigator's choice (topotecan or irinotecan) in patients with relapsed small cell lung cancer (Sclc; Lagoon trial). ASCO American Society of Clinical Oncology, 59th Annual Meeting, Posater, Abstract TPS8613, Jun. 2-6, 2023.
Besse et al., A phase III study of lurbinectedin alone or in combination with irinotecan vs investigator's choice (topotecan or irinotecan) in patients with relapsed small cell lung cancer (Sclc; Lagoon trial). J Clin Oncol. 2023;41 (Suppl 16), Abstract TPS8613.
Bhamidipati et al., Lurbinectedin, a DNA minor groove inhibitor for neuroendocrine neoplasms beyond small cell lung cancer. Oncoscience. Jun. 14, 2023;10:22-23.
Bhavnani et al., Zepzelca (lurbinectedin) and Atezolizumab (Tecentriq) Combination Granted U.S. Fda Priority Review for First-Line Maintenance Treatment of Extensive-Stage Small Cell Lung Cancer. Press Release, 7 pages, Jun. 10, 2025.
Blay et al., Efficacy and safety of trabectedin as an early treatment for advanced or metastatic liposarcoma and leiomyosarcoma. Future Oncol. Jan. 2014;10(1):59-68. pre-publication editon.
Blay, Treatment of advanced soft tissue sarcoma by histological subtype: wish, prediction or reality? Future Oncol. Sep. 2019;15(26s):5-10. pre-publication edition.
Bleehen et al., Controlled trial of twelve versus six courses of chemotherapy in the treatment of small-cell lung cancer. Report to the Medical Research Council by its Lung Cancer Working Party. Br J Cancer. Apr. 1989;59(4):584-90.
Blume-Jensen et al., Oncogenic kinase signalling. Nature. May 17, 2001;411(6835):355-65.
Bodey et al., Genetically engineered monoclonal antibodies for direct anti-neoplastic treatment and cancer cell specific delivery of chemotherapeutic agents. Curr Pharm Des. Feb. 2000;6(3):261-76.
Borbe et al., Failure of taxol-based combination chemotherapy for malignant glioma cannot be overcome by G2/M checkpoint abrogators or altering the p53 status. Cancer Chemother Pharmacol. 1999;44(3):217-27.
Borgoni et al., Depletion of tumor-associated macrophages switches the epigenetic profile of pancreatic cancer infiltrating T cells and restores their anti-tumor phenotype. Oncoimmunology. Nov. 13, 2017;7(2):e1393596, pre-publication edition.

(56) References Cited

OTHER PUBLICATIONS

Boyne et al., Comparative Effectiveness of Lurbinectedin for the Treatment of Relapsed Small Cell Lung Cancer in the Post-Platinum Setting: A Real-World Canadian Synthetic Control Arm Analysis. Target Oncol. Sep. 2023;18(5):697-705.
Bray et al., Global cancer statistics 2018: GLOBOCAN estimates of incidence and mortality worldwide for 36 cancers in 185 countries. CA Cancer J Clin. Nov. 2018;68(6):394-424.
Bredberg et al., Ciprofloxacin-induced inhibition of topoisomerase II in human lymphoblastoid cells. Antimicrob Agents Chemother. Mar. 1991;35(3):448-50.
Bria et al., Gemcitabine-based combinations for inoperable pancreatic cancer: have we made real progress? A meta- analysis of 20 phase 3 trials. Cancer. Aug. 1, 2007;110(3):525-33.
Brichacek, Top 200 Brand-Name Drugs by Retail Dollars in 2006. Njardarson Group, Cornell University, 1 page, (2006).
Brichacek, Top 200 Generic Drugs by Retail Dollars in 2006. Njardarson Group, Cornell University, 1 page, (2006).
Broto et al., Randomized, Open, Prospective, Phase II Clinical Trial of Doxorubicin (DOXO) vs. Trabectedin Plus DOXO in the First-Line Treatment of Patients (pts) with Advanced Non-operable and/or Metastatic Soft Tissue Sarcomas (STS): Geis-20 Study. 37th ESMO Congress, 1 page, (2012).
Broto et al., Randomized, Open, Prospective, Phase II Clinical Trial of Doxorubicin (DOXO) vs. Trabectedin Plus DOXO in the First-Line Treatment of Patients (pts) with Advanced Non-operable and/or Metastatic Soft Tissue Sarcomas (STS): Geis-20 Study. Annals of Oncology. Sep. 2012;23(Suppl 9):ix490, Abstract 1517TiP.
Brown et al., Epigenomics and epigenetic therapy of cancer. Trends Mol Med. 2002;8(4 Suppl):S43-8.
Brown et al., NCI's anticancer drug screening program may not be selecting for clinically active compounds. Oncol Res. 1997;9(5):213-5.
Bui-Nguyen et al., A phase IIb multicentre study comparing the efficacy of trabectedin to doxorubicin in patients with advanced or metastatic untreated soft tissue sarcoma: the TRUSTS trial. Eur J Cancer. Jul. 2015;51(10):1312-20.
Buolamwini et al., Novel anticancer drug discovery. Curr Opin Chem Biol. Aug. 1999;3(4):500-9.
Burd et al., Oxidation of Indole and Indole Derivatives Catalyzed by Nonheme Chloroperoxidases. Applied Biochemistry and Microbiology. 2001;37(3):248-250.
Byfield et al., Carrier-dependent and carrier-independent transport of anti-cancer alkylating agents. Nature. Nov. 19, 1981;294(5838):281-3.
Cable et al., The Biosynthesis of Tuberin from Tyrosine and Glycine; Observations on the Stereochemistry Associated with the Conversion of Glycine through Methylenetetrahydrofolate into Methenyltetrahydrofolate. J Chem Soc Perkin Trans 1. 1987:1593-1598.
Calabresi et al., Chemotherapy of Neoplastic Diseases. Goodman & Gilman's The Pharmcological Basis of Therapeutics, Ninth Edition, McGraw-Hill, New York. Section X, pp. 1225-1229, (1996).
Calip et al., EP.17.35 Treatment-Associated Interstitial Lung Disease in Extensive-Stage Small Cell Lung Cancer. IASLC 2025 World Conference on Lung Cancer, Abstract Book. Page 1901, (2025).
Camorani et al., Trabectedin modulates the senescence-associated secretory phenotype and promotes cell death in senescent tumor cells by targeting NF-KB. Oncotarget. Apr. 13, 2018;9(28):19929-19944.
CAMPTOSTAR Label. 46 pages, Final Package Insert Apr. 20, 2000.
Carbone, Molecular Modalities in the Treatment of Lung Cancer. Oncology. Oct. 1, 1999;13(10):12 pages.
Carter, Improving the efficacy of antibody-based cancer therapies. Nat Rev Cancer. Nov. 2001;1(2):118-29.
Casagrande et al., Emerging Approaches to Study Microenvironmental Interactions and Drug Activity in Classical Hodgkin Lymphoma. Cancers (Basel). May 14, 2022;14(10):2427, 25 pages.
Casagrande et al., In Doxorubicin-Adapted Hodgkin Lymphoma Cells, Acquiring Multidrug Resistance and Improved Immunosuppressive Abilities, Doxorubicin Activity Was Enhanced by Chloroquine and GW4869. Cells. Nov. 29, 2023;12(23):2732, 21 pages.
Casagrande et al., In ovarian cancer maraviroc potentiates the antitumoral activity and further inhibits the formation of a tumor-promoting microenvironment by trabectedin. Biomed Pharmacother. Mar. 2024;172:116296, 13 pages.
Casanova et al., Phase II Study of 3-hour Infusion Ecteinascidin-743 (ET-743) in Pretreated Adult and Pediatric Patients with Advanced or Recurrent Sarcomas: Preliminary Results. 24th Annual Meeting SIOP. 1 page, Sep. 2002.
Cassier et al., Trabectedin and its potential in the treatment of soft tissue sarcoma. Ther Clin Risk Manag. Feb. 2008;4(1):109-16.
Castelli et al., Modulation of the myeloid compartment of the immune system by angiogenic- and kinase inhibitor-targeted anti-cancer therapies. Cancer Immunol Immunother. Jan. 2015;64(1):83-9.
Caves et al., Patent Expiration, Entry, and Competition in the U.S. Pharmaceutical Industry. Brookings Papers on Economic Activity: Microeconomics. 66 pages, Jan. 1, 1991.
Cecil Textbook of Medicine, 21st edition. W.B. Saunders Company, Philadelphia. Chapter 198, pp. 1060-1074, (2000).
Cendrowicz et al., The Role of Macrophages in Cancer Development and Therapy. Cancers (Basel). Apr. 18, 2021;13(8):1946, 22 pages.
Center for Drug Evaluation and Research, Application No. 207953Orig1s000, Administrative and Correspondence Documents. 362 pages, Oct. 23, 2015.
Center for Drug Evaluation and Research, Application No. 207953Orig1s000, Chemistry Review(s). 35 pages, Oct. 23, 2015.
Center for Drug Evaluation and Research, Application No. 207953Orig1s000, Clinical Pharmacology and Biopharmaceutics Review(s). 65 pages, Oct. 23, 2015.
Lee et al., Anti-angiogenic therapy using thalidomide combined with chemotherapy in small cell lung cancer: a randomized, double-blind, placebo-controlled trial. J Natl Cancer Inst. Aug. 5, 2009;101(15):1049-57.
Lee et al., DCMiC: a double-cylinder micro-chamber platform for high-throughput drug screening and modeling of microenvironmental resistance in Ewing sarcoma. Lab Chip. Jan. 20, 2026;26(2):257-272.
Lee et al., Phase III Soft Tissue Sarcoma Trials: Success or Failure? Curr Treat Options Oncol. Mar. 2017;18(3):19, 16 pages.
Lemery, Yondelis Supplement Approval, NDA 207953/S-009. FDA, U.S. Food & Drug Administration. 4 pages, Dec. 23, 2025.
Li et al., Bidirectional Regulation in the Tumour Microenvironment: The Interaction Between Tumour-Associated Macrophages and T Cells Reshapes the Paradigm of Cancer Immunotherapy. Immunology. Jan. 7, 2026. 22 pages.
Li et al., Characterization of ARC-111 as a novel topoisomerase I-targeting anticancer drug. Cancer Res. Dec. 1, 2003;63(23):8400-7.
Li et al., Sensitivity of soft tissue sarcoma cell lines to chemotherapeutic agents: identification of ecteinascidin-743 as a potent cytotoxic agent. Clin Cancer Res. Sep. 2001;7(9):2908-11.
Liao et al., unctionalized graphene oxide NPs as a nanocarrier for drug delivery system in quercetin/ lurbinectedin as dual sensitive therapeutics for A549 lung cancer treatment. Heliyon. May 14, 2024;10(11):e31212, 12 pages.
Libertini et al., Activity of chemotherapy in a series of patients with locally advanced or metastatic pleomorphic rhabdomyosarcoma: A retrospective analysis. 2014 ASCO Annual Meeting. 2 pages, Abstract 10592, (2014).
Libertini et al., Activity of chemotherapy in a series of patients with locally advanced or metastatic pleomorphic rhabdomyosarcoma: A retrospective analysis. 50th ASCO Annual Meeting. 1 page, May 30- Jun. 3, 201h.
Libre et al., Lurbinectedin versus platinum rechallenge in relapsed extensive stage small cell lung cancer: A retrospective cohort study. J Clin Oncol. May 2024;42(Suppl 16):Abstract e20110.

(56) References Cited

OTHER PUBLICATIONS

Libre et al., Lurbinectedin vs. Platinum Rechallenge in Extensive Stage Small Cell Lung Cancer after Platinum Doublet, A Multicenter Retrospective Study. J Thorac Oncol. Sep. 2024;19(10):S213, Abstract P1.13B.01.
Lichter et al., Biological Activities Exerted by Extracts of Ecteinascidia Turbinata. Food and Drugs from the Sea Proceedings. pp. 117-127, (1972).
Liechti et al., Salicylanilides as inhibitors of the protein tyrosine kinase epidermal growth factor receptor. Eur J Med Chem. Jan. 2004;39(1):11-26.
Liguori et al., Tumor-associated macrophages as incessant builders and destroyers of the cancer stroma. Cancers (Basel). Sep. 28, 2011;3(4):3740-61.
Liu et al., Evaluation of drug combination effect using a Bliss independence dose-response surface model. Stat Biopharm Res. 2018;10(2):112-122.
Liu et al., Host obesity alters the ovarian tumor immune microenvironment and impacts response to standard of care chemotherapy. J Exp Clin Cancer Res. Jul. 12, 2023;42(1):165, 12 pages.
LiverTox: Clinical and Research Information on Drug-Induced Liver Injury. Severity Grading in Drug Induced Liver Injury. livertox.nih.gov. 3 pages, May 4, 2019.
Lopez-Guerrero et al., Trabectedin therapy as an emerging treatment strategy for recurrent platinum-sensitive ovarian cancer. Chin J Cancer. Jan. 2015;34(1):41-9.
Lorusso et al., Efficacy and safety of trabectedin for the treatment of advanced uterine or ovarian carcinosarcoma: Results of a phase II multicenter clinical trial (MITO-26). Gynecol Oncol. Dec. 2022;167(3):436-443. pre-publication edition.
Lorusso et al., Prospective phase II trial of trabectedin in BRCA-mutated and/or BRCAness phenotype recurrent ovarian cancer patients: the MITO 15 trial. Ann Oncol. Mar. 2016;27(3):487-93.
Lorusso et al., Single-Agent Trabectedin Versus Physician's Choice Chemotherapy in Patients With Recurrent Ovarian Cancer With BRCA-Mutated and/or BRCAness Phenotype: A Randomized Phase III Trial. J Clin Oncol. May 1, 2024;42(13):1488-1498. pre-publication edition.
Low, Metabolic Changes of Drugs and Related Organic Compounds. Wilson and Gisvold's Textbook of Organic Medicinal and Pharmaceutical Chemistry, Tenth Edition. Jaime N. Delgado (Ed.), Lippincott-Raven Publishers, Philadelphia. Chapter 3, pp. 43-122, (1998).
Lown et al., Molecular mechanisms of binding and single-strand scission of deoxyribonucleic acid by the antitumor antibiotics saframycins A and C. Biochemistry. Feb. 2, 1982;21(3):419-28.
Lown et al., Structure and conformation of saframycin R determined by high field 1H and 13C NMR and its interactions with DNA in solution. J Antibiot (Tokyo). Sep. 1983;36(9):1184-94.
Lu et al., Aligning organ-specific toxicities with formulation strategies: a rational design approach to chemotherapy optimization. Int J Pharm. Nov. 10, 2025;684:126121, 28 pages.
Lubomirov et al., CYP3A Genotype Is Associated With Variability in the Exposure and Clearance of the Novel Oncogenic Transcription Inhibitor Lurbinectedin. Clin Transl Sci. Apr. 2025;18(4):e70173, 10 pages.
Luo et al., Circumventing resistance within the Ewing sarcoma microenvironment by combinatorial innate immunotherapy. J Immunother Cancer. Sep. 12, 2024;12(9):e009726, 27 pages.
Lustberg et al., Management of neutropenia in cancer patients. Clin Adv Hematol Oncol. Dec. 2012;10(12):825-6.
Mabuchi et al., The activity of trabectedin as a single agent or in combination with everolimus for clear cell carcinoma of the ovary. Clin Cancer Res. Jul. 1, 2011;17(13):4462-73.
Mabuchi, The Activity of Trabectedin as a Single Agent or in Combination with Everolimus for Clear Cell Carcinoma of the Ovary. 17th International Meeting of the ESGO. 1 page, (2011).
Mabuchi, The Activity of Trabectedin as a Single Agent or in Combination with Everolimus for Clear Cell Carcinoma of the Ovary. International Journal of Gynecological Cancer. Oct. 2011;21(Suppl 3):Poster Shift II. 1 page.
Machiels et al., Effects of cytochrome P450 inducer and inhibitor coadministration on the pharmacokinetics of trabectedin in patients with advanced or metastatic solid tumors. 2014 ASCO Annual Meetings. 2 pages, Abstract E13520, (2014).
Mack et al., Dissociation constants and lipophilicity of catecholamines and related compounds. Naunyn Schmiedebergs Arch Pharmacol. Dec. 1979;310(1):1-9.
Magriotis, Synthetic Approaches to the Stereochemically Complex Antiutumor Drug Ecteinascidin-743: A Marine Natural Product by the Name Yondelis or Trabectidin. Stereochemistry and Global Connectivity: The Legacy of Ernest L. Eliel, vol. 2, American Chemical Society. Chapter 5, pp. 61-78, (2017).
Mai et al., Inhibition of Telomerase and the Alternative Lengthening Telomere Pathway Induces Cell Death in Multiple Myeloma. 21st International Myeloma Society Annual Meeting. Pages S193-S194, Abstract p. 273, Sep. 2024.
Malik et al., Tumor-associated macrophages: A sentinel of innate immune system in tumor microenvironment gone haywire. Cell Biol Int. Oct. 2024; 48(10):1406-1449.
Mantovani et al., Pharmacological modulation of monocytes and macrophages. Curr Opin Pharmacol. Aug. 2014;17:38-44.
Mantovani et al., Tumour-associated macrophages as treatment targets in oncology. Nat Rev Clin Oncol. Jul. 2017; 14(7):399-416.
Manzanares et al., Advances in the chemistry and pharmacology of ecteinascidins, a promising new class of anti-cancer agents. Curr Med Chem Anticancer Agents. Nov. 2001;1(3):257-76.
Markman, Docetaxel plus trabectedin appears active in recurrent or persistent ovarian and primary peritoneal cancer after up to three prior regimes: A phase II study of the Gynecologic Oncology Group. Gynecologic Oncology. 2011;122 (2):462.
Martin Broto et al., Trabectedin with concurrent low-dose of radiation therapy for metastatic soft tissue sarcomas: A phase II trial of Spanish, French and Italian sarcoma groups. Annals of Oncology. Oct. 2019;30(Suppl 5):V686-V687, Abstract 1674PD.
Martin et al., Trial watch: Clinical trial cycle times continue to increase despite industry efforts. Nat Rev Drug Discov. Mar. 2017;16(3):157.
Martin-Broto et al., Randomized phase II trial of doxorubicin vs. trabectedin plus doxorubicin in first line treatment of patients with advanced non-resectable or metastatic soft tissue sarcomas: a Spanish Group for Sarcoma Research (GEIS) study. European Journal of Cancer. 2013;49:S875, Abstract 3800.
Martin-Broto et al., Trabectedin with Concurrent Low-dose of Radiation Therapy for Metastatic Soft Tissue Sarcomas (Trasts): A Multicenter European, Single Arm Phase II Trial of Spanish, French and Italian Sarcoma Groups. CTOS 24th Annual Meeting. 1 page, Poster (2019).
Martin-Broto et al., Trabectedin with Concurrent Low-dose of Radiation Therapy for Metastatic Soft Tissue Sarcomas (Trasts): A Multicenter European, Single Arm Phase II Trial of Spanish, French and Italian Sarcoma Groups. CTOS 24th Annual Meeting. Page 490, Poster 224, Abstract 3255113, (2019).
Martin-Broto et al., Trabectedin with concurrent low-dose of radiation therapy for metastatic soft tissue sarcomas: A phase II trial of Spanish, French and Italian sarcoma groups TRASTS Trial). Annals of Oncology. Oct. 2019; 30(Suppl 5):V686-V687, Abstract 1674PD. 2019 ESMO Congress. 1 page, Poster, (2019).
Martin-Broto, Randomized Phase II Trial of Trabectedin Plus Doxorubicin vs Doxorubicin in Advanced or Metastatic Soft Tissue Sarcoma Patients. GEIS-20, slideshow, 20 pages, (2013).
Martinez et al., A new, more efficient, and effective process for the synthesis of a key pentacyclic intermediate for production of ecteinascidin and phthalascidin antitumor agents. Org Lett. Apr. 6, 2000;2(7):993-6.
Martinez et al., Enantioselective synthesis of saframycin A and evaluation of antitumor activity relative to ecteinascidin/saframycin hybrids. Org Lett. Jul. 15, 1999;1(1):75-7.
Demetri et al., Trabectedin (T) or Dacarbazine (D) for Treatment of Patients (pts) with Advanced Leiomyosarcoma (LMS) or Liposarcoma

(56) References Cited

OTHER PUBLICATIONS (LPS) After Prior Chemotherapy: Histology-specific Subgroup Analysis of a Randomized Phase-3 Study. CTOS 20th Annual. pp. 220-221, Abstract 137, (2015).
Denton et al., Myelolytic Treatments Enhance Oncolytic Herpes Virotherapy in Models of Ewing Sarcoma by Modulating the Immune Microenvironment. Mol Ther Oncolytics. Oct. 18, 2018;11:62-74.
Desai et al., Real-World Outcomes With Lurbinectedin in Second-Line Setting and Beyond for Extensive Stage Small Cell Lung Cancer. Clin Lung Cancer. Dec. 2023;24(8):689-695. pre-publication edition.
Desai et al., Systematic review and network meta-analysis: evaluation of systemic therapies for platinum refractory or resistant small cell lung cancer. Lung Cancer. Dec. 2025;210:108812, 8 pages.
Dick et al., Building on bortezomib: second-generation proteasome inhibitors as anti-cancer therapy. Drug Discov Today. Mar. 2010;15(5-6):243-9.
Digklia et al., Trabectedin and Durvalumab Combination Is Feasible and Active in Relapsing Ovarian Cancer. Clin Cancer Res. May 2, 2022;28(9):1745-1747.
Diken et al., CIMT 2013: advancing targeted therapies—report on the 11th Annual Meeting of the Association for Cancer Immunotherapy, May 14-16, 2013, Mainz, Germany. Hum Vaccin Immunother. Sep. 2013;9(9):2025-32.
Dimasi et al., Innovation in the pharmaceutical industry: New estimates of R&D costs. J Health Econ. May 2016;47:20-33.
D'INALCI et al., In human tumor xenografts the resistance of ET-743 or to cisplatin can be overcome by giving the two drugs in combination. European Journal of Cancer. Nov. 2002;38(Suppl 7):34.
D'INCALCI et al., A review of trabectedin (ET-743): a unique mechanism of action. Mol Cancer Ther. Aug. 2010;9(8):2157-63.
D'INCALCI et al., In human tumor xenografts to ET-743 or to cisplatin can be overcome by giving the two drugs in combination. 14th EORTC-NCI-AARC Symposium. Page S34, Abstract 97, Nov. 20, 2002.
D'Incalci et al., The Combination of ET-743 and Cisplatin (DDP): From a Molecular Pharmacology Study to a Phase I Clinical Trial. AACR Annual Meeting. Abstract 404, Apr. 6-10, 2002.
D'Incalci et al., Trabectedin, a drug acting on both cancer cells and the tumour microenvironment. Br J Cancer. Aug. 12, 2014;111(4):646-50.
Dingemans et al., Small-cell lung cancer: ESMO Clinical Practice Guidelines for diagnosis, treatment and follow-up. Ann Oncol. Jul. 2021;32(7):839-853.
Disis et al., Cancer vaccines for the treatment and prevention of non small-cell lung cancer. Clin Lung Cancer. May 2000; 1(4):294-301.
Dolmatova et al., Tumor-Associated Macrophages as Potential Targets for Anti-Cancer Activity of Marine Invertebrate-Derived Compounds. Curr Pharm Des. 2021;27(28):3139-3160.
Domine et al., Supportive measures to control myelosuppression and costs for patients with SCLC with lurbinectedin, CAV or topotecan with or without triladdib: A review on the basis of clinical trials. Annals of Oncology. 2023;34(S2):S1074-S1075, Abstract 2024P.
Domine et al., Supportive treatments to control myelosuppression and related costs with lurbinectedin, CAV and topotecan with or without trilaciclib in relapsed SCLC: a review on the basis of clinical trials. ESMO Congress. 1 page, poster, Oct. 20-24, 2023.
Donald et al., Complete protection by high-dose dexamethasone against the hepatotoxicity of the novel antitumor drug yondelis (ET-743) in the rat. Cancer Res. Sep. 15, 2003;63(18):5902-8.
Dorai et al., Development of a hammerhead ribozyme against BCL-2. II. Ribozyme treatment sensitizes hormone- resistant prostate cancer cells to apoptotic agents. Anticancer Res. Sep. 1997-Oct. 17(5A):3307-12.
Dorwald, Preface. Side Reactions in Organic Synthesis, A Guide to Successful Synthesis Design. Wiley-VCH Verlag Gmbh & Co. KgaA, Weinheim. Page IX, (2005).
Draetta et al., Cell Cycle Control and Cancer. Annual Reports in Medicinal Chemistry, vol. 31. Academic Press, San Diego. Chapter 25, pp. 241-246, (1996).
Drewinko et al., Combination chemotherapy in vitro with adriamycin. Observations of additive, antagonistic, and synergistic effects when used in two-drug combinations on cultured human lymphoma cells. Cancer Biochem Biophys. May 1976;1(4):187-95.
Druker et al., Lessons learned from the development of an abl tyrosine kinase inhibitor for chronic myelogenous leukemia. J Clin Invest. Jan. 2000;105(1):3-7.
Du et al., FDA-approved drugs featuring macrocycles or medium-sized rings. Arch Pharm (Weinheim). Jan. 2025;358(1):e2400890, 24 pages.
Duffaud et al., LMS-2: A Phase II Single-arm Multicenter Study of Trabectedin in Combination with Doxorubicin as First Line Treatment of Metastatic and/or Locally Advanced Leiomyosarcoma of Uterine (U-LMS) or Soft-tissue (ST-LMS) Origin: Results from Both Cohorts, for the French Sarcoma Group (FSG). CTOS 18th Annual Meeting. pp. 101-102, Paper 012, (2013).
Dwyer et al., The use of concanavalin A to study the immunoregulation of human T cells. Clin Exp Immunol. Nov. 1981;46(2):237-49.
Dy et al., A phase II trial of imatinib (ST1571) in patients with c-kit expressing relapsed small-cell lung cancer: a CALGB and NCCTG study. Ann Oncol. Nov. 2005;16(11):1811-6.
Eckardt et al., Phase III study of oral compared with intravenous topotecan as second-line therapy in small-cell lung cancer. J Clin Oncol. May 20, 2007;25(15):2086-92.
Eckhardt et al., Activity of ecteinascidin, a novel marine cytotoxic, against primary human tumor colony-forming units. Proceedings of the American Association for Cancer Research. Mar. 1996;37:409, Abstract 2791.
Eckhardt et al., Ecteinascidin-743. Drugs Fut. 1997;22(11):1279.
Edwards et al., Topotecan, pegylated liposomal doxorubicin hydrochloride, paclitaxel, trabectedin and gemcitabine for advanced recurrent or refractory ovarian cancer: a systemic review and economic evaluation. Health Technology Assessment. Jan. 2015; 19(7):521 pages.
Enea et al., Tumour-infiltrating immune cells as a predictive factor in advanced or metastatic leiomyosarcomas: comparison between uterine and non-uterine tumours. Virchows Archiv. 2023;483(Suppl 1):S257, Abstract E-PS-10-021.
Erba et al., Ascites interferes with the activity of lurbinectedin and trabectedin: Potential role of their binding to alpha 1-acid glycoprotein. Biochem Pharmacol. Nov. 15, 2017;144:52-62. pre-publication edition.
Erba et al., Combination of yondelis (ET-743) and oxaliplatin in experimental ovarian cancer. AARC-NCI-EORTC International Conference on Molecular Targets and Cancer Therapeutics. Abstract C247, Nov. 17-21, 2003.
Erba et al., ET-743 and Cisplatin (DDP) Show in Vitro and in Vivo Synergy Against Human Sarcoma and Ovarian Carcinoma Cell Lines. AACR NCI-EORTC Conference on Molecular Targets and Cancer Therapeutics. Abstract 406, Oct. 29-Nov. 2, 2001.
Erba et al., Isolation and characterization of an IGROV-1 human ovarian cancer cell line made resistant to Ecteinascidin-743 (ET-743). Br J Cancer. May 2000;82(10):1732-9.
Erba et al., Mode of action of Ecteinascidin 743, a natural marine compound with antitumoral activity. Annals of Oncology. 1998;9:139, Abstract 535.
Erba et al., Synergistic cytotoxic effect of ET-743 and cisplatin. Clinical Cancer Research. Nov. 2000;6:Abstract 209.
Erba et al., The unique biological features of the marine product Yondelis (ET-743, trabectedin) are shared by its analog ET-637, which lacks the C ring. Oncol Res. 2004;14(11-12):579-87.
Esmo et al., ESMO Minimum Clinical Recommendations for diagnosis, treatment and follow-up of small-cell lung cancer (SCLC). Ann Oncol. Aug. 2001;12(8):1051-2.
Evans et al., Cabazitaxel Versus Topotecan in Patients with Small-Cell Lung Cancer with Progressive Disease During or After First-Line Platinum-Based Chemotherapy. J Thorac Oncol. Aug. 2015;10(8):1221-8.

(56) References Cited

OTHER PUBLICATIONS

Faircloth et al., Ecteinascidin-743 (ET743): In Vitro (IVT) and In Vivo (INV) Results in Solid Tumor Models. The European Journal of Cancer. 1996;32A(Supp. 1):S5, Abstract 24 O.
Faircloth et al., In Vivo Combinations of Chemotherapeutic Agents with Ecteinascidin 743 (ET743) Against Solid Tumors. AACR NCI-EORT Conference. Abstract 387, Nov. 2001.
Falcon et al., Phase I results on the efficacy, safety and pharmacokinetics of lurbinectedin and irinotecan in advanced solid tumors. Invest New Drugs. Aug. 2025;43(4):955-967.
Fathima et al., Marine Derived Drug Lurbinectidin: A Potential Anticancer Agent. Indian Journal of Pharmacology. Dec. 2021;53:S105-S106. Sub-Code-1541, Ref No. Ze9KlgUD.
FDA Approval Label, Doxorubicin Hydrochloride for Injection, USP. 29 pages, May 8, 2003.
FDA, Challenge and Opportunity on the Critical Path to New Medical Products. Innovation Stagnation. 38 pages, Mar. 2004.
FDA, FDA Briefing Document, Pediatric Oncology Subcommittee of the Oncologic Drugs Advisory Committee (ODAC). 17 pages, Jun. 21, 2017.
Ferguson et al., Differential cellular retention of vincristine and vinblastine by cultured human promyelocytic leukemia HL-60/CI cells: the basis of differential toxicity. Cancer Res. Nov. 1985;45(11 Pt 1):5480-8.
Martinez et al., Phthalascidin, a synthetic antitumor agent with potency and mode of action comparable to ecteinascidin 743. Proc Natl Acad Sci U S A. Mar. 30, 1999;96(7):3496-501.
Martinez-Serra et al., Yondelis® (ET-743, Trabectedin) sensitizes cancer cell lines to CD95-mediated cell death: new molecular insight into the mechanism of action. Eur J Pharmacol. May 11, 2011;658(2-3):57-64.
Martin-Liberal et al., Systemic chemotherapy for inoperable, locally advanced, recurrent or metastatic uterine leiomyosarcoma. Clin Oncol (R Coll Radiol). Jun. 2013;25(6):343-5.
Marur, Yondelis, Supplement Approval. Nda 207953/S-006. 3 pages, Jun. 3, 2020.
Massuti et al., Trabectedin in patients with advanced non-small-cell lung cancer (NSCLC) with XPG and/or ERCC1 overexpression and BRCA1 underexpression and pretreated with platinum. Lung Cancer. Jun. 2012; 76(3):354-61.
Matera et al., What Is New in Small Cell Lung Cancer. Hematol Oncol Clin North Am. Jun. 2023;37(3):595-607.
McCauley et al., NR2B-selective N-methyl-D-aspartate antagonists: synthesis and evaluation of 5-substituted benzimidazoles. J Med Chem. Apr. 8, 2004;47(8):2089-96.
McCumber et al., Modulation of the EBL Immune System by ETE. 19th National Meeting Reticuloendothelial Society. 1982;32(1):67, Abstract 48.
McGovern et al., Systemic Therapy in Metastatic or Unresectable Well-Differentiated/Dedifferentiated Liposarcoma. Front Oncol. Nov. 30, 2017;7:292, 8 pages.
McGrath et al., A Graphical Journey of Innovative Organic Architectures That Have Improved Our Lives. Journal of Chemical Education. Dec. 2010;87(12):1348-1349.
McLeod et al., Clinically relevant drug-drug interactions in oncology. Br J Clin Pharmacol. Jun. 1998;45(6):539-44.
McMeekin et al., A phase II study of trabectedin (ET-743) as a second line therapy in patients with persistent or recurrent endometrial carcinoma. ASCO 40th Annual Meeting. 1 page, (2004).
McMeekin et al., A phase II study of trabectedin (ET-743) as a second line therapy in patients with persistent or recurrent endometrial carcinoma. Journal of Oncology. 2004;22(14S):2 pages, Abstract 5086.
McMeekin et al., Single-agent trabectedin as second-line therapy of persistent or recurrent endometrial cancer: Results of a multicenter phase II study. Gynecologic Oncology. 2009;14:288-292.
Meco et al., Effective combination of ET-743 and doxorubicin in sarcoma: preclinical studies. Cancer Chemother Pharmacol. Aug. 2003;52(2):131-8.
Mendelsohn et al., The EGF receptor family as targets for cancer therapy. Oncogene. Dec. 27, 2000;19(56):6550-65.
Menjon Beltran et al., Clinical Experience with Trabectedin in Monotherapy or with Doxorrubicine Hidroclorure in Patients with Metastatic Cancer. A Retrospective Review. Intl J Gynecological Cancer. Nov. 2014;24(9 Suppl 4):1031.
Messersmith et al., Phase I trial of weekly trabectedin (ET-743) and gemcitabine in patients with advanced solid tumors. Cancer Chemother Pharmacol. Dec. 2008;63(1):181-8.
Meunier et al., Mechanism of oxidation reactions catalyzed by cytochrome p450 enzymes. Chem Rev. Sep. 2004;104 (9):3947-80.
Meunier et al., Peroxidase-catalyzed O-demethylation reactions. Quinone-imine formation from 9-methoxyellipticine derivatives. J Biol Chem. Sep. 5, 1985;260(19):10576-82.
Meyer et al., Lurbinectedin in prostatic small cell and neuroendocrine carcinoma. J Clin Oncol. Jan. 2024;42(Suppl 4):Abstract 164.
Meyer et al., The Use of Lurbinectedin for the Treatment of Small Cell and Neuroendocrine Carcinoma of the Prostate. Clin Genitourin Cancer. Oct. 2024;22(5):102172, 9 pages.
Mikami et al., Structural studies on minor components of saframycin group antibiotics saframycins F, G and H. J Antibiot (Tokyo). Jun. 1988;41(6):734-40.
Minotti et al., Anthracyclines: molecular advances and pharmacologic developments in antitumor activity and cardiotoxicity. Pharmacol Rev. Jun. 2004;56(2):185-229.
Mirsalis et al., Toxicity of Ecteinascidin 743 in female Fischer-344 rats administered i.v. in a multiple-dose regimen. Proceedings of the American Association for Cancer Research. Mar. 1997;38:309, Abstract 2073.
Mirzapoiazova et al., Teriflunomide in Vitro or Leflunomide in Vivo Treatment Increases the Efficacy of Lurbinectedin in Sclc. J Thorac Oncol. 2024; 19(10):S314.
Mirzapoiazova et al., Teriflunomide/leflunomide synergize with chemotherapeutics by decreasing mitochondrial fragmentation via DRP1 in SCLC. iScience. May 27, 2024;27(6):110132, 37 pages.
MJH Life Sciences, Gleevec Is Approved for Chronic Myelogenous Leukemia. Oncology NEWS International. Jun. 1, 2001;10(6):5 pages.
Modica-Napolitano et al., Selective damage to carcinoma mitochondria by the rhodacyanine MKT-077. Cancer Res. Feb. 1, 1996;56(3):544-50.
Monk et al., A phase II evaluation of trabectedin in the treatment of advanced, persistent, or recurrent uterine leiomyosarcoma: a gynecologic oncology group study. Gynecol Oncol. Jan. 2012;124(1):48-52.
Monk et al., A randomized, open-label study comparing trabectedin and pegylated liposomal doxorubicin with pegylated liposomal doxorubicin alone for the treatment of advanced-relapsed epithelial ovarian, primary peritoneal, or fallopian tub cancer (ET743-OVC-3006). Gynecologic Oncology. 2019; 154:12-13, Abstract 20.
Monk et al., A randomized, open-label study comparing trabectedin and pegylated liposomal doxorubicin with pegylated liposomal doxorubicin alone for the treatment of advanced-relapsed epithelial ovarian, primary peritoneal, or fallopian tub cancer (ET743-OVC-3006). Sgo 50th Annual Meeting on Women's Cancer Hawaii F-O. 25 pages, slideshow, Mar. 16-19, 2019.
Monk et al., Activity of docetaxel plus trabectedin in recurrent or presistent ovarian and primary peritoneal cancer: A phase II study of the Gynecologic Oncology Group (Gog). Asco 46th Annual Meeting. J Clin Oncol. 2010;28(15):Abstract 5046, 1 page.
Monk et al., Activity of docetaxel plus trabectedin in recurrent or presistent ovarian and primary peritoneal cancer: A phase II study of the Gynecologic Oncology Group (Gog). J Clin Oncol. 2010;28(15):Abstract 5046, 2 pages.
Monk et al., Docetaxel plus trabectedin appears active in recurrent or persistent ovarian and primary peritoneal cancer after up to three prior regimens: a phase II study of the Gynecologic Oncology Group. Gynecol Oncol. Mar. 2011;120(3):459-63.
Moore et al., NMR-Based Model of an Ecteinascidin 743-DNA Adduct. J Am Chem Soc. 1997;119:5475-5476.
Moore et al., Sequencing evaluation of ET-743 combinations with standard chemotherapy agents against a panel of human tumor cell lines. Clin Cancer Res. Nov. 2000;6:Abstract 504.

(56) References Cited

OTHER PUBLICATIONS

Moore et al., Sequencing evaluation of ET-743 combinations with standard chemotherapy agents against a panel of human tumor cell lines. Proceedings of the 11th NCI-EORTC-AACR Symposium. 1 page, poster, (2000).
Moore et al., The NMR model of an ecteinascidin 743-DNA adduct. Proceedings of the American Association for Cancer Research. Mar. 1997;38;314, Abstract 2105.
Morales, Marine Natural Products Chemistry of a Caribbean Tunicate and a Palau Sponge. Thesis, Submitted in partial fulfillment of the requirements for the degree of Doctor of Philosophy in Chemistry. 302 pages, (1999).
Moreno et al., Impact of a Moderate CYP3A4 Inducer (Bosentan) on Lurbinectedin Pharmacokinetics and Safety in Patients with Advanced Solid Tumors: An Open-Label, Two-Way, Crossover, Phase Ib Drug-Drug Interaction Study. Pharmaceuticals (Basel). Jan. 30, 2024;17(2):182, 16 pages.
Moreno et al., Lurbinectedin (LRB) pharmacokinetics (PK) and safety when co-administered with itraconazole (ITZ) in patients with advanced solid tumor. Annals of Oncology. 2023;34(S2):S475, Abstract 679P.
Moreno et al., Lurbinectedin (LRB) pharmacokinetics (PK) and safety when co-administered with itraconazole (ITZ) in patients with advanced solid tumor. ESMO Congress. 1 page, poster, Oct. 20-24, 2023.
Moreno et al., Pharmacokinetics and Safety of Lurbinectedin Administrated with Itraconazole in Cancer Patients: A Drug-Drug Interaction Study. Mar Drugs. Apr. 16, 2024;22(4):178, 18 pages.
Morgan et al., Systematic therapy for unresectable or metastatic soft-tissue sarcomas: past, present, and future. Curr Oncol Rep. Aug. 2011;13(4):331-49.
Mosmann et al., Rapid colorimetric assay for cellular growth and survival: application to proliferation and cytotoxicity assays. J Immunol Methods. Dec. 16, 1983;65(1-2):55-63.
Moura et al., Immune-checkpoint genes as predictive biomarkers of trabectedin in advanced soft-tissue sarcoma (STS): A Spanish Group for Research on Sarcomas (GEIS) translational study. ASCO American Society of Clinical Oncology, 56th Annual Meeting, Virtual, May 31-Jun. 4, 2020. J Clin Oncol. 2020;38(15 Suppl.), Abstract 11546.
Moura et al., Immune-checkpoint genes as predictive biomarkers of trabectedin in advanced soft-tissue sarcoma (STS): A Spanish Group for Research on Sarcomas (GEIS) translational study. CTOS 2020 Annual Meeting, Virtual, 2 pages. Nov. 18-21, 2020.
Moura et al., Immune-checkpoint Genes as Predictive Biomarkers of Trabectedin in Advanced Soft-tissue Sarcoma (STS): A Spanish Group for Research on Sarcomas (GEIS) Translational Study. CTOS 2020 annual Meeting. 1 page, Abstract 3465320, (2020).
Moura et al., Immune-checkpoint genes as predictive biomarkers of trabectedin in advanced soft-tissue sarcoma (STS): A Spanish Group for Research on Sarcomas (GEIS) translational study. CTOS 2020 annual Meeting. 1 page, poster, (2020).
Santamaria et al., Lurbinectedin (PM01183) specifically targets RNA Pol II for degradation via the proteasome pathway in a transcription dependent fashion. 26th EORTC-NCI-AACR Symposium on Molecular Targets and Cancer Therapeutics. 1 page, Poster, Nov. 18-21, 2014.
Santamaria et al., Synergistic combination of lurbinectedin and PARP inhibitors in breast cancer tumor cell lines. AACR Annual Meeting. Abstract 2520, Apr. 18-22, 2015.
Santamaria et al., Synergistic combination of PM1183 and PARP inhibitors in breast cancer cells. AACR American Association for Cancer Research, 106th Annual Meeting. Abstract 2520, 1 page, poster, Apr. 18-22, 2015.
Santamaria et al., TC-NER Dependent Degradation of RNA Pol II In Response to Lurbinectedin (PM01183). 24th EORTC-NCI-AACR Symposium on Molecular Targets and Cancer Therapeutics. 1 pages, poster, Nov. 6-9, 2012.
Santamaria et al., TC-NER Dependent Degradation of RNA Pol II In Response to Lurbinectedin (PM01183). Eur J Cancer. 2012;48(Suppl 6):66, Abstract 218.
Santamaria Nunez et al., Lurbinectedin inhibits active transcription affecting tumor cell burden and its inflammatory microenvironment. 15th International Congress on Targeted Anticancer Therapies, TAT 2017. Abstract O10.4, Mar. 6-8, 2017.
Santamaria Nunez et al., Lurbinectedin reverses platinum dependent IRF1 overexpression and nuclear localization, partially responsible for resistance to platinum drugs in ovarian cancer. Proceedings of the American Association for Cancer Research. Apr. 2017;58:311, Abstract 1211.
Santamaria Nunez et al., Lurbinectedin reverses platinum-dependent IRF1 overexpression and nuclear localization, partially responsible for resistance to platinum drugs in ovarian cancer. AACR American Association for Cancer Research, 108th Annual meeting. 1 page, poster, Apr. 1-5, 2017.
Santamaria-Nunez et al., Lurbinectedin specifically targets transcription in cancer cells, triggering DNA breaks and degradation of phosphorylated Pol Ii. Aacr American Association for Cancer Research, 107th Annual Meeting. 1 page, poster, Apr. 16-20, 2016.
Santamaria-Nunez et al., Lurbinectedin specifically targets transcription in cancer cells, triggering DNA breaks and degradation of phosphorylated Pol Ii. Aacr Annual Meeting, Abstract 3039, Apr. 19, 2016.
Sanz-Garcia et al., Efficacy and Safety of Lurbinectedin (PM1183) in Ewing Sarcoma: Results from a Phase 2 Study. CTOS Connective Tissue Oncology Society, 22nd Annual Meeting. p. 83-84, Abstract 048, #2768194, Nov. 8-11, 2017.
Sauri et al., Lurbinectedin (PM01183) administered once (D1) every 3 weeks (q3w) in combination with capecitabine (XEL) in patients (pts) with metastatic breast (MBC), colorectal (CRC) or pancreatic (PaC) cancer. 41st ESMO European Cancer Congress. 1 page, poster, Oct. 7-11, 2016.
Sauri et al., Lurbinectedin (PM01183) administered once (D1) every 3 weeks (q3w) in combination with capecitabine (XEL) in patients (pts) with metastatic breast (MBC), colorectal (CRC) or pancreatic (PaC) cancer. Annals of Oncology. Oct. 2016;27:vi127, Abstract 392P.
Sauri et al., Lurbinectedin (PM01183) on Days (D) 1 & 8 in Combination with Capecitabine (XEL) in Patients (pts) with Metastatic Breast (MBC), Colorectal (CRC) or Pancreatic (PAC) Cancer. Annals of Oncology. 2014;25(Suppl 4):iv146, Abstract 482P.
Sauri et al., Lurbinectedin (PM01183) on Days (D) 1 & 8 in Combination with Capecitabine (XEL) in Patients (PTS) with Metastatic Breast (MBC), Colorectal (CRC) or Pancreatic (PAC) Cancer. Annals of Oncology. 2014;25(Suppl 4):iv161, Abstract 482P.
Sauri et al., Lurbinectedin (PM01183) on Days (D) 1 & 8 in Combination with Capecitabine (XEL) in Patients (pts) with Unresectable Metastatic Breast (MBC), Colorectal (CRC) or Pancreatic Cancer: Preliminary Results of an Ongoing Phase Ib Study. 39th ESMO Congress. 1 page, poster, Sep. 26-30, 2014.
Scherpereel et al., Novel therapies for malignant pleural mesothelioma. Lancet Oncol. Mar. 2018;19(3):e161-e172.
Schreeder et al., EMERGE 402: Real-world Characteristics and Safety of Lurbinectedin in Small-cell Lung Cancer (Sclc). J Thorac Oncol. 2023;18(3 Suppl):e43, Abstract PP01.77.
Schultz et al., ATR inhibition augments the efficacy of lurbinectedin in small cell lung cancer. bioRxiv. 37 pages, Dec. 19, 2022.
Schultz et al., ATR inhibition augments the efficacy of the lurbinectedin in small cell lung cancer. Cancer Res. 82(12 Suppl):Abstract 2153.
Serzan et al., Drugs in development for small cell lung cancer. J Thorac Dis. Oct. 2020;12(10):6298-6307.
Shi et al., Comparison of the second-line treatments for patients with small cell lung cancer sensitive to previous platinum-based chemotherapy: A systematic review and Bayesian network analysis. Front Oncol. Mar. 16, 2023;13:1154685, 10 pages.
Shinn et al., Lurbinectedin: A New Treatment Option for Relapsed/Refractory Small-Cell Lung Cancer. Ann Pharmacother. Sep. 2021;55(9):1172-1179.

(56) References Cited

OTHER PUBLICATIONS

Simona et al., Lurbinectedin improves macular edema in a case of central retinal vein occlusion. Am J Ophthalmol Case Rep. Nov. 6, 2022;28:101743, 4 pages.
Singh et al., FDA Approval Summary: Lurbinectedin for the Treatment of Metastatic Small Cell Lung Cancer. Clin Cancer Res. May 1, 2021;27(9):2378-2382.
Soares et al., PM01183, a marine-derived product, shows activity toward platinum-resistant cells and attenuates nucleotide excision repair. AACR American Association for Cancer Research, 102nd Annual Meeting. Abstract 5431, Apr. 2-6, 2011.
Soares et al., PM01183, a novel marine-derived ecteinascidin, shows activity toward platinum-resistant cells and attenuates nucleotide excision repair. AACR American Association for Cancer Research, 102nd Annual Meeting. Poster, Apr. 2-6, 2011.
Soares et al., The marine product PM01183 (Trptamicidin) shows activity toward platinum-resistant cells and attenuates nucleotide excision repair. 22nd EORTC-NCI-AACR Symposium on Molecular Targets and Cancer Therapeutics. 1 page, poster, Nov. 16-19, 2010.
Soares et al., The marine-derived product PM01183 shows activity toward platinum-resistant cells and attenuates nucleotide excision repair. Eur J Cancer. 2010;8(7):166-167, Abstract 522.
Soria et al., Novel Cytotoxic Drugs in Lung Cancer. J Thorac Oncol. Jan. 2017;12(1S):S85-S86, Abstract SC05.02.
Spigel et al., EMERGE-201: Phase 2 Basket Study of Lurbinectedin Monotherapy in Advanced or Metastatic Solid Tumors. J Thorac Oncol. Mar. 2023;18(3Suppl):e31, Abstract PP01.50.
Subbiah et al., Activity of Lurbinectedin (Zepsyre, PM1183) as single agent in patients with advanced Ewing's sarcoma. 15 pages, slideshow, (2017).
Subbiah et al., Activity of lurbinectedin in second-line SCLC patients candidates for platinum re-challenge. Annals of Oncology. 2020;31(S4):S1034-S1035, Abstract 1784P.
Subbiah et al., Activity of Lurbinectedin in Second-line SCLC Patients Candidates for Platinum Re-challenge. ESMO Virtual Congress 2020. Poster, Sep. 19-21, 2020.
Subbiah et al., Activity of Lurbinectedin in Second-line SCLC Patients Who Are Candidates for Platinum Rechallenge. 2020 North America Conference on Lung Cancer. 1 page, Abstract MO01.10, Oct. 16-17, 2020.
Subbiah et al., Activity of Lurbinectedin in Second-line SCLC Patients Who Are Candidates for Platinum Re-challenge. IASLC 2020 North America Conference on Lung Cancer. Abstract 109, poster, Oct. 16-17, 2020.
Subbiah et al., Antitumor activity of lurbinectedin in second-line small cell lung cancer patients who are candidates for re-challenge with the first-line treatment. Lung Cancer. Dec. 2020;150:90-96.
Subbiah et al., Antitumor Activity of Lurbinectedin, a Selective Inhibitor of Oncogene Transcription, in Patients with Relapsed Ewing Sarcoma: Results of a Basket Phase II Study. Clin Cancer Res. Jul. 1, 2022;28(13):2762-2770.
Subbiah et al., Efficacy and safety of lurbinectedin (PM1183) in Ewing sarcoma: Final results from a phase 2 study. ASCO American Society of Clinical Oncology, 54th Annual Meeting. 1 page, poster, Jun. 1-5, 2018.
Subbiah et al., Efficacy and safety of lurbinectedin (PM1183) in Ewing sarcoma: Final results from a phase 2 study. J Clin Oncol. 2018;36, Abstract 11519.
Subbiah et al., Lurbinectedin Is Safe and Active in Relapsed Small-Cell Lung Cancer. Cancer Discov. Jun. 1, 2020;10(6):757. 2 pages.
Subbiah et al., New Targets, Biomarkers, and Systemic Therapies. J Thorac Oncol. 2021;16(10 Suppl)S844-S845, Abstract MA16-SCLC.
Subbiah et al., Phase 2 Basket Trial of Lurbinectedin in Second-Line SCLC: Characteristics and Outcomes in Treatment Responders. 2020 North America Conference on Lung Cancer. Poster MO01.08, Oct. 16-17, 2020.
Subbiah et al., Phase 2 Basket Trial of Lurbinectedin in Second-line Small-cell Lung Cancer: Characteristics and Outcomes in Treatment Responders. IASLC 2020 North America Conference on Lung Cancer. Abstract 111, Oct. 16-17, 2020.
Subbiah et al., Subsequent Systemic Therapy After Lurbinectedin Discontinuation in Patients With Small-cell Lung Cancer. 2021 World Conference on Lung Cancer. 7 pages, slideshow, Sep. 8-14, 2021.
Subbiah, Efficacy and Safety of Lurbinectedin (PM1183) in Ewing Sarcoma. 2018 ASCO Annual Meeting, 10 pages, slideshow, (2018).
Sundstrom et al., Second-line chemotherapy in recurrent small cell lung cancer. Results from a crossover schedule after primary treatment with cisplatin and etoposide (EP-regimen) or cyclophosphamide, epirubicin, and vincristin (CEV-regimen). Lung Cancer. May 2005;48(2):251-61.
Takahashi et al., Antitumor activity of lurbinectedin toward ovarian clear cell carcinoma. AACR American Association for Cancer Research, 106th Annual Meeting. 1 page, poster, Apr. 18-22, 2015.
Takahashi et al., Antitumor activity of lurbinectedin toward ovarian clear cell carcinoma. AACR Annual Meeting. Abstract 1642, Apr. 16-22, 2015.
Takahashi et al., Phase I study of lurbinectedin in Japanese patients with pretreated advanced tumours: Final results. Annals of Oncology. 2020;31(S4):S478, Abstract 551P.
Barber et al., Hematologic toxicities of small molecule tyrosine kinase inhibitors. Target Oncol. Dec. 2011;6(4):203-15.
Brittain, Polymorphism in Pharmaceutical Solids. Marcel Dekker, Inc., New York. 25 pages, (1999).
Curt et al., Brief Report: Real-World Outcomes of Lurbinectedin in Veterans With Small Cell Lung Cancer. Clin Lung Cancer. Apr. 2026;27(3):17-21.
Izak et al., Management of thrombocytopenia. F1000Prime Rep. Jun. 2, 2014;6:45, 10 pages.
Merriam Webster, hematologic. 7 pages, (2026).
PharmaMar, PharmaMar announces data presentations for both its molecules Yondelis and lurbinectedin at ASCO 2018. Press Release, 5 pages, May 17, 2018.
PharmaMar, PharmaMar announces encouraging results in clinical trials of lurbinectedin in endometrial and breast cancer. Press Release, 4 pages, Jun. 13, 2017.
PharmaMar, PharmaMar announces new data with its compounds Yondelis and lurbinectedin during ASCO 2017. 4 pages, May 18, 2017.
PharmaMar, PharmaMar announces partnership with 8th National Race to End Women's Cancer in support of "End Women's Cancer Weekend" in Washington, D.C. Press Release, 2 pages, Nov. 4, 2017.
PharmaMar, PharmaMar announces positive results in its lurbinectedin monotherapy trial for small cell lung cancer. Press Release, 2 pages, Mar. 25, 2019.
PharmaMar, PharmaMar announces positive results of its APLICOV trial against COVID-19. Press Release, 3 pages, Oct. 16, 2020.
PharmaMar, PharmaMar announces results of its APLICOVPC study in adult patients with COVID-19 requiring hospital admission. Press Release, 5 pages, May 26, 2021.
PharmaMar, PharmaMar announces Singapore Health Sciences Authority approval of Zepzelca (lurbinectedin) for the treatment of metastatic Small Cell Lung Cancer. Press Release, 4 pages, Sep. 22, 2021.
PharmaMar, PharmaMar announces that Australia approves Zepzelca (lurbinectedin) for the treatment of metastatic Small Cell Lung Cancer. Press Release, 4 pages, Sep. 14, 2021.
PharmaMar, PharmaMar announces that it has received payment of $100 million from Jazz Pharmaceuticals for the approval of Zepzelca (lurbinectedin) in the U.S. Press Release, 3 pages, Jun. 29, 2020.
PharmaMar, PharmaMar announces that it has received the upfront payment of $200 million from the license agreement with Jazz for lurbinectedin in the United States. Press Release, 3 pages, Jan. 29, 2020.
PharmaMar, PharmaMar announces that its Phase I study on Japanese patients with lurbinectedin in monotherapy has achieved its objective. Press Release, 2 pages, Aug. 27, 2019.

(56) References Cited

OTHER PUBLICATIONS

PharmaMar, PharmaMar announces that lurbinectedin has received acceptance for its clinical trial application in China. Press Release, 3 pages, Jun. 29, 2020.
PharmaMar, PharmaMar announces that TGA has granted the "Provisional Approval Pathway" for lurbinectedin in relapsed Small Cell Lung Cancer in Australia. Press Release, 3 pages, Jun. 3, 2020.
PharmaMar, PharmaMar announces that the ATLANTIS study has reached the goal of patient recruitment. Press Release, 3 pages, Jul. 30, 2018.
PharmaMar, PharmaMar announces that the NCCN (National Compreshensive Cancer Network) has added Zepzelca (lurbinectedin) to Clinical Practice Guidelines in Oncology in the U.S. Press Release, 3 pages, Jul. 13, 2020.
PharmaMar, PharmaMar announces that Zepsyre (lurbinectedin) shows noteworthy clinical activity in metastatic breast cancer with mutations in BRCA 1/2. Press Release, 2 pages, Nov. 8, 2018.
PharmaMar, PharmaMar announces the addition of Ali Zeaiter as new Director of Clinical Development. Press Release, 2 pages, Oct. 1, 2018.
PharmaMar, PharmaMar announces the approval of Aplidin in Australia for the treatment of multiple myeloma. Press Release, 3 pages, Dec. 11, 2018.
PharmaMar, PharmaMar announces the approval of Zepzelca (lurbinectedin) for the treatment of metastatic Small Cell Lung Cancer in Israel. Press Release, 2 pages, Jan. 31, 2023.
PharmaMar, PharmaMar announces the approval of Zepzelca (lurbinectedin) for the treatment of metastatic small Cell Lung Cancer in Oman. Press Release, 1 page, Jul. 19, 2023.
PharmaMar, PharmaMar announces the approval of Zepzelca (lurbinectedin) for the treatment of metastatic Small Cell Lung Cancer in South Korea. Press Release, 2 pages, Sep. 23, 2022.
PharmaMar, PharmaMar announces the approval of Zepzelca (lurbinectedin) for the treatment of metastatic Small Cell Lung Cancer in Switzerland. Press Release, w pages, Mar. 8, 2023.
PharmaMar, PharmaMar announces the approval of Zepzelca (lurbinectedin) for the treatment of metastatic Small Cell Lung Cancer in Taiwan. Press Release, 4 pages, Jul. 11, 2023.
PharmaMar, PharmaMar announces the approval of Zepzelca (lurbinectedin) for the treatment of metastatic Small Cell Lung Cancer in the United Arab Emirates. Press Release, 3 pages, Sep. 1, 2021.
PharmaMar, PharmaMar announces the approval of Zepzelca (lurbinectedin) for the treatment of relapsed Small Cell Lung Cancer in Hong Kong. Press Release, e pages, Dec. 12, 2023.
PharmaMar, PharmaMar announces the approval of Zepzelca (lurbinectedin) for the treatment of relapsed stage III or metastatic small cell lung cancer in Canada. Press Release, 3 pages, Sep. 30, 2021.
PharmaMar, PharmaMar announces the data to be presented at ESMO 2022. Press Release, 4 pages, Sep. 8, 2022.
PharmaMar, PharmaMar announces the full approval of Zepzelca (lurbinectedin) for the treatment of metastatic Small Cell Lung Cancer in Mexico. Press Release, 2 pages, Jan. 24, 2023.
PharmaMar, PharmaMar announces the full approval of Zepzelca (lurbinectedin) for the treatment of metastatic Small Cell Lung Cancer in Peru. Press Release, 2 pages, Nov. 7, 2023.
PharmaMar, PharmaMar announces the meeting of its patient recruitment target in the phase II study with lurbinectedin as a single agent in small-cell lung cancer. Press Release, 2 pages, Nov. 14, 2018.
PharmaMar, PharmaMar announces the U.S. FDA approval of lurbinectedin (Zepzelca) for the treatment of metastatic Small Cell Lung Cancer. Press Release, 4 pages, Jun. 15, 2020.
PharmaMar, PharmaMar appoints Lara Vadillo as Communication Director. Press Release, 2 pages, Dec. 14, 2021.
PharmaMar, PharmaMar approves Zelnova' sale agreement and will submit the transaction for approval to the General Shareholders' Meeting in Jun. 2019. Press Release, 2 pages, May 23, 2019.
PharmaMar, PharmaMar begins the Nereida clinical trial with plitidepsin for treating immunosuppressed patients with COVID-19. Press Release, 3 pages, Apr. 20, 2023.
PharmaMar, PharmaMar closes recruitment for the Phase III Neptuno trial with Plitidepsin for the treatment of COVID-19. Press Release, 2 pages, Feb. 16, 2023.
PharmaMar, PharmaMar continues to execute commercially in 2016, adds new partner for pipeline asset, and sees pipeline progress. Press Release, 6 pages, Feb. 24, 2017.
PharmaMar, PharmaMar demonstrates its progress in R&D in New York. Press Release, 3 pages, Apr. 27, 2017.
PharmaMar, PharmaMar discovers new data on the mechanism of action of plitidepsin in tumor cells. Press Release, 3 pages, Apr. 17, 2018.
PharmaMar, PharmaMar enlarges its facilities to meet its upcoming business challenges. Press Release, 2 pages, Feb. 11, 2021.
PharmaMar, PharmaMar enters into a new licensing agreement with Janssen for Yondelis. Press Release, 2 pages, Aug. 26, 2019.
PharmaMar, PharmaMar gets the approval of Zepzelca (lurbinectedin) for the treatment of metastatic Small-Cell Lung Cancer in Macao, China. Press Release, 3 pages, Dec. 4, 2023.
PharmaMar, PharmaMar Goup's GENOMICA diagnostic kits for COVID-19 coronavirus receive CE conformity marking. Press Release, 3 pages, Mar. 6, 2020.
PharmaMar, PharmaMar group announces 2017 earnings results. Press Release, 2 pages, Feb. 28, 2018.
PharmaMar, PharmaMar Group Announces Financial Results as of Sep. 30, 2025. Press Release, 3 pages, Oct. 30, 2025.
PharmaMar, PharmaMar Group Announces Financial Results for First Half 2025. Press Release, 4 pages, Jun. 30, 2025.
PharmaMar, PharmaMar Group announces financial results for fiscal year 2024. Press Release, 4 pages, Feb. 28, 2025.
PharmaMar, PharmaMar Group announces results for the first half of 2019. Press Release, 2 pages, Jul. 29, 2019.
PharmaMar, PharmaMar group obtained a net profit of euro3 million in the first half of 2018. Press Release, 3 pages, Jul. 26, 2017.
PharmaMar, PharmaMar Group Presents Financial Results for the First Half of 2024. Press Release, 4 pages, Jul. 30, 2024.
Flick et al., Synthetic Approaches to the New Drugs Approved During 2020. J Med Chem. Jul. 28, 2022;65(14):9607-9661.
Forster et al., Activity of lurbinectedin (PM01183) as single agent and in combination in patients with endometrial cancer. ASCO American Society of Clinical Oncology, 53rd Annual Meeting, 1 page, poster, Jun. 2-5, 2017.
Forster et al., Activity of lurbinectedin (PM01183) as single agent and in combination in patients with endometrial cancer. J Clin Oncol. 2017;35, Abstract 5586.
Forster et al., Clinical activity of lurbinectedin (PM01183) in combination with doxorubicin (DOX) in small cell lung cancer (SCLC) patients (pts): preliminary results of a phase Ib study subpopulation analysis. IASLC 15th World Conference on Lung Cancer. Abstract 954. Oct. 27-31, 2013.
Forster et al., Clinical activity of lurbinectedin (PM01183) in combination with doxorubicin (DOX) in small cell lung cancer (SCLC) patients (pts): preliminary results of a phase lb study subpopulation analysis. IASLC 15th World Conference on Lung Cancer. Poster, Oct. 27-31, 2013.
Forster et al., Lurbinectedin (PM01183) in Combination with Cisplatin, with or without Aprepitant, in Patients with Advanced Solid Tumors. 18th ECCO, 40th ESMO European Cancer Congress. 1 page, poster, Sep. 25-29, 2015.
Forster et al., Lurbinectedin (PM01183) with doxorubicin (DOX), an active treatment as second-line therapy in small cell lung cancer (Sclc). Asco American Society of Clinical Oncology, 51st Annual Meeting. 1 page, poster. May 29-Jun. 2, 2015.
Forster et al., Lurbinectedin (PM01183) with doxorubicin (DOX), an active treatment as second-line therapy in small cell lung cancer (Sclc). Asco American Society of Clinical Oncology, 51st Annual Meeting. 7 pages, slideshow. May 29-Jun. 2, 2015.
Forster et al., Lurbinectedin (PM01183) with doxorubicin (DOX), an active treatment as second-line therapy in small cell lung cancer (Sclc). J Clin Oncol. 2015;33:Abstract 7509.

(56) References Cited

OTHER PUBLICATIONS

Forster et al., Overall Survival with Lurbinectedin Plus Doxorubicin in Relapsed SCLC. Results from an Expansion Cohort of a Phase Ib Trial. IASLC 19th World Conference on Lung Cancer. 1 page, poster, (2018).
Forster et al., Overall Survival with Lurbinectedin Plus Doxorubicin in Relapsed SCLC. Results from an Expansion Cohort of a Phase IB Trial. IASLC 19th World Conference on Lung Cancer. Page 358, Abstract P1.12-20, (2018).
Forster et al., Phase I study of lurbinectedin (PM01183) in combination with cisplatin (C) with or without aprepitant (Ap) in patients (pts) with advanced solid tumors. Eur J Cancer. 2015;51(Suppl 3):S60, Abstract 316.
Forster et al., Phase I study of lurbinectedin (PM01183) in combination with cisplatin (CDDP) with or without aprepitant in patients (pts) with advanced solid tumors. Eur J Cancer. Jan. 28, 2017;72(Suppl 1):S134, Abstract 1324.
Foucquier et al., Analysis of drug combinations: current methodological landscape. Pharmacol Res Perspect. Jun. 2015;3(3):e00149, 11 pages.
Foy et al., Targeting DNA damage in SCLC. Lung Cancer. Dec. 2017;114:12-22.
Frapolli et al., Lurbinectedin (PM01183): Antineoplastic Activity in Murine and Human Experimental Models. 24th EORTC-NCI-AACR Symposium on Molecular Targets and Cancer Therapeutics. 1 page, poster, Nov. 6-9, 2012.
Frapolli et al., Lurbinectedin (PM01183): Antineoplastic Activity in Murine and Human Experimental Models. Eur J Cancer. Nov. 7, 2012;48(Suppl 6):66-67, Abstract 220.
Gaillard et al., CORAIL trial: Randomized phase III study of lurbinectedin (PM01183) versus pegylated liposomal doxorubicin (PLD) or topotecan (T) in patients with platinum-resistant ovarian cancer. J Clin Oncol. 2016;34:Abstract TPS5597.
Gaillard et al., CORAIL trial: Randomized phase III study of lurbinectedin (PM01183) versus pegylated liposomal doxorubicin or topotecan in patients with platinum-resistant ovarian cancer (Proc). Asco American Society of Clinical Oncology. 52nd Annual Meeting. 1 page, poster, Jun. 3-7, 2016.
Gaillard et al., Lurbinectedin versus pegylated liposomal doxorubicin or topotecan in patients with platinum-resistant ovarian cancer: A multicenter, randomized, controlled, open-label phase 3 study (CORAIL). Gynecol Oncol. Nov. 2021;163(2):237-245.
Galmarini et al., Lurbinectedin (PM01183) synergizes with topoisomerase I inhibitors in vitro and in vivo. AACR Annual Meeting. Abstract 5499, Apr. 6-10, 2013.
Galmarini et al., Lurbinectedin (PM01183) synergizes with topoisomerase I inhibitors in vitro and in vivo. AACR Annual Meeting. Abstract 5499, poster, Apr. 6-10, 2013.
Galmarini, New marine anticancer agents in development. PharmaMar, New Cytotoxics and Vaccines, Symposium IX. slideshow, 28 pages, Jun. 22-25, 2010.
Ganti et al., Efficacy of lurbinectedin in a clinical trial versus other standard of care in a real-world comparator arm in relapsed/refractory small cell lung cancer patients. J Clin Oncol. 2022;40(Suppl 16):Abstract e20619.
Ganti et al., Lurbinectedin vs an External Control arm in Patients with Small Cell Lung Cancer. Journal of Thoracic Oncology. Mar. 2023;18(3S):e42-e43, Abstract PP01.76.
Gedminas et al., Lurbinectedin Inhibits the EWS-WT1 Transcription Factor in Desmoplastic Small Round Cell Tumor. Mol Cancer Ther. Aug. 2, 2022;21(8):1296-1305.
Gedminas et al., Lurbinectedin Targets the EWS-WT1 Transcription Factor in Desmoplastic Small Round Cell Tumor. Pediatr Blood Cancer. 2019;66(Suppl 2):S146-S147, Abstract 308.
Glisson et al., Recurrent small cell lung cancer: update. Semin Oncol. Feb. 2003;30(1):72-8.
Gordon et al., Saint: Results of a Phase 1/2 Study of Safety/Efficacy Using Safe Amounts of Ipilimumab, Nivolumab and Trabectedin as First Line Treatment of Advanced Soft Tissue Sarcoma. ASCO 55th Annual Meeting. 1 page, Jun. 1, 2019.
Gourd, 2018 ASCO Annual Meeting. The Lancet Oncology. 2018;19(7):865-866.
Gourd, Lurbinectedin for BRCA-mutated advanced breast cancer. Lancet Oncol. Nov. 2018;19(11):e582.
Grazziotin-Soares et al., The marine product Tryptamicidin shows activity toward platinum-resistant cells and attenuates nucleotide excision repair. 31st EORTC PAMM-Group Winter meeting. 20 pages, slideshow, Jan. 28-30, 2010.
Grazziotin-Soares et al., The Marine Products Yondelis and Tryptamicidin (PM01183) show activity toward platinum-resistant cells and attenuates nucleotide excision repair. EORTC PAMM-Group Winter meeting. 1 page, abstract, Jan. 28-30, 2010.
Gros et al., Lurbinectedin in Refractory Diffuse Malignant Peritoneal Mesothelioma: Report of Two Cases. Front Oncol. Jun. 18, 2021;11:704295, 5 pages.
Guillen et al., Combination of PM1183 with doxorubicin induces a synergistic antitumor activity in SCLC tumor xenografts. AACR American Association for Cancer Research, 106th Annual Meeting. 1 page, poster, Apr. 18-22, 2015.
Guillen et al., In vivo combination studies of PM01183 with alkylating, antimetabolites, DNA-topoisomerase inhibitors and tubulin binding agents. AACR American Association for Cancer Research, 102nd Annual Meeting. 1 page, Abstract 3538, Apr. 2-6, 2011.
Guillen et al., In vivo combination studies of PM01183 with alkylating, antimetabolites, DNA-topoisomerase inhibitors and tubulin binding agents. AACR American Association for Cancer Research, 102nd Annual Meeting. 1 page, Abstract 3538, Poster, Apr. 2-6, 2011.
Guillen et al., Lurbinectedin (PM01183) in vivo synergizes the antitumor activity of taxanes. AACR Annual Meeting. Abstract 5495, Apr. 6-10, 2013.
Guillen et al., Lurbinectedin (PM01183) synergizes in vivo the antitumor activity of doxorubicin in SCLC tumor xenografts. AACR Annual Meeting. Abstract 2542, Apr. 20, 2015.
Guillen et al., Lurbinectedin (PM1183) in vivo Synergizes the Antitumor Activity of Taxanes. AACR American Association for Cancer Research, Annual Meeting. Abstract 5495, poster, Apr. 6-10, 2013.
Gupta et al., High SLFN11 expression correlates with sensitivity to lurbinectedin in small cell lung cancer (SCLC) models. Cancer Res. 2023;83(7 Suppl):Abstract 2145.
Hanvesakul et al., EMERGE 402 Phase 4 Observational Study: Safety and Outcomes in Patients With SCLC Receiving Treatment With Lurbinectedin. J Thorac Oncol. 2021;16(10 Suppl):S1189-S1190, Abstract P64.02.
Hanvesakul et al., Indirect treatment comparison of lurbinectedin versus other second-line treatments for small-cell lung cancer. J Comp Eff Res. May 2023; 12(5):e220098, 18 pages.
Hanvesakul et al., Systematic Literature Review of Second-line Treatments for Small-cell Lung Cancer. Value in Health. Jan. 2022;25(1 Suppl):S37-S38, Abstract POSC28.
Hanvesakul, Emerge 402 Phase 4 Observational Study: Safety and Outcomes in Patients With SCLC Receiving Treatment With Lurbinectedin. 2021 World Conference on Lung Cancer. 9 pages, slideshow, Sep. 8-14, 2021.
Hao et al., Current Strategies for Extensive Stage Small Cell Lung Cancer Beyond First-line Therapy. Clin Lung Cancer. Jan. 2022;23(1):14-20.
Harlow et al., Lurbinectedin Inactivates teh EWS/FLI1 Transcripton Factor By Redistributing the Protein within the Nucleus. AACR American Association for Cancer Research, 107th Annual Meeting. 1 page, poster, Apr. 16-20, 2016.
Harlow et al., PM01183 inactivates the EWS/FLI1 transcription factor by redistributing the protein within the nucleus. AACR Annual Meeting. Abstract LB-177, Apr. 18, 2016.
Harlow et al., PM01183 shows an improved therapeutic index relative to trabectedin and suppresses EWS/FLI1 activity at clinically achievable concentrations. AACR American Association for Cancer Research, 105th Annual Meeting, 1 page, poster, Apr. 5-9, 2014.

(56) References Cited

OTHER PUBLICATIONS

Harlow et al., PM01183 shows an improved therapeutic index relative to trabectedin and suppresses EWS/FLI1 activity at clinically achievable concentrations. AACR Annual Meeting. Abstract 3962, Apr. 8, 2014.
Cheng et al., Efficacy and safety of lurbinectedin as second-line therapy in Chinese patients with small cell lung cancer: Preliminary results of a phase 1 study. ASCO American Society of Clinical Oncology, 58th Annual Meeting. 1 page, Poster, Jun. 3-7, 2022.
Cheng et al., Efficacy and safety of lurbinectedin as second-line therapy in Chinese patients with small cell lung cancer: Preliminary results of a phase 1 study. J Clin Oncol. 2022;40(Suppl 16):526s, Abstract 8580.
Cheuvart et al., Doxorubicin paclitaxel in pretreated advanced small-cell lung cancer: a large real-life retrospective study. Transl Lung Cancer Res. Oct. 31, 2025;14(10):4412-4421.
Chou et al., Quantitative analysis of dose-effect relationships: the combined effects of multiple drugs or enzyme inhibitors. Adv Enzyme Regul. 1984;22:27-55.
Chou, Theoretical basis, experimental design, and computerized simulation of synergism and antagonism in drug combination studies. Pharmacol Rev. Sep. 2006;58(3):621-81.
Chu et al., Treatment of small cell lung cancer: recent advances. Curr Opin Oncol. Jan. 1, 2022;34(1):83-88.
Clark et al., Small-Cell Lung Cancer: Treatment Progress and Prospects. Oncology. 1998;12(5):647-58.
Clinical Pharmacology, Clinical Drug Interaction Studies—Cytochrome P450 Eyzme—and Transporter-Mediated Drug Interactions, Guidance for Industry. U.S. Department of Health and Human Services, Food and Drug Administration, Center for Drug Evaluation and Research (CDER). 27 pages, Jan. 2020.
Clinicaltrials.gov, History of Changes for Study: NCT02611024. Pharmacokinetic Study of PM01183 in Combination With Irinotecan in Patients With Selected Solid Tumors. 7 pages, Nov. 26, 2021.
Clinicaltrials.gov, Study to Assess Safety, Tolerability, Efficacy of PM01183 and Atezolizumab in Patients w/ Advanced Small Cell Lung Cancer. NCT04253145. 8 pages, Nov. 18, 2023.
Cortesi et al., Exceptional response to lurbinectedin and irinotecan in BRCA-mutated platinum-resistant ovarian cancer patient: a case report. Ther Adv Chronic Dis. Jan. 13, 2022;13:20406223211063023, 6 pages.
Costanzo et al., Promoters of ASCL1- and NEUROD1-dependent genes are specific targets of lurbinectedin in SCLC cells. EMBO Mol Med. Apr. 7, 2022;14(4):e14841, 17 pages.
Cote et al., A Phase 1b lead-in to a randomized phase 2 trial of lurbinectedin plus doxorubicin in leiomyosarcom (Lms). Ctos Connective Tissue Oncology Society, 27th Annual Meeting. Abstract TPS11592, Nov. 16-19, 2022.
Cote et al., A Phase 1b lead-in to a Randomized Phase 2 Trial of Lurbinectedin plus Doxorubicin in Leiomyosarcom: Results from the Phase 1b Soft-Tissue Sarcoma Lead-In. CTOS Connective Tissue Oncology Society, 27th Annual Meeting. Poster, Nov. 16-19, 2022.
Cote et al., A phase 1b lead-in to a randomized phase 2 trial of lurbinectedin plus doxorubicin in leomyosarcoma (Lms). Asco American Society of Clinical Oncology, 58th Annual Meeting. 1 page, Poster, Jun. 3-7, 2022.
Cote et al., A phase 1b lead-in to a randomized phase 2 trial of lurbinectedin plus doxorubicin in leomyosarcoma (Lms). J Clin Oncol. 2022;40(Suppl 16):684s, Abstract TPS11592.
Cote et al., Lurbinectedin in Combination with Irinotecan in Patients (PTS) with Soft Tissue Sarcomas (Sts). Ctos 2020 Annual Meeting. 1 page, abstract, Control ID: 3463926, Nov. 18-21, 2020.
Cote et al., Lurbinectedin in combination with irinotecan in patients (PTS) with soft tissue sarcomas (Sts). Ctos 2020 Annual Meeting. 1 page, poster, Nov. 8-21, 2020.
Cote et al., Phase II Study of PM01183 as a Single Agent or in Combination with Conventional Chemotherapy in Metastatic and/or Unresectable Soft Tissue Sarcomas. CTOS Connective Tissue Oncology Society, 21st Annual Meeting. p. 351, Abstract P2-Poster 097, Nov. 9-12, 2016.
Cristina Mendonca Nogueira et al., New FDA oncology small molecule drugs approvals in 2020: Mechanism of action and clinical applications. Bioorg Med Chem. Sep. 1, 20215;46:116340, 28 pages.
Cruz et al., Analysis of secondary mutations in BRCA1/2 genes as a mechanism of resistance of PM01183 in BRCA-mutation carriers. AACR-NCI-EORTC International Conference on Molecular Targets and Cancer Therapeutics. Abstract B117, Oct. 19-23, 2013.
Cruz et al., Analysis of secondary mutations in BRCA1/2 genes as a mechanism of resistance of PM01183 in BRCA-mutation carriers. AACR-NCI-EORTC International Conference on Molecular Targets and Cancer Therapeutics. Poster, 1 page, Oct. 19-23, 2013.
Cruz et al., Development of xenoimplants from genuine BRCA1/2 mutant breast cancer (BC) for the identification of predictive biomarkers, mechanisms of resistance against poly(ADP-ribose) polymerase (PARP) inhibitors and evaluation of novel therapies. 26th EORTC-NCI-AACR Symposium on Molecular Targets and Cancer Therapeutics. 1 page, poster, Nov. 18-21, 2014.
Cruz et al., Development of xenoimplants from genuine BRCA1/2 mutant breast cancer (BC) for the identification of predictive biomarkers, mechanisms of resistance against poly(ADP-ribose) polymerase (PARP) inhibitors and evaluation of novel therapies. Eur J Cancer. 2014;50(Suppl 6):82, Abstract 244.
Cruz et al., Lurbinectedin (PM01183) exhibits antitumor activity in PARP-inhibitor resistant germline BRCA PDX and lacks cross-resistance with cisplatin. 41st ESMO European Cancer Congress. 18 pages, slideshow, Oct. 7-11, 2016.
Cruz et al., Lurbinectedin (PM01183) exhibits antitumor activity in PARP-inhibitor resistant germline BRCA PDX and lacks cross-resistance with cisplatin. Annals of Oncology. 2016;27(Suppl 6):vi526, Abstract 15200.
Davies et al., Treatment of recurrent small cell lung cancer. Hematol Oncol Clin North Am. Apr. 2004;18(2):387-416.
De La Torre et al., An Analysis of FDA Drug Approvals from the Perspective of Molecules. Molecules. Jan. 25, 2021;26(3):627, 14 pages.
Desai, Real-World Experience of Lurbinectedin beyond the second line in Small Cell Lung Cancer. IASLC, 2022 Targeted Therapies of Lung Cancer Meeting. 10 pages, slideshow, Feb. 22-26, 2022.
Devgun et al., Microarray Data Analysis, Structure Prediction, and In silico Docking of Drugs for Inhibiting Overexpression of High Mobility Group A1 in Human Malignant Neoplasias. Intl J Pharm Sci Res. 2020;12(5):448-456.
Dingemans et al., Small-cell lung cancer: ESMO Clinical Practice Guidelines for diagnosis, treatment and follow-up. Ann Oncol. Jul. 2021;32(7):839-853. pre-publication edition.
Dumoulin, Lurbinectedin in pre-treated patients with SCLC and mesothelioma. 2021 World Conference on Lung Cancer. 11 pages, slideshow. Sep. 8-14, 2021.
Dumoulin, Lurbinectedin in Pre-Treated Patients With Small Cell Lung Cancer and Malignant Pleural Mesothelioma in a Real World Setting. J Thorac Oncol. 2021;16(10 Suppl):S1180, Abstract P63.01.
Estrin et al., Real-world (RW) outcomes of second-line (2L) small cell lung cancer (SCLC) patients treated with lurbinectedin. Annals of Oncology. 2022;33(S7):s1250, Abstract 1529P.
Estrin et al., Real-world (RW) outcomes of second-line (2L) small cell lung cancer (SCLC) patients treated with lurbinectedin. Annals of Oncology. ESMO Congress 2022. Abstract 1539P, 1 page, (2022).
European Pharmacopoeia 7.1, Index. pp. 3481-3527, (2011).
European Pharmacopoeia 7.2, Contents of Supplement 7.2. pp. XXV-XXVI, (2011).
Falcon et al., Lurbinectedin (LUR) in combination with Irinotecan (IRI) in patients (pts) with advanced endometrial carcinoma. ASCO American Society of Clinical Oncology, 57th Annual Meeting. 1 page, poster, Jun. 4-8, 2021.
Falcon et al., Lurbinectedin (LUR) in combination with irinotecan (IRI) in patients (pts) with advanced endometrial carcinoma. J Clin Oncol. 2021;39(15 Suppl):333s, Abstract 5586.

(56) References Cited

OTHER PUBLICATIONS

Farago et al., Atlantis: Global, randomized phase III study of lurbinectedin (L) with doxorubicin (DOX) vs. CAV or topotecan (T) in small-cell lung cancer after platinum therapy. ASCO American Society of Clinical Oncology, 54th Annual Meeting. 1 page, poster, Jun. 1-5, 2018.
Farago et al., Atlantis: Global, randomized phase III study of lurbinectedin (L) with doxorubicin (DOX) vs. CAV or topotecan (T) in small-cell lung cancer after platinum therapy. J Clin Oncol. 2018;36, Abstract TPS8587.
Farago et al., Atlantis: Phase III Study of PM01183 with Doxorubicin vs. CAV or Topotecan in Small-Cell Lung Cancer After Platinum Therapy. Journal of Thoracic Oncology. 2017;12(11S2):S2400, Abstract P2.04-008.
Fernandez et al., Drug-exposure response models for safety and efficacy in the use of doxorubicin plus lurbinectedin. ICPAD Workshop 2017. Paper No. 11. poster, Sep. 13-14, 2017.
Fernandez Teruel et al., Pharmacokinetic and Pharmacodynamic Modeling of Neutropenia for Lurbinectedin. Basic & Clinical Pharmacology & Toxicology. 2014;115(Suppl 2):20-21, Abstract 53.
Fernandez-Teruel et al., Integrated exposure-response analysis of efficacy and safety of lurbinectedin to support the dose regimen in small-cell lung cancer. Cancer Chemother Pharmacol. May 2022;89(5):585-594.
Fernandez-Teruel et al., Lurbinectedin (PM01183) Efficacy in Platinum-Resistant/Refractory Ovarian Cancer (PRROC) Patients Correlates with Drug Exposure Using Pharmacokinetic/Pharmacodynamic (PK/PD) Modelling. ESGO19, European Gynaecological Oncology Congress 2015. 1 page, poster, Oct. 24-27, 2015.
Fernandez-Teruel et al., Lurbinectedin (PM01183) Efficacy in Platinum-Resistant/Refractory Ovarian Cancer (PRROC) Patients Correlates with Drug Exposure Using Pharmacokinetic/Pharmacodynamic (PK/PD) Modelling. J Gynecol Cancer. 2015;25(Suppl 19):433, Abstract ESGO-0843.
Fernandez-Teruel et al., Population Pharmacokinetic-Pharmacodynamic Modeling and Covariate Analyses of Neutropenia and Thrombocytopenia in Patients With Solid Tumors Treated With Lurbinectedin. J Clin Pharmacol. Sep. 2021;61(9):1206-1219. pre-publication edition.
Ferrara et al., Progress in the Management of Advanced Thoracic Malignancies in 2017. J Thorac Oncol. Mar. 2018;13(3):301-322.
Fisher et al., Time-dependent covariates in the Cox proportional-hazards regression model. Annu Rev Public Health. 1999;20:145-57.
Mccall et al., Phase I Study of Palliative Radiotherapy with Lurbinectedin in Patients with Extensive Stage Small Cell Lung Cancer. J Thorac Oncol. 2022 Sept; 17(9 Suppl): S541, Abstract EP14.03-003.
Mclellan, Zepsyre, Product Analysis. <www.datamonitorhealthcare.com.> 13 pages, Aug. 17, 2017.
Medsafe, The Importance of Cytochrome P450 3A4. Drug Metabolism. Mar. 2014;35(1):4-6.
Menna et al., Lurbinectedin, an Anticancer Drug of Natural Origin, Effectively Reduces Retinal Macular Edema: A Case Report. Asian Journal of Research and Reports in Ophthalmology. 2020;3(2):24-31.
Metaxas et al., A phase I trial of lurbinectedin in combination with cisplatin in patients with advanced solid tumors. Invest New Drugs. Feb. 2022;40(1):91-98.
Metaxas et al., Lurbinectedin as second- or third-line palliative therapy in malignant pleural mesothelioma: an international, multi-centre, single-arm, phase II trial (SAKK 17/16). Ann Oncol. Apr. 2020;31(4):495-500.
Metaxas et al., Lurbinectedin Monotherapy in Patients with Progressive Malignant Pleural Mesothelioma. A Multicenter, Single Arm, Phase II Trial. ESMO 2018. Abstract SAKK 17/19, Poster, (2018).
Metaxas et al., SAKK 17/16—Lurbinectedin as second or third line palliative chemotherapy in malignant pleural mesothelioma (MPM): A multi-center, single-arm phase II trial. Annals of Oncology. Oct. 2019;30(Suppl 5):v748, Abstract 1843O.
Metaxas et al., SAKK 17/16: Lurbinectedin as second or third line palliative chemotherapy in malignant pleural mesothelioma (MPM): A multi-center, single-arm phase II trial. Annals of Oncology. 2019 ESMO Congress. Slideshow. 10 pages. (2019).
Metaxas et al., SAKK 17/16: Lurbinectedin as second or third line palliative chemotherapy in malignant pleural mesothelioma (MPM): A multi-center, single-arm phase II trial. Annals of Oncology. 2019;30(Suppl 5):v748, Abstract 1316.
Mukherjee et al., Simultaneously Inhibiting BCL2 and MCL1 Is a Therapeutic Option for Patients with Advanced Melanoma. Cancers (Basel). Aug. 5, 2020;12(8):2182, 16 pages.
Nair et al., Efficacy and safety of second-line (2L) therapy in patients with relapsed small cell lung cancer (Sclc): A systematic literature review (Slr). J Clin Oncol. 2022;40(Suppl 16):Abstract e20576.
Olmedo et al., Efficacy and safety of lurbinectedin and doxorubicin in relapsed small cell lung cancer. Results from an expansion cohort of a phase I study. Invest New Drugs. Oct. 2021;39(5):1275-1283.
Olmedo Garcia et al., Activity of lurbinectedin as single agent and in combination in patients with advanced small cell lung cancer (SCLC). 42nd ESMO European Cancer Congress. 1 page, poster, Sep. 8-12, 2017.
Olmedo Garcia et al., Activity of lurbinectedin as single agent and in combination in patients with advanced small cell lung cancer (SCLC). Annals of Oncology. 2017;28(Suppl 5):v539-v540, Abstract 1529PD.
Papachristos et al., Lurbinectedin-induced thrombocytopenia: the role of body surface area. Cancer Chemother Pharmacol. May 2022;89(5):573-575.
Parkes et al., Systemic Treatment Strategies for Patients with Hereditary Breast Cancer Syndromes. Oncologist. Jun. 2017;22(6):655-666.
Patel et al., An overview of lurbinectedin as a new second-line treatment option for small cell lung cancer. Ther Adv Med Oncol. May 2, 20219;13:17588359211020529, 9 pages.
Paz-Ares et al., Clinical activity of lurbinectedin (PM01183) in combination with gemcitabine (GEM) in non-small cell lung cancer (NSCLC) patients (pts): IASLC 15th World Conference on Lung Cancer. Poster, 1 page, 2013.
Paz-Ares et al., Clinical activity of lurbinectedin (PM01183) in combination with gemcitabine (GEM) in non-small cell lung cancer (NSCLC) patients (pts): preliminary subgroup analysis of a phase lb study. J Thorac Oncol. Otober 27-31, 2013;8(Suppl 2):Abstract 995.
Paz-Ares, Lurbinectedin/Doxorubicin versus CAV or Topotecan in relapsed SCLC patients: Phase III randomized Atlantis Trial. 2021 World Conference on Lung Cancer. 15 pages, Sep. 8-14, 2021.
Paz-Ares, Lurbinectedin/Doxorubicin versus CAV or Topotecan in Relapsed SCLC Patients: Phase III Randomized Atlantis Trial. J Thorac Oncol. 16(10 Suppl):S844-S845, Abstract PL02.03.
Perez-Fidalgo et al., Cell proliferation inhibitors and apoptosis promoters. EJC Suppl. Aug. 22, 2020;15:73-76.
Pernice at al., Development of a liquid chromatography/tandem mass spectrometry assay for the quantification of PM01183 (lurbinectedin), a novel antineoplastic agent, in mouse, rat, dog, Cynomolgus monkey and mini-pig plasma. J Pharm Biomed Anal. May 10, 2016;123:37-41.
Petty et al., Emerging Strategies for the Treatment of Small Cell Lung Cancer: A Review. JAMA Oncol. pp. E1-E11, published online Dec. 15, 2022 .
Pharma Mar, S.A., CNMV Informe Financiero Semestral Correspondiente Al Ano. 21 pages, Dec. 31, 2021.
Pharma Mar, S.A., CNMV Informe Financiero Semestral Correspondiente Al Ano. 21 pages, Dec. 31, 2022.
Pharma Mar, S.A., CNMV Informe Financiero Semestral Correspondiente al Ano. 24 pages, Jun. 30, 2021.
Pharma Mar, S.A., CNMV Informe Financiero Semestral Correspondiente Al Ano. 33 pages, Jun. 30, 2023.
Pharmamar, CNMV Informe Financiero Semestral Correspondiente al Ano. 21 pages, Dec. 31, 2023.
Pharmamar, CNMV Informe Financiero Semestral Correspondiente al Ano. 33 pages, Jun. 6, 2024.

(56) References Cited

OTHER PUBLICATIONS

Pharmamar, CNMV Informe Financiero Semestral Correspondiente al Ano. 35 pages, Jun. 30, 2025.
PharmaMar, Consolidated Non-Financial Information Statement 2018. 60 pages, Feb. 28, 2019.
PharmaMar, Consolidated Non-Financial Information Statement 2019. 64 pages, Feb. 26, 2020.
PharmaMar, Consolidated Non-Financial Information Statement 2021. 102 pages, Feb. 28, 2022.
PharmaMar, Consolidated Non-Financial Information Statement 2022. 120 pages, Feb. 28, 2023.
PharmaMar, Consolidated Non-Financial Information Statement 2023. 150 pages, Feb. 28, 2024,.
PharmaMar, Corporate Presentation. Slideshow. 169 pages, Jan. 2018.
PharmaMar, Corporate Presentation. Slideshow. 25 pages, Jan. 2018.
PharmaMar, Financial information as of Sep. 30, 2025. Slideshow. 19 pages, (2025).
PharmaMar, General Meeting of Shareholders 2019. Slideshow. 71 pages, Jun. 26, 2019.
PharmaMar, Inside Information. 7 pages, Nov. 10, 2020.
PharmaMar, Investment Highlights. Slideshow. 31 pages, Jun. 2018.
PharmaMar, Junta General de Accionistas 2017. Slideshow. 76 pages, Jun. 29, 2017.
PharmaMar, Junta General de Accionistas 2020. Slideshow. 52 pages, Jun. 15, 2020.
PharmaMar, Lurbinectedin data in Progressive Malignant Pleural Mesothelioma presented at ESMO. Press Release, 3 pages, Oct. 1, 2019.
PharmaMar, Other Relevant Information. 1 page, Jul. 27, 2023.
PharmaMar, Other Relevant Information. 13 pages, Sep. 6, 2023.
PharmaMar, Other Relevant Information. 4 pages, Jul. 5, 2023.

* cited by examiner

COMBINATION OF LURBINECTEDIN AND IMMUNE CHECKPOINT INHIBITORS

CROSS REFERENCE TO RELATED APPLICATIONS

This application is a continuation of U.S. application Ser. No. 18/023,804, filed on Feb. 28, 2023, which is a U.S. National Stage Application filed under 35 U.S.C. § 371, based on International Patent Application No. PCT/EP 2021/074425, filed on Sep. 3, 2021, which claims priority to International Patent Application No. PCT/EP 2020/074860, filed on Sep. 4, 2020. The entire contents of each of the above applications are incorporated herein by reference.

FIELD OF THE INVENTION

The present invention relates to therapeutic treatment of cancers, particularly solid tumours, with combination therapy using lurbinectedin and immune checkpoint inhibitors.

BACKGROUND TO THE INVENTION

Immune checkpoint inhibitor (ICI) therapy is a form of cancer immunotherapy. The therapy targets immune checkpoints, key regulators of the immune system that when stimulated can dampen the immune response to an immunologic stimulus. Some cancers can protect themselves from attack by stimulating immune checkpoint targets. Checkpoint therapy can block inhibitory checkpoints, restoring immune system function, and permitting the immune system to respond to the cancer.

Key immune checkpoint inhibitors target the molecules CTLA4, PD-1, and PD-L1. PD-1 is the transmembrane programmed cell death 1 protein (also called PDCD1 and CD279), which interacts with PD-L1 (PD-1 ligand 1, or CD274). PD-L1 on the cell surface binds to PD1 on an immune cell surface, which inhibits immune cell activity. Among PD-L1 functions is a key regulatory role on T cell activities. It appears that (cancer-mediated) upregulation of PD-L1 on the cell surface may inhibit T cells that might otherwise attack. Antibodies that bind to either PD-1 or PD-L1 and therefore block the interaction may allow the T-cells to attack the tumour.

A number of ICI therapies targeting these molecules have been approved for a wide range of uses, and more therapies and cancer targets are under investigation. Approved ICIs include ipilimumab (targeting CTLA-4); nivolumab, pembrolizumab, and cemiplimab (targeting PD-1); and atezolizumab, avelumab, and durvalumab (targeting PD-L1).

Lurbinectedin, also known as PM01183 and initially called tryptamicidin, is a synthetic tetrahydropyrrolo[4,3,2-de]quinolin-8(1H)-one alkaloid analogue with antineoplastic activity, and the subject of WO 03/014127. Lurbinectedin is a selective inhibitor of oncogenic transcription, induces DNA double-strand break generating apoptosis, and modulates the tumor microenvironment. For example, by inhibiting active transcription in tumor-associated macrophages, lurbinectedin downregulates IL-6, IL-8, CCL2, and VEGF.

The chemical structure of lurbinectedin is represented as follows:

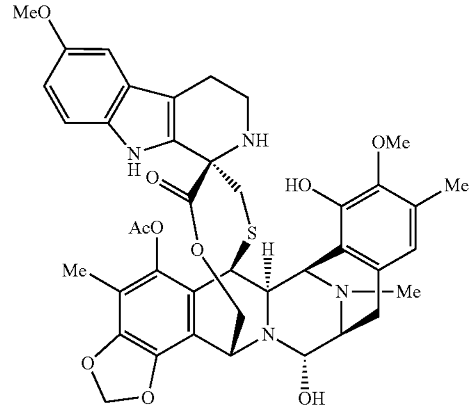 [SMILES: COc1ccc2[nH]c3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

Lurbinectedin has demonstrated highly potent in vitro activity against solid and non-solid tumour cell lines as well as significant in vivo activity in several xenografted human tumor cell lines in mice, such as those for breast, kidney and ovarian cancer. It is a selective inhibitor of the oncogenic transcription programs on which many tumours are particularly dependent. Together with its effect on cancer cells, lurbinectedin inhibits oncogenic transcription in tumour-associated macrophages, downregulating the production of cytokines that are essential for the growth of the tumour. Transcriptional addiction is an acknowledged target in those diseases, many of them lacking other actionable targets.

There is a need for further effective cancer therapies.

SUMMARY OF THE INVENTION

The present inventors have surprisingly determined that combination therapy using lurbinectedin and an ICI may be effective in treatment of certain cancer types.

Accordingly, the present invention provides a method of treatment of a solid tumour, the method comprising administering a combination therapy of lurbinectedin and an immune checkpoint inhibitor to a patient, preferably a human patient, in need thereof, thereby treating the solid tumour.

The immune checkpoint inhibitor may comprise an immunoglobulin molecule, preferably an antibody, targeting an immune checkpoint molecule. By "targeting" is meant that the immunoglobulin molecule is an agonist of the immune checkpoint molecule, and/or that it specifically binds to the immune checkpoint molecule so as to block activation of the immune checkpoint, thereby enhancing immune function or response. The immune checkpoint molecule may be selected from CTLA-4, PD-1, and PD-L1. In preferred embodiments the immune checkpoint molecule is PD-1. In some embodiments, a plurality of immune checkpoint molecules may be targeted; for example, CTLA-4 and PD-1, or CTLA-4 and PD-L1, or CTLA-4 and PD-1 and PD-L1; preferably CTLA-4 and PD-1.

In some embodiments, the immune checkpoint inhibitor comprises a monoclonal antibody which specifically binds CTLA-4, or which specifically binds PD-1, or which specifically binds PD-L1. Examples of such monoclonal antibodies include pembrolizumab, nivolumab, ipilimumab, avelumab, atezolizumab, durvalumab, cemiplimab (REGN2810), camrelizumab (SHR1210), envafolimab (KN035), sintilimab (IBI308), spartalizumab (PDR001), tislelizumab (BGB-A317), prolgolimab (BCD-100), toripalimab (JS001), dostarlimab (TSR-042, WBP-285), tremelimumab (ticilimumab, CP-675,206).

Particularly preferred combinations include lurbinectedin and atezolizumab; lurbinectedin and pembrolizumab; lurbinectedin and nivolumab and ipilimumab; lurbinectedin and durvalumab; and lurbinectedin and dostarlimab.

In some embodiments, the immune checkpoint inhibitor comprises a peptide inhibitor of PD-1/PD-L1 interaction, or a small molecule inhibitor. Examples of such include AUNP12, CA-170, and BMS-986189.

The lurbinectedin and the immune checkpoint inhibitor may be administered concurrently, separately or sequentially. Multiple administrations of either the lurbinectedin, or the immune checkpoint inhibitor, or both, may be given. Other administration schedules may be used.

Lurbinectedin may be administered in cycles once every one to four weeks, preferably once every three weeks. A particular administration cycle is once every 21 days.

Any suitable administration route may be used, for example, subcutaneous, intravenous, intraperitoneal. Different administration routes may be used for the lurbinectedin and the immune checkpoint inhibitor. Preferably the lurbinectedin is administered by intravenous infusion; for example, 3.2 $mg/m^2$ by intravenous infusion every 21 days or three weeks, or 3.2 $mg/m^2$ by intravenous infusion over 60 minutes every 21 days or three weeks. The lurbinectedin may be administered in cycles once every one to four weeks, preferably once every three weeks. The lurbinectedin may be administered at a dose of 1 to 5 $mg/m^2$ body surface area, 1 to 2.5 $mg/m^2$ body surface area, 1 to 2 $mg/m^2$ body surface area, 2 to 3 $mg/m^2$ body surface area, about 3 $mg/m^2$ body surface area, 3 to 3.5 $mg/m^2$ body surface area, 2 to 3.2 $mg/m^2$ body surface area, 1 $mg/m^2$, 1.5 $mg/m^2$, 2 $mg/m^2$, 2.4 $mg/m^2$, 2.5 $mg/m^2$, 2.6 $mg/m^2$, or 3.2 $mg/m^2$ body surface area.

The lurbinectedin may be administered as an infusion, preferably with an infusion time of up to 24 hours, 1 to 12 hours, 1 to 6 hours and most preferably 1 hour.

The lurbinectedin may be administered in the form of a pharmaceutically acceptable salt selected from the hydrochloride, hydrobromide, hydroiodide, sulfate, nitrate, phosphate, acetate, trifluoroacetate, maleate, fumarate, citrate, oxalate, succinate, tartrate, malate, mandelate, methanesulfonate p-toluenesulfonate, sodium, potassium, calcium and ammonium salts, ethylenediamine, ethanolamine, N,N-dialkylenethanolamine, triethanolamine and basic amino acids salts.

Preferably the immune checkpoint inhibitor is administered by intravenous infusion; for example, 200 mg every 3 weeks administered as an intravenous infusion over 30 minutes.

Preferably the solid tumour is malignant. In some embodiments, the solid tumour is a carcinoma. In one embodiment of the invention, the solid tumour is selected from the group consisting of prostate cancer, breast cancer, lung cancer, colorectal cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer, and sarcomas. For example, the solid tumour may be selected from the group consisting of cancers of the prostate gland, breast, skin, colon, lung, and urinary organs. In another embodiment, the solid tumour may be selected from the groups consisting of prostate cancer, melanomas, cervical cancer, oesophageal cancer, and head and/or neck cancer. In preferred embodiments, the solid tumour is a melanoma.

In some embodiments, the solid tumour may be a sarcoma. In some embodiments, the solid tumour may be a lymphoma.

In some embodiments, the solid tumour expresses PD-L1. In some embodiments, the method may further comprise determining whether the tumour to be treated expresses PD-L1 prior to beginning treatment. Any suitable test may be used; for example, immunohistochemistry may be used to detect PD-L1 expression on the cell surface of tumour cells.

The treatment may result in one or more of the following outcomes: reduction in tumour size; delay in growth of tumour; prolongation of life of the patient; remission. These outcomes may be in comparison to a control subject (or hypothetical control subject) not given the treatment, or given an alternative treatment.

The above features also apply to the following aspects of the invention, unless otherwise noted.

A further aspect of the present invention provides a method of prolonging survival of a patient having a solid tumour, the method comprising administering a combination therapy of lurbinectedin and an immune checkpoint inhibitor to a patient in need thereof, thereby prolonging survival of the patient.

Also provided is a method of delaying disease progression of a solid tumour in a patient, the method comprising administering a combination therapy of lurbinectedin and an immune checkpoint inhibitor to a patient in need thereof, thereby delaying disease progression of the solid tumour.

Yet further provided is a method of reducing or delaying growth of a solid tumour, the method comprising administering a combination therapy of lurbinectedin and an immune checkpoint inhibitor to a patient in need thereof, thereby reducing or delaying growth of the solid tumour.

A still further aspect of the invention provides a method of selecting a patient having a solid tumour for combination therapy, the method comprising determining whether the solid tumour expresses PD-L1, and if so, selecting the patient for combination therapy wherein the combination therapy comprises administering a combination therapy of lurbinectedin and an immune checkpoint inhibitor. Preferably the immune checkpoint inhibitor comprises an immunoglobulin which targets PD-1 or PD-L1. The method may further comprise providing said combination therapy to the patient.

Also provided by the present invention is use of lurbinectedin in the manufacture of a medicament for the treatment of a solid tumour, wherein said treatment comprises administering a combination therapy of lurbinectedin and an immune checkpoint inhibitor to a patient in need thereof.

The invention also provides use of an immune checkpoint inhibitor in the manufacture of a medicament for the treatment of a solid tumour, wherein said treatment comprises administering a combination therapy of lurbinectedin and an immune checkpoint inhibitor to a patient in need thereof.

Yet further provided is use of lurbinectedin and an immune checkpoint inhibitor in the manufacture of a medicament for the treatment of a solid tumour, wherein said treatment comprises administering a combination therapy of lurbinectedin and an immune checkpoint inhibitor to a patient in need thereof.

The invention further provides lurbinectedin for use in a method of treatment of a solid tumour, wherein said treatment comprises administering a combination therapy of lurbinectedin and an immune checkpoint inhibitor to a patient in need thereof.

Also provided is an immune checkpoint inhibitor for use in a method of treatment of a solid tumour, wherein said treatment comprises administering a combination therapy of lurbinectedin and an immune checkpoint inhibitor to a patient in need thereof.

The invention further provides lurbinectedin and an immune checkpoint inhibitor for use in a method of treatment of a solid tumour, wherein said treatment comprises administering a combination therapy of lurbinectedin and an immune checkpoint inhibitor to a patient in need thereof.

Dosage forms, pharmaceutical packages and preparations, and kits of parts are also provided by the invention. These may comprise lurbinectedin and/or an immune checkpoint inhibitor packaged for use in a method of treatment of a solid tumour, wherein said treatment comprises administering a combination therapy of lurbinectedin and an immune checkpoint inhibitor to a patient in need thereof. The dosage forms, packages, preparations and kits may further comprise instructions for providing treatment to a patient.

Figure 1:
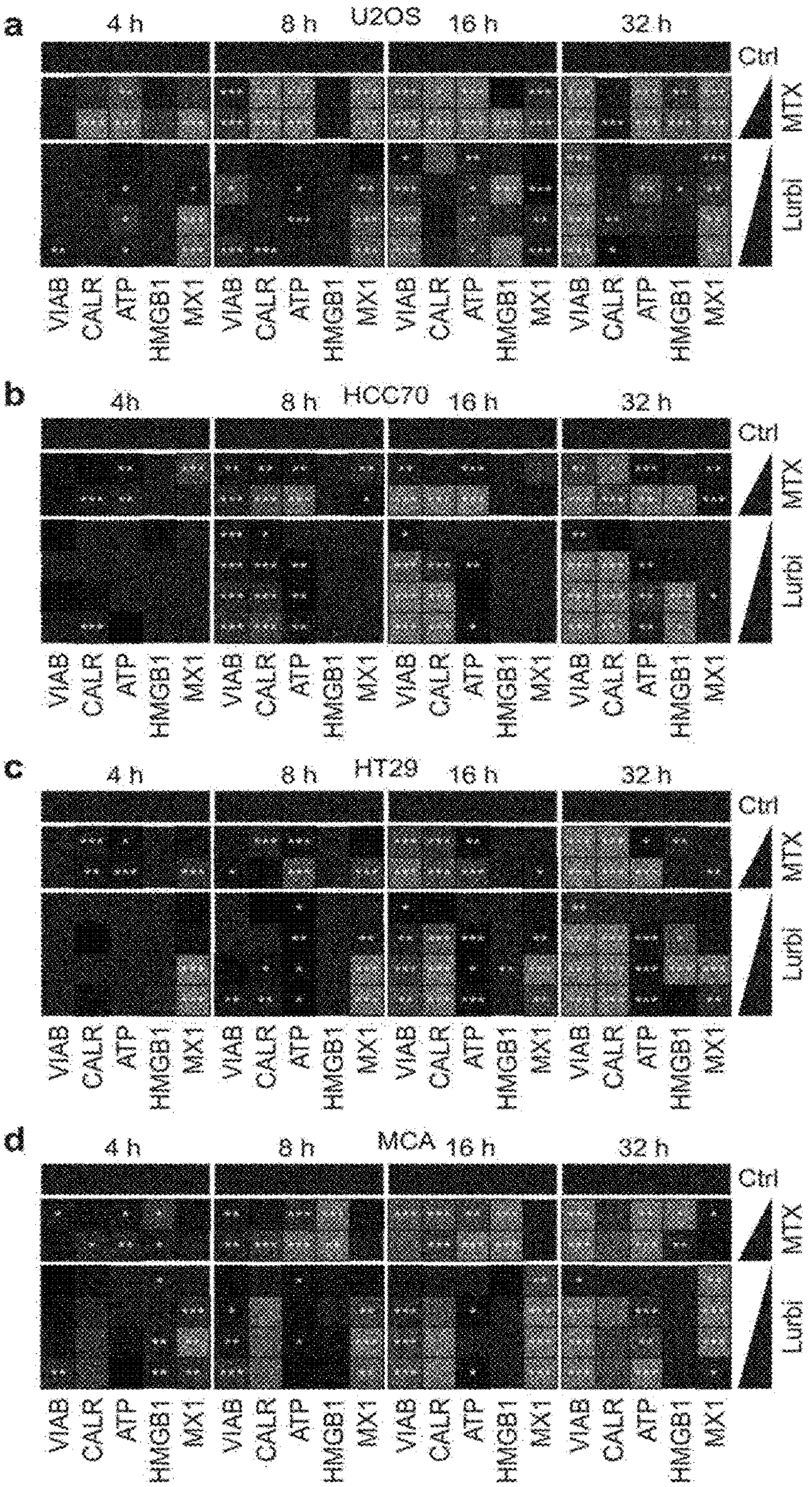
FIG. 1. Immunogenic cell death assessment in solid tumours.

(a) Human osteosarcoma U2OS (a), human breast cancer HCC70 (b) human colon cancer HT29 cells (c) and murine methylcholantrene-induced fibrosarcoma MCA205 cells (d) were treated with lurbinectedin (Lurbi, 1 nM, 10 nM, 100 nM and 1 μM) for the indicated times. Subsequently, the cells were stained with 1 μM Hoechst 33342 and 1 μM propidium iodide and assessed for the loss of viability by automated image acquisition. Images were segmented, cellular debris was excluded and the number of cells with normal nuclear morphology was enumerated. Cells stably expressing CALR-GFP were treated as above. Following the cells were fixed with 3.7% of PFA, stained with 1 μM Hoechst 33342 and assessed by automated image acquisition. Images were segmented, cellular debris was excluded and CALR-GFP granularity (a surrogate marker of CALR exposure) was evaluated in the cytoplasmic region of cells with normal nuclear morphology. Wild type cells were treated as above and then assessed for cytoplasmic quinacrine granularity (after staining with the ATP-sensitive dye quinacrine together with Hoechst 33342) by automated image acquisition, segmentation and analysis. Cells stably expressing HMGB1-GFP were treated as above and then assessed for nuclear HMGB1-GFP fluorescence intensity. The cells were fixed and stained with Hoechst 33342 and images were acquired, segmented and analyzed. WT cells were treated as above and following the media was changed and the cells were incubated for 48 hours before the supernatant was used to treat MX1-GFP biosensor cells for additional 48 hours. The cells were fixed and stained with Hoechst 33342 before type 1 IFN responses were monitored by means of automated microscopy as an increase in GFP fluorescence intensity. Mitoxantrone (MTX, 1 and 3 μM) was used as a positive control. The means of quadruplicate assessments and p-values are depicted as heat maps. (*$p<0.01$; $p<0.005$; *$p<0.001$, two-tailed Student's t test).

Figure 2:
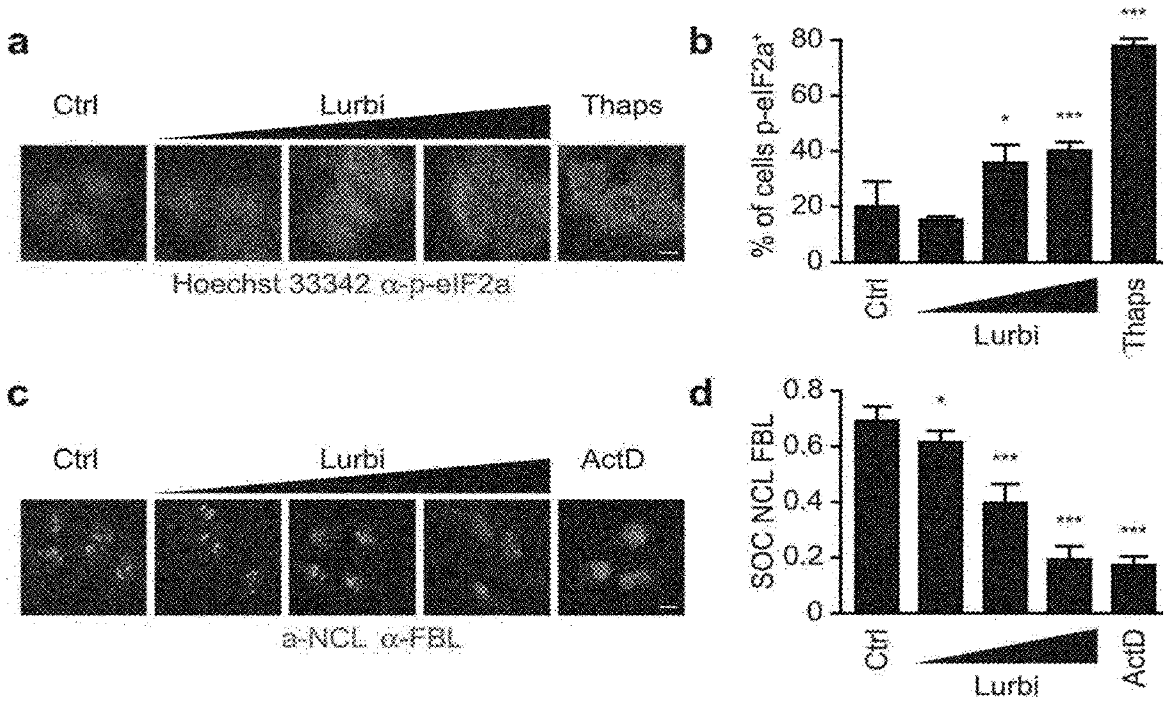

FIG. 2. Traits of immunogenic cell death.

Human osteosarcoma U2OS cells were treated with 10, 50 or 100 nM lurbinectedin (Lurbi) for 6 hours. Thapsigargin (Thaps, 3 μM) was used as a positive control. The cells were fixed with 3.7% PFA and DNA was stained with 1 μM Hoechst 33342. Following the phosphorylation of the eukaryotic translation initiation factor 2 alpha (eIF2a) was assessed with phosphoneoepitope-specific antibody and was monitored by means of automated microscopy as an increase in cytoplasmic fluorescence intensity. (a,b) The level of transcription was measured in U2OS cell treated as above with Lurbi. The transcription inhibitor actinomycin D (ActD) was used as a control. The cells were fixed as above and following the colocalization of nucleolin and fibrillarin was assessed as an indicator for transcriptional activity (c,d) Scale bar equals 10 μm and bar charts depict mean values±SD of quadruplicate assessments (*$p<0.01$; *$p<0.001$, two-tailed Student's t test).

Figure 3:
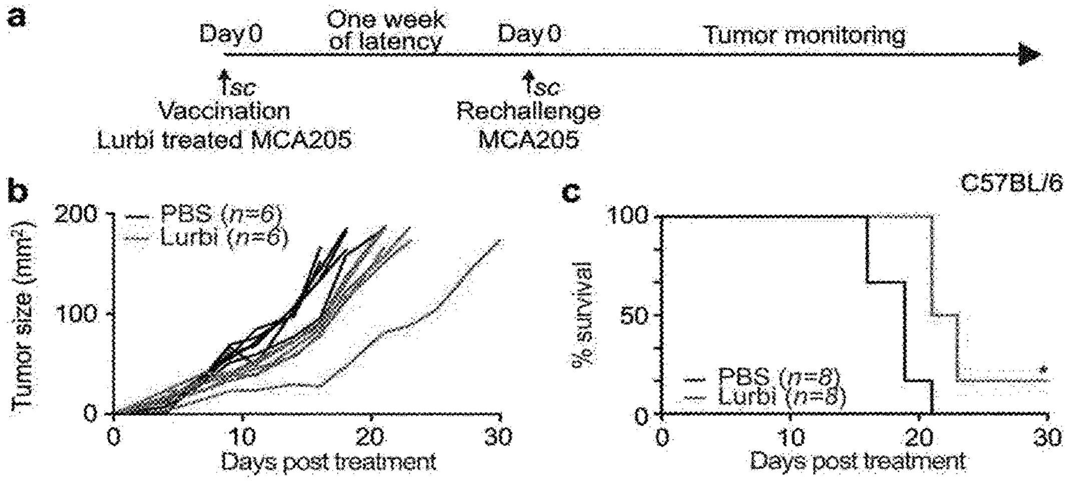

FIG. 3. Anticancer vaccination efficacy of lurbinectedin-treated cells.

MCA205 cells treated for 20 h with 1 μM lurbinectedin were inoculated subcutaneously (s.c.) into immunocompetent C57BL/6 mice, which were rechallenged 7 days later s.c. with living cells of the same type. The tumour growth was measured until endpoints were reached and overall survival was evaluated regularly for the following 30 days (n=6). (*p<. 01, two-tailed Student's t test, compared to all other groups). Data were analyzed with TumGrowth.

Figure 4:
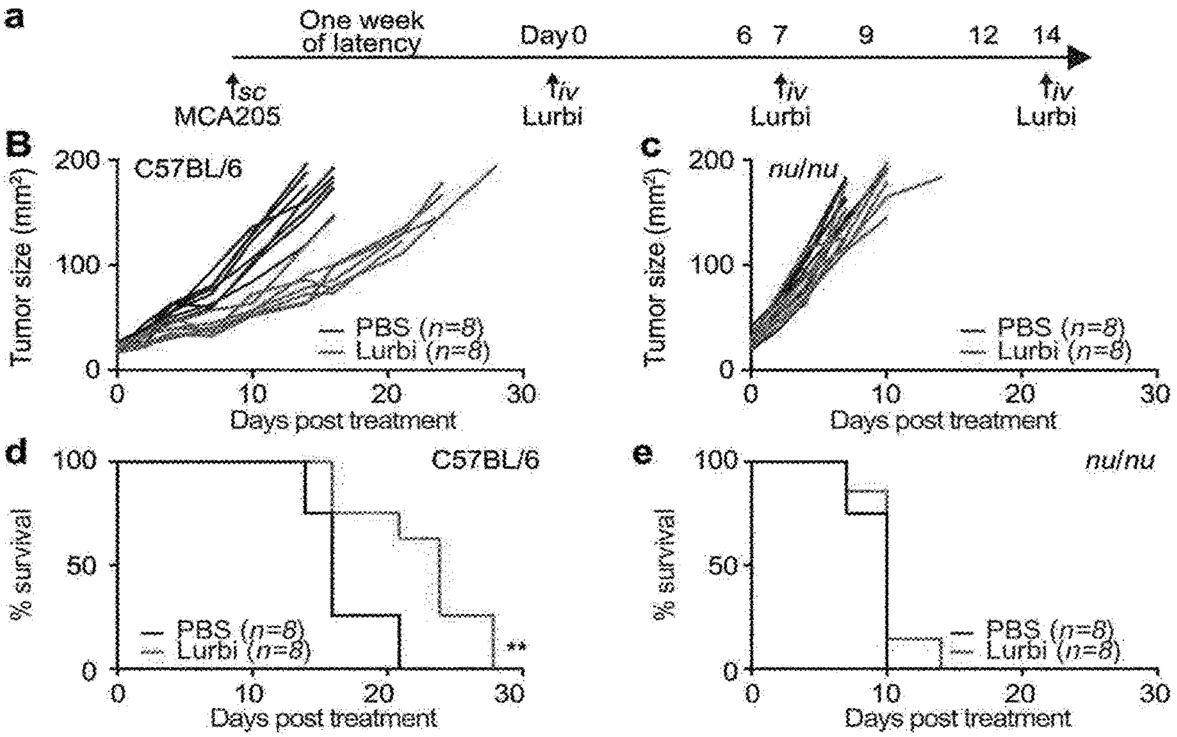

FIG. 4. Therapeutic efficacy of lurbinectedin in immunocompetent and immunodeficient hosts.

Live MCA205 cells were injected subcutaneously (s.c.) into immunocompetent C57BL/6 mice or immunodeficient nu/nu mice as depicted in the scheme in (a) When tumours became palpable, mice were intravenously (i.v.) injected with 0.14 mg/Kg lurbinectedin (on day 1, 7 and 14). Tumour growth was assessed regularly for the following 30 days. Data is depicted as tumour growth curves (b,d) and overall survival plots (c,e). Data were analyzed with TumGrowth.

Figure 5:
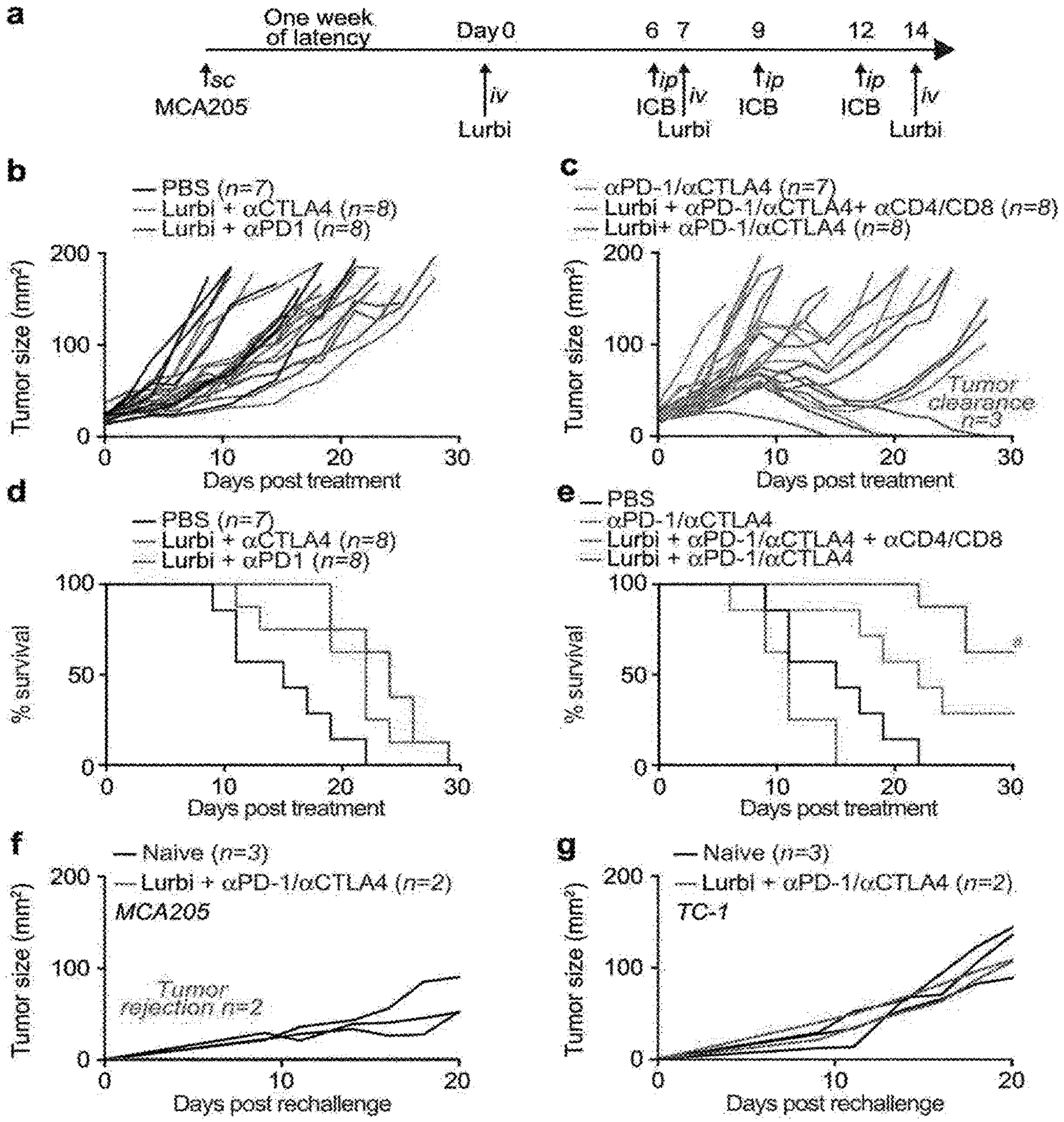

FIG. 5. Sequential lurbinectedin treatment with double immune checkpoint blockade exhibits systemic antitumor immunity C57BL/6 mice were inoculated subcutaneously (s.c.) with murine fibrosarcoma MCA205. Palpable tumours were treated with sequential intravenous (i.v.) injections of 0.14 mg/Kg lurbinectedin (Lurbi) as indicated in (a). Single- or double-immune checkpoint blockade was mounted by sequential intraperitoneal (i.p.) injections of monoclonal antibodies targeting CTLA-4 or PD-1 at day 6, 9 and 12 post treatment and tumour growth (b,c) and overall survival (d,e) were assessed regularly for the following 30 days. (f,g) The generation of immunological memory was assessed in cured animals by rechallenge with MCA205 and TC-1. Naïve animals were used as controls. Individual tumour growth curves are depicted. Data were analyzed with TumGrowth.

Figure 6:
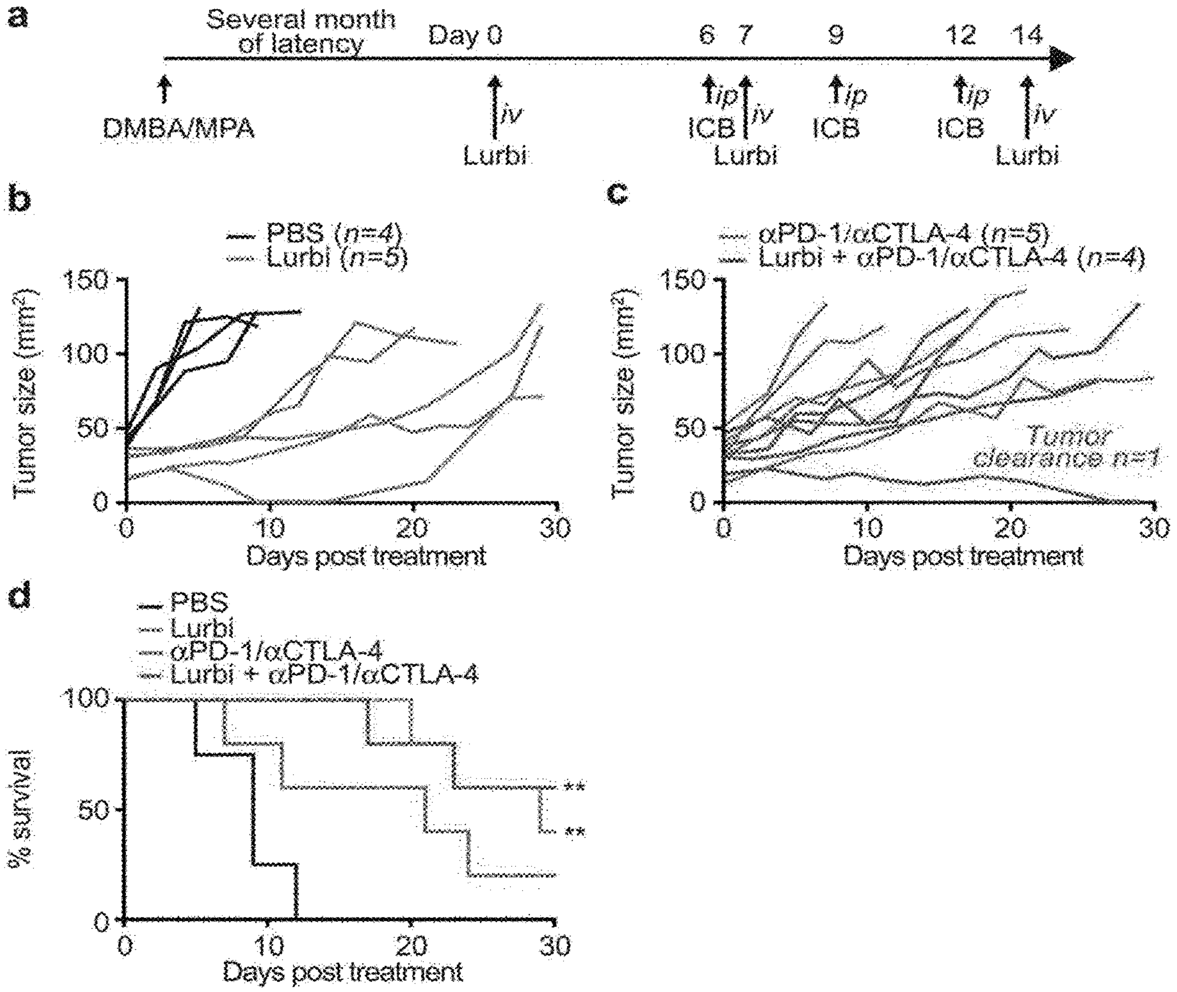

FIG. 6. Lurbinectedin retards the growth of spontaneous tumours.

Medroxyprogesterone acetate (MPA) pellets (50 mg, 90-day release) were implanted subcutaneously into the interscapular area of immunocompetent C57BL/6 mice. Then the animals received 1 mg dimethylbenzantracene (DMBA) administered by oral gavage 6× during 7 weeks. When spontaneous tumours became palpable mice were randomly assigned to receive 0.14 mg/Kg lurbinectedin (Lurbi) alone or in combination with double immune checkpoint blockade with monoclonal antibodies targeting CTLA-4 and PD-1 at day 6, 9 and 12 post treatment (a). The tumour area and overall survival were measured regularly until ethical endpoints were reached (b,c,d). Data were analyzed with TumGrowth (https://github.com/kroemerlab).

DETAILED DESCRIPTION OF THE INVENTION

In the present application, a number of general terms and phrases are used, which should be interpreted as follows.

The term "treating", as used herein, unless otherwise indicated, means reversing, attenuating, alleviating or inhibiting the progress of the disease or condition to which such term applies, or one or more symptoms of such disorder or condition. The term "treatment", as used herein, unless otherwise indicated, refers to the act of treating as "treating" is defined immediately above.

"Patient" includes humans, non-human mammals (e.g., dogs, cats, rabbits, cattle, horses, sheep, goats, swine, deer, and the like) and non-mammals (e.g., birds, and the like).

Lurbinectedin is a synthetic alkaloid, having the following structure:

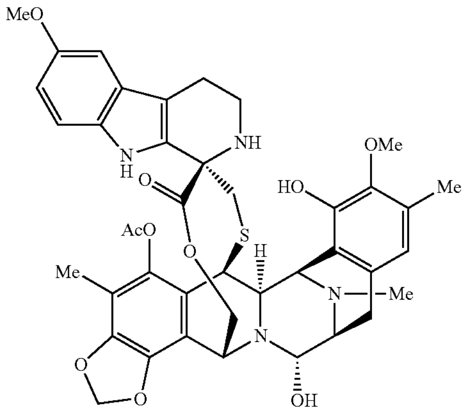 [SMILES: COc1ccc2[nH]c3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

Information regarding its mechanism of action and in vivo efficacy can be found in 100th AACR Annual Meeting, Apr. 18-22, 2009, Denver, CO, Abstract Nr. 2679 and Abstract Nr. 4525; Leal J F M et. al. Br. J. Pharmacol. 2010, 161, 1099-1110; and Belgiovine, C et al. Br. J. Cancer, 2017; 117 (5): 628-638;

Further information regarding the clinical development of PM01183 (lurbinectedin) can be found in:

Elez, M E. et. al. Clin. Cancer Res. 2014, 20 (8), 2205-2214;

50th ASCO Annual Meeting, May 30-Jun. 3, 2014, Chicago, IL, Abstract 5505;

26th EORTC-NCI-AACR Symposium on Molecular Targets and Cancer Therapeutics; Nov. 18-21, 2014, Barcelona, Spain, published in Eur. J. Cancer 2014, 50 (Suppl. 6), pages 13-14, Abs. No. 23.

51th ASCO Annual Meeting, May 29-Jun. 2, 2015, Chicago, IL, Abstract No. TPS2604 and Abstract Nr. 7509, published in J. Clin. Oncol. 33, 2015 (suppl);

54th ASCO Annual Meeting, Jun. 1-5, 2018, Chicago, IL, Abstract No. 11519, published in J. Clin. Oncol. 36, 2018 (suppl);

Cruz, C. et al. J. Clin. Oncol. 2018; in press 1-21;

54th ASCO Annual Meeting, Jun. 1-5, 2018, Chicago, IL, Abstract No. 8570, published in J. Clin. Oncol. 36, 2018 (suppl);

The term "lurbinectedin" is intended here to cover any pharmaceutically acceptable salt, ester, solvate, hydrate, prodrug, or any other compound which, upon administration to the patient is capable of providing (directly or indirectly) the compound as described herein. However, it will be appreciated that non-pharmaceutically acceptable salts also fall within the scope of the invention since those may be useful in the preparation of pharmaceutically acceptable salts. The preparation of salts can be carried out by methods known in the art.

For instance, pharmaceutically acceptable salts of the compounds provided herein are synthesized from the parent compounds, which contain a basic or acidic moiety, by conventional chemical methods. Generally, such salts are, for example, prepared by reacting the free acid or base of these compounds with a stoichiometric amount of the appropriate base or acid in water or in an organic solvent or in a mixture of both. Generally, nonaqueous media like ether, ethyl acetate, ethanol, 2-propanol or acetonitrile are preferred. Examples of the acid addition salts include mineral acid addition salts such as, for example, hydrochloride, hydrobromide, hydroiodide, sulfate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic amino acids salts.

Any compound that is a prodrug of lurbinectedin is within the scope and spirit of the invention. The term "prodrug" is used in its broadest sense and encompasses those derivatives that are converted in vivo to PM01183. The prodrug can hydrolyze, oxidize, or otherwise react under biological conditions to provide PM01183. Examples of prodrugs include, but are not limited to, derivatives and metabolites of PM01183 that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by Burger in "Medicinal Chemistry and Drug Discovery" 6th ed. (Donald J. Abraham ed., 2001, Wiley) and "Design and Applications of Prodrugs" (H. Bundgaard ed., 1985, Harwood Academic Publishers).

In addition, any drug referred to herein may be in crystalline or amorphous form either as free compounds or as solvates (e.g. hydrates) and it is intended that all forms are within the scope of the present invention. Methods of solvation are generally known within the art.

Moreover, lurbinectedin for use in accordance with the present invention may be prepared following the synthetic process such as the one disclosed in WO 03/014127, which is incorporated herein by reference.

In a preferred embodiment of the combination of the present invention, the molar ratio of lurbinectedin or a pharmaceutically acceptable salt or stereoisomer thereof to immune checkpoint inhibitor in said combination is from 1:1000 to 1000:1. Further molar ratios include 1:700 to 700:1, 1:500 to 500:1, 1:300 to 300:1, 1:100 to 100:1, and 1:50 to 50:1.

Pharmaceutical compositions comprising lurbinectedin or a pharmaceutically acceptable salt or ester thereof, and a pharmaceutically acceptable carrier may be formulated according to the chosen route of administration. Examples of the administration form include without limitation oral, topical, parenteral, sublingual, rectal, vaginal, ocular and intranasal. Parenteral administration includes subcutaneous injections, intravenous, intramuscular, intrasternal injection or infusion techniques. Preferably the compositions are administered parenterally. Pharmaceutical compositions can be formulated so as to allow a compound to be bioavailable upon administration of the composition to an animal, preferably human. Compositions can take the form of one or more dosage units, where for example, a tablet can be a single dosage unit, and a container of a compound may contain the compound in liquid or in aerosol form and may hold a single or a plurality of dosage units.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous, or liquid so as to provide an aerosol composition useful in, for example inhalatory administration. Powders may also be used for inhalation dosage forms. The term "carrier" refers to a diluent, adjuvant or excipient, with which the compound according to the present invention is administered. Such pharmaceutical carriers can be liquids, such as water and oils including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, disaccharides, and the like. In addition, auxiliary, stabilizing, thickening, lubricating and coloring agents can be used. In one embodiment, when administered to an animal, the compounds and compositions and pharmaceutically acceptable carriers are sterile. Water is a preferred carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more for the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agent such as sucrose or saccharin; a flavoring agent such as peppermint, methyl salicylate or orange flavoring; and a coloring agent.

When the composition is in the form of a capsule (e.g. a gelatin capsule), it can contain, in addition to materials of the above type, a liquid carrier such as polyethylene glycol, cyclodextrins or a fatty oil.

The composition can be in the form of a liquid, e.g. an elixir, syrup, solution, emulsion or suspension. The liquid can be useful for oral administration or for delivery by injection. When intended for oral administration, a composition can comprise one or more of a sweetening agent, preservatives, dye/colorant and flavour enhancer. In a composition for administration by injection, one or more of a surfactant, preservative, wetting agent, dispersing agent, suspending agent, buffer, stabilizer and isotonic agent can also be included.

The preferred route of administration is parenteral administration including, but not limited to, intradermal, intramuscular, intraperitoneal, intravenous, subcutaneous, intranasal, epidural, intracerebral, intraventricular, intrathecal, intravaginal or transdermal. The preferred mode of administration is left to the discretion of the practitioner, and will depend in part upon the site of the medical condition. In a more preferred embodiment, the compounds according to the present invention are administered intravenously. Infusion times of up to 24 hours are preferred to be used, more preferably 1 to 12 hours, with 1 to 6 hours being most preferred. Short infusion times which allow treatment to be carried out without an overnight stay in a hospital are especially desirable. However, infusion may be 12 to 24 hours or even longer if required. Infusion may be carried out at suitable intervals of, for example, 1 to 4 weeks, preferably once every three weeks.

Liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides, polyethylene glycols, glycerin, or other solvents; antibacterial agents such as benzyl alcohol or methyl paraben; and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant.

The compositions comprise an effective amount of a lurbinectedin and/or an immune checkpoint inhibitor such that a suitable dosage will be obtained. The correct dosage will vary according to the particular formulation, the mode of application, and its particular site and host. Other factors like age, body weight, sex, diet, time of administration, rate of excretion, condition of the host, drug combinations, reaction sensitivities and severity of the disease should be taken into account. Administration can be carried out continuously or periodically within the maximum tolerated dose.

The dose will be selected according to the dosing schedule, having regard to the existing data on preferred administration routes and dosages for each compound.

In specific embodiments, it can be desirable to administer lurbinectedin or an immune checkpoint inhibitor locally to the area in need of treatment. In one embodiment, administration can be by direct injection at the site (or former site) of a cancer, tumour or neoplastic or pre-neoplastic tissue.

Pulmonary administration can also be employed, e.g. by use of an inhaler or nebulizer, and formulation with an aerosolizing agent, or via perfusion in a fluorocarbon or synthetic pulmonary surfactant. In certain embodiments, lurbinectedin can be formulated as a suppository, with traditional binders and carriers such as triglycerides.

The present compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

The pharmaceutical compositions can be prepared using methodology well known in the pharmaceutical art. For example, a composition intended to be administered by injection can be prepared by combining lurbinectedin with water, or other physiologically suitable diluent, such as phosphate buffered saline, so as to form a solution. A surfactant can be added to facilitate the formation of a homogeneous solution or suspension.

Preferred compositions comprising lurbinectedin may invention include:

- Pharmaceutical compositions comprising lurbinectedin and a disaccharide. Particularly preferred disaccharides are selected from lactose, trehalose, sucrose, maltose, isomaltose, cellobiose, isosaccharose, isotrehalose, turanose, melibiose, gentiobiose, and mixtures thereof.
- Lyophilised pharmaceutical compositions comprising lurbinectedin and a disaccharide. Particularly preferred disaccharides are selected from lactose, trehalose, sucrose, maltose, isomaltose, cellobiose, isosaccharose, isotrehalose, turanose, melibiose, gentiobiose, and mixtures thereof.

The ratio of lurbinectedin to the disaccharide in embodiments of the present invention is determined according to the solubility of the disaccharide and, when the formulation is freeze dried, also according to the freeze-dryability of the disaccharide. It is envisaged that this lurbinectedin:disaccharide ratio (w/w) can be about 1:10 in some embodiments, about 1:20 in other embodiments, about 1:50 in still other embodiments. It is envisaged that other embodiments have such ratios in the range from about 1:5 to about 1:500, and still further embodiments have such ratios in the range from about 1:10 to about 1:500.

The composition comprising lurbinectedin may be lyophilized. The composition comprising lurbinectedin is usually presented in a vial which contains a specified amount of such compound.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

The invention will now be described further with reference to the following example.

EXAMPLE

Introduction

Primary or transplantable tumours react to anthracycline-based chemotherapy with durable response in syngeneic immunocompetent mice yet fail to do so in immunodeficient hosts (1-3). Consistently, retrospective clinical studies in patients with solid tumours subjected to chemotherapy showed that severe lymphopenia negatively affects prognosis, (4,5) which points to the fact that chemotherapy-elicited anticancer immunity plays a critical role for the outcome of anticancer therapy. (6,7) Based on these findings, (1-3) we introduced the hypothesis that some chemotherapeutic agents can induce immunogenic cell death (ICD) in tumours and convert them into a therapeutic vaccine, hence stimulating an immune response that can control residual cancer cells.

Selected chemotherapeutics such as anthracyclines and oxaliplatin are able to induce ICD (1-3) while many other antineoplastic agents including cisplatin and mitomycin C fail to do so. Cancer cells undergoing ICD can evoke anticancer immunity and protect against a subsequent challenge with living cells exhibiting the same antigenic profile in mice (1-3) or elicit anticancer immune responses during chemotherapy in patients. (8) Distinctive properties of immunogenic cell death include the exposure of calreticulin (CALR) at the cytoplasmic surface, (3,8,9) the autophagy-dependent liberation of ATP from stressed and dying cells, (10,11) the cell death-associated exodus of nuclear high mobility group box 1 (HMGB1) (12,13) and the stimulation of an autocrine or paracrine type-1 interferon response. (14) CALR serves as a de novo uptake signal and stimulates the engulfment of dying cancer cells by dendritic cells (DCs). (3) HMGB1 binds to toll-like receptor-4 (TLR4) entities on DC, eliciting MYD88-dependent signaling that facilitates tumor antigen processing. (3,15) ATP ligates purinergic receptors of the P2X type and thus activates the NLRP3 inflammasome to stimulate the production of interleukin-1β (IL-1B) by DC and eventually interferon-γ (IFNγ) by CD8+ cytotoxic T lymphocytes (CTL). (10,16) The sum of danger associated molecular patterns (DAMP) emitted during ICD is necessary to generate anticancer immunity, thus tumours growing in Tlr4−/−, P2rx7−/−, Myd88−/−, Nlrp3−/−, Il1r−/−, Ifnγ−/−, Ifnγr−/−, Fpr1−/−, athymic or CD8+ T cell-depleted mice fail to respond to immunogenic chemotherapeutic regimens. Loss-of-function mutations of FPR1, P2RX7 or TLR4 in breast cancer are negatively correlated with clinical response to adjuvant chemotherapy with anthracyclines. (3,10,13,14,17-19) These results imply the obligate contribution of anticancer immune responses to the success of ICD-inducing chemotherapies. Here, we investigated the capacity of lurbinectedin to stimulate the emission of immunogenic DAMPs and tested anticancer immune responses in three experimental in vivo models. Our results support the contention that lurbinectedin causes immunogenic cell death in tumours and creates anticancer immunity.

Results and Discussion

Emission of Immunogenic Signals by Lurbinectedin

The known parameters determining ICD are the translocation of CALR to the surface of the plasma membrane, the autophagy-dependent liberation of ATP and the release of the non-histone binding protein HMGB1, which occur before, during and after apoptosis, respectively. The production of type I interferons (IFNs) has been added to the list of ICD hallmarks as it controls autocrine or paracrine circuits that underlie cancer immunosurveillance.

In a systematic screening campaign, the capacity of lurbinectedin to induce immunogenic cell death in cancer cells was assessed in human osteosarcoma U2OS cells stably expressing fluorescent biosensors for the detection of CALR-relocation (as a surrogate marker for CALR surface exposure), HMGB1 release and Type I IFN responses together with U2OS WT cells stained with the ATP-sensitive dye quinacrine. ICD-related parameters were measured at 4, 8, 16 and 32 hours post exposure to lurbinectedin from 1 nM to 1 μM by robotized epifluorescence microscopy followed by automated image analysis (FIG. 1). The induction of cell death was evaluated based on changes in the nuclear morphology visualized by means of the DNA intercalating dye Hoechst 33342. Lurbinectedin caused a dose- and time-dependent drop in cellular viability comparable to mitoxantrone (MTX) that was used at 1 and 3 μM as a positive control throughout all experiments. The translocation of a CALR-GFP (green fluorescent protein) fusion protein from the perinuclear ER to the cellular periphery was measured by assessing cytoplasmic "granularity" (see Materials and Methods) as an indicator for the formation of CALR-containing vesicles and as a surrogate marker for CALR exposure. Lurbinectedin, similar to MTX, induced a time- and dose-dependent increase in CALR-granularity as compared to untreated controls. The reduction of intracellular ATP (as an indicator for ATP release) was assessed by measuring the decrease in the cytoplasmic granularity of ATP containing vesicles stained with the fluorescent probe quinacrine. As compared to untreated controls a significant decrease in ATP signal similar to MTX was detectable for lurbinectedin. The effect was dose-dependent and decreased over time in line with the fragile nature of the metabolite. HMGB1 release was detected as a loss in the nuclear fluorescence of an HMGB1-GFP chimera. A significant decrease in nuclear GFP signal was detected for MTX and lurbinectedin at medium to late time points. Type I interferon (IFN) production was measured using U2OS biosensor cells stably expressing a GFP under the control of the MX1 (a Type I IFN response gene) promoter. To this aim the supernatant of U2OS cells following treatment and additional 48 hours incubation with fresh media was used to treat the biosensor cells. Following the type 1 IFN response was monitored by means an increase in GFP fluorescence intensity. A significant increase in de novo GFP signal intensity was detected for both lurbinectedin and MTX throughout all time points (FIG. 1(*a*)). Similar results were obtained when the approach was repeated in human breast cancer HCC70 cells (FIG. 1(*b*)), human colon carcinoma HT29 (FIG. 1(*c*)) and mouse fibrosarcoma MCA205 cells (FIG. 1(*d*)). Next, we investigated the capacity of lurbinectedin to activate two additional characteristics of common ICD inducers, the phosphorylation of the eukaryotic translation initiation factor 2 alpha (eIF2α) and the inhibition of general transcription. Indeed, lurbinectedin led to a dose-dependent phosphorylation of eIF2α monitored by fluorescence microscopy upon immunostaining with a phosphoneoepitope-specific antibody (FIG. 2(*a,b*)). Lurbinectedin also inhibited mRNA transcription at a level comparable to a known transcription-inhibitor, as assessed by visualizing the dissociation of nucleolin and fibrillarin by microscopy (FIG. 2(*b,c*)), an accepted proxy of suppressed transcription. (21) Lurbinectedin holds many of the described in vitro parameters of ICD, thus qualifying for further in vivo investigations in immunocompetent animals, which remains the gold standard assay for the determination of ICD-mediated anticancer immunity.

Anticancer Immunity Induced by Lurbinectedin

In order to assess the capacity of lurbinectedin to stimulate anticancer immunity in a monotherapeutic approach and to convert tumour cells into a therapeutic vaccine we exposed murine fibrosarcoma cells to the drug in vitro (in conditions previously established to induce a sufficient amplitude of cell death) and then injected the dying cancer cells into syngeneic immunocompetent mice. One week later, the animals were re-challenged injecting live tumour cells of the same kind into the opposite flank, (FIG. 3(*a*)). In this setting, a decrease of tumour growth can be interpreted as sign of a productive anticancer immune response. Indeed, lurbinectedin-treated cells significantly reduced tumour growth (p=0.0094) (FIG. 3(*b*)) and led to an increase in overall survival (FIG. 3(*c*)). As compared to know ICD inducers (1-3) the vaccination effects observed here were rather limited yet statistically significant. Next we evaluated the effect of lurbinectedin on established cancers growing on immunocompetent or immunodeficient mice. MCA 205 tumours were implanted subcutaneously on immunocompetent C57BL/6 as well as in athymic nu/nu mice. When the tumours became palpable, the animals were treated with three consecutive intravenous injections of 0.18 mg/kg lurbinectedin on day 1, 7 and 14. (FIG. 4(*a*)). The treatment with lurbinectedin had significant therapeutic benefit in immunocompetent animals. The tumour growth was significantly reduced as compared to control animals ($p<0.0001$) (FIG. 4(*b*)) and overall survival was increased (FIG. 4(*c*)). This effect was exclusively observed when tumours grew on immunocompetent mice, yet was lost when the tumours proliferated on athymic (nu/nu) mice (FIG. 4(*d,e*)). These results underscore the obligate contribution of the immune system to the chemotherapeutic activity of lurbinectedin.

Combinatorial Effects of Lurbinectedin and αPD-1/αCTLA-4 Double Immune Checkpoint Blockade Given the capacity of lurbinectedin to induce immune-dependent anticancer effects on established tumours, we investigated whether this agent could sensitize cancers to therapy with immune checkpoint blockers targeting CTLA-4 or PD-1. For this, established MCA205 fibrosarcomas were treated with Lurbinectedin as before and subjected to immunotherapy with antibodies specific for CTLA-4, PD-1 or a combination of both on day 6, 9 and 12, when the anticancer immune response in the tumour peaks (FIG. 5(*a*)). Tumor monitoring led to the deduction that the most efficient therapeutic regimen was a combination of all three anticancer agents (lurbinectedin, αCTLA-4 and αPD-1). Single ICB therapies are also shown to be effective (FIG. 5(*b-e*)). The combination of lurbinectedin with αCTLA-4/αPD-1 dual checkpoint blockade in tumour-bearing animals significantly extended life expectancy and, moreover, led to tumour clearance in 3/8 mice in the time frame of the experiment (FIG. 5(*e*)). The effect of lurbinectedin with αCTLA-4/αPD-1 dual checkpoint blockade was abrogated in conditions in which CD4+ and CD8+ cytotoxic T lymphocytes (CTLs) were depleted. Mice that had been rendered tumour-free for more than 50 days rejected tumours upon rechallenge with the same cancer cell type from which they had been cured (MCA205), yet developed cancers when rechallenged with TC1 tumour cells (FIG. 5(*f,g*)). Thus, mice that had been cured by a combination of systemic lurbinectedin-based chemotherapy and immunotherapy had established a specific anticancer immune response that generated immunological memory.

Lurbinectedin Retards the Growth of Carcinogen-Induced and Spontaneous Breast Cancer To explore the potential lurbinectedin for the therapy of breast cancer, we took advantage of a hormone/carcinogen induced breast cancer model activated by the continuous stimulation of progesterone receptors by medroxyprogesterone acetate (MPA) and the repeated exposure to the DNA-damaging agent dimethylbenzantracene (DMBA). This induced model of breast cancer is known to be modulated by the immune system. (22) We treated mice with palpable MPA/DMBA-induced tumours by systemic injection with lurbinectedin alone or in combination with double immune checkpoint blockade neutralizing CTLA-4 and PD-1 (FIG. 6(*a*)). Both interventions significantly reduced tumour growth and increased overall survival. However, only the combination with αCTLA-4/αPD-1 yielded tumour clearance in the time frame of the experiment (FIG. 6(*b-d*)).

Concluding Remarks

The results of this study suggest that lurbinectedin efficiently induces cell death in a broad panel of solid tumours. This procedure likely does not only cause the cells to succumb to disintegration but rather triggers traits of immunogenic cell death, including the phosphorylation of eIF2a and the release of danger associated molecular patterns (DAMPs). Irrespective of the exact molecular mechanisms accounting for these effects, there are a number of evidences advocating for lurbinectedin-triggered cancer-specific immunogenicity. Thus, animals that had been cured by lurbinectedin from established cancers became resistance to rechallenge with the same cancer type. The therapeutic effect of lurbinectedin was neutralized in conditions in which either the host was immunocompromised or T-cell had been depleted. Furthermore, the recapitulation in a heterogeneous spontaneous tumour model of effects that were previously observed in homogenous transplanted tumours indicates that the results presented here hold a high translational value.

Altogether, these results convincingly demonstrate that lurbinectedin mediated immunochemotherapy may be advantageously combined with clinically established immune checkpoint blockade regimens.

Materials & Methods

Cell Culture and Chemicals

All media and cell culture supplements were from Thermo Fisher Scientific (Carlsbad, CA, US). Lurbinectedin was provided by PharmaMar (Madrid, Spain). Cell culture plastics and consumables were purchased from Greiner Bio-One (Kremsmünster, Austria). Human osteosarcoma U2OS cells previously genetically altered as described earlier, 23 murine methylcholanthrene-induced fibrosarcoma MCA-205 cells and murine lung cancer TC-1 cells were cultured in Glutamax®-containing DMEM medium supplemented with 10% fetal bovine serum (FBS), and 10 mM HEPES. Cells were cultured in a temperature-controlled environment at 37° C. with a humidified atmosphere containing 5% CO2.

Automated Image Acquisition and Analysis

One day before the experiment $5\times10^3$ cells were seeded in 96-well µClear imaging plates (Greiner BioOne) and let adhere under standard culture conditions. The following day cells were treated with lurbinectedin at 0.001, 0.01, 0.1 and 1 µM for 4, 8, 16 or 32 hours. Then cells were fixed with 3.7% formaldehyde supplemented with 1 µg/ml Hoechst 33342 for 30 min at RT. The fixative was changed to PBS and the plates were analyzed by automated microscopy. For the detection of ATP enriched vesicles, the cells were labeled after 4, 8, 16 or 32 hours of incubation with the fluorescent dye quinacrine (as described before (23)). In short, cells were incubated with 5 µm quinacrine and 1 µg/ml Hoechst 33342 in Krebs-Ringer solution (125 mM NaCl, 5 mM KCl, 1 mM $MgSO_4$, 0.7 mM $KH_2PO_4$, 2 mm $CaCl_2$), 6 mM glucose and 25 mM Hepes, pH 7.4) for 30 minutes at 37° C. Thereafter, cells were rinsed with Krebs-Ringer and viable cells were microscopically examined. For automated fluorescence microscopy a robot-assisted Molecular Devices IXM XL BioImager (Molecular Devices, Sunnyvale, CA, USA) equipped with SpectraX light source (Lumencor, Beaverton, OR, USA), adequate excitation and emission filters (Semrock, Rochester, NY, USA) and a 16-bit monochromes sCMOS PCO.edge 5.5 camera (PCO Kelheim, Germany) and a 20× PlanAPO objective (Nikon, Tokyo, Japan) was used to acquire a minimum of 9 view fields, followed by automated image processing with the custom module editor within the MetaXpress software (Molecular Devices). Depending on the utilized biosensor cell line the primary region of interest (ROI) was defined by a polygon mask around the nucleus allowing for the enumeration of cells, the detection of morphological alterations of the nucleus and nuclear fluorescence intensity. Cellular debris was excluded from the analysis and secondary cytoplasmic ROIs were used for the quantification of CALR-GFP or quinacrine containing vesicles. For the latter, the images were segmented and analyzed for GFP granularity by comparing the standard deviation of the mean fluorescence intensity of groups of adjacent pixels (coefficient of variation) within the cytoplasm of each cell to the mean fluorescence intensity in the same ROI using the MetaXpress software (Molecular Devices).

In Vivo Experimentation

Six- to eight-week-old female wild-type C57BL/6 and nu/nu mice were obtained from Envigo France (Huntingdon, UK) and were kept in the animal facility at the Gustave Roussy Campus Cancer in a specific pathogen-free and temperature-controlled environment with 12 h day, 12 h night cycles and received food and water ad libitum. Animal experiments were conducted in compliance with the EU Directive 63/2010 and protocols 2013_094A and were approved by the Ethical Committee of the Gustave Roussy Campus Cancer (CEEA IRCIV/IGR no. 26, registered at the French Ministry of Research). As described, (24,25) MCA205 tumours were established in C57BL/6 mice by subcutaneously (s.c.) injection of $5\times10^5$ cells. When tumours became palpable, 0.18 mg/Kg lurbinectedin was injected sequentially once a week intravenously into the tail vein and animal well-being and tumour growth were monitored. A total of 0.5 mg of anti-CD8 (clone 2.43 BioXCell BE 0061) and anti-CD4 (clone GK1.5 BioXCell BE 0003-1) intraperitoneal (i.p.) injections were repeated every 7 days to assure the complete depletion of both T cell populations during the whole experiment. Mice were sacrificed when tumour size reached end-point or signs of obvious discomfort associated to the treatment were observed following the EU Directive 63/2010 and our Ethical Committee advice. Tumour-free animals were kept for more than 30 days before testing the generation of immunological memory by s.c. rechallenge with $5\times10^5$ TC-1 in one flank and $5\times10^5$ MCA205 cells injected in the contralateral flank. Animals were monitored and tumour growth documented regularly until end-points were reached. Statistical analysis was performed by applying 2-way ANOVA analysis followed by Bonferroni's test comparing to control conditions (*$p<0.05$, **$p<0.01$ and *$p<0.001$). Murine fibrosarcoma MCA205 cells were incubated with 1 µM lurbinectedin for 24 h, resulting in approximately 70% cell death. For vaccination experiments, $3\times10^5$ dying MCA205 cells were inoculated s.c. into the left flanks of six-week-old female C57BL/6 mice. Seven to ten days later, animals were re-challenged in the opposite flank with $3\times10^5$ living MCA205 cells, and tumour growth and incidence were monitored. Six-week-old female C57BL/6 mice (n=12 per group) underwent surgical implantation of slow-release medroxyprogesterone acetate (MPA) pellets (50 mg, 90-day release; Innovative Research of America, Sarasota, Fl, US) s.c. Two-hundred µL of 5 mg/mL dimethylbenzantracene (DMBA, Sigma Aldrich, St. Louis, MO, US) dissolved in corn oil was administered by oral gavage once per week for 7 weeks.

Immune Checkpoint Blockade

Double or single immune checkpoint blockade was applied by repeated intraperitoneal injections of monoclonal antibody specific to PD-1 (200 µg, Clone 29F.1A12, BioXcell, West Lebanon, NH, USA) or CTLA-4 (200 µg, Clone 9D9, BioXcell) at day 6, 9 and 12 upon initiation of the treatment with lurbinectedin. Animals were monitored regularly and the tumour growth was documented until ethical end-points were reached. Statistical analysis was performed employing 2-way ANOVA analysis followed by Bonferroni's test comparing to control conditions (*$p<0.05$, **$p<0.01$ and *$p<0.001$).

Statistical Procedures

Unless otherwise specified, experiments were performed in quadruplicate instances. Data were analyzed with the freely available software R (https://www.r-project.org). Significances were calculated using a student t-test with Welch correction. Thresholds for each assay were applied based on the Gaussian distribution of positive and negative controls. In vivo tumour growth was analyzed with the help of the TumGrowth software package (26) freely available at https://github.com/kroemerlab.

REFERENCES

1. Casares N, Pequignot M O, Tesniere A, et al. Caspase-dependent immunogenicity of doxorubicin-induced tumor cell death. J Exp Med. 2005; 202 (12): 1-9. doi: 10.1084/jem.20050915.
2. Mattarollo S R, Loi S, Duret H, Ma Y, Zitvogel L, Smyth M J. Pivotal role of innate and adaptive immunity in anthracycline chemotherapy of established tumors. Cancer Res. 2011; 71 (14): 4809-4820. doi: 10.1158/0008-5472.CAN-11-0753.
3. Obeid M, Tesniere A, Ghiringhelli F, et al. Calreticulin exposure dictates the immunogenicity of cancer cell death. Nat Med. 2007; 13 (1): 54-61. doi: 10.1038/nm1523.
4. Ray-Coquard I, Cropet C, Van Glabbeke M, et al. Lymphopenia as a prognostic factor for overall survival in advanced carcinomas, sarcomas, and lymphomas. Cancer Res. 2009; 69 (13): 5383-5391. doi: 10.1158/0008-5472.CAN-08-3845.
5. Fridman W H, Zitvogel L, Sautes-Fridman C, Kroemer G. The immune contexture in cancer prognosis and treatment. Nat Rev Clin Oncol. 2017; 14 (12): 717-734. doi: 10.1038/nrclinonc.2017.101.
6. Lesterhuis W J, Haanen J B, Punt C J. Cancer immunotherapy-revisited. Nat Rev Drug Discovery. 2011; 10 (8): 591-600. doi: 10.1038/nrd3500.
7. Zitvogel L, Kepp O, Kroemer G. Immune parameters affecting the efficacy of chemotherapeutic regimens. Nat Rev Clin Oncol. 2011; 8 (3): 151-160. doi: 10.1038/nrclinonc.2010.223.
8. Zappasodi R, Pupa S M, Ghedini G C, et al. Improved clinical outcome in indolent B-cell lymphoma patients vaccinated with autologous tumor cells experiencing immunogenic death. Cancer Res. 2010; 70 (22): 9062-9072. doi: 10.1158/0008-5472.CAN-10-1825.
9. Fucikova J, Kralikova P, Fialova A, et al. Human tumor cells killed by anthracyclines induce a tumor-specific immune response. Cancer Res. 2011; 71 (14): 4821-4833. doi: 10.1158/0008-5472.CAN-11-0950.
10. Ghiringhelli F, Apetoh L, Tesniere A, et al. Activation of the NLRP3 inflammasome in dendritic cells induces IL-1beta-dependent adaptive immunity against tumors. Nat Med. 2009; 15 (10): 1170-1178. doi: 10.1038/nm.2028.
11. Michaud M, Martins I, Sukkurwala A Q, et al. Autophagy-dependent anticancer immune responses induced by chemotherapeutic agents in mice. Science. 2011; 334 (6062): 1573-1577. doi: 10.1126/science.1208347.
12. Apetoh L, Ghiringhelli F, Tesniere A, et al. The interaction between HMGB1 and TLR4 dictates the outcome of anticancer chemotherapy and radiotherapy. Immunol Rev. 2007; 220:47-59. doi: 10.1111/j.1600-065X.2007.00573.x.
13. Tesniere A, Schlemmer F, Boige V, et al. Immunogenic death of colon cancer cells treated with oxaliplatin. Oncogene. 2010; 29 (4): 482-491. doi: 10.1038/onc.2009.356.
14. Sistigu A, Yamazaki T, Vacchelli E, et al. Cancer cell-autonomous contribution of type I interferon signaling to the efficacy of chemotherapy. Nat Med. 2014; 20 (11): 1301-1309. doi: 10.1038/nm.3708.
15. Apetoh L, Ghiringhelli F, Tesniere A, et al. Toll-like receptor 4-dependent contribution of the immune system to anticancer chemotherapy and radiotherapy. Nat Med. 2007; 13 (9): 1050-1059. doi: 10.1038/nm1622.
16. Ma Y, Adjemian S, Mattarollo S R, et al. Anticancer chemotherapy-induced intratumoral recruitment and differentiation of antigen-presenting cells. Immunity. 2013; 38 (4): 729-741. doi: 10.1016/j.immuni.2013.03.003.
17. Vacchelli E, Ma Y, Baracco E E, et al. Chemotherapy-induced antitumor immunity requires formyl peptide receptor 1. Science. 2015; 350 (6263): 972-978. doi: 10.1126/science.aad0779.
18. Kroemer G, Senovilla L, Galluzzi L, Andre F, Zitvogel L. Natural and therapy-induced immunosurveillance in breast cancer. Nat Med. 2015; 21 (10): 1128-1138. doi: 10.1038/nm.3944.
19. Vacchelli E, Enot D P, Pietrocola F, Zitvogel L, Kroemer G. Impact of pattern recognition receptors on the prognosis of breast cancer patients undergoing adjuvant chemotherapy. Cancer Res. 2016; 76 (11): 3122-3126. doi: 10.1158/0008-5472.CAN-16-0294.
20. Santamaría Nuñez G, Robles C M, Giraudon C, et al. Lurbinectedin specifically triggers the degradation of phosphorylated RNA polymerase II and the formation of DNA breaks in cancer cells. Mol Cancer Ther. 2016; 15 (10): 2399-2412. doi: 10.1158/1535-7163.MCT-16-0172.
21. Peltonen K, Colis L, Liu H, et al. A targeting modality for destruction of RNA polymerase I that possesses anticancer activity. Cancer Cell. 2014; 25 (1): 77-90. doi: 10.1016/j.ccr.2013.12.009.
22. Pietrocola F, Pol J, Vacchelli E, et al. Caloric restriction mimetics enhance anticancer immunosurveillance. Cancer Cell. 2016; 30 (1): 147-160. doi: 10.1016/j.ccell.2016.05.016.
23. Martins I, Kepp O, Schlemmer F, et al. Restoration of the immunogenicity of cisplatin-induced cancer cell death by endoplasmic reticulum stress. Oncogene. 2011; 30 (10): 1147-1158. doi: 10.1038/onc.2010.500.
24. Iribarren K, Buque A, Mondragon L, et al. Anticancer effects of anti-CD47 immunotherapy in vivo. Oncoimmunology. 2019; 8 (3): 1550619. doi: 10.1080/2162402X.2018.1550619.
25. Zhou H, Mondragon L, Xie W, et al. Oncolysis with DTT-205 and DTT-304 generates immunological memory in cured animals. Cell Death Dis. 2018; 9 (11): 1086. doi: 10.1038/s41419-018-1127-3.
26. Enot D P, Vacchelli E, J acquelot N, Zitvogel L, TumGrowth: K G. An open-access web tool for the statistical analysis of tumor growth curves. Oncoimmunology. 2018; 7 (9): e1462431. doi: 10.1080/2162402X.2018.1490854.

The invention claimed is:

1. A method of treatment of lung cancer, the method comprising administering to a patient in need thereof a compound of the following formula:

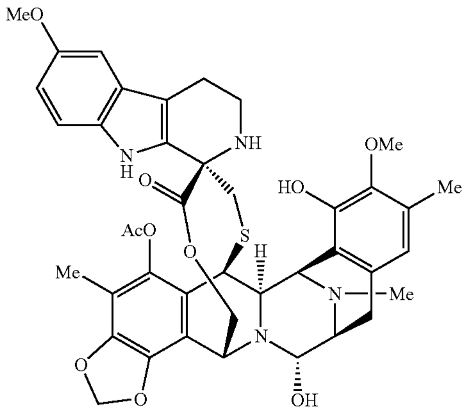 [SMILES: COc1ccc2[nH]c3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

wherein the compound is administered in combination with atezolizumab; and wherein the compound is administered every 21 days by intravenous infusion at a dose of 3.2 $mg/m^2$.

2. The method according to claim 1, wherein atezolizumab is administered every 21 days.

3. The method according to claim 1, wherein the compound is administered as a 1-hour infusion.

4. The method according to claim 1, wherein the compound and atezolizumab are administered concurrently, separately or sequentially.

5. The method according to claim 1, wherein multiple administrations of either the compound, or atezolizumab, or both, are given.

6. The method according to claim 1, wherein atezolizumab is administered by intravenous infusion.

7. The method according to claim 1, wherein atezolizumab is administered subcutaneously.

8. The method according to claim 1, wherein the lung cancer expresses PD-L1.

9. The method according to claim 1, wherein the method further comprises determining whether the tumor to be treated expresses PD-L1 prior to beginning treatment.

10. The method according to claim 1, wherein the treatment results in one or more of: reduction in tumor size; delay in growth of tumor; prolongation of life of the patient; delay in disease progression; remission.

11. The method according to claim 1, wherein the method comprises prolonging survival of a patient having a lung cancer, delaying disease progression of a lung cancer in a patient and/or reducing or delaying growth of a lung cancer tumor.

12. The method according to claim 2, wherein the compound is administered as a 1-hour infusion.

13. The method according to claim 12, wherein the compound and atezolizumab are administered concurrently, separately or sequentially.

14. The method according to claim 13, wherein atezolizumab is administered by intravenous infusion.

15. The method according to claim 14, wherein the lung cancer expresses PD-L1.

16. The method according to claim 15, wherein the method further comprises determining whether the tumor to be treated expresses PD-L1 prior to beginning treatment.

17. The method according to claim 16, wherein the treatment results in one or more of: reduction in tumor size; delay in growth of tumor; prolongation of life of the patient; delay in disease progression; remission; and/or wherein the method comprises prolonging survival of a patient having a lung cancer, delaying disease progression of a lung cancer in a patient and/or reducing or delaying growth of a lung cancer tumor.

18. The method according to claim 13, wherein atezolizumab is administered subcutaneously.

19. The method according to claim 18, wherein the lung cancer expresses PD-L1.

20. The method according to claim 19, wherein the method further comprises determining whether the tumor to be treated expresses PD-L1 prior to beginning treatment.

21. The method according to claim 20, wherein the treatment results in one or more of: reduction in tumor size; delay in growth of tumor; prolongation of life of the patient; delay in disease progression; remission; and/or wherein the method comprises prolonging survival of a patient having a lung cancer, delaying disease progression of a lung cancer in a patient and/or reducing or delaying growth of a lung cancer tumor.

22. The method according to claim 3, wherein the compound and atezolizumab are administered concurrently, separately or sequentially.

23. The method according to claim 22, wherein atezolizumab is administered by intravenous infusion.

24. The method according to claim 23, wherein the lung cancer expresses PD-L1.

25. The method according to claim 24, wherein the method further comprises determining whether the tumor to be treated expresses PD-L1 prior to beginning treatment.

26. The method according to claim 22, wherein atezolizumab is administered subcutaneously.

27. The method according to claim 26, wherein the lung cancer expresses PD-L1.

28. The method according to claim 27, wherein the method further comprises determining whether the tumor to be treated expresses PD-L1 prior to beginning treatment.

29. The method according to claim 28, wherein the treatment results in one or more of: reduction in tumor size; delay in growth of tumor; prolongation of life of the patient; delay in disease progression; remission; and/or wherein the method comprises prolonging survival of a patient having a lung cancer, delaying disease progression of a lung cancer in a patient and/or reducing or delaying growth of a lung cancer tumor.

* * * * *